(12) United States Patent
Porszasz-Reisz

(10) Patent No.: US 8,222,478 B2
(45) Date of Patent: Jul. 17, 2012

(54) CONDITIONAL MST OVEREXPRESSING CONSTRUCT AND CONDITIONAL MYOSTATIN OVEREXPRESSING TRANSGENIC MOUSE

(75) Inventor: Suzanne Porszasz-Reisz, Lakewood, CA (US)

(73) Assignee: Charles Drew University of Medicine and Science, Lynwood, CA (US)

( * ) Notice: Subject to any disclaimer, the term of this patent is extended or adjusted under 35 U.S.C. 154(b) by 225 days.

(21) Appl. No.: 12/398,994

(22) Filed: Mar. 5, 2009

(65) Prior Publication Data

US 2010/0169986 A1    Jul. 1, 2010

Related U.S. Application Data

(60) Provisional application No. 61/034,083, filed on Mar. 5, 2008.

(51) Int. Cl.
*A01K 67/00* (2006.01)
*A01K 67/033* (2006.01)
*A01K 67/027* (2006.01)

(52) U.S. Cl. ................................. 800/8; 800/14; 800/18

(58) Field of Classification Search .................. 800/8, 14
See application file for complete search history.

(56) References Cited

OTHER PUBLICATIONS

Reisz-Porszasz, Am J Physiol Endocrinol Metab, 2003, 285:E876-E888.*
Artaza, Journal of Endocrinology, 2007, 194:63-76.*
Sigmund, 2000, Arterioscler. Thromb. Vasc. Biol. 20: 1425-1429.*
Moens et al. 1993, Development 119: 485-499.*
Lee, 2004, Annual Review of Cell and Developmental Biology, 20:61-86.*
Petridou et al. 2003, Transgenic Research 12: 693-706.*
BD Biosciences Tet-Off and Tet-On gene expression systems user manual. Cat. No. 630921, 630922 Published: Feb. 3, 2004.
Clontech: Tet-Off and Tet-On gene expression systems user manual. Cat. No. PT30001-1. Publisshed Jun. 25, 1999.
Fiers, et al., "Complete nucleotide sequence of SV40 DNA", Nature, 273(5658): 113-120, (1978).
Larochelle, et al., "Efficient muscle-specific transgene expression after adenovirus-mediated gene transfer in mice using a 1.35kb muscle creatine kinase promoter/enhancer", Gene Ther., 4: 465-472, (1997).
Lourenco, et al., "A cell-based bicistronic lentiviral reporter system for identification of inhibitors of the hepatitis C virus internal ribosome entry site", J. Virol. Methods, 158(1-2): 152-159, (2009).
McPherron, et al., Regulation of skeletal muscle mass in mice by a new TGF-β superfamily member, Nature, 387(6628): 83-90, (1997).
Mulligan, et al., "Expression of a bacteria gene in mammalian cells", Science, 209(4463): 1422-1427, (1980).
Pavlakis, et al., "Expresion of two human growth hormone genes in monkey cells infected by simian virus 40 recombinants", PNAS, 78(12): 7398-7402, (1981).
Shield, et al., "E-box sites and a proximal regulatory region of the muscle creatine kinase gene differentially regulate expression in diverse skeletal muscles and cardiac muscle of transgenic mice", Mol. Cell Biol., 16: 5058-5068, (1996).
Zimmers, et al., "Induction of cachexia in mice by systemically administered myostatin", Science, 296: 1486-1488, (2002).

* cited by examiner

*Primary Examiner* — Valarie Bertoglio
(74) *Attorney, Agent, or Firm* — James A. Fox; Arnold & Porter LLP

(57) ABSTRACT

Provided herein are novel nucleic acid sequences, vectors comprising such nucleic acid sequences, host cells comprising such vectors, and transgenic animals comprising such nucleic acid sequences, and related molecules and methods relating thereto. Such novel nucleic acid sequences, vectors comprising such nucleic acid sequences, host cells comprising such vectors, and transgenic animals comprising such nucleic acid sequences, and related molecules and methods provide conditional overexpression of genes, such as myostatin, and transgenic animals conditionally overexpression genes, such as myostatin.

6 Claims, 108 Drawing Sheets

*Myostatin transgenic mice*

- *Mst overexpressing construct*

- *Conditional Mst overexpressing construct*

Figures 1, 1A:
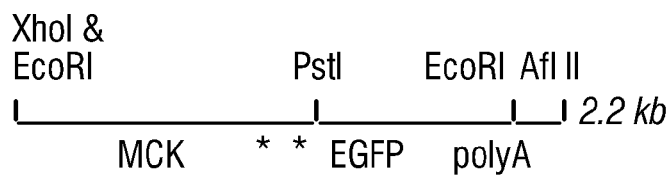

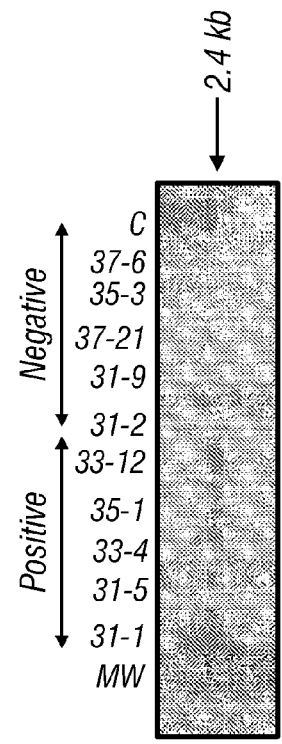
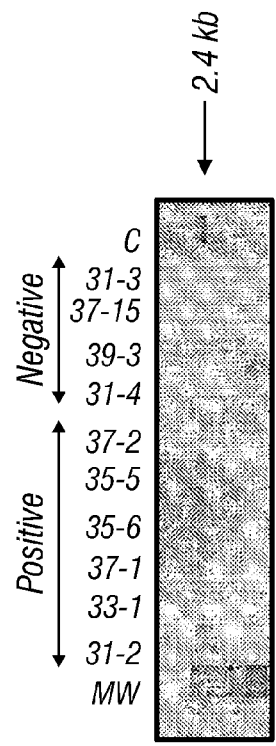
FIG. 3A
FIG. 3B
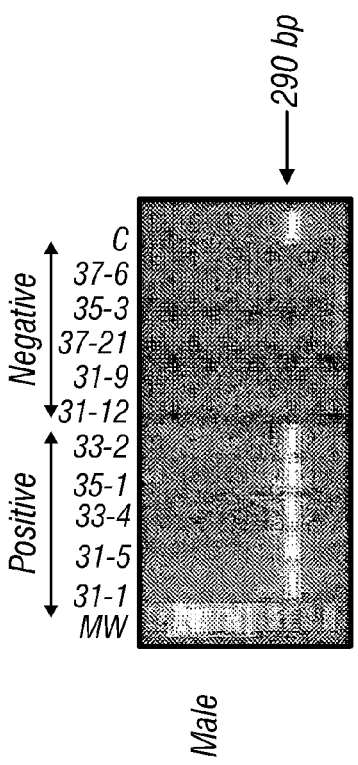
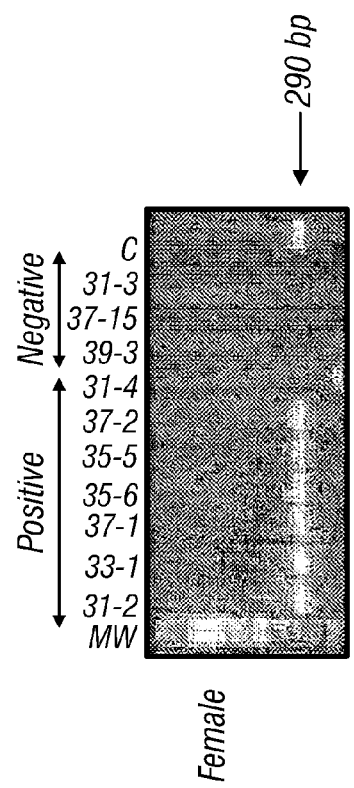

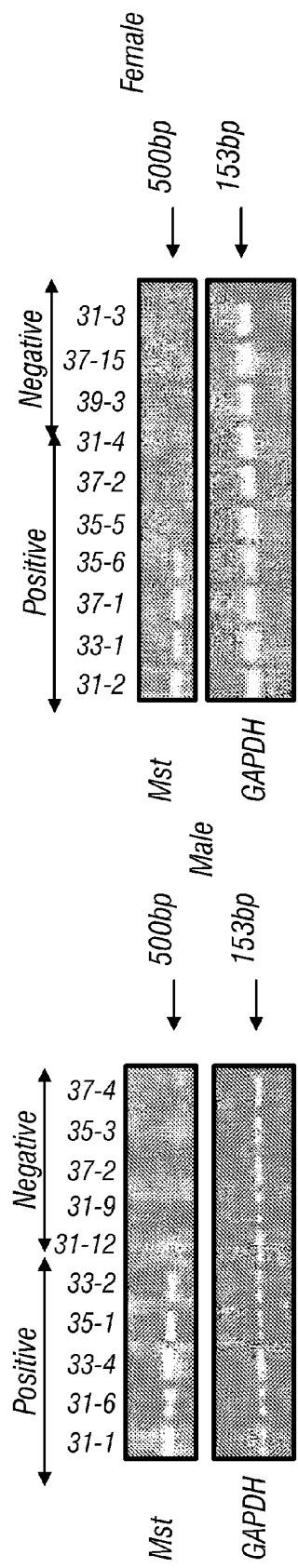
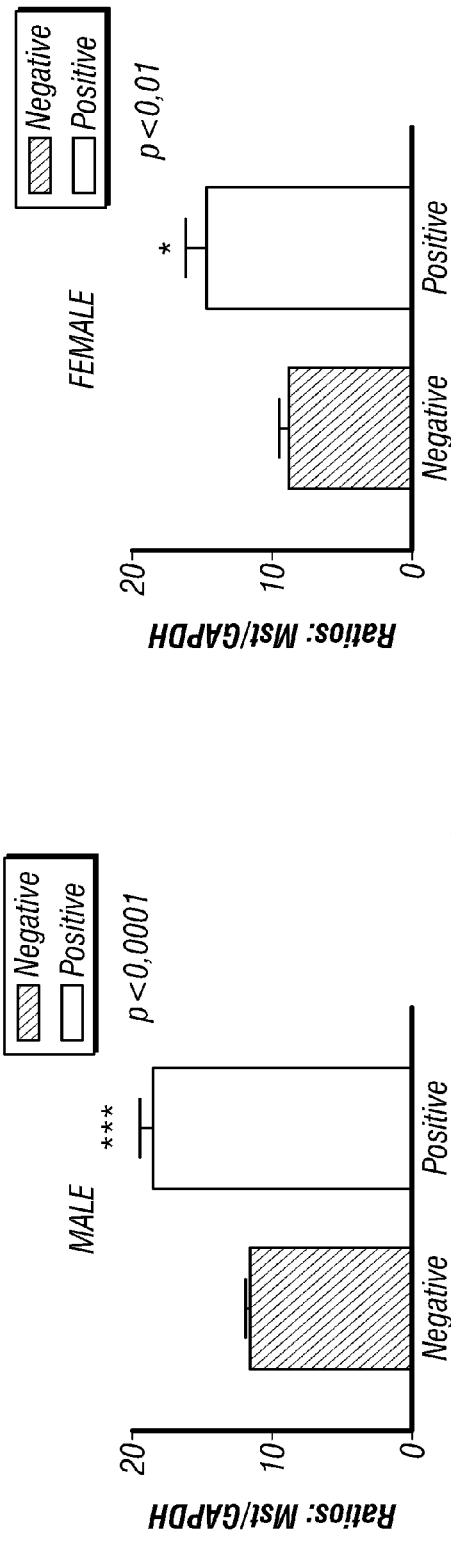
FIG. 5A
FIG. 5B

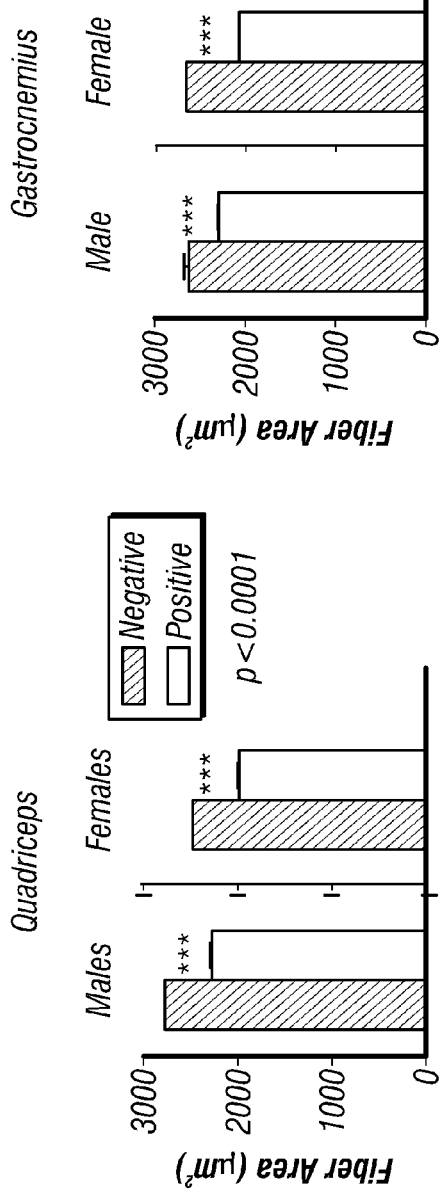
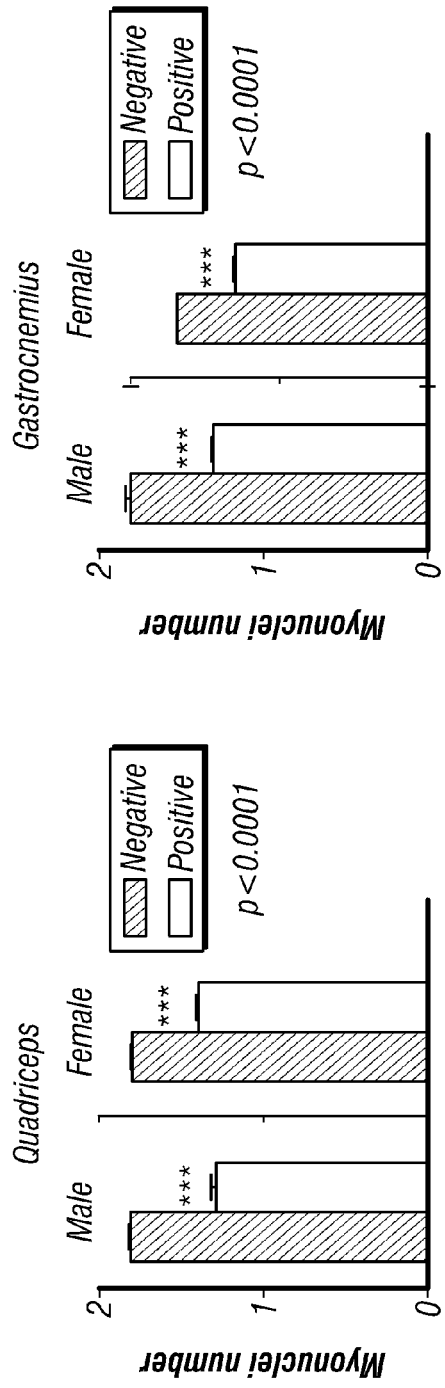
FIG. 7A
FIG. 7B

  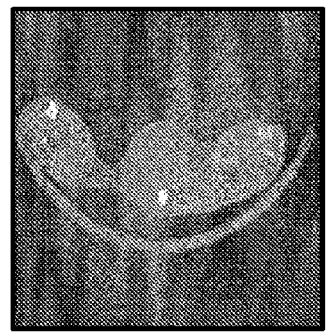
FIG. 10A    FIG. 10B    FIG. 10C
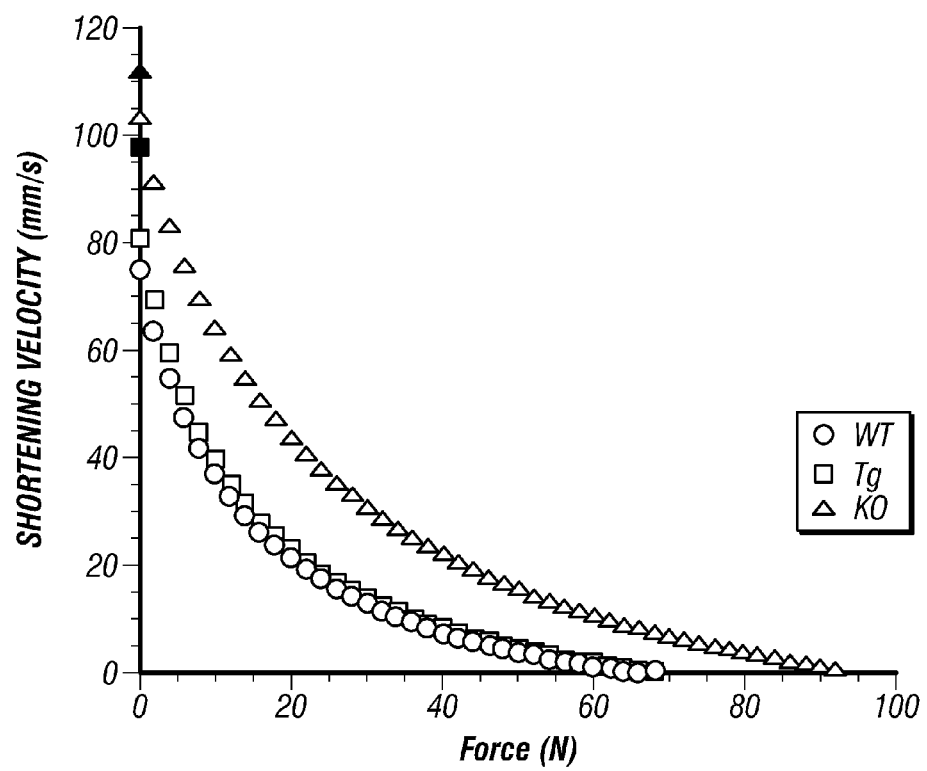
FIG. 11

CMOT transgene

```
cttaagatacattgatgagtttggacaaaccacaactagaatgcagtgaaaaaaatgctttatttgtgaaatttgtg
atgctattgctttatttgtaaccattataagctgcaataaacaagttaacaacaacaattgcattcattttatgttt
caggttcaggggggaggtgtgggaggttttttaaagcaagtaaaacctctacaaatgtggtatggctgattatgatct
agagtcgcggccgctttacttgtacagctcgtccatgccgagagtgatcccggcggcggtcacgaactccagcagga
ccatgtgatcgcgcttctcgttggggtctttgctcagggcggactgggtgctcaggtagtggttgtcgggcagcagc
acggggccgtcgccgatgggggtgttctgctggtagtggtcggcgagctgcacgctgccgtcctcgatgttgtggcg
gatcttgaagttcaccttgatgccgttcttctgcttgtcggccatgatatagacgttgtggctgttgtagttgtact
ccagcttgtgccccaggatgttgccgtcctccttgaagtcgatgcccttcagctcgatgcggttcaccagggtgtcg
ccctcgaacttcacctcggcgcgggtcttgtagttgccgtcgtccttgaagaagatggtgcgctcctggacgtagcc
ttcgggcatggcggacttgaagaagtcgtgctgcttcatgtggtcggggtagcggctgaagcactgcacgccgtagg
tcaggtggtcacgagggtgggccagggcacgggcagcttgccggtggtgcagatgaacttcagggtcagcttgccg
taggtggcatcgccctcgccctcgccggacacgctgaacttgtggccgtttacgtcgccgtccagctcgaccaggat
gggcaccacccggtgaacagctcctcgcccttgctcaccatggttgtggccatattatcatcgtgttttttcaaagg
aaaaccacgtcccgtggttcggggggcctagacgttttttttaacctcgactaaacacatgtaaagcatgtgcaccg
aggcccccagatcagatcccatacaatggggtaccttctgggcatccttcagccccttgttgaatacgcttgaggaga
gccatttgactctttccacaactatccaactcacaacgtggcactggggttgtgccgcctttgcaggtgtatcttat
acacgtggcttttggccgcagaggcacctgtcgccaggtgggggttccgctgcctgcaaagggtcgctacagacgt
tgtttgtcttcaagaagcttccagaggaactgcttccttcacgacattcaacagaccttgcattcctttggcgagag
gggaaagacccctaggaatgctcgtcaagaagacagggccaggtttccgggccctcacattgccaaaagacggcaat
atggtggaaaataacatatagacaaacgcacaccggccttattccaagcggcttcggccagtaacgttagggggggg
ggagggagaggggcggatcccgggcccgcggtaccgtcgactgcagaattcactagtgattaaattatattgtcgac
tcatgagcacccacagcggtctactaccatggctggaattttcccatatattatttgttctttgccattaaaatata
gcatattaatgggagacatttttgtcggagtgcagcaagggcctgctgagcctctggggtttgcttggtgcacaaga
tgagtatgcggatatttttgtaaaaacacaaattcacactctcctgagcagtaattggcctatatctttttgggtgc
gataatccagtcccatccaaaggcttcaaaatcgaccgtgaggggggtagcggcagcaccgggattccgtggagtgct
catcgcagtcaagcccaaagtctctccgggacctcttgggtgtgtctgtcaccttgacttctaaaaagggattcagc
ccatcttctcctggtcctgggaaggttacagcaagatcatggccattctcatccaaagctttgatttcaatgcctaa
gttggattcaggctgtttgagccaatttttgcaacactgtcttcacatcaatactctgccaaataccagtgcctgggc
tcatgtcaagtttcagagatcggattccagtataccttgtaccgtcttttcatgggtttgatgagtctcaggatttgc
acaaacactgttgtaggagtcttgacgggtctgagatatatccacagttgggcttttactactttgttgtactgtat
tttagagctaaatttaaaaaagcaacatttgggcttgccatccgcttgcattagaaagtcagactctgtaggcatgg
taatgattgtttccgtggtagcgtgataatcgtcatcttccaaagagccatcactgctgtcatccctctggacgtcg
tactgatcgatcagttcccggagtggaggcgctcttggcagaagttgtcttatagcatctttgctgatgttaggagc
tgtttccaggcgcagcttactgaggatttgaattttatggcttctattctggagtacctcgtgttttgtctccacg
cacatgcattacacagcccctcttttccacattttcttctctcactgccctcatttagatccactgggccagca
gcaatcagcatgaacaggtaaatataaacatacatttgcagttttgcatcatggctggatccgggcccataagagc
gtaatctggaacatcgtatgggtacatggtgtctagctcgcgtcagctgactagaggatccccgggtaccgagctcg
aattcggggccgcggaggctggatcggtcccggtgtcttctatggaggtcaaaacagcgtggatggcgtctccaggc
gatctgacggttcactaaacgagctctgcttatataggcctccaccgtacacgcctactcgacccgggtaccgagc
tcgactttcacttttctctatcactgatagggagtggtaaactcgactttcacttttctctatcactgatagggagt
ggtaaactcgactttcacttttctctatcactgatagggagtggtaaactcgactttcacttttctctatcactgat
agggagtggtaaactcgactttcacttttctctatcactgatagggagtggtaaactcgactttcacttttctctat
cactgatagggagtggtaaactcgactttcacttttctctatcactgatagggagtggtaaactcgactttcacttt
tctctatcactgatagggagtggtaaactcgagatctcgagctcaagcttcgaattatcgaattcctgcagcccgat
```

FIG. 18

```
ctcagctgaggtgcaaaaggctcctgtcatattgtgtcctgctctggtctgccttccacagcttgggggccacctag
cccacctctccctagggatgagagcagccactacgggtctaggctgcccatgtaaggaggcaaggcctggggacacc
cgagatgcctggttataattaacccagacatgtggctgccccccccccccaacacctgctgcctgagcctcacccc
caccccggtgcctgggtcttaggctctgtacaccatggaggagaagctcgctctaaaaataaccctgtccctggtgg
atccagggtgaggggcaggctgagggcggccacttccctcagccgcaggtttgttttcccaagaatggttttttctgc
ttctgtagcttttcctgtcaattctgccatggtggagcagcctgcactgggcttctgggagaaaccaaaccgggttc
taacctttcagctacagttattgcctttcctgtagatgggcgactacagccccaccccaccccgtctcctgtatc
cttcctgggcctggggatcctaggctttcactggaaattcccccaggtgctgtaggctagagtcacggctcccaa
gaacagtgcttgcctggcatgcatggttctgaacctccaactgcaaaaaatgacacataccttgaccttggaaggc
tgaggcaggggattgccatgagtgcaaagccagactgggtggcatagttagaccctgtctcaaaaaaccaaaaaca
attaaataactaaagtcaggcaagtaatcctactcgggagactgaggcagagggattgttacatgtctgaggccagc
ctggactacatagggtttcaggctagccctgtctacagagtaaggccctatttcaaaaacacaaacaaaatggttct
cccagctgctaatgctcaccaggcatgaagcctggtgagcattagcaatgaaggcaatgaaggagggtgctggctac
aatcaaggctgtggggactgagggcaggctgtaacaggcttggggccagggcttatacgtgcctgggactcccaa
agtattactgttccatgttcccggcgaagggccagctgtccccgccagctagactcagcacttagtttaggaacca
gtgagcaagtcagcccttggggcagcccatacaaggccatgggctgggcaagctgcacgcctgggtccgggtggg
cacggtgcccgggcaacgagctgaaagctcatctgctctcaggggcccctccctggggacagcccctcctggctagt
cacaccctgtaggctcctctatataacccaggggcacaggggctgcccccaagctggccgctctagaggatccccgg
gactagaattcaccatgtctagattagataaaagtaaagtgattaacagcgcattagagctgcttaatgaggtcgga
atcgaaggtttaacaacccgtaaactcgcccagaagcttggtgtagagcagcctacactgtattggcatgtaaaaaa
taagcgggctttgctcgacgccttagccattgagatgttagataggcaccatactcacttttgccctttaaaaggggg
aaagctggcaagatttttttacgcaataacgctaaaagttttagatgtgctttactaagtcatcgcaatggagcaaaa
gtacattcagatacacggcctacagaaaaacagtatgaaactctcgaaaatcaattagccttttttatgccaacaagg
ttttcactagagaacgcgttatatgcactcagcgctgtggggcattttactttaggttgcgtattggaagatcaag
agcatcaagtcgctaaagaagaaagggaaacacctactactgatagtatgccgccattattacgacaagctatcgaa
ttatttgatcaccaaggtgcagagccagccttcttattcggccttgaattgatcatatgcggattagaaaaacaact
taaatgtgaaagtgggtccgcgtacagccgcgcgcgtacgaaaaacaattacgggtctaccatcgagggcctgctcg
atctcccggacgacgacgcccccgaagaggcggggctggcggctccgcgcctgtcctttctccccgcgggacacacg
cgcagactgtcgacggccccccgaccgatgtcagcctgggggacgagctccacttagacggcgaggacgtggcgat
ggcgcatgccgacgcgctagacgatttcgatctggacatgttgggggacggggattccccggggtccgggatttaccc
cccacgactccgcccctacggcgctctggatatggccgacttcgagtttgagcagatgtttaccgatgcccttgga
attgacgagtacggtgggatggatccccgggtaccggtcgccaccatggtgagcaagggcgaggagctgttcaccgg
ggtggtgcccatcctggtcgagctggacggcgacgtaaacggccacaagttcagcgtgtccggcgagggcgagggcg
atgccacctacggcaagctgaccctgaagttcatctgcaccaccggcaagctgcccgtgccctggcccaccctcgtg
accaccctgacctgggcgtgcagtgcttcagccgctaccccgaccacatgaagcagcacgacttcttcaagtccgc
catgcccgaaggctacgtccaggagcgcaccatcttcttcaaggacgacggcaactacaagacccgcgccgaggtga
agttcgagggcgacaccctggtgaaccgcatcgagctgaagggcatcgacttcaaggaggacggcaacatcctgggg
cacaagctggagtacaactacatcagccacaacgtctatatcaccgccgacaagcagaagaacggcatcaaggccaa
cttcaagatccgccacaacatcgaggacggcagcgtgcagctcgccgaccactaccagcagaacacccccatcggcg
acggccccgtgctgctgcccgacaaccactacctgagcacccagtccgccctgagcaaagaccccaacgagaagcgc
gatcacatggtcctgctggagttcgtgaccgccgcgggatcactctcggcatggacgagctgtacaagtaaagcgg
ccgcgactctagatcataatcagccataccacatttgtagaggttttacttgctttaaaaaacctcccacacctccc
cctgaacctgaaacataaaatgaatgcaattgttgttgttaacttgtttattgcagcttataatggttacaaataaa
gcaatagcatcacaaatttcacaaataaagcatttttttcactgcattctagttgtggtttgtccaaactcatcaat
gtatcttaag
```

FIG. 18 (Cont'd)

CMOT=pFin plasmid sequence
(pMCK/Tet-ON-BFP//TRE/HA-Mst/IRES-EGFP)

Bicistronic bridge:

```
ctcgactttc acttttctct atcactgata gggagtggta aactcgagat ctcgagctca agcttcgaat
tatcgaattc ctgcagcccg atctcagctg aggtgcaaaa ggctcctgtc atattgtgtc ctgctctggt
ctgccttcca cagcttgggg gccacctagc ccacctctcc ctagggatga gagcagccac tacgggtcta
ggctgcccat gtaaggaggc aaggcctggg gacacccgag atgcctggtt ataattaacc cagacatgtg
gctgccccc cccccccaac acctgctgcc tgagcctcac ccccacccccg gtgcctggt cttaggctct
gtacaccatg gaggagaagc tcgctctaaa ataaccctg tccctggtgg atccagggtg aggggcaggc
tgagggcggc cacttccctc agccgcaggt ttgttttccc aagaatggtt tttctgcttc tgtagctttt
cctgtcaatt ctgccatggt ggagcagcct gcactgggct tctgggagaa accaaaccgg gttctaacct
ttcagctaca gttattgcct ttcctgtaga tgggcgacta cagccccacc cccaccccccg tctcctgtat
ccttcctggg cctggggatc ctaggctttc actggaaatt tcccccagg tgctgtaggc tagagtcacg
gctcccaaga acagtgcttg cctggcatgc atggttctga acctccaact gcaaaaaatg acacatacct
tgacccttgg aaggctgagg caggggatt gccatgagtg caaagccaga ctgggtggca tagttagacc
ctgtctcaaa aaaccaaaaa caattaaata actaaagtca ggcaagtaat cctactcggg agactgaggc
agagggattg ttacatgtct gaggccagcc tggactacat agggtttcag gctagccctg tctacagagt
aaggccctat ttcaaaaaca caaacaaaat ggttctccca gctgctaatg ctcaccaggc atgaagcctg
gtgagcatta gcaatgaagg caatgaagga gggtgctggc tacaatcaag gctgtggggg actgagggca
ggctgtaaca ggcttggggg ccagggctta tacgtgcctg ggactcccaa agtattactg ttccatgttc
ccggcgaagg gccagctgtc ccccgccagc tagactcagc acttagttta ggaaccagtg agcaagtcag
cccttggggc agcccataca aggccatggg gctgggcaag ctgcacgcct gggtccgggg tgggcacggt
gcccgggcaa cgagctgaaa gctcatctgc tctcaggggc ccctccctgg ggacagcccc tcctggctag
tcacaccctg taggctcctc tatataaccc aggggcacag gggctgcccc caagctggcc gctctagagg
atccccggga ctagaattca ccatgtctag attagataaa agtaaagtga ttaacagcgc attagagctg
cttaatgagg tcggaatcga aggtttaaca acccgtaaac tcgcccagaa gcttggtgta gagcagccta
cactgtattg gcatgtaaaa aataagcggg ctttgctcga cgccttagcc attgagatgt tagataggca
ccatactcac ttttgccctt taaaagggga aagctggcaa gatttttac gcaataacgc taaagttttt
agatgtgctt tactaagtca tcgcaatgga gcaaagtac attcagatac acggcctaca gaaaaacagt
atgaaactct cgaaaatcaa ttagccttt tatgccaaca aggtttttca ctagagaacg cgttatatgc
actcagcgct gtgggcatt ttactttagg ttgcgtattg gaagatcaag agcatcaagt cgctaaagaa
gaaagggaaa cacctactac tgatagtatg ccgccattat tacgacaagc tatcgaatta tttgatcacc
aaggtgcaga gccagccttc ttattcggcc ttgaattgat catatgcgga ttagaaaaac aacttaaatg
tgaaagtggg tccgcgtaca gccgcgcgcg tacgaaaaac aattacgggt ctaccatcga gggcctgctc
gatctcccgg acgacgacgc ccccgaagag gcggggctgg cggctccgcg cctgtccttt ctccccgcgg
gacacacgcg cagactgtcg acggcccccc cgaccgatgt cagcctgggg gacgagctcc acttagacgg
cgaggacgtg gcgatggcgc atgccgacgc gctagacgat ttcgatctgg acatgttggg ggacggggat
tccccgggtc cgggatttac ccccacgac tccgcccct acggcgctct ggatatggcc gacttcgagt
ttgagcagat gtttaccgat gcccttggaa ttgacgagta cggtgggatg gatcccggg taccggtcgc
caccatggtg agcaagggcg aggagctgtt caccggggtg gtgcccatcc tggtcgagct ggacggcgac
gtaaacggcc acaagttcag cgtgtccggc gagggcgagg gcgatgccac ctacggcaag ctgaccctga
agttcatctg caccaccggc aagctgcccg tgcctggcc caccctcgtg accaccctga cctgggcgt
gcagtgcttc agccgctacc ccgaccacat gaagcagcac gacttcttca gtccgccat gcccgaaggc
tacgtccagg agcgcaccat cttcttcaag gacgacggca actacaagac ccgcgccgag gtgaagttcg
agggcgacac cctggtgaac cgcatcgagc tgaagggcat cgacttcaag gaggacggca acatcctggg
gcacaagctg gagtacaact acatcagcca caacgtctat atcaccgccg acaagcagaa gaacggcatc
aaggccaact tcaagatccg ccacaacatc gaggacggca gcgtgcagct cgccgaccac taccagcaga
acacccccat cggcgacggc cccgtgctgc tgcccgacaa ccactacctg agcacccagt ccgccctgag
```

*FIG. 19*

```
caaagacccc aacgagaagc gcgatcacat ggtcctgctg gagttcgtga ccgccgccgg gatcactctc
ggcatggacg agctgtacaa gtaaagcggc cgcagacatg ataag Tet-on polyA. a gcttcttaag
gcgtaaattg taagcgttaa tattttgtta aaattcgcgt taaattttg ttaaatcagc tcattttta
accaataggc cgaaatcggc aaaatcccct ataaatcaaa agaatägacc
gagatatggtcgatcggagtgctcacttgacccactctgcttatatagacctcccaccgtacacgcctacccgccat
ttgcgtcaatgggggcggagttgttatgacattttggaaagtcccgttgattttggtgccaaaacaaactcccattga
cgtcaatgggcgggggtcgtttgggcggtcagccaggcgggccatttaccgtaagttatgtaacgcggaactccatat
atgggctatgaactaatgaccccgtaattgattactattaataacta
atgcatggcggtaatacggttatccacagaatcaggggataacgcaggaaagaacatgtgagcaaaaggccagcaaa
aggccaggaaccgtaaaaaggccgcgttgctggcgtttttccataggctccgcccccctgacgagcatcacaaaaat
cgacgctcaagtcagaggtggcgaaacccgacaggactataaagataccaggcgtttccccctggaagctccctcgt
gcgctctcctgttccgaccctgccgcttaccggatacctgtccgcctttctcccttcgggaagcgtggcgctttctc
atagctcacgctgtaggtatctcagttcggtgtaggtcgttcgctccaagctgggctgtgtgcacgaaccccccgtt
cagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaact
acggctacactagaaggacagtatttggtatctgcgctctgctgaagccagttaccttcggaaaaagagttggtagc
tcttgatccggcaaacaaaccaccgctggtagcggtggtttttttgtttgcaagcagcagattacgcgcagaaaaaa
aggatctcaagaagatcctttgatcttttctacggggtctgacgctcagtggaacgaaaactcacgttaagggattt
tggtcatgagattatcaaaaaggatcttcacctagatccttttaaattaaaaatgaagttttaaatcaatctaaagt
atatatgagtaaacctgaggctatggcagggcctgccgcccccgacgttggctgcgagccctgggccttcacccgaact
tggggggtgggtgggaaaaggaagaaacgcgggcgtattggccccaatggggtctcggtggggtatcgacagagt
gccagccctgggaccgaaccccgcgtttatgaacaaacgacccaacaccgtgcgttttattctgtcttttattgcc
gtcatagcgcgggttccttccggtattgtctccttccgtgtttcagttagcctcccccctagggtgggcgaagaactc
cagcatgagatccccgcgctggaggatcatccagccggcgtcccggaaaacgattccgaagcccaacctttcataga
aggcggcggtggaatcgaaatctcgtgatggcaggttggcgtcgcttggtcggtcatttcgaaccccagagtcccg
ctcagaagaactcgtcaagaaggcgatagaaggcgatgcgctgcgaatcgggagcggcgataccgtaaagcacgagg
aagcggtcagcccattcgccgccaagctcttcagcaatatcacggggtagccaacgctatgtcctgatagcggtccgc
cacacccagccggccacagtcgatgaatccagaaaagcggccattttccaccatgatattcggcaagcaggcatcgc
catgggtcacgacgagatcctcgccgtcgggcatgctcgccttgagcctggcgaacagttcggctggcgcgagcccc
tgatgctcttcgtccagatcatcctgatcgacaagaccggcttccatccgagtacgtgctcgctcgatgcgatgttt
cgcttggtggtcgaatgggcaggtagccggatcaagcgtatgcagccgccgcattgcatcagccatgatggatactt
tctcggcaggagcaaggtgagatgacaggagatcctgccccggcacttcgcccaatagcagccagtcccttcccgct
tcagtgacaacgtcgagcacagctgcgcaaggaacgcccgtcgtggccagccacgatagccgcgctgcctcgtcttg
cagttcattcagggcaccggacaggtcggtcttgacaaaaagaaccgggcgcccctgcgctgacagccggaacacgg
cggcatcagagcagccgattgtctgttgtgcccagtcatagccgaatagcctctccacccaagcggccggagaacct
gcgtgcaatccatcttgttcaatcatgcgaaacgatcctcatcctgtctcttgatcgatctttgcaaaagcctaggc
ctccaaaaaagcctcctcactacttctggaatagctcagaggccgaggcggcctcggcctctgcataaataaaaaa
attagtcagccatggggcggagaatgggcggaactgggcggagttaggggcgggatgggcggagttaggggcgggac
tatggttgctgactaattgagatgcatgctttgcatacttctgcctgctggggagcctggggactttccacacctgg
ttgctgactaattgagatgcatgctttgcatacttctgcctgctggggagcctggggactttccacaccctaactga
cacacattccacagctggttctttccgcctcaggactcttcctttttcaatattattgaagcatttatcagggttat
tgtctcatgagcggatacatatttgaatgtatttagaaaaataaacaaatagggttccgcgcacatttccccgaaa
agtgccacctgacgcgcccgtagcggcgcattaagcgcggcgggtgtggtggttacgcgcagcgtgaccgctacac
ttgccagcgccctagcgcccgctcctttcgctttcttcccttcctttctcgccacgttcgccggctttccccgtcaa
gctctaaatcgggggctcccttagggttccgatttagtgctttacggcacctcgaccccaaaaaacttgattaggg
tgatggttcacgtagtgggccatcgccctgatagacggtttttcgccctttgacgttggagtccacgttctttaata
gtggactcttgttccaaactggaacaacactcaacccatctctcggtctattcttttgatttataagggattttgccg
atttcggcctattggttaaaaaatgagctgatttaacaaaaatttaacgcgaattttaacaaaatattaacgcttac
aatttacgccttaagatacattgatgagtttggacaaaccacaactagaatgcagtgaaaaaaatgctttatttgtg
aaatttgtgatgctattgctttatttgtaaccattataagctgcaataaacaagttaacaacaacaattgcattcat
```

```
tttatgtttcaggttcagggggaggtgtgggaggttttttaaagcaagtaaaacctctacaaatgtggtatggctga
ttatgatctagagtcgcggccgctttacttgtacagctcgtccatgccgagagtgatcccggcggcggtcacgaact
ccagcaggaccatgtgatcgcgcttctcgttggggtctttgctcagggcggactgggtgctcaggtagtggttgtcg
ggcagcagcacggggccgtcgccgatgggggtgttctgctggtagtggtcggcgagctgcacgctgccgtcctcgat
gttgtggcggatcttgaagttcaccttgatgccgttcttctgcttgtcggccatgatatagacgttgtggctgttgt
agttgtactccagcttgtgccccaggatgttgccgtcctccttgaagtcgatgcccttcagctcgatgcggttcacc
agggtgtcgccctcgaacttcacctcggcgcgggtcttgtagttgccgtcgtccttgaagaagatggtgcgctcctg
gacgtagccttcgggcatggcggacttgaagaagtcgtgctgcttcatgtggtcggggtagcggctgaagcactgca
cgccgtaggtcagggtggtcacgagggtgggccagggcacggggcagcttgccggtggtgcagatgaacttcagggtc
agcttgccgtaggtggcatcgccctcgccctcgccggacacgctgaacttgtggccgtttacgtcgccgtccagctc
gaccaggatgggcaccaccccggtgaacagctcctcgcccttgctcaccatggttgtggccatattatcatcgtgtt
tttcaaaggaaaaccacgtccccgtggttcgggggggcctagacgttttttttaacctcgactaaacacatgtaaagca
tgtgcaccgaggccccagatcagatcccatacaatggggtaccttctgggcatccttcagcccttgttgaatacgc
ttgaggagagccatttgactctttccacaactatccaactcacaacgtggcactgggggttgtgccgcctttgcaggt
gtatcttatacacgtggcttttggccgcagaggcacctgtcgccaggtgggggggttccgctgcctgcaaagggtcgc
tacagacgttgtttgtcttcaagaagcttccagaggaactgcttccttcacgacattcaacagaccttgcattcctt
tggcgagaggggaaagacccctaggaatgctcgtcaagaagacagggccaggtttccgggccctcacattgccaaaa
gacggcaatatggtggaaaataacatatagacaaacgcacaccggccttattccaagcggcttcggccagtaacgtt
agggggggggagggagaggggc
ggatcccgggcccgcggtaccgtcgactgcagaattcactagtgattaaattatattgtcgac
tcatgagcacccacagcggtctactaccatggctggaattttcccatatattatttgttctttgccattaaaatata
gcatattaatgggagacatttttgtcggagtgcagcaagggcctgctgagcctctggggtttgcttggtgcacaaga
tgagtatgcggatatttttgtaaaaacacaaattcacactctcctgagcagtaattggccttatatcttttgggtgc
gataatccagtcccatccaaaggcttcaaaatcgacgtgagggggtagcggcagcaccgggattccgtggagtgct
catcgcagtcaagcccaaagtctctccgggacctcttgggtgtgtctgtcaccttgacttctaaaaagggattcagc
ccatcttctcctggtcctgggaaggttacagcaagatcatggccattctcatccaaagctttgatttcaatgcctaa
gttggattcaggctgtttgagccaattttgcaacactgtcttcacatcaatactctgccaaataccagtgcctgggc
tcatgtcaagtttcagagatcggattccagtataccttgtaccgtctttcatgggtttgatgagtctcaggatttgc
acaaacactgttgtaggagtcttgacgggtctgagatatatccacagttgggcttttactactttgttgtactgtat
tttagagctaaatttaaaaaagcaacatttgggcttgccatccgcttgcattagaaagtcagactctgtaggcatgg
taatgattgtttccgtggtagcgtgataatcgtcatcttccaaagagccatcactgctgtcatccctctggacgtcg
tactgatcgatcagttcccggagtggaggcgctcttggcagaagttgtcttatagcatctttgctgatgttaggagc
tgtttccaggcgcagcttactgaggatttgaattttatggcttctattctggagtacctcgtgttttgtctccacg
cacatgcattacacagcccctcttttccacattttcttctctctcactgccctcatttagatccactgggccagca
gcaatcagcatgaacaggtaaatataaacatacatttgcagttttgcatcatggctggatccgggcccat
aagagcgtaatctggaacatcgtatgggtacatggtgtctagctcgcgtcagctgactagaggatccccgggtaccg
agctcgaattcggggccgcggaggctggatcggtcccggtgtcttctatggaggtcaaaacagcgtggatggcgtct
ccaggcgatctgacggttcactaaacgagctctgcttatataggcctcccaccgtacacgcctactcgaccgggta
ccgagctcgactttcacttttctctatcactgatagggagtggtaaactcgactttcacttttctctatcactgata
gggagtggtaaactcgactttcacttttctctatcactgatagggagtggtaaactcgactttcacttttctctatc
actgatagggagtggtaaactcgactttcacttttctctatcactgatagggagtggtaaactcgactttcactttt
ctctatcactgatagggagtggtaaactcgactttcacttttctctatcactgatagggagtggtaaa
```

FIG. 19 (Cont'd)

CMOT plasmid

10273 base pairs

Graphic map | Table by enzyme name

```
                                    Eco88I BstYI Sau3AI Sfr274I BsoBI
                                    XhoI PaeR7I MboI BglII XhoI PaeR7I
   TthHB8I               TspRI      Sfr274I DpnII MflI DpnI BcoI TaqI
ctcgactttcacttttctctatcactgatagggagtggtaaactcgagatctcgagctcaagcttcgaattatcg base pairs
gagctgaaagtgaaaagagatagtgactatccctcaccatttgagctctagagctcgagttcgaagcttaatagc 1 to 75
   TaqI                             Ama87I TaqI NdeII XhoII Eco88I CviJI
                                    BcoI BsoBI BstX2I Kzo9I AvaI Ecl136II
                                    AvaI TthHB8I Bsp143I Ama87I TthHB8I EcoICRI Psp1246I CviJI Bsp119I TaqI TspEI Fsp4HI NdeII BstDEI DdeI PspN4I
    SduI Eco24I SstI TthHB8I NspV TthHB8I Tsp509I BbvI Sau3AI PvuII MnlI
    AluI Bbv12I Alw21I SfuI TaqI Sse9I AcsI SfcI PstI MboI DdeI NspBII NlaIV
aattcctgcagcccgatctcagctgaggtgcaaaaggctcctgtcatattgtgtcctgctctggtctgccttcca base pairs
ttaaggacgtcgggctagagtcgactccacgttttccgaggacagtataacacaggacgagaccagacggaaggt 76 to 150
    Asp7I SacI BsiHKAI LspI Bpu14I Sse9I BstSFI CviJI Bsp143I MspA1I
     BmyI FriOI HindIII BstBI TspEI EcoRI BsoFI Bst71I DpnI CviJI CviJI
    Bsp1286I BanII AluI Csp45I Tsp509I ApoI ItaI DpnII Kzo9I AluI BstDEI BslI Cfr13I HaeIII       StyI EcoT14I ItaI              BbvI BsiYI
    AluI BsiYI AspS9I BsuRI  Eco130I BfaI BsoFI             CviJI Hsp92II
    CviJI Esp1396I PalI BfaI AvrII MaeI FokI CviJI     MaeI BsoFI NlaIII
cagcttgggggccacctagcccacctctccctagggatgagagcagccactacgggtctaggctgcccatgtaag base pairs
gtcgaaccccggtggatcgggtggagagggatccctactctcgtcggtgatgcccagatccgacgggtacattc 151 to 225
    Bsc4I Van91I NlaIV MaeI MnlI BssTlI BstF5I BbvI       BfaI Fsp4HI Bsc4I
    AccB7I AsuI PspN4I CviJI ErhI BsaJI    Fsp4HI           ItaI  BslI
    PflMI Sau96I CviJI       BlnI BseDI    Bst71I           Bst71I CviJI EcoRII MvaI BcoI SfaNI ScrFI TruII  Hsp92II Bst71I
         AatI BsuRI BstNI BsmFI EcoRII MvaI MseI AflIII CviJI
    MnlI Pme55I BsaJI MspR9I AvaI BstOI TspEI     BspLU11I BsoFI
gaggcaaggcctgggacaccccgagatgcctggttataattaacccagacatgtgctgcccccccccccccaac base pairs
ctccgttccggaccctgtgggctctacggaccaatattaattgggtctgtacaccgacggggggggggggttg 226 to 300
         StuI Eco147I Bst2UI BsoBI MspR9I Tsp509I  BstXI Fsp4HI
         HaeIII BseDI ScrFI Eco88I Bst2UI Tru9I    NlaIII BbvI
         PalI SseBI BstCI Ama87I BstNI Sse9I       NspI ItaI BbvI             BsiYI MspI BshNI BseDI ScrFI SspBI Eco130I BstDSI
    BspMI MwoI  MnlI    BseDI BcnI Eco64I BsaJI MspR9I Bsp1407I BssT1I NlaIII
     BsoFI BstDEI       HphI Bsc4I NciI MspR9I EcoRII MvaI CviJI RsaI NcoI DsaI
acctgctgcctgagcctcaccccccacccccggtgcctgggtcttaggctctgtacaccatggaggagaagctcgct base pairs
tggacgacggactcggagtgggggtggggccacggacccagaatccgagacatgtggtacctcctcttcgagcga 301 to 375
    Fsp4HI CviJI       BsaJI MslI ScrFI NlaIV BstOI BstDEI AfaI BsaJI Bsp19I
     ItaI DdeI         BslI HpaII BanI PspN4I Bst2UI BsrGI ErhI EcoT14I
       Bst71I          BsiSI HapII AccB1I BstNI DdeI Csp6I StyI BseDI
```

FIG. 20

```
CviJI          BslI Bst2UI NdeII BstI DpnI BsaJI ScrFI MnlI EaeI HaeIII
   Cac8I         BseDI MspR9I DpnII MflI NlaIV AlwI Bst2UI Cac8I CfrI PalI
  BseRI         Bsc4I BstNI MvaI Sau3AI Kzo9I BseDI MvaI HphI BstDEI CviJI
ctaaaaataaccctgtccctggtggatccagggtgaggggcaggctgagggcggccacttccctcagccgcaggt base pairs
gattttattgggacagggaccacctaggtcccactccccgtccgactcccgccggtgaagggagtcggcgtcca 376 to 450
    AluI         BsaJI BstOI BstYI Bsp143I EcoRII MspR9I BsiYI MnlI ItaI AciI
  MnlI           EcoRII ScrFI BstX2I XhoII AclWI BstOI BslI CviJI Fsp4HI DdeI
 Hsp92II         BsiYI BsmFI MboI BamHI PspN4I BstNI Bsc4I DdeI BsoFI BsuRI MnlI AciI                                          NcoI BstDSI Fsp4HI  BsgI
 BstDEI        BsiYI          MwoI             Tsp509I StyI BseDI Hsp92II Bsc4I
  CviJI BspMI Bsc4I          SfcI CviJI        Sse9I  Eco130I NlaIII BbvI BslI
ttgtttttcccaagaatggttttttctgcttctgtagcttttcctgtcaattctgccatggtggagcagcctgcact base pairs
aacaaaagggttcttaccaaaaagacgaagacatcgaaaaggacagttaagacggtaccacctcgtcggacgtga 451 to 525
   Fsp4HI       BslI            BstSFI           TspEI  ErhI EcoT14I ItaI Cac8I
    ItaI                         AluI                  BssT1I Bsp19I CviJI BsiYI
   BsoFI                                                BsaJI DsaI BsoFI Bst71I BsrI            NciI
    BseII           MspI MspR9I        SfcI                   Bsc4I
    BseNI           BsiSI ScrFI        CviJI                  SfcI BslI      SfcI
gggcttctgggagaaaccaaaccggttctaacctttcagctacagttattgcctttcctgtagatgggcgacta base pairs
cccgaagaccctctttggtttggcccaagattggaaagtcgatgtcaataacggaaaggacatctacccgctgat 526 to 600
   TspRI          HpaII           AluI                BstSFI           BstSFI
    CviJI         HapII           BstSFI               BsiYI
    BsrSI         BcnI BstOI Sau96I BsuRI BstNI BstYI Bsp143I
 MwoI                Bsm3I          BseDI MvaI AspS9I EcoRII Bst2UI Sau3AI Kzo9I
  CviJI              Alw26I         EcoRII Bst2UI CviJI BslI BstOI DpnII BamHI
cagccccaccccaccccgtctcctgtatccttcctgggcctggggatcctaggctttcactggaaatttcccc base pairs
gtcgggtggggtggggcagaggacataggaaggacccggaccccctaggatccgaaagtgacctttaaagggg 601 to 675
               BsmAI     BsaJI ScrFI HaeIII BsiYI MspR9I MboI MflI
               Esp3I         BstNI Cfr13I PalI BsaJI ScrFI NdeII BstI
                             MspR9I AsuI Bsc4I BseDI MvaI BstX2I XhoII NlaIV StyI EcoT14I BseNI Tsp509I Bst2UI BfaI PleI Cac8I ScrFI NlaIII EcoT22I
   ErhI BsaJI CviJI Sse9I EcoRII MvaI MaeI MaeIII BstOI MwoI BbuI Zsp2I
  DpnI BlnI AlwI TspRI AcsI BseDI ScrFI CviJI CviJI EcoRII Cac8I NspI Mph1
ccaggtgctgtaggctagagtcacggctcccaagaacagtgcttgcctggcatgcatggttctgaacctccaact base pairs
ggtccacgacatccgatctcagtgccgagggttcttgtcacgaacggaccgtacgtaccaagacttggaggttga 676 to 750
 PspN4I AclWI MaeI BseII BsaJI MspR9I BstSFI NlaIV BstNI MvaI Hsp92II NlaI
  AvrII BssT1I BfaI BsrI ApoI BstOI SfcI HinfI PspN4I MspR9I PpuI0I NsiI MnlI
     Eco130I BseDI BsrSI TspEI BstNI AlwNI Tsp45I TspRI Bst2UI PaeI SphI Hsp92II
```

FIG. 20 (Cont'd)

```
                        BsaJI BslI
                        StyI  Bsc4I                    MwoI          BseLI
03I                     Eco130I CviJI MnlI             NlaIII CviJI  BsrSI
gcaaaaaatgacacataccttgacccttggaaggctgaggcaggggattgccatgagtgcaaagccagactggg base pairs
cgttttttactgtgtatggaactgggaaccttccgactccgtccccctaacggtactcacgtttcggtctgaccc 751 to 825
II                    FrhI BseDI BstDEI                Hsp92II         BseNI
                      BssTlI BsiYI                                     BsrI
                      EcoT14I DdeI MseI                          BsoBI
                  AtsI  BsmAI           Tsp509I                       Eco88I
                     Tth111I            Sse9I                         Ama87I
tggcatagttagaccctgtctcaaaaaaccaaaaacaattaaataactaaagtcaggcaagtaatcctactcggg base pairs
accgtatcaatctgggacagagttttttggttttttgttaatttattgatttcagtccgttcattaggatgagccc 826 to 900
                  AspI  Alw26I          TspEI                         BcoI
                                        Tru9I                         AvaI
                                        TruII NspI    PalI CviJI ScrFI          BfaI
BsmAI               AflIII BstDEI Cac8I Bst2UI         PstNHI    BstSFI
 Alw26I     MnlI     BspLU11I HaeIII BstOI             CviJI     AccI
agactgaggcagagggattgttacatgtctgaggccagcctggactacataggtgtttcaggctagccctgtctac base pairs
tctgactccgtctccctaacaatgtacagactccggtcggacctgatgtatcccaaagtccgatcgggacagatg 901 to 975
    DdeI MnlI     MaeIII  NlaIII CviJI BstNI Mval       NheI CviJI SfcI
    BstDEI                Hsp92II BsuRI MspR9I           MaeI
                              DdeI MnlI EcoRII                Cac8I DraII CviJI                     MspA1I MwoI    Bst2UI      EcoRII
        AsuI HaeIII                     AluI Fsp4HI    BstOI  Hsp92II
        Cfr13I PalI                     PvuII ItaI    EcoRII ScrFI  BstNI
agagtaaggccctatttcaaaaacacaaacaaaatggttctcccagctgctaatgctcaccaggcatgaagcctg base pairs
tctcattccgggataaagtttttgtgtttgttttaccaagagggtcgacgattacgagtggtccgtacttcggac 976 to
1050
         Sau96I BsuRI                   CviJI BbvI     BstNI NlaIII
         EcoO109I                       NspBII Bst71I  MspR9I   CviJI
         AspS9I                          BsoFI         HphI Mval BstOI MvaI
 Bst2UI                                                BstDEI    MaeIII
   MwoI      BsrDI      BsrDI MnlI Cac8I      CviJI    DdeI MnlI CviJI
gtgagcattagcaatgaaggcaatgaaggaggggtgctggctacaatcaaggctgtgggggactgagggcaggctg base pairs
cactcgtaatcgttacttccgttacttcctcccacgaccgatgttagttccgacaccccctgactcccgtccgac 1051 to
1125
MspR9I       MwoI                             CviJI              BsmFI Cac8I
  ScrFI
    HphI
```

*FIG. 20 (Cont'd)*

```
           NlaIV EcoRII Bst2UI BsaJI Bst2UI                      BcnI ScrFI
         AsuI HaeIII BstNI CviJI BstNI HinfI                    BsiSI Bsc4I
      CviJI Cfr13I CviJI BstOI MaeII BstOI BsmFI              NlaIII MspI BsiYI
taacaggcttgggggccagggcttatacgtgcctgggactcccaaagtattactgttccatgttcccggcgaagg base pairs
attgtccgaaccccggtcccgaatatgcacggaccctgagggtttcataatgacaaggtacaagggccgcttcc 1126 to
1200
      Sau96I PalI BseDI MvaI BseDI MvaI                     Hsp92II HapII
      AspS9I BsuRI MspR9I BsaAI MspR9I PleI                   NciI MspR9I
       PspN4I BsaJI ScrFI EcoRII ScrFI                         HpaII BslI Sau96I Cac8I BsmFI      DdeI              BsrI              BssT1I Fsp4HI
   AspS9I PvuII AciI BfaI                  BseNI              ErhI BseDI CviJI
     CviJI AluI FauI AluI  PleI DdeI    NlaIV BsrSI         CviJI EcoT14I Bst71I
gccagctgtccccgccagctagactcagcacttagtttaggaaccagtgagcaagtcagcccttggggcagccc base pairs
cggtcgacaggggcggtcgatctgagtcgtgaatcaaatcccttggtcactcgttcagtcgggaaccccgtcggg 1201 to
1275
Cfr13I BsuRI MspA1I MaeI     BstDEI    PspN4I TspRI          Eco130I BsoFI
  HaeIII CviJI  Cac8I HinfI                BseII             StyI HglI ItaI
   AsuI PalI NspBII CviJI BstDEI                             BsaJI MwoI BovI CviJI BssT1I NlaIII CviJI Cac8I BstNI Cfr13I Eco47I BsiYI BseDI BmyI
  BslI Eco130I BseDI Hsp92II ItaI BsgI BstOI SinI AvaII BslI HapII ScrFI
    HaeIII NcoI DsaI BstXI Fsp4HI BsaJI ScrFI Sau96I PspN4I BsaJI SduI
atacaaggccatggggctgggcaagctgcacgcctgggtccggggtgggcacggtgcccgggcaacgagctgaaa base pairs
tatgttccggtaccccgacccgttcgacgtgcggacccaggccccaccgtgccacgggcccgttgctcgacttt 1276 to
1350
Bsc4I BsuRI BsaJI Bsp19I Cac8I BovI BseDI MvaI HgiEI Bsc4I HpaII MspR9I
  BsiYI ErhI EcoT14I CviJI AluI Bst71I MspR9I Bme18I AspS9I MspI NciI Bsp1286I
     PalI StyI BstDSI MwoI BsoFI EcoRII Bst2UI AsuI NlaIV BsiSI BcnI Eco64I NlaIV Eco88I SduI HpaII SrfI AluI Sau96I HaeIII BmyI Bsc4I BsiYI MvaI EcoRII
 Acc3II Cfr9I BsoBI BcnI ScrFI CviJI PspOMI PspN4I Bsp1286I BsaJI BstOI CviJI
  BanI Ama87I BseDI BmyI HapII CviJI Cfr13I DraII CviJI FriOI MnlI BstNI BsmFI
gctcatctgctctcaggggcccctccctggggacagcccctcctggctagtcacaccctgtaggctcctctatat base pairs
cgagtagacgagagtcccgggagggaccctgtcggggaggaccgatcagtgtgggacatccgaggagatata 1351 to
1425
BshNI BcoI BsaJI BsiSI MspR9I AluI Bsp120I NlaIV BsuRI ApaI BseDI Bst2UI BstNI
   PspAI XmaI NciI MspI SmaI DdeI AsuI AspS9I SduI BanII EcoRII ScrFI BstOI
    PspN4I AvaI Bsp1286I PspALI BstDEI Eco0109I PalI Eco24I BslI MspR9I MnlI
```

FIG. 20 (Cont'd)

```
    MaeI BstSFI BseDI ScrFI BmyI ItaI CviJI HaeIII XbaI BstYI Sau3AI Kzo9I
  Bst2UI SfcI PspN4I BstOI Bsp1286I Bsc4I EaeI BsuRI AccBSI NdeII BstI NlaIV
 MspR9I Tsp45I MnlI BstNI SduI Fsp4HI BsiYI CviJI AciI BfaI MboI MflI MnlI
aacccaggggcacaggggctgcccccaagctggccgctctagaggatccccgggactagaattcaccatgtctag base pairs
ttgggtccccgtgtccccgacggggggttcgaccggcgagatctcctaggggccctgatcttaagtggtacagatc 1426 to
1500
    MvaI MaeIII BseRI MspR9I AlwNI BbvI AluI PalI ItaI MaeI BstX2I XhoII AclWI
    CviJI CviJI BsaJI Bst2UI CviJI Bst71I CfrI BsoFI BsrBI DpnII BamHI DpnI
   ScrFI BfaI NlaIV EcoRII MvaI BsoFI BslI Cac8I Fsp4HI BstD102I Bsp143I PspN4I BsaJI Eco88I HpaII MaeI TspEI XbaI Tru9I AspLEI BbvI  HinfI
  Ama87I BsoBI HapII BfaI ApoI MaeI MseI HhaI Fsp4HI MnlI       Tru1I
 BseDI AvaI NciI ScrFI BsmFI Tsp509I HinP1I CviJI Tru9I TfiI    Tru9I
attagataaaagtaaagtgattaacagcgcattagagctgcttaatgaggtcggaatcgaaggtttaacaacccg base pairs
taatctattttcatttcactaattgtcgcgtaatctcgacgaattactccagccttagcttccaaattgttgggc 1501 to
1575
   BccI XmaI MspI SmaI AcsI HphI BfaI Hin6I BsoFI MseI  TthHB8I MseI
  AlwI Cfr9I BcnI PspAII EcoRT Hsp92II HspAI AluI Bst7lI TaqI
    PspAI BsiSI MspR9I Sse9I NlaIII Tru1I CfoI ItaI Tru1I BbvI                           MwoI
             AluI      ItaI          NspI             FauI
          HindIII      BsoFI     TspRI     NlaIII     Cac8I      TthHB8I
taaactcgcccagaagcttggtgtagagcagcctacactgtattggcatgtaaaaaataagcgggctttgctcga base pairs
atttgagcgggtcttcgaaccacatctcgtcggatgtgacataaccgtacatttttattcgcccgaaacgagct 1576 to
1650
          CviJI       Fsp4HI          Hsp92II        AciI     TaqI
          BstXI       CviJI                                   CviJI
                      Bst71I BbiII DdeI               NlaIV               DraI
HinlI HgaI               BshNI               Tru1I         Cac8I
    AcyI    MslI         Eco64I              Tru9I BsiYI   CviJI
cgccttagccattgagatgttagataggcaccatactcactttttgcccttttaaaagggggaaagctggcaagattt base pairs
gcggaatcggtaactctacaatctatccgtggtatgagtgaaaacgggaaatttccccttcgaccgttctaaa 1651 to
1725
   BsaHI CviJI           BanI                MseI BslI     AluI
   Msp17I BstDEI         AccB1I              EcoNI
   Hsp92I                PspN4I              Bsc4I AfaI
                                 DdeI      MslI BsrDI Csp6I
tttacgcaataacgctaaaagttttagatgtgctttactaagtcatcgcaatggagcaaaagtacattcagatac base pairs
aaatgcgttattgcgattttcaaaatctacacgaaatgattcagtagcgttacctcgttttcatgtaagtctatg 1726 to
1800
                         BstDEI                    RsaI
```

FIG. 20 (Cont'd)

```
SfcI
   PalI                                  Tsp509I
    HaeIII              TthHB8I Sse9I CviJI                          MaeI
acggcctacagaaaaacagtatgaaactctcgaaaatcaattagcctttttatgccaacaaggttttttcactaga base pairs
tgccggatgtctttttgtcatactttgagagcttttagttaatcggaaaaatacggttgttccaaaaagtgatct 1801 to
                                                                             1875
   CviJI                      TaqI   TspEI                           BfaI
   BsuRI
     BstSFI BstUI          Hin6I AspLEI                       Bsp143I
    ThaI           HinP1I CfoI                        MboI DpnI AflIII  MwoI  DdeI Aor51HI HaeII                DpnII MboII  SfaNI
gaacgcgttatatgcactcagcgctgtggggcattttactttaggttgcgtattggaagatcaagagcatcaagt base pairs
cttgcgcaatatacgtgagtcgcgacaccccgtaaaatgaaatccaacgcataaccttctagttctcgtagttca 1876 to
                                                                             1950
   MluI Bsh1236I BstDEI AfeI Bsp143II            NdeII
     AccII          HspAI HhaI                   Sau3AI
     MvnI        Eco47III BstH2I                 Kzo9I Tsp509I MboI
                                            ItaI         TthHB8I  BclI
            MboII                          BsoFI         CviJI Sse9I  FbaI
cgctaaagaagaaaggGaaacacctactactgatagtatgccgccattattacgacaagctatcgaattatttga base pairs
gcgatttcttctttcccttTgtggatgatgactatcatacggcggtaataatgctgttcgatagcttaataaact 1951 to
                                                                             2025
                              Fsp4HI            AluI  TspEI     DpnII
                                AciI                  TaqI      NdeII
                                                                Ksp22I Kzo9I BssT1I CviJI             TspEI MboI DpnI
   Bsp143I BseDI MwoI      PalI Sse9I NdeII FauNDI          TruII
   Sau3AI BsaJI BsgI       HaeIII   FbaI Sau3AI AciI        Tru9I
tcaccaaggtgcagagccagcctTcttattcggccttgaattgatcatatgcggattagaaaaacaacttaaatg base pairs
agtggttccacgtctcggtcggaagaataagccggaacttaactagtatacgcctaatctttttgttgaatttac 2026 to
                                                                             2100
      DpnI StyI MslI  CviJI        CviJI    DpnII Kzo9I                MseI
      Eco130I HphI Cac8I           BsuRI    BclI Bsp143I
      ErhI EcoT14I                     Tsp509I Ksp22I NdeI HgiEI AspS9I AciI BsoFI ThaI MvnI Cac8I Bsh1236I AfaI TaqI Eco0109I
       Eme18I PspN4I Csp6I Fsp4HI AccII HhaI AccII Pf1123II Tsp509I DraII
         Cfr13I NlaIV Bsh1236I ItaI BsePI AciI ThaI PspLI RsaI TthHB8I AspS9I
tgaaagtgggtccgcgtacagccgcgcgcgtacgaaaaacaattacgggtctaccatcgagggcctgctcgatct base pairs
actttcacccaggcgcatgtcggcgcgcgcatgcttttgttaatgcccagatggtagctcccggacgagctaga 2101 to
                                                                             2175
```

FIG. 20 (Cont'd)

```
          SinI AvaII AccII RsaI HinPlI BstJI CfoI BstUI SunI Sse9I Cfr13I HaeIII
          Sau96I ThaI BstUI CviJI BssHII Bsh1236I MvnI BsiWI TspEI Sau96I CviJI
          AsuI Eco47I MvnI AfaI HspAI Hin6I AspLEI SplI Csp6I AccI AsuI MnlI

Cac8I Sau3AI BcnI Hin1I HgaI Ksp632I BsoFI PspN4I BstUI   BseDI MvnI FauI
PalI NdeII BsiSI HapII Hsp92I Bam1104I Cac8I NlaIV Hin6I AspLEI AccII KspI
   TthHB8I Kzo9I MspI Msp17I BslI EarI CviJI AciI ThaI AciI BsaJI BstUI Sfr3
cccggacgacgacgcccccgaagaggcggggctggcggctccgcgcctgtcctttctccccgcgggacacacgcg base pairs
gggcctgctgctgcgggggcttctccgccccgaccgccgaggcgcggacaggaaagaggggcgccctgtgtgcgc 2176 to
                                                                            2250
    DpnII DpnI HpaII BpiII Bsc4I MnlI MwoI CviJI AccII HhaI BstDSI Bsh1236I
    TaqI Bsp143I MspR9I AcyI BsiYI AciI Fsp4HI HspAI Bsh1236I DsaI NspBII SstII
 BsuRI MboI NciI ScrFI BsaHI MboII FauI ItaI HinP1I MvnI CfoI ThaI MspAlI Cfr42I AciI AccII AspLEI HindII CviJI Bsh1285I BstOI Ec1l36II BmyI SacI BsiHKAI
SacII ThaI MvnI TthHB8I AspS9I PspN4I CviJI MspR9I AluI AspHI BanII BstDEI
  03I HinPlI HhaI AccI Sau96I NlaIV PshAI BstNI BsmFI Bsp1286I FriOI DdeI
cagactgtcgacggccccccgaccgatgtcagcctgggggacgagctccacttagacggcgaggacgtggcgat base pairs
gtctgacagctgccggggggctggctacagtcggaccccctgctcgaggtgaatctgccgctcctgcaccgcta 2251 to
                                                                            2325
    BsmFI BstJI SalI HincII HaeIII BstMCI BseDI MvaI CviJI Bbv12I Alw21I
      HspAI Bsh1236I Cfr13I PalI BsiEI EcoRII Bst2UI SduI Eco24I SstI MaeII
        Hin6I CfoI TaqI AsuI BsuRI BsaOI BsaJI ScrFI EcoICRI Psp124BI MnlI AspLEI NspI AccII HhaI ManI Bse8I Bsp143I NspI         BcoI XmaI HpaII SmaI
   Hin6I PaeI SphI BstUI CfoI TthHB8I MboI AflIII      TfiI Ama87I NciI HapII
   HinPlI NlaIII ThaI Bsh1236I BsaBI DpnII DpnI    BsmFI   BsaJI Eco88I MspI
ggcgcatgccgacgcgctagacgatttcgatctggacatgttgggggacgggattccccgggtccgggatttac base pairs
ccgcgtacggctgcgcgatctgctaaagctagacctgtacaaccccctgccccctaaggggcccaggccctaaatg 2326 to
                                                                            2400
    HspAI Cac8I HinPlI HgaI BfaI TaqI NdeII BspLJ11I    Hinfl Cfr9I BsiSI ScrFI
       HhaI Hsp92II Hin6I AspLEI BsrBRI Sau3AI NlaIII       BseDI AvaI BcnI PspALI
      CfoI BbuI HspAI MvnI MaeI Bsh1365I Kzo9I Hsp92II      PspAI Bso3I MspR9I HgiEI PspN4I NciI PleI HspAI    CfrI                                BssT1I
  SinI AvaII BslI HapII AciI AspLEI  EaeI      TaqI                     EzhI
Cfr13I Eco47I BsiYI BcnI HinPlI Bsp143II BsuRI                          SfaNI
ccccacgactccgcccctacggcgctctggatatggccgacttcgagtttgagcagatgtttaccgatgccct base pairs
ggggtgctgaggcgggggatgccgcgagacctataccggctgaagctcaaactcgtctacaaatggctacggga 2401 to
                                                                          2475
  Bme18I AspS9I HpaII HinfI HhaI HaeII CviJI TthHB8I                    Eco130I
     AsuI Bsc4I MspI MspR9I CfoI BstH2I PalI                            StyI
    Sau96I NlaIV BsiSI ScrFI Hin6I    HaeIII                            BsaJI Tsp509I            NdeII BamHI DpnI BseDI AvaI NciI ScrFI Acc65I RsaI
   BseDI       AfaI    DpnII Bsp143I AclWI PspAI BsiSI MspR9I Asp718I AfaI
   EcoT14I   Csp6I     BstYI Sau3AI PspN4I BcoI XmaI HpaII Eco64I NlaIV BslI
tggaattgacgagtacggtgggatggatccccgggtaccggtcgccaccatggtgagcaagggcgaggagctgtt base pairs
accttaactgctcatgccaccctacctaggggcccatggccagcggtggtaccactcgttcccgctcctcgacaa 2476 to
                                                                            2550
```

FIG. 20 (Cont'd)

```
          RsaI      BstF5I MflI Xzo9I AlwI Eco88I MspI SmaI BshNI Bsc4I
   Sse9I            BstX2I BstI NlaIV Ama87I BsoBI HapII BanI Csp6I AgeI
   TspEI            MboI FokI XhoII BsaJI Cfr9I BcnI PspALI AccB1I PspN4I

PinAI Cfr10I BsaOI BssT1I Bsp19I BseRI BsaJI ScrFI PspN4I BstOI TthHB8I HaeIII
   BsaWI HpaII Bsh1285I EcoT14I Hsp92II MspI MspR9I AccB1I BstF5I MvaI CviJI
     BsiYI HapII Eco130I BseDI NlaIII BsiSI NciI Eco64I Bsp1286I MspR9I AluI
caccggggtggtgcccatcctggtcgagctggacggcgacgtaaacggccacaagttcagcgtgtccggcgaggg base pairs
gtggcccaccacgggtaggaccagctcgacctgccgctgcatttgccggtgttcaagtcgcacaggccgctccc 2551 to
2625
   BssAI BsiSI BsiEI StyI BstDSI MnlI HpaII BcnI BanI SduI EcoRII ScrFI MaeII
     BsrFI MspI BstMCI NcoI DsaI HphI AluI BseDI MslI NlaIV BstNI Bst2UI EaeI
       Bse118I KpnI ErhI BsaJI MslI CviJI HapII HphI BshNI BmyI FokI TaqI CfrI MspI                                         Cfr10I MwoI ItaI  BsaJI BsiYI
 PalI HapII            AluI                    BsrFI HapII Fsp4HI EcoRII
 CviJI MwoI SfaNI      Cac8I        Eco57I     BsgI HpaII AluI Bst71I Bsp1286I
cgagggcgatgccacctacggcaagctgaccctgaagttcatctgcaccaccggcaagctgccgtgccctggcc base pairs
gctcccgctacggtggatgccgttcgactgggacttcaagtagacgtggtggccgttcgacgggcacgggaccgg 2626 to
2700
   HpaII    BcgI        CviJI               BssAI MspI BsoFI  Bsc4I BslI
  BsuRI MnlI                                Bse118I CviJI MwoI SduI BmyI
  BsiSI MnlI                                  BsiSI Cac8I BbvI BseDI BstNI MvaI AsuI MslI Bsc4I BstNI Cac8I      ItaI                 ItaI
   BstOI Sau96I BsuRI BssSI BseDI MvaI      CviJI                BsoFI
       ScrFI AspS9I MaeIII BsaJI ScrFI TspRI BsoFI             NlaIII BbvI
caccctcgtgaccaccctgacctggggcgtgcagtgcttcagccgctaccccgaccacatgaagcagcacgactt base pairs
gtgggagcactggtgggactggaccccgcacgtcacgaagtcggcgatgggctggtgtacttcgtcgtgctgaa 2701 to
2775
      MspR9I HaeIII BsiI BslI BstOI MwoI       Eco57I           Hsp92II
       Bst2UI CviJI MnlI EcoRII MspR9I BsgI     Fsp4HI           Fsp4HI
        Cfr13I PalI Tsp45I BsiYI Bst2UI          AciI             Bst71I MspR9I HhaI
             Hsp92II        BstNI HinP1I
   MboII  AciI       CviJI EcoRII MvaI CfoI   MboII
cttcaagtccgccatgcccgaaggctacgtccaggagcgcaccatcttcttcaaggacgacggcaactacaagac base pairs
gaagttcaggcggtacgggcttccgatgcaggtcctcgcgtggtagaagaagttcctgctgccgttgatgttctg 2776 to
2850
              NlaIII    MaeII ScrFI Hin6I
                         BstOI HspAI
```

FIG. 20 (Cont'd)

```
                            Bst2UI AspLEI

Hin6I AciI BsaJI TthHB8I     BstNI HphI          AluI
     ThaI MvnI CfoI MnlI          EcoRII ScrFI   TaqI          TaqI
     HinP1I AspLEI BslI  MnlI     BsaJI MspR9I AciI  CviJI Eco57I            MnlI
ccgcgccgaggtgaagttcgagggcgacaccctggtgaaccgcatcgagctgaagggcatcgacttcaaggagga base pairs
ggcgcggctccacttcaagctcccgctgtgggaccacttggcgtagctcgacttcccgtagctgaagttcctcct 2851 to
                                                                                2925
     HspAI Bsh1236I BsiYI       BseDI Bst2UI       TthHB8I          TthH38I
     AccII FauI Bsc4I HphI      MslI MvaI          SfaNI            SfaNI
     BstUI HhaI BseDI TaqI      BstOI BstNI ScrFI       BomI
       BseDI Bst2UI AluI Csp6I
       EcoRII FokI Bsp1286I          CviJI MaeII       HphI
cggcaacatcctggggcacaagctggagtacaactacatcagccacaacgtctatatcaccgccgacaagcagaa base pairs
gccgttgtaggaccccgtgttcgacctcatgttgatgtagtcggtgttgcagatatagtggcggctgttcgtctt 2926 to
                                                                                3000
     BsaJI MspR9I CviJI RsaI                                 AciI
     BstF5I SduI      GsuI
     BstOI MvaI BmyI  AfaI BsuRI     MboI Bsp143I              Bst71I AluI
          CviJI     BstX2I DpnI  TthH38I   ItaI  ItaI BbvI
   MooII SfaNI      BstYI MflI AlwI   MnlI BsoFI BsoFI Bst71I
gaacggcatcaaggccaacttcaagatccgccacaacatcgaggacggcagcgtgcagctcgccgaccactacca base pairs
cttgccgtagttccggttgaagttctaggcggtgttgtagctcctgccgtcgcacgtcgagcggctggtgatggt 3001 to
                                                                                3075
              HaeIII   DpnII XhoII AciI      Fsp4HI Fsp4HI Cac8I
              PalI     NdeII Kzo9I   TaqI      BbvI  CviJI
                       Sau3AI AclWI                Cac8I BsgI HaeIII   BsoFI                 BmyI  BseNI BstDEI
              AsuI PalI ItaI                 Bsp1286I AciI
              Cfr13I BsuRI BbvI            DdeI SduI BsiHKAI
gcagaacacccccatcggcgacggccccgtgctgctgcccgacaaccactacctgagcacccagtccgccctgag base pairs
cgtcttgtgggggtagccgctgccggggcacgacgacgggctgttggtgatggactcgtgggtcaggcgggactc 3076 to
                                                                                3150
              Sau96I NlaIV Bst71I           BstDEI Alw21I BsrI
              AspS9I PspN4I                 AspHI BsrSI DdeI
              CviJI   Fsp4HI                Bbv12I BseI ThaI Bsh1236I DpnI Hsp92II BomI  Fsp4HI HapII NdeII AlwI
       Hin6I MvnI NdeII NlaIII AsuI GsuI  BsoFI MspI BcnI Sau3AI
        HinP1I AspLEI Bsp143I Sau96I AspS9I ItaI HpaII ScrFI Bsp143I
caaagaccccaacgagaagcgcgatcacatggtcctgctggagttcgtgaccgccgcgggatcactctcggcat base pairs
gtttctggggttgctcttcgcgctagtgtaccaggacgacctcaagcactggcggcgccctagtgagagccgta 3151 to
                                                                                3225
```

FIG. 20 (Cont'd)

```
                    HspAI BstUI MboI Cfr13I HgiEI Tsp45I Bsc4I BsiYI MboI DpnI
                      HhaI CfoI Sau3AI SinI AvaII MaeIII  BslI NciI DpnII AclWI
                     AccII DpnII Kzo9I Bme18I Eco47I  AciI BsiSI MspR9I Kzo9I

Bsp1407I    BsoFI ItaI CviJI BsaOI Bsh1236I Sau3AI BsrBRI
  NlaIII SspBI       CfrI Fsp4HI BsuRI AccII HinfI DpnII MamI    MnlI
     CviJI AfaI     EaeI NotI HaeIII Bsh1285I PleI MboI DpnI CviJI
ggacgagctgtacaagtaaagcggccgcgactctagatcataatcagccataccacatttgtagaggttttactt  base pairs
cctgctcgacatgttcatttcgccggcgctgagatctagtattagtcggtatggtgtaaacatctccaaaatgaa  3226 to
                                                                              3300
   Hsp92II Csp6I     BstZI EclXI PalI BstMCI AciI BfaI Kzo9I Bsh1365I
      AluI RsaI       CciNI Eco52I BsiEI BstUI XbaI NdeII BsaBI
      BsrGI           EagI XmaIII AciI ThaI MvnI MaeI Bsp143I Bse8I MunI          HincII
                                                      Mva1269I        MseI
      TruII                                            MfeI BsaMI     Tru9I
      Tru9I       MnlI       MnlI
gctttaaaaaaacctcccacacctcccccctgaacctgaaacataaaatgaatgcaattgttgttgttaacttgttt base pairs
cgaaatttttttggagggtgtggaggggggacttggactttgtattttacttacgttaacaacaacaattgaacaaa 3301 to
                                                                                3375
    MseI                                               BsmI Tsp509I HpaI
     DraI                                               Sse9I       TruII
                                                        TspEI       HindII AluI                     ApoI
    ItaI Bst71I                  AcsI
    BsoFI    MaeIII              SfaNI                                TspRI
attgcagcttataatggttacaaataaagcaatagcatcacaaatttcacaaataaagcatttttttttcactgcat  base pairs
taacgtcgaatattaccaatgtttatttcgttatcgtagtgttttaaagtgtttatttcgtaaaaaaagtgacgta  3376 to
                                                                                3450
    Fsp4HI                            Sse9I
    CviJI                             TspEI
     BbvI                             Tsp509I BsaMI                     MspCI   Tsp509I                     AcsI
   Mva1269I                   Bst98I  Sse9I     TruII    TruII
                              BspTI   MseI      Tru9I    Tru9I Tsp5
tctagttgtggtttgtccaaactcatcaatgtatcttaaggcgtaaattgtaagcgttaatattttgttaaaatt  base pairs
agatcaacaccaaacaggtttgagtagttacatagaattccgcatttaacattcgcaattataaaacaattttaa  3451 to
                                                                              3525
    BsmI                           AflII TruII     MseI         MseI ApoI
    MaeI                           Vha464I TspEI         SspI        Sse9I
    BfaI                           BfrI Tru9I                        TspEI BstUI AcsI    MseI
    ThaI MseI ApoI                       TruII    PalI
     09I Tru9I Tsp509I     CviJI         Tru9I    HaeIII
cgcgttaaattttttgttaaatcagctcattttttaaccaataggccgaaatcggcaaaatcccttataaatcaaa  base pairs
gcgcaatttaaaaacaattttagtcgagtaaaaaattggttatccggctttagccgttttagggaatatttagttt  3526 to
                                                                                3600
```

FIG. 20 (Cont'd)

```
    Bsh1236I TspEI        AluI      MseI          CviJI
    AccII Sse9I  Tru9I                            BsuRI
    MvnI Tru1I   Tru1I

MaeI BstX2I AciI
         AluI  DpnII MflI DpnI                                      AfaI
         CviJI BstYI Bsp143I              CviJI              MnlI  Csp6I
agaatagaccgagagctagcggatctgacggttcactaaaccagctctgcttatatagacctcccaccgtacacg base pairs
tcttatctggctctcgatcgcctagactgccaagtgatttggtcgagacgaatatatctggagggtggcatgtgc 3601 to
                                                                             3675
             NheI Cac8I Sau3AI AclWI      AluI                       RsaI
             PstNHI MboI XhoII AlwI
              BfaI NdeII Kzo9I NlaIV
                                                                    BshNI
         FauI      HgaI     AciI                  BsmFI              Eco64I
cctacccgccatttgcgtcaatggggcggagttgttatgacatttttggaaagtcccgttgattttggtgccaaaa base pairs
ggatgggcggtaaacgcagttaccccgcctcaacaatactgtaaaacctttcagggcaactaaaaccacggtttt 3676 to
                                                                              3750
    AciI                                                             BanI
                                                                     AccB1I
                                                                     PspN4I MaeII                      MspR9I CviJI FauI
         BbiII AatII                EcoRII MvaI AsuI CviJI
         Hin1I AcyI   AciI       AciI BstNI BglI AspS9I       MaeIII
caaactcccattgacgtcaatgggcggggggtcgttgggcggtcagccaggcgggccatttaccgtaagttatgta base pairs
gtttgagggtaactgcagttacccgcccccagcaacccgccagtcggtccgcccggtaaatggcattcaatacat 3751 to
                                                                              3825
         Msp17I        FauI        CviJI ScrFI Cac8I PalI
         Hsp92I                    BstOI MwoI AciI BsuRI
         BsaHI                     Bst2UI Sau96I HaeIII MvnI                                     AseI         Mph1103I
    AccII      BsiYI              Tsp509I    Tru9I        NsiI
      AciI     Bsc4I              Sse9I      AsnI Tru1I   Zsp2I AciI
acgcggaactccatatatgggctatgaactaatgaccccgtaattgattactattaataactaatgcatggcggt base pairs
tgcgccttgaggtatatacccgatacttgattactggggcattaactaatgataattattgattacgtaccgcca 3826 to
                                                                             3900
    ThaI        BslI                TspEI      VspI     Ppu10I Hsp92II
    BstUI              CviJI                   PshBI          EcoT22I
    Bsh1236I                                   MseI           NlaIII NspI       Cac8I    CviJI MspR9I
                                    NlaIII    PalI     BsiYI BstNI
              HinfI                 BspLU11I    HaeIII BslI BsuRI
aatacggttatccacagaatcaggggataacgcaggaaagaacatgtgagcaaaaggccagcaaaaggccaggaa base pairs
ttatgccaataggtgtcttagtcccctattgcgtcctttcttgtacactcgttttccggtcgttttccggtcctt 3901 to
                                                                              3975
```

```
                        TfiI                      AflIII      CviJI Bsc4I EcoRII
                                              Hsp92II    BsuRI      HaeIII
                                                                  PalI BstOI

CviJI ThaI MwoI
   NlaIV BsiYI Fsp4HI Bsh1236I          PspN4I
   Bst2UI BsII BsuRI AccII              CviJI AciI           SfaNI     TthH38I
   ccgtaaaaaggccgcgttgctggcgttttttccataggctccgccccctgacgagcatcacaaaaatcgacgctc base pairs
   ggcattttttccggcgcaacgaccgcaaaaaggtatccgaggcggggggactgctcgtagtgtttttagctgcgag 3976 to
                                                                                4050
   MvaI Bsc4I BsoFI BstUI               NlaIV                         TaqI   HgaI
   ScrFI      HaeIII MvnI Cac8I
       PspN4I PalI ItaI AciI Bst2JI       BstOI AluI      BssSI
                                        BstOI       EcoRII MvaI      HinP1I
   DrdI       MnlI                      EcoRII MvaI BsaJI Bst2JI MnlI HhaI
   aagtcagaggtggcgaaacccgacaggactataaagataccaggcgtttccccctggaagctccctcgtgcgctc base pairs
   ttcagtctccaccgctttgggctgtcctgatatttctatggtccgcaaagggggaccttcgaggagcacgcgag 4051 to
                                                                                4125
                                        BstNI      BseDI ScrFI       BsiI
                                        MspR9I     BstNI CviJI       HspAI
                                        ScrFI     MspR9I             Hin6I BsaWI                                    AspLEI
             ItaI Bsc4I HapII                                 Hin6I HaeII
             BsoFI BsII MspI        AciI                      HinP1I BstH2I
   tcctgttccgaccctgccgcttaccggatacctgtccgcctttctcccttcgggaagcgtggcgctttctcatag base pairs
   aggacaaggctgggacggcgaatggcctatggacaggcggaaagagggaagcccttcgcaccgcgaaagagtatc 4126 to
                                                                                4200
   AspLEI        Fsp4HI BsiSI                                  HspAI Bsp143II
     CfoI         AciI HpaII                                   HhaI
                      BsiYI                                    CfoI Bsp1286I
   CviJI                                                         VncI BmyI
        SfcI   DdeI                      CviJI           Alw44I Alw21I
   ctcacgctgtaggtatctcagttcggtgtaggtcgttcgctccaagctgggctgtgtgcacgaacccccgttca base pairs
   gagtgcgacatccatagagtcaagccacatccagcaagcgaggttcgacccgacacacgtgcttgggggcaagt 4201 to
                                                                                4275
        BstSFI BstDEI                            AluI CviJI     SduI BsiHKAI
```

FIG. 20 (Cont'd)

```
       AluI                                            ApaLI Bpv12I
                                                         AspHI

NspBII HinP1I CfoI HapII          MspI                      BsrI
       BstMCI AciI BbvI BsaWI              BcnI ScrFI                BseNI
   CviJI BsiEI BsoFI Hin6I BsiSI    HinfI  BsiSI                     TspRI
   gcccgaccgctgcgccttatccggtaactatcgtcttgagtccaacccggtaagacacgacttatcgccactggc base pairs
   cgggctggcgacgcggaataggccattgatagcagaactcaggttgggccattctgtgctgaatagcggtgaccg 4276 to
   4350
        Bsh1285I ItaI HhaI HpaII          PleI NciI MspR9I                    BsrSI
        BsaOI Fsp4HI Bst71I MspI               HpaII                          BseII
          MspA1I HspAI AspLEI MaeIII           HapII ItaI      BseII
        Bst71I BsrSI
         Fsp4HI TspRI              Mn1I     AciI         BstSFI              PalI
                                                                             HaeIII
   agcagccactggtaacaggattagcagagcgaggtatgtaggcggtgctacagagttcttgaagtggtggcctaa base pairs
   tcgtcggtgaccattgtcctaatcgtctcgctccatacatccgccacgatgtctcaagaacttcaccaccggatt 4351 to
   4425
         BbvI   MaeIII                              SfcI                   CviJI
           CviJI BseNI                                                     BsuRI
    BsoFI   AlwNI BsrI AspLEI        BseNI
      BsiYI                        Hin6I         MaeIII
      BslI      MaeI               HinP1I        Eco57I
   ctacggctacactagaaggacagtatttggtatctgcgctctgctgaagccagttaccttcggaaaaagagttgg base pairs
   gatgccgatgtgatcttcctgtcataaaccatagacgcgagacgacttcggtcaatggaagcctttttctcaacc 4426 to
   4500
     Bsc4I       BfaI              HspAI       CviJI BsrI
       CviJI                        HhaI             BsrSI
                                    CfoI             BseII Sau3AI HapII                                          Bst71I AccII
          NdeII HpaII        AciI                             Fsp4HI HspAI
     CviJI Kzo9I MspI       NspBII   AciI          Cac8I BbvI MwoI BstUI
   tagctcttgatccggcaaacaaaccaccgctggtagcggtggtttttttgtttgcaagcagcagattacgcgcag base pairs
   atcgagaactaggccgtttgtttggtggcgaccatcgccaccaaaaaaacaaacgttcgtcgtctaatgcgcgtc 4501 to
   4575
     AluI DpnII BsiSI       MspA1I                       BsoFI   HinP1I
       MboI DpnI AlwI                                    ItaI    ThaI
       Bsp143I AclWI                                             Hin6I HhaI    NdeII Kzo9I BstX2I XhoII DpnII
   Bsh1236I Sau3AI AclWI MboI DpnI AlwI Kzo9I        BstDEI             MseI
         BstYI MflI AlwI Sau3AI MboII Sau3AI         HgaI TspRI         MaeII
   aaaaaaaggatctcaagaagatccctttgatcttttctacggggtctgacgctcagtggaacgaaaactcacgtta base pairs
   ttttttttcctagagttcttctaggaaactagaaaagatgccccagactgcgagtcaccttgcttttgagtgcaat 4576 to
   4650
```

FIG. 20 (Cont'd)

```
     CfoI  DpnII XhoII BstYI Bsp143I MboI DpnI        DdeI                 Tru9I
  MvnI     BstX2I DpnI DpnII MflI AclWI Bsp143I                            Tru1I
AspLEI     MboI Bsp143I NdeII Kzo9I NdeII

MboI Bsp143I BfaI Sau3AI AclWI Sse9I    Tru1I
              NlaIII       BstX2I DpnI MaeI BstX2I DpnI Tru1I Tru1I
        BspHI              BstYI MflI AlwI DpnII MflI AlwI TspEI   Tru9I
agggattttggtcatgagattatcaaaaaggatcttcacctagatcctttttaaattaaaaatgaagttttaaatc   base pairs
tccctaaaaccagtactctaatagttttttcctagaagtggatctaggaaaatttaattttttacttcaaaatttag 4651 to
                                                                              4725
          RcaI                DpnII XhoII MooII MboI XhoII MseI Tru9I DraI
            Hsp92II           NdeII Kzo9I HphI NdeII Kzo9I DraI MseI MseI
                              Sau3AI AclWI BstYI Bsp143I Tru9I Tsp509I CvnI CviJI     DraII CviJI Fsp4HI    BsoFI  BsaJI Eco24I
                 DdeI Bsu36I    AsuI HaeIII BsoFI BsiYI   Bst71I SduI
           MaeIII AocI MnlI      Cfr13I PalI Cac8I Bsc4I  BbvI EcoRII
aatctaaagtatatatgagtaacctgaggctatggcagggcctgccgccccgacgttggctgcgagccctgggcc  base pairs
ttagatttcatatatactcattggactccgataccgtcccggacggcggggctgcaaccgacgctcgggacccgg  4726 to
                                                                              4800
              Eco81I         Sau96I BsuRI ItaI BslI ItaI CviJI BmyI
              Bse21I         EcoO109I MwoI MaeII CviJI Cac8I Bsp1286I
              BstDEI         AspS9I AlwNI AciI    Fsp4HI BseDI FriOI ScrFI AspS9I BsiYI                   MvnI FauI   HaeIII EslI
BstNI Cfr13I PalI Bsc4I                 AccII     AsuI PalI BsiYI BsaI
BanII MvaI AsuI HphI           MboII Cac8I    Cfr13I BsuRI    Alw26I
ttcacccgaacttggggggtggggtggggaaaaggaagaaacgcgggcgtattggccccaatgggggtctcggtgg base pairs
aagtgggcttgaaccccccacccccaccccttttccttctttgcgcccgcataaccggggttaccccagagccacc 4801 to
                                                                              4875
   BstOI Sau96I BsuRI               ThaI AciI  Sau96I NlaIV    Eco31I
      Bst2UI CviJI BslI             BstUI      AspS9I PspN4I   BsmAI
      MspR9I HaeIII                 Bsh1236I     CviJI Bsc4I EcoRII MspR9I Sau96I BsmFI MvnI
              BsaJI BstOI Cfr13I Eco47I AccII
     TthHB8I     Cac8I BslI ScrFI Bme18I NlaIV BstUI
ggtatcgacagagtgccagccctgggaccgaaccccgcgtttatgaacaaacgacccaacaccgtgcgttttatt base pairs
ccatagctgtctcacggtcgggaccctggcttgggcgcaaatacttgtttgctgggttgtggcacgcaaaataa  4876 to
                                                                             4950
      TaqI        CviJI BstNI MvaI AsuI PspN4I FauI
                  BseDI BsiYI SinI AvaII ThaI AciI
                  Bsc4I Bst2UI HgiEI AspS9I Bsh1236I ThaI Bsh1236I MspI                              StyI
              HspAI BstUI PspN4I                              Eco13
           MwoI HhaI AspLEI BsiSI      Alw26I        CviJI   AvrII
ctgtcttttttattgccgtcatagcgcgggttccttccggtattgtctccttccgtgtttcagttagcctcccct base pairs
gacagaaaaataacggcagtatcgcgcccaaggaaggccataacagaggaaggcacaaagtcaatcggagggga  4951 to
                                                                             5025
```

FIG. 20 (Cont'd)

```
                   HinP1I CfoI NlaIV HapII   BsmAI                       MnlI
                    Hin6I MvnI FauI HpaII                                ErhI
                     AccII AciI BsaWI                                    FlnI

EcoT14I             BstX2I Kzo9I HspAI Bsh1236I CfoI Bsp143I MroNI Bse118I
   OI BfaI              NlaIII Bsp143I ThaI MvnI HhaI MboI GsuI AclWI CviJI
     MaeI BslI MboII   GsuI BstYI MboI DpnI AccII Bsc4I AspLEI Kzo9I FokI BsrFI
agggtgggcgaagaactccagcatgagatccccgcgctggaggatcatccagccggcgtcccggaaaaacgattcc base pairs
tcccacccgcttcttgaggtcgtactctaggggcgcgacctcctagtaggtcggccgcagggccttttgctaagg 5026 to
                                                                              5100
BssT1I Bsc4I         BpmI DpnII Sau3AI AlwI BstJI BslI NdeII MnlI BstF5I NgoAIV
   BsaJI BsiYI        Hsp92II XhoII HinP1I FauI BsiYI Sau3AI DpnI BssAI
     BseDI             NdeII MflI AclWI Hin6I AciI DpnII BpmI AlwI NgoMI Cac8I AcyI BcnI BsmFI ItaI                                 BbiII
    HpaII BbiII BsiSI ScrFI BsoFI HinfI                          HinlI HgaI
     MspI Msp17I NciI MspR9I Fsp4HI TthH38I     BsiI         BspMI BsaHI
gaagcccaacctttcatagaaggcggcggtggaatcgaaatctcgtgatggcaggttgggcgtcgcttggtcggt base pairs
cttcggggttggaaagtatcttccgccgccaccttagctttagagcactaccgtccaaccgcagcgaaccagcca 5101 to
                                                                             5175
      HapII Hsp92I HpaII TfiI AciI   TaqI       BssSI       MwoI AcyI
Cfr10I NaeI BsaHI MspI HinfI    TfiI                         Msp17I
 BsiSI Hin1I HgaI HapII CviJI                                Hsp92I BstBI Bpu14I    AciI                              HhaI BbvI
       LspI NspV       DdeI BstD102I                     Hin6I BsoFI TfiI
      TthH38I    HinfI BsmFI BsrBI                       HinP1I Fsp4HI catttcgaaccccagagtcccgctcagaagaactcgtcaagaaggcgatagaaggcgatgcgctgcgaatcggga base pairs
gtaaagcttggggtctcagggcgagtcttcttgagcagttcttccgctatcttccgctacgcgacgcttagccct 5176 to
                                                                             5250
      SfuI TaqI   PleI AccBSI                            HspAI CfoI HinfI
       Csp45I        FauI    MboII                        SfaNI ItaI
       Bsp119I       BstDEI                                AspLEI Bst71I BsrBI                                          MboII
   ItaI AciI       MnlI              ItaI         Ksp632I
   BsoFI         BsiI  AciI        BsoFI CviJI   Eam1104I        CviJI
gcggcgataccgtaaagcacgaggaagcggtcagcccattcgccgccaagctcttcagcaatatcacgggtagcc base pairs
cgccgctatggcatttcgtgctccttcgccagtcgggtaagcggcggttcgagaagtcgttatagtgccatcgg 5251 to
                                                                             5325
   Fsp4HI         BssSI        CviJI    Fsp4HI AluI SapI
    AccBSI                               AciI      EarI
    BstD102I                                       Eco57I CpoI AsuI AciI NgoMI BsiSI CfrI BsuRI    ItaI BsuRI
             BsiYI HgiEI AspS9I NgoAIV HapII CviJI HinfI BsoFI AciI
              Bsc4I Bme18I AvaII MroNI Bse118I HaeIII TfiI   FaeI CviJI
aacgctatgtcctgatagcggtccgccacacccagccggccacagtcgatgaatccagaaaagcggccatttttcc base pairs
ttgcgatacaggactatcgccaggcggtgtgggtcggccggtgtcagctacttaggtcttttcgccggtaaaagg 5326 to
                                                                              5400
```

FIG. 20 (Cont'd)

```
          BslI Sau96I Eco47I BsrFI MspI EaeI PalI       CfrI PalI
           Cfr13I RsrII    BssAI Cfr10I NaeI TthHB8I    Fsp4HI
           SinI CspI AciI CviJI HpaII Cac8I TaqI         HaeIII

ErhI EcoT14I MaeIII Sau3AI AlwI     BbuI
             MslI BsaJI NlaIII BstX2I XhoII      NlaIII
 NlaIII    Cac8I   MwoI BssT1I BstDSI BstYI Bsp143I MnlI  PaeI       CviJI
accatgatattcggcaagcaggcatcgccatgggtcacgacgagatcctcgccgtcgggcatgctcgccttgagc base pairs
tggtactataagccgttcgtccgtagcggtacccagtgctgctctaggagcggcagcccgtacgagcggaactcg 5401 to
                                                                             5475
    Hsp92II          SfaNI NcoI Bsp19I DpnII MflI AclWI Cac8I SphI    EcoRII
                       Eco130I DsaI Tsp45I MboI Kzo9I   Hsp92II
                     StyI BseDI Hsp92II NdeII DpnI       NspI MspR9I         Hin6I MvnI CviJI MwoI SapI NdeII  FokI Bsp143I Cfr10I
BstNI          HinP1I CfoI SduI BanII MboII Sau3AI DpnII TthHB8I HpaII
   ScrFI    CviJI HhaI AspLEI BmyI SfaNI  DpnII DpnI MboI DpnI BsrFI HapII
ctggcgaacagttcggctggcgcgagcccctgatgctcttcgtccagatcatcctgatcgacaagaccggcttcc base pairs
gaccgcttgtcaagccgaccgcgctcggggactacgagaagcaggtctagtaggactagctgttctggccgaagg 5476 to
                                                                             5550
      MvaI      Cac8I AccII Cac8I Eco24I EarI MboI  BstF5I Kzo9I Bse118I
BstOI         HspAI BstUI Bsp1286I Eam1104I Bsp143I Sau3AI  BssAI MspI
Bst2JI         ThaI Bsh1236I FriCI Ksp632I Kzo9I NdeII TaqI BsiSI CviJI AfaI  Bbv12I TaqI                    MspI MboI AclWI
       Csp6I  AspHI TthHB8I                 BsiSI Sau3AI
    BstF5I  SduI Alw21I         TthHB8I    BspMI DpnII DpnI  MwoI
atccgagtacgtgctcgctcgatgcgatgtttcgcttggtggtcgaatgggcaggtagccggatcaagcgtatgc base pairs
taggctcatgcacgagcgagctacgctacaaagcgaaccaccagcttacccgtccatcggcctagttcgcatacg 5551 to
                                                                             5625
    FokI MaeII Bsp1286I  SfaNI        TaqI        CviJI NdeII AlwI
      RsaI  BmyI BsiHKAI                          HpaII Bsp143I
        BsaAI Cac8I                               HapII Kzo9I CviJI ItaI                                          MboI Bsp143I
Fsp4HI AciI         CviJI                              BstX2I DpnI
   Bst71I  BsrDI     NlaIII                     HphI   BstYI MflI
agccgccgcattgcatcagccatgatggatactttctcggcaggagcaaggtgagatgacaggagatcctgcccc base pairs
tcggcggcgtaacgtagtcggtactacctatgaaagagccgtcctcgttccactctactgtcctctaggacgggg 5626 to
```

*FIG. 20 (Cont'd)*

```
BsoFI BsoFI     SfaNI  Hsp92II                              DpnII XhoII
ItaI  Fsp4HI                                                NdeII Kzo9I
  BbvI                                                      Sau3AI AclWI

NciI ScrFI         BbvI  BsmFI          Tth111I    BmyI PvuII BsoFI FspI
 BseDI HapII       ItaI  BseI        Tsp45I AtsI     Bsp1286I MspA1I Hin6I
 AlwI HpaII      BsoFI BsrSI       FauI Eco57I   TthHB8I Alw21I NspBII HspAI
ggcacttcgcccaatagcagccagtcccttcccgcttcagtgacaacgtcgagcacagctgcgcaaggaacgccc base pairs
ccgtgaagcgggttatcgtcggtcagggaagggcgaagtcactgttgcagctcgtgtcgacgcgttccttgcggg 5701 to
                                                                             5775
 BsaJI MspI       Fsp4HI BseNI      AciI   TspRI   TaqI   SduI BsiHKAI HinP1I
 BsiSI MspR9I      CviJI BsrI        MaeIII MaeII    AspHI CviJI Fsp4HI AviII
  BcnI              Bst71I             AspI        Bov12I AluI ItaI BbvI AspLEI PalI BalI    TtaI AccII HhaI ItaI          NlaIV BsiSI
   HhaI CfrI MluNI    CviJI ThaI AciI Fsp4HI       BshNI Bsp1286I
    Bst71I CviJI CviJI BsoFI Hin6I AspLEI MnlI     Eco64I BmyI HapII
gtcgtggccagccacgatagccgcgctgcctcgtcttgcagttcattcagggcaccggacaggtcggtcttgaca base pairs
cagcaccggtcggtgctatcggcgcgacggagcagaacgtcaagtaagtcccgtggcctgtccagccagaactgt 5776 to
                                                                             5850
Acc16I EaeI MscI MwoI   HinP1I Bsh1236I BovI       BanI SduI MspI
   MwoI BsuRI     Fsp4HI BstUI CfoI Bst71I         Acc31I BsaWI DrdI
  CfoI HaeIII Cac8I      HspAI MvnI BsoFI          PspN4I HpaII NciI KasI Hin1I HspAI EheI HaeII Hin6I HpaII Fsp4HI BbvI
       MspI MspR9I BbiII BsaHI HhaI BstH2I CfoI MspI BsoFI fsp4HI      BmyI
      BsiSI ScrFI Msp17I Hin6I CfoI BbeI HhaI BsiSI BsiYI BsoFI       SduI
aaaagaaccgggcgcccctgcgctgacagccggaacacggcggcatcagagcagccgattgtctgttgtgcccag base pairs
ttttcttggcccgcggggacgcgactgtcggccttgtgccgccgtagtctcgtcggctaacagacaacacgggtc 5851 to
                                                                             5925
      HpaII Eco64I Hsp92I NlaIV Bsp143II AspLEI HapII ItaI ItaI       Bsp1286I
      HapII BanI AccB1I NarI PspN4I HinP1I MwoI Bsc4I AciI CviJI
       BcnI BshNI HinP1I AcyI AspLEI HspAI CviJI BslI SfaNI Bst71I BseNI                     EagI Eco52I BsiSI BstMCI
                           CfrI Ec1XI BsuRI HapII
 BsrI          CviJI       EaeI XmaIII AciI MspI Cac8I              NlaIII
tcatagccgaatagcctctccacccaagcggccggagaacctgcgtgcaatccatcttgttcaatcatgcgaaac base pairs
agtatcggcttatcggagaggtgggttcgccggcctcttggacgcacgttaggtagaacaagttagtacgctttg 5926 to
                                                                             6000
     CviJI       MnlI       BstZI ItaI PalI Bsh1285I                Hsp92II
BsrSI                       BsoFI HaeIII BsiEI BsaOI
BseII                       Fsp4HI CviJI HpaII BspMI MboI DpnI AlwI    NdeII BanIII BscI DpnII CviJI BlnI MaeI AatI Sse3I
DpnII MamI Bse8I BsmAI Bsp143I BspXI ClaI Bsp143I BsaJI BfaI CviJI MnlI
 Bsp143I AclWI FokI MboI DpnI Bsp106I NdeII AvrII BssT1I StuI Eco147I
gatcctcatcctgtctcttgatcgatctttgcaaaagcctaggcctccaaaaaagcctcctcactacttctggaa base pairs
ctaggagtaggacagagaactagctagaaacgttttcggatccggaggttttttcggaggagtgatgaagacctt 6001 to
                                                                             6075
```

FIG. 20 (Cont'd)

```
      Kzo9I Bsh1365I Alw26I Kzo9I Bsa29I BseCI Kzo9I StyI  BseDI HaeIII CviJI
NdeII BsaBI  MnlI    DpnII TthHB8I TaqI  MboI  DpnI  Eco130I Pme55I BsuRI BseRI
Sau3AI Bsr3RI BstF5I Sau3AI BspDI  Bsu15I Sau3AI ErhI EcoT14I PalI MnlI

BsuRI BglI CviJI BseDI                   BssT1I DsaI Bsc4I
   DdeI   PalI BseDI ItaI AciI PalI        Tsp509I ErhI EcoT14I BsiYI
  CviJI   HaeIII MwoI PalI BsaJI BsuRI     Sse9I   CviJI BsaJI NlaIII
tagctcagaggccgaggcggcctcggcctctgcataaataaaaaaattagtcagccatggggcggagaatgggc base pairs
atcgagtctccggctccgccggagccggagacgtatttatttttttttaatcagtcggtaccccgcctcttacccg 6076 to
                                                                              6150
   AluI    CviJI SfiI Fsp4HI MnlI MnlI       TspEI   Eco130I Bsp19I AciI
   BstDEI MnlI   MnlI HaeIII HaeIII                  StyI BseDI Hsp92II
          BsaJI BsoFI BsuRI CviJI                    NcoI BstDSI BslI AciI           FokI                                      Cac8I
        BseII             MwoI              BsmFI         Tsp509I    Zsp2I
    AciI  BsrSI      AciI     AciI        AciI            Sse9I      Ppu10I
ggaactgggcggagttaggggcgggatgggcggagttaggggcgggactatggttgctgactaattgagatgcat base pairs
ccttgacccgcctcaatccccgccctacccgcctcaatccccgccctgataccaacgactgattaactctacgta 6151 to
                                                                              6225
     BseNI            FauI                   FauI         TspEI      SfaNI
     BsrI             BstF5I                                         NsiI
                                                                     EcoT22I BbuI MwoI             BsaJI ScrFI        MspR9I                  Cac8I
     Hsp92II               CviJI MspR9I       BstNI       Tsp509I    Zsp2I
   Mph1103I    Cac8I    NlaIV BstNI BsmFI SexAI ScrFI     Sse9I      Ppu10I Mph11
gctttgcatacttctgcctgctggggagcctggggactttccacacctggttgctgactaattgagatgcatgct base pairs
cgaaacgtatgaagacggacgaccccctcggacccctgaaaggtgtggaccaacgactgattaactctacgtacga 6226 to
                                                                              6300
   PaeI SphI           PspN4I BstOI       EcoRII MvaI     TspEI      SfaNI
   NlaIII              EcoRII Bst2UI      BstOI                      NsiI
   NspI                BseDI MvaI         Bst2UI                     EcoT22I BbuI MwoI              BsaJI ScrFI                                MspA1I
   Hsp92II                CviJI MspR9I                               AluI
   O3I        Cac8I    NlaIV BstNI BsmFI                             PvuII
ttgcatacttctgcctgctggggagcctggggactttccacacctaactgacacacattccacagctggttctt base pairs
aacgtatgaagacggacgaccccctcggacccctgaaaggtgtggattgactgtgtgtaaggtgtcgaccaagaa 6301 to
                                                                              6375
   PaeI SphI           PspN4I BstOI                                  CviJI
   NlaIII              EcoRII Bst2UI                                 NspBII
   NspI                BseDI MvaI CvnI MnlI    EarI                                  NlaIII
       DdeI Bsu36I Eam1104I                       Alw26I BstD102I
     AciI AccI PleI        SspI                   BspHI        AccBSI
tccgcctcaggactcttcctttttcaatattattgaagcatttatcagggttattgtctcatgagcggatacata base pairs
aggcggagtcctgagaaggaaaaagttataataacttcgtaaatagtcccaataacagagtactcgcctatgtat 6376 to
                                                                              6450
```

FIG. 20 (Cont'd)

```
      Eco81I HinfI                                              RcaI    BsrBI
      Bse21I      Ksp632I                                       BsmAI  AciI
      BstDEI      MboII                                              Hsp92II ThaI MvnI                         Hin6I
                                  HinP1I HhaI                        ThaI
                                NlaIV Hin6I AspLEI                   HinP1I
    tttgaatgtatttagaaaaataaacaaatagggggttccgcgcacatttccccgaaaagtgccacctgacgcgccc base pairs
    aaacttacataaatcttttttatttgtttatccccaaggcgcgtgtaaagggggcttttcacggtggactgcgcggg 6451 to
    6525
                                  PspN4I BstUI CfoI                  HspAI
                                       HspAI Bsh1236I                AccII
                                       AccII AciI                    BstUI HhaI Bsc4I HinP1I Tru9I Hin6I CfoI AciI ThaI MvnI BsoFI Bst71I    HhaI MaeI
     MvnI SfcI Fsp4HI AspLEI HinP1I AspLEI FauI Hin6I CfoI BbvI        HspAI Bsp143II
       CfoI BslI ItaI HhaI MwoI ThaI Bsh1236I HinP1I HhaI ItaI AciI Cac8I CfoI BfaI
    tgtagcggcgcattaagcgcggcgggtgtggtggttacgcgcagcgtgaccgctacacttgccagcgccctagcg base pairs
    acatcgccgcgtaattcgcgccgcccacaccaccaatgcgcgtcgcactggcgatgtgaacggtcgcgggatcgc 6526 to
    6600
    Bsh1236I BsoFI AciI TruII AccII BsoFI MaeIII BstUI Fsp4HI MwoI  HinP1I BstH2I
    HgaI BstSFI HspAI CfoI HspAI BstUI ItaI HspAI Bsh1236I MaeIII   Hin6I HaeII
    AspLEI BsiYI Hin6I MseI HhaI MvnI Fsp4HI AccII AspLEI Tsp45I    AspLEI HinP1I Hin6I BstH2I MwoI                      BsrFI MspI NaeI
        CfoI FauI BstD102I                  BssAI BsiSI CviJI HhaI Cac8I BsrBI MboII       MaeII MroNI Cfr10I    CviJI
    cccgctcctttcgctttcttcccttcctttctcgccacgttcgccggctttccccgtcaagctctaaatcggggg base pairs
    gggcgaggaaagcgaaagaagggaaggaaagagcggtgcaagcggccgaaaggggcagttcgagatttagccccc 6601 to
    6675
        AspLEI AciI                MwoI Bse118I Cac8I   AluI
      HspAI HaeII AccBSI                  NgoMI HpaII
        Bsp143II                          NgoAIV HapII Bsp1286I                     NlaIV
     PspN4I                        BshNI TaqI
    CviJI Eco24I NlaIV             Eco64I MnlI             HphI   MaeII
    ctcccctttaggggttccgatttagtgctttacggcacctcgaccccaaaaaaacttgattagggtgatggttcacgt base pairs
    gagggaaatcccaaggctaaatcacgaaatgccgtggagctgggggttttttgaactaatcccactaccaagtgca 6676 to
    6750
    NlaIV FriCI PspN4I          BanI  TthHB8I                       BsaAI
      SduI BanII                AccB1I
      BmyI                        PspN4I AspS9I
     DraIII CviJI                                         TruII
        Cfr13I BsuRI                MaeII HinfI MaeII  Tru9I   HinfI
    agtgggccatcgcccctgatagacggttttttcgcccttttgacgttggagtccacgttcttttaatagtggactcttg base pairs
    tcacccggtagcgggactatctgccaaaaaagcgggaaactgcaacctcaggtgcaagaaattatcacctgagaac 6751 to
    6825
```

FIG. 20 (Cont'd)

```
        Sau96I                                         DrdI PleI    MseI         PleI
     AsuI PalI
       HaeIII

BseNI              BsiYI                                              PalI
       BsrSI              Bsc4I                                              HaeIII
ttccaaactggaacaacactcaaccctatctcggtctattcttttgatttataagggattttgccgatttcggcc  base pairs
aaggtttgaccttgttgtgagttgggatagagccagataagaaaactaaatattccctaaaacggctaaagccgg  6826 to
                                                                             6900
       BseNI              BslI                                               CviJI
       BsrI                                                                  BsuRI Tsp509I   BstUI Tsp509I
        TruII            TruII  TspEI    AccII ApoI       MseI         Tsp509I
        Tru9I    CviJI Tru9I   Sse9I    ThaI AcsI MseI   SsoI          Sse9I
tattggttaaaaaatgagctgatttaacaaaaatttaacgcgaattttaacaaaatattaacgcttacaatttac  base pairs
ataaccaattttttactcgactaaattgttttttaaattgcgcttaaaattgttttataattgcgaatgttaaatg  6901 to
                                                                              6975
     MseI    AluI    MseI    AcsI MseI MvnI TspEI      Tru9I      TspEI
                             ApoI TruII Sse9I Tru9I    TruII
                                  Tru9I Bsh1236I TruII MspCI                                                                    Tsp5
    Bst98I                             BsaMI                                 TspEI
    BspTI MseI                   MaeI  BsmI                                  Sse9I
gccttaagatacattgatgagtttggacaaaccacaactagaatgcagtgaaaaaaatgctttatttgtgaaatt  base pairs
cggaattctatgtaactactcaaacctgtttggtgttgatcttacgtcacttttttttacgaaataaacactttaa  6976 to
                                                                             7050
    AflII TruII                 BfaI   Mva1269I                              AcsI
    Vha464I                             TspRI                                ApoI
    BfrI Tru9I C9I                               ItaI        HincII Tsp509I
                                  BsoFI       TruII  MunI     BsaMI
        SfaNI       MaeIII        CviJI       Tru9I  MfeI     BsmI
tgtgatgctattgctttatttgtaaccattataagctgcaataaacaagttaacaacaacaattgcattcatttt  base pairs
acactacgataacgaaataaacattggtaatattcgacgttatttgttcaattgttgttgttaacgtaagtaaaa  7051 to
                                                                             7125
                                  AluI Bst71I  MseI    Sse9I    Mva1269I
                                  Fsp4HI        HpaI    TspEI
                                     BbvI       HindII TruII
                MnlI    MnlI Tru9I         MnlI          CviJI
atgtttcaggttcaggggggaggtgtggaggtttttaaagcaagtaaaaccctctacaaatgtggtatggctgat  base pairs
tacaaagtccaagtcccccctccacaccctccaaaaatttcgttcattttggagatgtttacaccataccgacta  7126 to
                                                                             7200
```

FIG. 20 (Cont'd)

```
                                      MseI
                                      DraI

Bse8I Sau3AI BfaI  MvnI BsoFI Eco52I BsiEI Bsp1407I Hsp92II NciI  AclWI Fsp4HI
  BsrBRI Bsp143I ThaI BstZI NotI HaeIII Bsh1285I CviJI MboI  DpnI  HpaII BsoFI
  MamI  NdeII  XbaI AccII CfrI Fsp4HI CviJI BsaOI Csp6I NdeII Kzo9I MspI  AlwI
tatgatctagagtcgcggccgctttacttgtacagctcgtccatgccgagagtgatcccggcggcggtcacgaac  base pairs
atactagatctcagcgccggcgaaatgaacatgtcgagcaggtacggctctcactagggccgccgccagtgcttg  7201 to
                                                                              7275
  BsaBI MboI MaeI BstUI CciNI XmaIII AciI AciI BsrGI AluI Sau3AI BcnI ScrFI
  Bsh1365I DpnI PleI Bsh1236I EclXI PalI BstMCI RsaI NlaIII BsiSI HapII Bsc4I
   DpnII Kzo9I HinfI EaeI EagI ItaI BsuRI SspBI AfaI DpnII Bsp143I MspR9I ItaI MaeIII AsuI AspS9I Sau3AI Hin6I CfoI                 DdeI  Bov12I
    AciI   SinI AvaII NdeII DpnI AccII AspLEI             Bse1I BmyI BsiHKAI
  BslI BpmI HgiEI NlaIII Kzo9I ThaI HhaI      DdeI      AciI BsrSI Bsp1286I
tccagcaggaccatgtgatcgcgcttctcgttggggtctttgctcagggcggactgggtgctcaggtagtggttg  base pairs
aggtcgtcctggtacactagcgcgaagagcaaccccagaaacgagtcccgcctgacccacgagtccatcaccaac  7276 to
                                                                              7350
  BsiYI  Cfr13I Eco47I MboI HspAI Bsh1236I   BstDEI         BseNI AspHI
    Tsp45I Bme18I Hsp92II HinP1I MvnI                       BsrI SduI Alw21I
       GsuI Sau96I DpnII Bsp143I BstUI                          BstDEI Bst71I  NlaIV                                    Fsp4HI Fsp4HI
      ItaI    AsuI  HaeIII                                 AluI Bst71I
      BsoFI     Cfr13I CviJI                             Cac8I BbvI ItaI
tcgggcagcagcacggggccgtcgccgatgggggtgttctgctggtagtggtcggcgagctgcacgctgccgtcc  base pairs
agcccgtcgtcgtgccccggcagcggctaccccccacaagacgaccatcaccagccgctcgacgtgcgacggcagg 7351 to
                                                                              7425
        Fsp4HI      Sau96I PalI                            CviJI Cac8I Bst71I
           BbvI     AspS9I BsuRI                              BsoFI BsoFI
                    PspN4I                                    ItaI BsgI BbvI MboI Bsp143I                     PalI
  TaqI       BstX2I AciI     HphI             HaeIII
  TthHB8I    BstYI MflI AclWI MslI  SfaNI  MboII  EaeI  NlaIII MaeII
tcgatgttgtggcggatcttgaagttcaccttgatgccgttcttctgcttgtcggccatgatatagacgttgtgg  base pairs
agctacaacaccgcctagaacttcaagtggaactacggcaagaagacgaacagccggtactatatctgcaacacc  7426 to
                                                                              7500
            DpnII XhoII AlwI                  CfrI    Hsp92II
  MnlI      NdeII Kzo9I                         CviJI
            Sau3AI DpnI                         BsuRI BseDI Bst2UI                              TaqI
           AfaI  GsuI  BmyI BstOI FokI                        AluI
  CviJI    Csp6I  CviJI  SduI BstNI BstF5I  MnlI   TthHB8I   Eco57I
ctgttgtagttgtactccagcttgtgcccaggatgttgccgtcctccttgaagtcgatgcccttcagctcgatg  base pairs
gacaacatcaacatgaggtcgaacacgggtcctacaacggcaggaggaacttcagctacgggaagtcgagctac  7501 to
                                                                              7575
```

FIG. 20 (Cont'd)

```
            RsaI   AluI    Bsp1286I MvaI              TaqI  SfaNI   CviJI
                   BpmI    BsaJI MspR9I                              TthHB8I

EcoRII ScrFI

BstOI MslI                    HinP1I MvnI AciI
      BseDI ScrFI     MnlI      HphI BslI HhaI CfoI
SfaNI EcoRII Bst2JI TthHB8I  BsaJI Bsc4I AccII FauI                MboII
cggttcaccagggtgtcgccctcgaacttcacctcggcgcgggtcttgtagttgccgtcgtccttgaagaagatg base pairs
gccaagtggtcccacagcgggagcttgaagtggagccgcgcccagaacatcaacggcagcaggaacttcttctac 7576 to
                                                                              7650
    AciI BsaJI HphI    TaqI      BseDI Hin6I BstUI
       BstNI MvaI                MnlI BsiYI AspLEI
       MspR9I                HspAI ThaI Bsh1236I AspLEI ScrFI                               Bst71I
  Hin6I BstNI MvaI           AciI         ItaI            ItaI
  HinP1I BstOI MaeII     NlaIII   MboII   BsoFI  NlaIII   BsoFI
gtgcgctcctggacgtagccttcgggcatggcggacttgaagaagtcgtgctgcttcatgtggtcggggtagcgg base pairs
cacgcgaggacctgcatcggaagcccgtaccgcctgaacttcttcagcacgacgaagtacaccagccccatcgcc 7651 to
                                                                              7725
    HspAI EcoRII   CviJI      Hsp92II          Fsp4HI Hsp92II    Fsp4HI
      HhaI MspR9I                              BcvI
      CfoI Bst2JI AciI                             Sau96I EcoRII MvaI BsiYI ItaI Cac8I
    MwoI       BsgI           BssSI HaeIII BstNI Bsc4I MwoI AluI BssAI
       Eco57I Cac8I       Tsp45I MslI Cfr13I BsuRI MspR9I SduI Fsp4HI BsrFI
ctgaagcactgcacgccgtaggtcagggtggtcacgagggtgggccagggcacgggcagcttgccggtggtgcag base pairs
gacttcgtgacgtgcggcatccagtcccaccagtgctcccacccggtcccgtgcccgtcgaacggccaccacgtc 7726 to
                                                                              7800
        TspRI           MaeIII  BsiI AspS9I BsaJI Bst2UI BmyI CviJI Bse118I
CviJI                           MnlI CviJI BseDI ScrFI Bsp1286I Bst71I
                                AsuI PalI BstOI BslI BsoFI BcvI Cfr1

HpaII                                HapII              PalI
      MspI       AluI                      HpaII              HaeIII
      HapII Eco57I Cac8I        SfaNI MnlI MnlI  MwoI     EaeI
atgaacttcagggtcagcttgccgtaggtggcatcgccctcgccctcgccggacacgctgaacttgtggccgttt base pairs
tacttgaagtcccagtcgaacggcatccaccgtagcgggagcgggagcggcctgtgcgacttgaacaccggcaaa 7801 to
                                                                              7875
      BsgI      CviJI                   BcgI  BsiST        CfrI
   BsiSI                                      MspI         CviJI
   OI MwoI                                                 BsuRI MspR9I Eco64I Bsp1286I MspI CviJI    NcoI BstDSI
                TthHB8I ScrFI BshNI BmyI MslI ScrFI BseRI   StyI BseDI
    MaeII       CviJI  BstNI BstF5I SduI BsiSI HapII  MnlI  Eco130I HphI
acgtcgccgtccagctcgaccaggatgggcaccaccccggtgaacagctcctcgcccttgctcaccatggttgtg base pairs
tgcagcggcaggtcgagctggtcctacccgtggtggggccacttgtcgaggagcgggaacgagtggtaccaacac 7876 to
                                                                              7950
```

FIG. 20 (Cont'd)

```
           AluI EcoRII MvaI AccB1I BsaJI BcnI HphI           ErhI EcoT14I
         TaqI BstOI FokI NlaIV BseDI HpaII AluI             BssT1I Bsp19I
           Bst2UI BanI PspN4I NciI MspR9I                   BsaJI DsaI

MsII HaeIII                        BsmFI     DraII PspN4I
 NlaIII PalI BalI                     BstDSI    AsuI NlaIV MaeI MseI
   BstXI BsuRI             MaeII BsaJI BslI  Cfr13I HaeIII  Tru9I
gccatattatcatcgtgtttttcaaaggaaaaccacgtccccgtggttcgggggcctagacgttttttttaacct base pairs
cggtataatagtagcacaaaaagtttccttttggtgcaggggcaccaagccccccggatctgcaaaaaaattgga 7951 to
8025
   EaeI CviJI                      BseDI BsiYI Sau96I CviJI MaeII
    CfrI MscI                      DsaI Bsc4I  Eco0109I BsuRI  TruII
 Hsp92II MluNI                                 AspS9I PalI BfaI NspI    VneI Bsp1286I Sau96I PalI NlaIV Bsp143I MflI AclWI BsiYI MnlI         NlaIII   Hsp92II Alw21I AsuI HaeIII NdeII DpnI BstX2I DpnI BslI
 ThHB8I  BspLU11I    NlaIII BnyI BsaJI Eco0109I PspN4I BstYI Sau3AI AlwI
cgactaaacacatgtaaagcatgtgcaccgaggccccagatcagatcccatacaatgggtaccttctgggcatc base pairs
gctgatttgtgtacatttcgtacacgtggctccggggtctagtctagggtatgttaccccatggaagacccgtag 8026 to
8100
 TaqI      AflIII    Alw44I Bbv12I Cfr13I CviJI DpnII Kzo9I MboI XhoII AccB7I
           Hsp92II   NspI SduI BsiHKAI DraII MnlI MboI DpnII Bsp143I Bsc4I
                     ApaLI AspHI BseDI AspS9I BsuRI Sau3AI NdeII Kzo9I PflMI Acc65I RsaI FokI
   Eco64I NlaIV SfaNI            CviJI
 Esp1396I BshNI PspN4I    MnlI     HinfI                          MaeII
cttcagcccttgttgaatacgcttgaggagagccatttgactctttccacaactatccaactcacaacgtggca base pairs
gaagtcggggaacaacttatgcgaactcctctcggtaaactgagaaaggtgttgataggttgagtgttgcaccgt 8101 to
8175
     Asp718I AflI Eco57I      BseRI       PleI                  DraIII
  Van91I AccB1I BstF5I
    BanI Csp6I KpnI  CviJI BsrI                           PmlI    PalI ItaI BshNI       MspR9I
   BseNI    ItaI MwoI             Eco72I  EaeI BsoFI Eco64I      BstCI
  TspRI  BsoFI      BspMI   AflIII BbrPI  HaeIII MwoI NlaIV EcoRII MvaI
ctggggttgtgccgcctttgcaggtgtatcttatacacgtggcttttggccgcagaggcacctgtcgccaggtgg base pairs
gaccccaacacggcggaaacgtccacatagaatatgtgcaccgaaaaccggcgtctccgtggacagcggtccacc 8176 to
8250
     BsrSI  Fsp4HI             MaeII CviJI CviJI AciI Acc3lI     BstNI
     Bse1I     AciI             BsaAI  CfrI Fsp4HI BanI PspN4I   ScrFI
                                 PmaCI     BsuRI BglI MnlI      Bst2UI
```

FIG. 20 (Cont'd)

```
  BsiYI    BsoFI    BslI                        MboII
BslI PspN4I ItaI Bsc4I                       BbsI  AluI            XmnI
     NlaIV AciI BbvI        SfcI   MaeII      BpuAI CviJI       MnlI
ggggttccgctgcctgcaaagggtcgctacagacgttgtttgtcttcaagaagcttccagaggaactgcttcctt base pairs
ccccaaggcgacggacgtttcccagcgatgtctgcaacaaacagaagttcttcgaaggtctccttgacgaaggaa  8251 to
                                                                              8325
Bsc4I    NspBII Bst71I    BstSFI              Bbv16II                  Asp700I
         MspA1I Cac8I                          BpiI
    Fsp4HI   BsiYI                                  HindIII BlnI BseDI           BpiI
                          BsaMI              ErhI BsaJI BsaMI     Bbv16II
                          BsmI       MnlI    AvrII MaeI Mval269I  MboII
cacgacattcaacagaccttgcattcctttggcgagagggaaagaccccctaggaatgctcgtcaagaagacagg base pairs
gtgctgtaagttgtctggaacgtaaggaaaccgctctccccttctgggatccttacgagcagttcttctgtcc   8326 to
                                                                            8400
                   Mval269I              Eco130I  BsmI          BpuAI
                                         StyI  EcoT14I          BbsI
                                         BssT1I BfaI            Cfr13I AspS9I BstNI MvaI BcnI Sau96I HaeIII BnyI ApaI BslI                      BsiSI
     CviJI MspR9I MspI Cfr13I EcoO109I Bsp1286I Bsc4I                      Bse118I
  Sau96I EcoRII BsiSI MspR9I AspS9I PalI Ecc24I BsrDI                      BssAI
gccaggtttccgggccctcacattgccaaaagacggcaatatggtggaaaataacatatagacaaacgcacaccg base pairs
cggtccaaaggcccgggagtgtaacggttttctgccgttataccacctttattgtatatctgtttgcgtgtggc  8401 to
                                                                             8475
   HaeIII BstOI HpaII ScrFI AsuI CviJI SduI BanII                       BsrFI
   AsuI BsuRI ScrFI NciI Bsp1286I NlaIV PspN4I MnlI                     CfrI
     PalI Bst2UI HapII PspOMI DraII BsuRI FriOI BsiYI                   HpaII CviJI     AciI  PalI BsrSI                       NdeII BstI  NlaIV Eco88I
   BsuRI     ItaI MwoI BsuRI MaeII                  DpnII MflI AciI PspAI
  MspI     BsoFI EaeI MaeIII Psp1406I     MnlI  MnlI Sau3AI Kzo9I BcoI
gccttattccaagcggcttcggccagtaacgttaggggggggggaggagagggcggatcccgggcccgcggta base pairs
cggaataaggttcgccgaagccggtcattgcaatccccccccctccctctcccgcctagggcccgggcgccat  8476 to
                                                                           8550
    HapII     Fsp4HI  HaeIII BsrI                    BstYI BamHI DpnI Cfr9I
  OI HaeIII    CviJI CviJI BseII                     BstX2I XhoII PspN4I
    PalI          CfrI    BseNI                     MboI Bsp143I Ama87I XmaI MspI Cfr13I NlaIV SduI BsaJI DsaI MvnI FauI AciI Acc65I PspN4I SfcI
   BseDI HpaII SmaI AsuI HaeIII Eco24I BstDSI Bsh1236I Eco64I Csp6I SalI HindII
 AclWI BsoBI HapII Bsp120I PalI Bsp1286I ApaI NspBII SstII BanI NlaIV TthHB8I
ccgtcgactgcagaattcactagtgattaaattatattgtcgactcatgagcacccacagcggtctactaccatg base pairs
ggcagctgacgtcttaagtgatcactaatttaatataacagctgagtactcgtgggtgtcgccagatgatggtac  8551 to
                                                                              8625
   AlwI BcnI PspALI AspS9I PspN4I BseDI ThaI MspA1I Cfr42I AccB1I XpnI HincII
   BsaJI NciI MspR9I Sau96I BsuRI Cac8I BanII BstJI Sfr303I Asp718I AfaI TaqI
    AvaI BsiSI ScrFI PspOMI CviJI BmyI FriOI AccII KspI SacII BshNI RsaI AccI
```

FIG. 20 (Cont'd)

```
     AcsI SpeI MseI TthHB8I PleI BmyI BsiHKAI StyI BseDI Hsp92II TruII PshBI
       TspEI BfaI Tsp509I HinfI SduI Bbv12I AccI BsaJI Bsp19I TspEI VspI TruII
    Sse9I AclNI TruII AccI BspHI Bsp1286I MspA1I BssT1I NlaIII ApoI AsnI MseI
gctggaattttcccatatattatttgttctttgccattaaaatatagcatattaatgggagacattttttgtcgga base pairs
cgaccttaaaagggtatataataaacaagaaacggtaattttatatcgtataattaccctctgtaaaaacagcct 8626 to
8700
     EcoRI MaeI Sse9I TaqI RcaI AspHI MwoI AciI NcoI DsaI CviJI Tru9I Tru9I
    PstI ApoI Tru9I SalI HindII Hsp92II NspBII ErhI EcoT14I Sse9I MseI MslI Alw26I
  BstSFI Tsp509I TspEI HincII NlaIII Alw21I Eco130I BstDSI AcsI Tsp509I AseI DrdI  Bst71I  DraII  BsuRI  Bsp1720I        Bsp1286I
      Fsp4HI Sau96I PalI CelII          ApaLI Bbv12I
     BsoFI Cfr13I CviJI DdeI CviJI      Alw44I Alw21I         AciI
gtgcagcaagggcctgctgagcctctggggtttgcttggtgcacaagatgagtatgcggatatttttgtaaaaac base pairs
cacgtcgttcccggacgactcggagacccccaaacgaaccacgtgttctactcatacgcctataaaaacatttttg 8701 to
8775
 BsmAI BbvI Eco0109I Cac8I BstDEI       VneI BmyI
     BsgI AsuI HaeIII BlpI MnlI          SduI BsiHKAI
   ItaI MwoI AspS9I Bpu1102I             AspHI Tsp509I                 BsuRI                              BsmFI
   TspEI                   Tsp509I                        BseII  Bsc4I
   Sse9I       DdeI       Sse9I HaeIII                     BsrSI  BstF5I
acaaattcacactctcctgagcagtaattggcctatatcttttgggtgcgataatccagtcccatccaaaggct base pairs
tgtttaagtgtgagaggactcgtcattaaccggaatatagaaaacccacgctattaggtcagggtaggtttccga 8776 to
8850
   AcsI         BstDEI  TspEI CviJI                       BseNI  FokI CviJI
   ApoI                       PalI                         BsrI   BslI
                                                                  BsiYI BstMCI  MnlI         MspI MspR9I      Bbv12I
            BsiEI BsiYI    ItaI Bst71I BcnI BseDI AspHI
       TthHB8I  Bsc4I    BsoFI BovI NciI BsaJI    SduI BsiHKAI CviJI
tcaaaatcgaccgtgaggggtagcggcagcaccgggattccgtggagtgctcatcgcagtcaagcccaaagtct base pairs
agttttagctggcactcccccatcgccgtcgtggccctaaggcacctcacgagtagcgtcagttcgggtttcaga 8851 to
8925
       TaqI     BslI    Fsp4HI  BsiSI ScrFI DsaI  Bsp1286I
        Bsh1285I        AciI   HpaII HinfI         BmyI
        BsaOI                  HapII TfiI BstDSI   Alw21I MspI MspR9I AsuI Psp5II MnlI                             MspR9I Bme18I
   BsiSI ScrFI HgiEI Eco47I Tsp45I                          BstNI Cfr13I
  Alw26I BcnI PpuMI DraII NlaIV HphI             HinfI CviJI  MboII ScrFI HgiEI
ctccgggacctcttgggtgtgtctgtcaccttgacttctaaaaagggattcagcccatcttctcctggtcctggg base pairs
gaggccctggagaacccacacagacagtggaactgaagatttttccctaagtcgggtagaagaggaccaggaccc 8926 to
9000
  BsmAI NciI Bme18I AvaII PspN4I                  TfiI           EcoRII MvaI
```

FIG. 20 (Cont'd)

```
       HpaII Cfr13I EcoO109I BsmFI                                        BstOI SinI
       HapII SinI Sau96I AspS9I MaeIII                                    Bst2UI Sau96I

AspS9I BstOI DpnII Kzo9I HaeIII FokI
    Eco47I BseDI MvaI Sau3AI NlaIII MluNI
         EcoRII MspR9I NdeII EaeI CviJI BalI AluI        DdeI    HinfI CviJI MwoI
    aaggttacagcaagatcatggccattctcatccaaagctttgatttcaatgcctaagttggattcaggctgtttg base pairs
    ttccaatgtcgttctagtaccggtaagagtaggtttcgaaactaaagttacggattcaacctaagtccgacaaac 9001 to
                                                                                  9075
    AsuI BslI BsaJI ScrFI Bsp143I PalI MscI CviJI          BstDEI   TfiI
      AvaII BsiYI Bst2UI MboI CfrI BsuRI BstF5I
        Bsc4I BstNI MaeIII DpnI Hsp92II HindIII BoiI                         Bsc4I PflMI BstNI ScrFI
       TspEI              Bov16II                       BseII BslI BsaJI MspR9I Bsp1286I
        Sse9I          TspRI                            BsrSI AlwNI Esp1396I SduI
    agccaatttttgcaacactgtcttcacatcaatactctgccaaataccagtgcctgggctcatgtcaagtttcaga base pairs
    tcggttaaaacgttgtgacagaagtgtagttatgagacggtttatggtcacggaccccgagtacagttcaaagtct 9076 to
                                                                                  9150
       CviJI                  BouAI                      BseNI AccB7I Van91I CviJI
         Tsp509I             BosI                        BsrI EcoRII BseDI Bst2UI
                              MboII                        TspRI BsiYI BstOI MvaI BmyI FriOI DpnII DpnI BseNI                       BsmAI
          Bsp143I AccI   RsaI                    PleI
     BanII NdeII TfiI Bse1I        NlaIII   HinfI Alw26I                 TspRI
    gatcggattccagtataccttgtaccgtctttcatgggtttgatgagtctcaggatttgcacaaacactgttgta base pairs
    ctagcctaaggtcatatggaacatggcagaaagtacccaaactactcagagtcctaaacgtgtttgtgacaacat 9151 to
                                                                                 9225
     NlaIII Sau3AI BsrSI  Csp6I        Hsp92II       DdeI
    Eco24I MboI Kzo9I BsrI AfaI                      BstDEI
       Hsp92II HinfI Bst1107I TspEI
                                 BsiYI          AfaI                          Sse9I
       HinfI    DdeI           Bsc4I          Csp6I             CviJI
    ggagtcttgacgggtctgagatatatccacagttgggcttttactactttgttgtactgtattttagagctaaat base pairs
    cctcagaactgcccagactctatataggtgtcaacccgaaaatgatgaaacaacatgacataaaatctcgattta 9226 to
                                                                                 9300
       PleI      BstDEI           BslI                    RsaI           AluI Tsp509I
                               CviJI                                         AcsI
                                                                             ApoI BstSFI
       DraI            AciI    SfcI      MslI
    Tru9I     CviJI    BstF5I    HinfI    NlaIII
    ttaaaaaagcaacatttgggcttgccatccgcttgcattagaaagtcagactctgtaggcatggtaatgattgtt base pairs
    aattttttcgttgtaaacccgaacggtaggcgaacgtaatctttcagtctgagacatccgtaccattactaacaa 9301 to
                                                                                 9375
```

FIG. 20 (Cont'd)

```
                    Cac8I    FokI                      AlwNI    Hsp92II
      MseI                   Cac8I                     PleI
      TruII

Hsp92I   DpnII
                                                         MnlI BsaHI AfaI Sau3AI
      BstDSI
      BsaJI                MboII  CviJI  MwoI        BstF5I HinlI AcyI NdeII
      tccgtggtagcgtgataatcgtcatcttccaaagagccatcactgctgtcatccctctggacgtcgtactgatcg base pairs
      aggcaccatcgcactattagcagtagaaggtttctcggtagtgacgacagtagggagacctgcagcatgactagc 9376 to
                                                                                9450
      BseDI                                     TspRI    FokI  Msp17I RsaI MboI
      DsaI                                                     BciII AatII Bsp143I
                                                               MaeII Csp6I Kzo9I DpnI BspXI BseCI Kzo9I HpaII Hin6I HaeII
         Bsp106I ClaI Bsp143I MspR9I AspLEI
         TthHB8I Bsu15I Sau3AI MspI HspAI CfoI            SfaNI            CviJI EcoRII
      atcagttccggagtggaggcgctcttggcagaagttgtcttatagcatctttgctgatgttaggaggtgtttcc base pairs
      tagtcaaggcctcacctccgcgagaaccgtcttcaacagaatatcgtagaaacgactacaatcctcgacaaagg 9451 to
                                                                                9525
          BanIII BscI NdeII NciI HapII MnlI BstH2I                AluI
          Bsa29I DpnII DcnI BcnI HinP1I Bsp143II
          BspDI TaqI MboI BsiSI ScrFI HhaI MwoI Bst2UI AspLEI AluI    TspEI              AfaI
      BstOI HspAI BsoFI DdeI AcsI              BpmI    BssSI         MslI
         MvaI CfoI BovI  Sse9I       CviJI     Csp6I MnlI      Alw26I Ppu1
      aggcgcagcttactgaggatttgaattttatggcttctattctggagtaccctcgtgttttgtctccacgcacat base pairs
      tccgcgtcgaatgactcctaaacttaaaaataccgaagataagacctcatggagcacaaaacagaggtgcgtgta 9526 to
                                                                                9600
      BstNI HinP1I CviJI BstDEI                Gsul     BsiI       BsmAI
      MspR9I HhaI Fsp4HI MnlI ApoI                      RsaI
      ScrFI Hin6I ItaI Bst71I Tsp509I Zsp2I                                     MboI Bsp143I AsuI Bse1I
      Hsp92II                                      BstX2I DpnI Sau96I HaeIII
         01 EcoT22I      MnlI        MboII  TspRI  BstYI nflI AlwI BsrSI
      gcattacacagcccctcttttttccacattttcttctctctcactgccctcatttagatccactgggccagcagca base pairs
      cgtaatgtgtcggggagaaaaaggtgtaaaagaagagagagtgacgggagtaaatctaggtgacccggtcgtcgt 9601 to
                                                                                9675
      NlaIII    CviJI                         MnlI DpnII XhoII Cfr13I BsrI
      NspI Mph1103I                           NdeII Kzo9I TspRI BseNI
      NsiI                                    Sau3AI AclWI AspS9I BsoFI Hsp92II                            DpnII BamHI NlaIV AclWI
         Fsp4HI                                   Hsp92II Sau3AI Kzo9I MspI
      PalI BbvI                      MwoI    SfaNI BstYI Bsp143I BsiSI
      atcagcatgaacaggtaaatataaacatacatttgcagttttgcatcatggctggatccgggcccataagagcg base pairs
      tagtcgtacttgtccatttatatttgtatgtaaacgtcaaaaacgtagtaccgacctaggcccgggtattctcgc 9676 to
                                                                                9750
```

FIG. 20 (Cont'd)

```
   BsuRI Bst71I                                       NlaIII NdeII XhoII HpaII
   Cac8I NlaIII                                       CviJI MboI BstI PspN4I
CviJI ItaI                                              BstX2I MflI DpnI HapII

Cfr13I NlaIV SduI BanII Hsp92II    AccII AluI BfaI MboI Bsp143I AclWI BcoI
  MspR9I AsuI BsuRI FriOI RsaI  BfaI     ThaI   PvuII    BstX2I XhoII PspN4I
 AlwI Bsp120I CviJI BmyI Csp6I    MaeI Cac8I HgaI MspA1I BstYI BamHI DpnI AlwI
 taatctggaacatcgtatgggtacatggtgtctagctcgcgtcagctgactagaggatccccgggtaccgagctc base pairs
 attagaccttgtagcataccccatgtaccacagatcgagcgcagtcgactgatctcctaggggcccatggctcgag 9751 to
 9825
  BcnI Sau96I PalI Bsp1286I NlaIII  CviJI Bsh1236I MaeI DpnII MflI MnlI BseDI
 NciI PspOMI HaeIII Eco24I AfaI    AluI MvnI CviJI    NdeII BstI NlaIV Ama87I
    ScrFI AspS9I PspN4I ApaI           BstJI NspBII    Sau3AI Kzo9I BsaJI PspAI Bso3I HapII BanI Csp6I Ecl136II Bbv12I BanII AcsI Cfr13I HaeIII BstDSI
 Cfr9I NciI MspR9I Acc65I AfaI EcoICRI Eco24I Alw21I ApoI NlaIV BsuRI DsaI BstJI
   Eco88I HpaII Eco64I NlaIV CviJI Bsp1286I FriOI Sse9I Sau96I CviJI BseDI AccII
 gaattcggggccgcggaggctggatcggtcccggtgtcttctatggaggtcaaaacagcgtggatggcgtctcca base pairs
 cttaagccccggcgcctccgacctagccagggccacagaagatacctccagttttgtcgcacctaccgcagaggt 9826 to
 9900
  AvaI BcnI PspALI BshNI RsaI AluI AspHI SacI SstI TspEI AspS9I BsoFI ItaI
    XmaI MspI SmaI AccB1I KpnI SduI BmyI TaqI BsiHKAI Tsp509I PalI Fsp4HI MvnI
     BsiSI ScrFI Asp718I PspN4I TthHB8I Psp1243I EcoRI AsuI PspN4I BsaJI ThaI MspA1I SacII MnlI Bsp143I AsuI Eco47I HpaII Bbv16II Hin1I HgaI BstNI GsuI Sau3AI
     SstII BglI MboI AlwI Sau96I BsiSI HapII BbsI BstF5I AcyI BsmBI ScrFI MboI
     Sfr303I CviJI Kzo9I SinI AvaII NciI ScrFI MboII Msp17I EcoRII BstCI BpmI ggcgatctgacggttcactaaacgagctctgcttatataggcctcccaccgtacacgcctactcgacccgggtac base pairs
 ccgctagactgccaagtgatttgctcgagacgaatatatccggagggtggcatgtgcggatgagctgggcccatg 9901 to
 9975
 Nsp3II Cfr42I DpnII DpnI Bme18I NlaIV BcnI BsmFI MnlI BbiII Alw26I MspR9I NdeII
     KspI AciI NdeII AclWI HgiEI PspN4I MspR9I BpiI FokI BsaHI Esp3I MvaI DpnII
     Bsh1236I MwoI Sau3AI Cfr13I AspS9I MspI BpuAI MwoI Hsp92I BsmAI Bst2UI Bsp143I AluI BmyI SacI BsiHKAI Eco147I TaqI Eco88I NciI MspR9I BshNI RsaI AluI
     DpnI Bsp1286I BanII StuI PalI RsaI BcoI AvaI BsiSI PspALI AccB1I KpnI SduI
     Kzo9I SduI Eco24I SstI HaeIII MnlI Ama87I BseDI MspI SmaI Asp718I PspN4I
 cgagctcgactttcacttttctctatcactgataggagtggtaaactcgactttcacttttctctatcactgat base pairs
 gctcgagctgaaagtgaaaagagatagtgactatccctcaccatttgagctgaaagtgaaaagagatagtgacta 9976 to
 10050
     CviJI AspHI FriOI Pme55I Sse3I TthHB8I BsaJI BcnI ScrFI Acc65I AfaI EcoICRI
     Ecl136II Bbv12I Alw21I CviJI Csp6I PspAI XmaI HpaII Eco64I Csp6I Ecl136II
       EcoICRI Psp124BI AatI BsuRI AfaI Cfr9I BsoBI HapII BanI NlaIV CviJI AspHI SacI SstI TspRI
    Bbv12I BanII TthHB8I
  Bsp1286I FriOI TspCI               TspRI              TthHB8I
 agggagtggtaaactcgactttcacttttctctatcactgataggagtggtaaactcgactttcacttttctct base pairs
 tccctcaccatttgagctgaaagtgaaaagagatagtgactatccctcaccatttgagctgaaagtgaaaagaga 10051 to
 10125
```

FIG. 20 (Cont'd)

```
       Eco24I Alw21I TthHB8I                           TaqI
   BmyI Psp124BI TaqI
TthHB8I TaqI BsiHKAI TaqI

TspRI          TthHB8I            TspRI           TthHB8I
atcactgataqggagtggtaaactcgactttcacttttctctatcactgataqggagtggtaaactcgactttca  base pairs
tagtgactatccctcaccatttgagctgaaagtgaaaagagatagtgactatccctcaccatttgagctgaaagt  10126 to
                                                                             10200
                 TaqI                                              TaqI TspRI            TthHB8I              TspRI
cttttctctatcactgataqggagtggtaaactcgactttcacttttctctatcactgataqggagtggtaaa  base pairs
gaaaagagatagtgactatccctcaccatttgagctgaaagtgaaaagagatagtgactatccctcaccattt  10201 to
                                                                           10273
                         TaqI
```

Table by Enzyme Name

| Enzyme name | No. cuts | Positions of sites | Recognition sequence |
|---|---|---|---|
| AatI | 3 | 234 6043 9941 | agg/cct |
| AatII | 2 | 3767 9439 | gacgt/c |
| Acc16I | 1 | 5762 | tgc/gca |
| Acc65I | 5 | 2509 8084 8547 9814 9971 | g/gtacc |
| AccB1I | 15 | 330 1328 1677 2509 2560 3741 5826 5861 6707 7903 8084 8232 8547 9814 9971 | g/gyrcc |
| AccB7I | 3 | 154 8079 9127 | ccannnn/ntgg |
| AccBSI | 5 | 1464 5200 5254 6443 6607 | gagcgg |
| AccI | 7 | 971 2150 2258 8554 8590 8614 | gt/mkac |

FIG. 20 (Cont'd)

```
                        9164
AccII       32    1880 2114 2124 2128 2218 2237    cg/cg
                  2248 2339 2853 3171 3252 3527
                  3828 3989 4570 4843 4912 4975
                  5059 5497 5798 6489 6520 6544
                  6564 6940 7215 7296 7614 8545
                  9789 9838
AciI        92    429 446 1216 1462 1639 1994 2079 ccgc
                  2115 2125 2204 2213 2219 2238
                  2415 2746 2787 2854 2893 2988
                  3031 3144 3204 3249 3253 3622
                  3684 3704 3777 3791 3803 3831
                  3899 3990 4018 4145 4164 4285
                  4395 4530 4539 4773 4846 4913
                  4978 5060 5126 5198 5254 5280
                  5296 5346 5351 5391 5631 5735
                  5799 5893 5956 6095 6141 6152
                  6162 6174 6183 6195 6380 6443
                  6490 6533 6547 6578 6605 7218
                  7222 7264 7327 7440 7578 7617
                  7684 7725 8190 8228 8260 8491
                  8533 8546 8613 8759 8877 9332
                  9839
AclNI       1     8569                             a/ctagt
AclWI       26    403 650 1473 2504 3029 3214 3625 ggatc
                  4513 4587 4599 4684 4697 5056
                  5071 5448 5615 5694 6005 7258
                  7443 8073 8536 9660 9734 9809
                  9851
AcsI        15    75 666 1484 3417 3521 3532 6931  r/aatty
                  6942 7046 8563 8630 8778 9297
                  9548 9826
AcyI        8     1650 2187 3764 5081 5160 5862    gr/cgyc
                  9436 9892
AfaI        22    352 1788 2117 2131 2489 2511     gt/ac
                  2954 3236 3670 5558 7231 7513
                  8086 8549 9173 9280 9442 9574
                  9772 9816 9952 9973
AfeI        1     1897                             agc/gct
AflII       2     3485 6978                        c/ttaag
AflIII      7     274 923 1878 2361 3942 8035 8210 a/crygt
AgeI        1     2512                             a/ccggt
AluI        60    56 62 97 153 369 485 565 1021    ag/ct
                  1205 1219 1300 1344 1351 1454
                  1537 1591 1713 2009 2296 2545
                  2578 2650 2683 2899 2947 3058
                  3232 3382 3549 3615 3644 4110
```

FIG. 20 (Cont'd)

|         |    |                                              |           |
|---------|----|----------------------------------------------|-----------|
|         |    | 4200 4246 4503 5300 5758 6078                |           |
|         |    | 6366 6661 6918 7085 7235 7409                |           |
|         |    | 7520 7560 7784 7817 7889 7922                |           |
|         |    | 8303 9037 9294 9517 9533 9785                |           |
|         |    | 9795 9822 9926 9979                          |           |
| Alw21I  | 14 | 58 2298 3134 4260 5565 5755 7337             | gwgcw/c   |
|         |    | 8052 8603 8743 8902 9824 9928                |           |
|         |    | 9981                                         |           |
| Alw26I  | 12 | 624 847 904 4870 4998 6017 6435              | gtctc     |
|         |    | 8688 8926 9201 9591 9898                     |           |
| Alw44I  | 3  | 4256 8048 8739                               | g/tgcac   |
| AlwI    | 26 | 403 650 1473 2504 3029 3214 3625             | ggatc     |
|         |    | 4513 4587 4599 4684 4697 5056                |           |
|         |    | 5071 5448 5615 5694 6005 7258                |           |
|         |    | 7443 8073 8536 9660 9734 9809                |           |
|         |    | 9851                                         |           |
| AlwNI   | 6  | 682 1443 4358 4766 9127 9352                 | cagnnn/ctg |
| Ama87I  | 11 | 43 51 245 895 1332 1474 2383                 | c/ycgrg   |
|         |    | 2505 8536 9810 9967                          |           |
| AocI    | 2  | 4749 6381                                    | cc/tnagg  |
| Aor51HI | 1  | 1897                                         | agc/gct   |
| ApaI    | 4  | 1371 8416 8543 9740                          | gggcc/c   |
| ApaLI   | 3  | 4256 8048 8739                               | g/tgcac   |
| ApoI    | 15 | 75 666 1484 3417 3521 3532 6931              | r/aatty   |
|         |    | 6942 7046 8563 8630 8778 9297                |           |
|         |    | 9548 9826                                    |           |
| AseI    | 2  | 3879 8677                                    | at/taat   |
| AsnI    | 2  | 3879 8677                                    | at/taat   |
| Asp700I | 1  | 8317                                         | gaann/nnttc |
| Asp718I | 5  | 2509 8084 8547 9814 9971                     | g/gtacc   |
| AspHI   | 14 | 58 2298 3134 4260 5565 5755 7337             | gwgcw/c   |
|         |    | 8052 8603 8743 8902 9824 9928                |           |
|         |    | 9981                                         |           |
| AspI    | 2  | 840 5745                                     | gacn/nngtc |
| AspLEI  | 36 | 1529 1898 2126 2220 2250 2329                | gcg/c     |
|         |    | 2341 2426 2814 2855 3171 4122                |           |
|         |    | 4189 4289 4463 4572 4975 5061                |           |
|         |    | 5237 5497 5763 5800 5864 5872                |           |
|         |    | 6491 6522 6535 6544 6566 6592                |           |
|         |    | 6600 7298 7614 7655 9472 9530                |           |
| AspS9I  | 36 | 159 638 983 1138 1199 1312 1367              | g/gncc    |
|         |    | 2109 2161 2263 2387 2697 3098                |           |
|         |    | 3181 3802 4763 4796 4854 4900                |           |
|         |    | 5345 6754 7283 7366 7767 8003                |           |
|         |    | 8057 8399 8412 8539 8710 8931                |           |
|         |    | 8992 9664 9736 9833 9852                     |           |
| AsuI    | 36 | 159 638 983 1138 1199 1312 1367              | g/gncc    |
|         |    | 2109 2161 2263 2387 2697 3098                |           |
|         |    | 3181 3802 4763 4796 4854 4900                |           |

*FIG. 20 (Cont'd)*

|         |    |                                         |              |
|---------|----|-----------------------------------------|--------------|
|         |    | 5345 6754 7283 7366 7767 8003           |              |
|         |    | 8057 8399 8412 8539 8710 8931           |              |
|         |    | 8992 9664 9736 9833 9852                |              |
| AtsI    | 2  | 840 5745                                | gacn/nngtc   |
| AvaI    | 11 | 43 51 245 895 1332 1474 2383            | c/ycgrg      |
|         |    | 2505 8536 9810 9967                     |              |
| AvaII   | 10 | 1312 2109 2387 3181 4900 5345           | g/gwcc       |
|         |    | 7283 8931 8992 9852                     |              |
| AviII   | 1  | 5762                                    | tgc/gca      |
| AvrII   | 5  | 180 650 5023 6038 8374                  | c/ctagg      |
| BalI    | 3  | 5782 7951 9021                          | tgg/cca      |
| BamHI   | 7  | 399 646 1469 2500 8532 9730 9805        | g/gatcc      |
| BanI    | 15 | 330 1328 1677 2509 2560 3741            | g/gyrcc      |
|         |    | 5826 5861 6707 7903 8084 8232           |              |
|         |    | 8547 9814 9971                          |              |
| BanII   | 13 | 58 1371 2298 4793 5503 6677 8416        | grgcy/c      |
|         |    | 8543 9134 9740 9824 9928 9981           |              |
| BanIII  | 2  | 6022 9448                               | at/cgat      |
| BbeI    | 1  | 5865                                    | ggcgc/c      |
| BbiII   | 8  | 1650 2187 3764 5081 5160 5862           | gr/cgyc      |
|         |    | 9436 9892                               |              |
| BbrPI   | 1  | 8213                                    | cac/gtg      |
| BbsI    | 4  | 8297 8397 9099 9866                     | gaagac       |
| BbuI    | 5  | 729 2333 5463 6226 6298                 | gcatg/c      |
| Bbv12I  | 14 | 58 2298 3134 4260 5565 5755 7337        | gwgcw/c      |
|         |    | 8052 8603 8743 8902 9824 9928           |              |
|         |    | 9981                                    |              |
| Bbv16II | 4  | 8297 8397 9099 9866                     | gaagac       |
| BbvI    | 40 | 87 197 216 285 309 518 1025 1273        | gcagc        |
|         |    | 1304 1447 1541 1607 2687 2768           |              |
|         |    | 3052 3059 3110 3383 4288 4353           |              |
|         |    | 4562 4788 5241 5628 5721 5762           |              |
|         |    | 5804 5905 6570 7089 7359 7413           |              |
|         |    | 7420 7704 7785 8263 8707 8881           |              |
|         |    | 9534 9674                               |              |
| BcgI    | 2  | 2637 7842                               | cgannnnntgc  |
| BclI    | 2  | 2023 2067                               | t/gatca      |
| BcnI    | 27 | 328 548 1191 1316 1333 1475 2177        | cc/sgg       |
|         |    | 2384 2391 2506 2554 3208 4322           |              |
|         |    | 5086 5699 5859 7258 7912 8411           |              |
|         |    | 8537 8884 8929 9459 9735 9811           |              |
|         |    | 9856 9968                               |              |
| BcoI    | 11 | 43 51 245 895 1332 1474 2383            | c/ycgrg      |
|         |    | 2505 8536 9810 9967                     |              |
| BfaI    | 28 | 166 181 208 651 690 962 1220            | c/tag        |
|         |    | 1397 1464 1481 1497 1871 2342           |              |
|         |    | 3258 3452 3616 4437 4690 5024           |              |
|         |    | 6039 6595 7013 7207 8007 8375           |              |
|         |    | 8570 9782 9800                          |              |

FIG. 20 (Cont'd)

```
BfrI       2   3485 6978                                c/ttaag
BglI       5   1266 3801 6092 8230 9841                 gccnnnn/nggc
BglII      1   47                                       a/gatct
BlnI       5   180 650 5023 6038 8374                   c/ctagg
BlpI       1   8717                                     gc/tnagc
Bme18I    10   1312 2109 2387 3181 4900 5345            g/gwcc
               7283 8931 8992 9852
BmyI      33   58 1326 1333 1371 1437 2298 2565         gdgch/c
               2694 2943 3134 4260 4793 5503
               5565 5755 5829 5922 6677 7337
               7528 7777 7906 8052 8416 8543
               8603 8743 8902 9134 9740 9824
               9928 9981
BpiI       4   8297 8397 9099 9866                      gaagac
BpmI       8   2953 3193 5046 5067 7280 7520            ctggag
               9573 9901
Bpu1102I   1   8717                                     gc/tnagc
Bpu14I     2   65 5180                                  tt/cgaa
BpuAI      4   8297 8397 9099 9866                      gaagac
Bsa29I     2   6022 9448                                at/cgat
BsaAI      4   1153 5560 6748 8213                      yac/gtr
BsaBI      4   2352 3265 6005 7202                      gatnn/nnatc
BsaHI      8   1650 2187 3764 5081 5160 5862            gr/cgyc
               9436 9892
BsaI       1   4870                                     ggtctc
BsaJI     67   180 235 326 334 356 392 403 504          c/cnngg
               635 641 650 675 775 1141 1157
               1262 1284 1308 1315 1332 1375
               1428 1473 2029 2235 2284 2382
               2473 2504 2523 2553 2693 2721
               2856 2880 2935 4102 4792 4895
               5023 5428 5697 6038 6087 6096
               6131 6254 6326 7528 7583 7607
               7770 7910 7940 7991 8053 8374
               8536 8543 8621 8891 8995 9127
               9377 9809 9836 9967
BsaMI      6   3353 3452 7021 7120 8351 8384            gaatgc
BsaOI      7   2274 2517 3250 4282 5957 7219            cgry/cg
               8861
BsaWI      5   2512 4148 4295 4985 5829                 w/ccggw
Bsc4I     52   153 221 326 392 408 463 523 588          ccnnnn/nnngg
               640 779 1195 1278 1313 1375 1453
               1702 2196 2388 2511 2693 2720
               2856 3206 3841 3963 3981 4147
```

FIG. 20 (Cont'd)

|  |  |  |  |
|---|---|---|---|
|  |  | 4426 4779 4810 4861 4896 5027 |  |
|  |  | 5060 5341 5885 6136 6528 6854 |  |
|  |  | 7262 7612 7775 7996 8078 8248 |  |
|  |  | 8268 8431 8843 8866 8994 9126 |  |
|  |  | 9257 |  |
| BscI | 2 | 6022 9448 | at/cgat |
| Bse118I | 8 | 2512 2675 5077 5360 5541 6643 | r/ccggy |
|  |  | 7788 8472 |  |
| Bse1I | 19 | 527 665 824 1249 3140 4349 4362 | actgg |
|  |  | 4479 5725 5926 6158 6836 7332 |  |
|  |  | 8179 8502 8836 9125 9164 9665 |  |
| Bse21I | 2 | 4749 6381 | cc/tnagg |
| Bse8I | 4 | 2352 3265 6005 7202 | gatnn/nnatc |
| BseCI | 2 | 6022 9448 | at/cgat |
| BseDI | 67 | 180 235 326 334 356 392 403 504 | c/cnngg |
|  |  | 635 641 650 675 775 1141 1157 |  |
|  |  | 1262 1284 1308 1315 1332 1375 |  |
|  |  | 1428 1473 2029 2235 2284 2382 |  |
|  |  | 2473 2504 2523 2553 2693 2721 |  |
|  |  | 2856 2880 2935 4102 4792 4895 |  |
|  |  | 5023 5428 5697 6038 6087 6096 |  |
|  |  | 6131 6254 6326 7528 7583 7607 |  |
|  |  | 7770 7910 7940 7991 8053 8374 |  |
|  |  | 8536 8543 8621 8891 8995 9127 |  |
|  |  | 9377 9809 9836 9967 |  |
| BseNI | 19 | 527 665 824 1249 3140 4349 4362 | actgg |
|  |  | 4479 5725 5926 6158 6836 7332 |  |
|  |  | 8179 8502 8836 9125 9164 9665 |  |
| BsePI | 1 | 2124 | g/cgcgc |
| BseRI | 6 | 366 1420 2545 6062 7928 8131 | gaggag |
| BsgI | 10 | 524 1306 2039 2673 2734 3058 | gtgcag |
|  |  | 7415 7739 7800 8706 |  |
| Bsh1236I | 32 | 1880 2114 2124 2128 2218 2237 | cg/cg |
|  |  | 2248 2339 2853 3171 3252 3527 |  |
|  |  | 3828 3989 4570 4843 4912 4975 |  |
|  |  | 5059 5497 5798 6489 6520 6544 |  |
|  |  | 6564 6940 7215 7296 7614 8545 |  |
|  |  | 9789 9838 |  |
| Bsh1285I | 7 | 2274 2517 3250 4282 5957 7219 | cgry/cg |
|  |  | 8861 |  |
| Bsh1365I | 4 | 2352 3265 6005 7202 | gatnn/nnatc |
| BshNI | 15 | 330 1328 1677 2509 2560 3741 | g/gyrcc |
|  |  | 5826 5861 6707 7903 8084 8232 |  |
|  |  | 8547 9814 9971 |  |
| BsiEI | 7 | 2274 2517 3250 4282 5957 7219 | cgry/cg |
|  |  | 8861 |  |
| BsiHKAI | 14 | 58 2298 3134 4260 5565 5755 7337 | gwgcw/c |
|  |  | 8052 8603 8743 8902 9824 9928 |  |
|  |  | 9981 |  |
| BsiI | 6 | 2710 4120 5147 5273 7763 9582 | ctcgtg |

FIG. 20 (Cont'd)

```
BsiSI      45   328  547 1191 1315 1333 1475 2177   c/cgg
                2384 2390 2506 2513 2553 2616
                2676 3207 4149 4296 4322 4512
                4986 5078 5086 5361 5542 5609
                5699 5830 5858 5880 5957 6644
                7258 7789 7849 7912 8410 8473
                8537 8883 8928 9459 9734 9811
                9856 9968
BsiWI      1    2129                                 c/gtacg
BsiYI      52   154  222  327  393  409  464  524  589   ccnnnnn/nngg
                641  780 1196 1279 1314 1376 1454
                1703 2197 2389 2512 2694 2721
                2857 3207 3842 3964 3982 4148
                4427 4780 4811 4862 4897 5028
                5061 5342 5886 6137 6529 6855
                7263 7613 7776 7997 8079 8249
                8269 8432 8844 8867 8995 9127
                9258
BslI       52   154  222  327  393  409  464  524  589   ccnnnnn/nngg
                641  780 1196 1279 1314 1376 1454
                1703 2197 2389 2512 2694 2721
                2857 3207 3842 3964 3982 4148
                4427 4780 4811 4862 4897 5028
                5061 5342 5886 6137 6529 6855
                7263 7613 7776 7997 8079 8249
                8269 8432 8844 8867 8995 9127
                9258
BsmAI      12   624  847  904 4870 4998 6017 6435   gtctc
                8688 8926 9201 9591 9898
BsmBI      2    624 9898                             cgtctc
BsmFI      22   243  394 1112 1164 1212 1384 1481   gggac
                2243 2293 2374 3731 4903 5087
                5196 5728 6198 6262 6334 7991
                8839 8934 9857
BsmI       6    3353 3452 7021 7120 8351 8384       gaatgc
BsoBI      11   43   51  245  895 1332 1474 2383    c/ycgrg
                2505 8536 9810 9967
BsoFI      70   84  194  213  282  306  427  443  515    gc/ngc
                1022 1270 1301 1444 1459 1538
                1604 1991 2122 2211 2684 2743
                2765 3049 3056 3107 3204 3247
                3380 3987 4142 4285 4350 4559
                4770 4785 5124 5238 5252 5293
                5389 5625 5631 5718 5759 5796
                5801 5891 5902 5954 6093 6531
                6545 6567 7086 7216 7262 7356
                7410 7417 7701 7723 7782 8187
                8225 8260 8489 8704 8875 9531
                9671 9836
```

FIG. 20 (Cont'd)

| | | | |
|---|---|---|---|
| Bsp106I | 2 | 6022 9448 | at/cgat |
| Bsp119I | 2 | 65 5180 | tt/cgaa |
| Bsp120I | 4 | 1367 8412 8539 9736 | g/ggccc |
| Bsp1286I | 33 | 58 1326 1333 1371 1437 2298 2565 2694 2943 3134 4260 4793 5503 5565 5755 5829 5922 6677 7337 7528 7777 7906 8052 8416 8543 8603 8743 8902 9134 9740 9824 9928 9981 | gdgch/c |
| Bsp1407I | 3 | 350 3234 7229 | t/gtaca |
| Bsp143I | 48 | 47 89 399 646 1469 1933 2023 2067 2170 2353 2500 3024 3172 3210 3260 3621 4508 4583 4594 4602 4680 4692 5051 5067 5443 5521 5530 5611 5689 6000 6019 6023 7203 7253 7291 7439 8063 8068 8532 9013 9150 9445 9449 9655 9730 9805 9847 9903 | /gatc |
| Bsp143II | 7 | 1899 2427 4190 5865 6593 6601 9473 | rgcgc/y |
| Bsp1720I | 1 | 8717 | gc/tnagc |
| Bsp19I | 8 | 356 504 1284 2523 5428 6131 7940 8621 | c/catgg |
| BspDI | 2 | 6022 9448 | at/cgat |
| BspHI | 3 | 4662 6434 8595 | t/catga |
| BspLU11I | 5 | 274 923 2361 3942 8035 | a/catgt |
| BspMI | 6 | 306 450 5156 5606 5969 8200 | acctgc |
| BspTI | 2 | 3485 6978 | c/ttaag |
| BspXI | 2 | 6022 9448 | at/cgat |
| BsrBI | 5 | 1464 5200 5254 6443 6607 | gagcgg |
| BsrBRI | 4 | 2352 3265 6005 7202 | gatnn/nnatc |
| BsrDI | 5 | 1066 1075 1778 5639 8426 | gcaatg |
| BsrFI | 8 | 2512 2675 5077 5360 5541 6643 7788 8472 | r/ccggy |
| BsrGI | 3 | 350 3234 7229 | t/gtaca |
| BsrI | 19 | 527 665 824 1249 3140 4349 4362 4479 5725 5926 6158 6836 7332 8179 8502 8836 9125 9164 9665 | actgg |
| BsrSI | 19 | 527 665 824 1249 3140 4349 4362 4479 5725 5926 6158 6836 7332 8179 8502 8836 9125 9164 9665 | actgg |
| BssAI | 8 | 2512 2675 5077 5360 5541 6643 7788 8472 | r/ccggy |
| BssHII | 1 | 2124 | g/cgcgc |
| BssSI | 6 | 2710 4120 5147 5273 7763 9582 | ctcgtg |
| BssT1I | 17 | 180 356 504 650 775 1262 1284 2029 2473 2523 5023 5428 6038 6131 7940 8374 8621 | c/cwwgg |
| Bst1107I | 1 | 9165 | gta/tac |

FIG. 20 (Cont'd)

```
Bst2UI      47  236  255  335  394  404  636  642  677   cc/wgg
                722  940  1036 1048 1142 1158 1309
                1377 1393 1430 2285 2570 2695
                2722 2807 2882 2936 3797 3970
                4091 4104 4794 4897 5476 6255
                6272 6327 7530 7584 7659 7771
                7896 8244 8403 8990 8996 9128
                9525 9899
Bst71I      40  87   197  216  285  309  518  1025 1273  gcagc
                1304 1447 1541 1607 2687 2768
                3052 3059 3110 3383 4288 4353
                4562 4788 5241 5628 5721 5762
                5804 5905 6570 7089 7359 7413
                7420 7704 7785 8263 8707 8881
                9534 9674
Bst98I      2   3485 6978                                c/ttaag
BstBI       2   65   5180                                tt/cgaa
BstD102I    5   1464 5200 5254 6443 6607                 gagcgg
BstDEI      33  93   98   310  341  420  438  785  904   c/tnag
                929  1112 1225 1232 1362 1654
                1763 1892 2302 3128 3146 4217
                4626 4749 5198 6079 6381 7318
                7336 8717 8792 9053 9199 9241
                9538
BstDSI      14  356  504  1284 2235 2523 5428 6131       c/crygg
                7940 7991 8543 8621 8891 9377
                9836
BstF5I      17  189  2500 2570 2936 5075 5529            ggatg
                5554 6011 6178 7536 7902 8101
                8843 9033 9330 9429 9891
BstH2I      7   1899 2427 4190 5865 6593 6601            rgcgc/y
                9473
BstI        7   399  646  1469 2500 8532 9730 9805       g/gatcc
BstMCI      7   2274 2517 3250 4282 5957 7219            cgry/cg
                8861
BstNI       47  236  255  335  394  404  636  642  677   cc/wgg
                722  940  1036 1048 1142 1158 1309
                1377 1393 1430 2285 2570 2695
                2722 2807 2882 2936 3797 3970
                4091 4104 4794 4897 5476 6255
                6272 6327 7530 7584 7659 7771
```

FIG. 20 (Cont'd)

|         |    |                                                                                                                                                     |              |
|---------|----|-----------------------------------------------------------------------------------------------------------------------------------------------------|--------------|
|         |    | 7896 8244 8403 8990 8996 9128<br>9525 9899                                                                                                           |              |
| BstOI   | 47 | 236 255 335 394 404 636 642 677<br>722 940 1036 1048 1142 1158 1309<br>1377 1393 1430 2285 2570 2695<br>2722 2807 2882 2936 3797 3970<br>4091 4104 4794 4897 5476 6255<br>6272 6327 7530 7584 7659 7771<br>7896 8244 8403 8990 8996 9128<br>9525 9899 | cc/wgg |
| BstSFI  | 15 | 81 480 566 584 598 683 972 1408<br>1806 4207 4398 6525 8277 8558<br>9353                                                                             | c/tryag      |
| BstUI   | 32 | 1880 2114 2124 2128 2218 2237<br>2248 2339 2853 3171 3252 3527<br>3828 3989 4570 4843 4912 4975<br>5059 5497 5798 6489 6520 6544<br>6564 6940 7215 7296 7614 8545<br>9789 9838 | cg/cg |
| BstX2I  | 20 | 47 399 646 1469 2500 3024 3621<br>4583 4594 4680 4692 5051 5443<br>5689 7439 8068 8532 9655 9730<br>9805                                             | r/gatcy      |
| BstXI   | 4  | 277 1291 1592 7947                                                                                                                                   | ccannnnn/ntgg |
| BstYI   | 20 | 47 399 646 1469 2500 3024 3621<br>4583 4594 4680 4692 5051 5443<br>5689 7439 8068 8532 9655 9730<br>9805                                             | r/gatcy      |
| BstZI   | 3  | 3247 5954 7216                                                                                                                                       | c/ggccg      |
| Bsu15I  | 2  | 6022 9448                                                                                                                                            | at/cgat      |
| Bsu36I  | 2  | 4749 6381                                                                                                                                            | cc/tnagg     |
| BsuRI   | 61 | 161 234 429 640 934 984 1140<br>1201 1283 1369 1458 1804 2058<br>2163 2264 2438 2598 2698 3014<br>3099 3249 3569 3804 3957 3968<br>3986 4420 4765 4798 4855 5364<br>5391 5782 5956 6043 6086 6095<br>6101 6756 6898 7218 7368 7480<br>7769 7869 7951 8005 8058 8224<br>8401 8414 8476 8497 8541 8712<br>8806 9021 9666 9738 9835 9941 | gg/cc |
| Cac8I   | 63 | 371 417 519 718 727 936 963 1087<br>1120 1203 1217 1298 1305 1456<br>1638 1715 2043 2126 2165 2208<br>2331 2648 2681 2729 3053 3060<br>3617 3802 3959 3996 4556 4767<br>4789 4845 4892 5079 5362 5416<br>5461 5493 5499 5565 5784 5970<br>6224 6243 6296 6315 6588 6602 | gcn/ngc |

FIG. 20 (Cont'd)

|       |     |                                           |           |
|-------|-----|-------------------------------------------|-----------|
|       |     | 6645 7407 7414 7738 7786 7819             |           |
|       |     | 8264 8543 8714 9322 9333 9668             |           |
|       |     | 9787                                      |           |
| CciNI | 2   | 3247 7216                                 | gc/ggccgc |
| CelII | 1   | 8717                                      | gc/tnagc  |
| CfoI  | 36  | 1529 1898 2126 2220 2250 2329             | gcg/c     |
|       |     | 2341 2426 2814 2855 3171 4122             |           |
|       |     | 4189 4289 4463 4572 4975 5061             |           |
|       |     | 5237 5497 5763 5800 5864 5872             |           |
|       |     | 6491 6522 6535 6544 6566 6592             |           |
|       |     | 6600 7298 7614 7655 9472 9530             |           |
| Cfr10I| 8   | 2512 2675 5077 5360 5541 6643             | r/ccggy   |
|       |     | 7788 8472                                 |           |
| Cfr13I| 36  | 159 638 983 1138 1199 1312 1367           | g/gncc    |
|       |     | 2109 2161 2263 2387 2697 3098             |           |
|       |     | 3181 3802 4763 4796 4854 4900             |           |
|       |     | 5345 6754 7283 7366 7767 8003             |           |
|       |     | 8057 8399 8412 8539 8710 8931             |           |
|       |     | 8992 9664 9736 9833 9852                  |           |
| Cfr42I| 3   | 2238 8546 9839                            | ccgc/gg   |
| Cfr9I | 7   | 1332 1474 2383 2505 8536 9810             | c/ccggg   |
|       |     | 9967                                      |           |
| CfrI  | 16  | 427 1456 2436 2596 3247 5362              | y/ggccr   |
|       |     | 5389 5780 5954 7216 7478 7867             |           |
|       |     | 7949 8222 8495 9019                       |           |
| ClaI  | 2   | 6022 9448                                 | at/cgat   |
| CpoI  | 1   | 5345                                      | cg/gwccg  |
| Csp45I| 2   | 65 5180                                   | tt/cgaa   |
| Csp6I | 22  | 351 1787 2116 2130 2488 2510              | g/tac     |
|       |     | 2953 3235 3669 5557 7230 7512             |           |
|       |     | 8085 8548 9172 9279 9441 9573             |           |
|       |     | 9771 9815 9951 9972                       |           |
| CspI  | 1   | 5345                                      | cg/gwccg  |
| CviJI | 231 | 56 62 86 97 112 153 161 169 196           | rg/cy     |
|       |     | 212 234 281 314 346 369 419 429           |           |
|       |     | 442 485 517 528 565 603 640 655           |           |
|       |     | 689 701 784 815 934 938 961 965           |           |
|       |     | 984 1021 1046 1089 1101 1122              |           |
|       |     | 1132 1140 1146 1201 1205 1219             |           |
|       |     | 1260 1272 1283 1291 1300 1344             |           |
|       |     | 1351 1369 1386 1396 1414 1443             |           |
|       |     | 1454 1458 1537 1591 1606 1640             |           |
|       |     | 1658 1713 1804 1844 2009 2041             |           |
|       |     | 2045 2058 2121 2163 2206 2213             |           |
|       |     | 2264 2283 2296 2438 2545 2578             |           |
|       |     | 2598 2650 2683 2698 2742 2799             |           |
|       |     | 2899 2947 2967 3014 3058 3099             |           |
|       |     | 3232 3249 3272 3382 3549 3569             |           |
|       |     | 3615 3644 3795 3804 3846 3957             |           |
|       |     | 3968 3986 4012 4110 4200 4246             |           |

FIG. 20 (Cont'd)

|  |  |  |  |
|---|---|---|---|
|  |  | 4251 4276 4355 4420 4431 4474 |  |
|  |  | 4503 4754 4765 4784 4791 4798 |  |
|  |  | 4855 4894 5016 5077 5104 5284 |  |
|  |  | 5300 5323 5360 5364 5391 5474 |  |
|  |  | 5491 5501 5545 5608 5627 5644 |  |
|  |  | 5720 5758 5782 5786 5795 5879 |  |
|  |  | 5904 5931 5939 5956 6037 6043 |  |
|  |  | 6055 6078 6086 6095 6101 6130 |  |
|  |  | 6253 6325 6366 6647 6661 6675 |  |
|  |  | 6756 6898 6918 7085 7195 7218 |  |
|  |  | 7235 7368 7409 7480 7500 7520 |  |
|  |  | 7568 7668 7725 7769 7784 7817 |  |
|  |  | 7869 7889 7922 7951 8005 8058 |  |
|  |  | 8106 8133 8217 8224 8303 8401 |  |
|  |  | 8414 8476 8491 8497 8541 8626 |  |
|  |  | 8712 8721 8806 8848 8915 8978 |  |
|  |  | 9021 9037 9068 9077 9132 9262 |  |
|  |  | 9294 9320 9411 9517 9533 9559 |  |
|  |  | 9611 9666 9727 9738 9785 9795 |  |
|  |  | 9822 9835 9844 9926 9941 9979 |  |
| CvnI | 2 | 4749 6381 | cc/tnagg |
| DdeI | 33 | 93 98 310 341 420 438 785 904 | c/tnag |
|  |  | 929 1112 1225 1232 1362 1654 |  |
|  |  | 1763 1892 2302 3128 3146 4217 |  |
|  |  | 4626 4749 5198 6079 6381 7318 |  |
|  |  | 7336 8717 8792 9053 9199 9241 |  |
|  |  | 9538 |  |
| DpnI | 48 | 49 91 401 648 1471 1935 2025 | ga/tc |
|  |  | 2069 2172 2355 2502 3026 3174 |  |
|  |  | 3212 3262 3623 4510 4585 4596 |  |
|  |  | 4604 4682 4694 5053 5069 5445 |  |
|  |  | 5523 5532 5613 5691 6002 6021 |  |
|  |  | 6025 7205 7255 7293 7441 8065 |  |
|  |  | 8070 8534 9015 9152 9447 9451 |  |
|  |  | 9657 9732 9807 9849 9905 |  |
| DpnII | 48 | 47 89 399 646 1469 1933 2023 | /gatc |
|  |  | 2067 2170 2353 2500 3024 3172 |  |
|  |  | 3210 3260 3621 4508 4583 4594 |  |
|  |  | 4602 4680 4692 5051 5067 5443 |  |
|  |  | 5521 5530 5611 5689 6000 6019 |  |
|  |  | 6023 7203 7253 7291 7439 8063 |  |
|  |  | 8068 8532 9013 9150 9445 9449 |  |
|  |  | 9655 9730 9805 9847 9903 |  |
| DraI | 6 | 1701 3305 4701 4720 7162 9302 | ttt/aaa |
| DraII | 9 | 983 1367 2161 4763 8003 8057 | rg/gnccy |
|  |  | 8413 8710 8931 |  |
| DraIII | 2 | 6751 8169 | cacnnn/gtg |
| DrdI | 4 | 4050 5839 6795 8692 | gacnnnn/nngtc |
| DsaI | 14 | 356 504 1284 2235 2523 5428 6131 | c/crygg |
|  |  | 7940 7991 8543 8621 8891 9377 |  |

*FIG. 20 (Cont'd)*

```
                    9836
EaeI         16     427  1456 2436 2596 3247 5362    y/ggccr
                    5389 5780 5954 7216 7478 7867
                    7949 8222 8495 9019
EagI          3     3247 5954 7216                   c/ggccg
Eam1104I      4     2200 5306 5516 6393              ctcttc
EarI          4     2200 5306 5516 6393              ctcttc
Ecl136II      5     56 2296 9822 9926 9979           gag/ctc
EclXI         3     3247 5954 7216                   c/ggccg
Eco130I      17     180  356  504  650  775 1262 1284 c/cwwgg
                    2029 2473 2523 5023 5428 6038
                    6131 7940 8374 8621
Eco147I       3     234 6043 9941                    agg/cct
Eco24I       13     58 1371 2298 4793 5503 6677 8416 grgcy/c
                    8543 9134 9740 9824 9928 9981
Eco31I        1     4870                             ggtctc
Eco47I       10     1312 2109 2387 3181 4900 5345    g/gwcc
                    7283 8931 8992 9852
Eco47III      1     1897                             agc/gct
Eco52I        3     3247 5954 7216                   c/ggccg
Eco57I       10     2662 2742 2905 4474 5308 5740    ctgaag
                    7568 7731 7811 8106
Eco64I       15     330 1328 1677 2509 2560 3741     g/gyrcc
                    5826 5861 6707 7903 8084 8232
                    8547 9814 9971
Eco72I        1     8213                             cac/gtg
Eco81I        2     4749 6381                        cc/tnagg
Eco88I       11     43 51 245 895 1332 1474 2383     c/ycgrg
                    2505 8536 9810 9967
EcoICRI       5     56 2296 9822 9926 9979           gag/ctc
EcoNI         1     1701                             cctnn/nnnagg
EcoO109I      9     983 1367 2161 4763 8003 8057     rg/gnccy
                    8413 8710 8931
EcoRI         4     75 1484 8563 9826                g/aattc
EcoRII       47     234  253  333  392  402  634  640  675  /ccwgg
                    720  938 1034 1046 1140 1156 1307
                    1375 1391 1428 2283 2568 2693
                    2720 2805 2880 2934 3795 3968
                    4089 4102 4792 4895 5474 6253
                    6270 6325 7528 7582 7657 7769
```

*FIG. 20 (Cont'd)*

| | | | |
|---|---|---|---|
| | | 7894 8242 8401 8988 8994 9126 9523 9897 | |
| EcoT14I | 17 | 180 356 504 650 775 1262 1284 2029 2473 2523 5023 5428 6038 6131 7940 8374 8621 | c/cwwgg |
| EcoT22I | 5 | 731 3893 6224 6296 9603 | atgca/t |
| EheI | 1 | 5863 | ggc/gcc |
| ErhI | 17 | 180 356 504 650 775 1262 1284 2029 2473 2523 5023 5428 6038 6131 7940 8374 8621 | c/cwwgg |
| Esp1396I | 3 | 154 8079 9127 | ccannnn/ntgg |
| Esp3I | 2 | 624 9898 | cgtctc |
| FauI | 20 | 1216 1640 2205 2238 2854 3684 3778 3804 4847 4913 4979 5060 5198 5735 6175 6196 6551 6605 7618 8546 | cccgc |
| FauNDI | 1 | 2072 | ca/tatg |
| FbaI | 2 | 2023 2067 | t/gatca |
| FokI | 17 | 189 2500 2570 2936 5075 5529 5554 6011 6178 7536 7902 8101 8843 9033 9330 9429 9891 | ggatg |
| FriOI | 13 | 58 1371 2298 4793 5503 6677 8416 8543 9134 9740 9824 9928 9981 | grgcy/c |
| Fsp4HI | 70 | 84 194 213 282 306 427 443 515 1022 1270 1301 1444 1459 1538 1604 1991 2122 2211 2684 2743 2765 3049 3056 3107 3204 3247 3380 3987 4142 4285 4350 4559 4770 4785 5124 5238 5252 5293 5389 5625 5631 5718 5759 5796 5801 5891 5902 5954 6093 6531 6545 6567 7086 7216 7262 7356 7410 7417 7701 7723 7782 8187 8225 8260 8489 8704 8875 9531 9671 9836 | gc/ngc |
| FspI | 1 | 5762 | tgc/gca |
| GsuI | 8 | 2953 3193 5046 5067 7280 7520 9573 9901 | ctggag |
| HaeII | 7 | 1899 2427 4190 5865 6593 6601 9473 | rgcgc/y |
| HaeIII | 61 | 161 234 429 640 934 984 1140 1201 1283 1369 1458 1804 2058 2163 2264 2438 2598 2698 3014 3099 3249 3569 3804 3957 3968 3986 4420 4765 4798 4855 5364 5391 5782 5956 6043 6086 6095 6101 6756 6898 7218 7368 7480 7769 7869 7951 8005 8058 8224 8401 8414 8476 8497 8541 8712 8806 9021 9666 9738 9835 9941 | gg/cc |

*FIG. 20 (Cont'd)*

```
HapII      45   328  547 1191 1315 1333 1475 2177  c/cgg
                2384 2390 2506 2513 2553 2616
                2676 3207 4149 4296 4322 4512
                4986 5078 5086 5361 5542 5609
                5699 5830 5858 5880 5957 6644
                7258 7789 7849 7912 8410 8473
                8537 8883 8928 9459 9734 9811
                9856 9968
HgaI       11  1653 2190 2340 3694 4048 4626       gacgc
                5085 5164 6521 9793 9896
HgiEI      10  1312 2109 2387 3181 4900 5345       g/gwcc
                7283 8931 8992 9852
HhaI       36  1529 1898 2126 2220 2250 2329       gcg/c
                2341 2426 2814 2855 3171 4122
                4189 4289 4463 4572 4975 5061
                5237 5497 5763 5800 5864 5872
                6491 6522 6535 6544 6566 6592
                6600 7298 7614 7655 9472 9530
Hin1I       8  1650 2187 3764 5081 5160 5862       gr/cgyc
                9436 9892
Hin6I      36  1527 1896 2124 2218 2248 2327       g/cgc
                2339 2424 2812 2853 3169 4120
                4187 4287 4461 4570 4973 5059
                5235 5495 5761 5798 5862 5870
                6489 6520 6533 6542 6564 6590
                6598 7296 7612 7653 9470 9528
HinP1I     36  1527 1896 2124 2218 2248 2327       g/cgc
                2339 2424 2812 2853 3169 4120
                4187 4287 4461 4570 4973 5059
                5235 5495 5761 5798 5862 5870
                6489 6520 6533 6542 6564 6590
                6598 7296 7612 7653 9470 9528
HincII      5  2259 3366 7101 8555 8591            gty/rac
HindII      5  2259 3366 7101 8555 8591            gty/rac
HindIII     4    60 1589 8301 9035                 a/agctt
HinfI      27   693 1162 1223 1554 2378 2408       g/antc
                3254 3917 4313 5095 5132 5190
                5242 5376 6386 6796 6818 7210
                8140 8592 8887 8972 9061 9156
                9195 9227 9349
HpaI        2  3366 7101                           gtt/aac
HpaII      45   328  547 1191 1315 1333 1475 2177  c/cgg
                2384 2390 2506 2513 2553 2616
                2676 3207 4149 4296 4322 4512
                4986 5078 5086 5361 5542 5609
                5699 5830 5858 5880 5957 6644
                7258 7789 7849 7912 8410 8473
                8537 8883 8928 9459 9734 9811
                9856 9968
HphI       21   321  411 1036 1054 1492 2030 2531  ggtga
```

*FIG. 20 (Cont'd)*

|        |    |                                      |         |
|--------|----|--------------------------------------|---------|
|        |    | 2554 2864 2888 2986 4690 4806        |         |
|        |    | 5679 6740 7455 7584 7608 7918        |         |
|        |    | 7941 8955                            |         |
| Hsp92I | 8  | 1650 2187 3764 5081 5160 5862        | gr/cgyc |
|        |    | 9436 9892                            |         |
| Hsp92II| 51 | 221 278 360 508 729 733 806 927      | catg/   |
|        |    | 1043 1187 1288 1495 1625 2333        |         |
|        |    | 2365 2527 2761 2791 3181 3226        |         |
|        |    | 3895 3946 4666 5050 5406 5432        |         |
|        |    | 5463 5649 5994 6135 6226 6298        |         |
|        |    | 6438 7245 7290 7485 7680 7710        |         |
|        |    | 7944 8039 8048 8599 8625 9020        |         |
|        |    | 9138 9186 9363 9601 9684 9726        |         |
|        |    | 9777                                 |         |
| HspAI  | 36 | 1527 1896 2124 2218 2248 2327        | g/cgc   |
|        |    | 2339 2424 2812 2853 3169 4120        |         |
|        |    | 4187 4287 4461 4570 4973 5059        |         |
|        |    | 5235 5495 5761 5798 5862 5870        |         |
|        |    | 6489 6520 6533 6542 6564 6590        |         |
|        |    | 6598 7296 7612 7653 9470 9528        |         |
| ItaI   | 70 | 84 194 213 282 306 427 443 515       | gc/ngc  |
|        |    | 1022 1270 1301 1444 1459 1538        |         |
|        |    | 1604 1991 2122 2211 2684 2743        |         |
|        |    | 2765 3049 3056 3107 3204 3247        |         |
|        |    | 3380 3987 4142 4285 4350 4559        |         |
|        |    | 4770 4785 5124 5238 5252 5293        |         |
|        |    | 5389 5625 5631 5718 5759 5796        |         |
|        |    | 5801 5891 5902 5954 6093 6531        |         |
|        |    | 6545 6567 7086 7216 7262 7356        |         |
|        |    | 7410 7417 7701 7723 7782 8187        |         |
|        |    | 8225 8260 8489 8704 8875 9531        |         |
|        |    | 9671 9836                            |         |
| KasI   | 1  | 5861                                 | g/gcgcc |
| KpnI   | 5  | 2513 8088 8551 9818 9975             | ggtac/c |
| Ksp22I | 2  | 2023 2067                            | t/gatca |
| Ksp632I| 4  | 2200 5306 5516 6393                  | ctcttc  |
| KspI   | 3  | 2238 8546 9839                       | ccgc/gg |
| Kzo9I  | 48 | 47 89 399 646 1469 1933 2023         | /gatc   |
|        |    | 2067 2170 2353 2500 3024 3172        |         |
|        |    | 3210 3260 3621 4508 4583 4594        |         |
|        |    | 4602 4680 4692 5051 5067 5443        |         |
|        |    | 5521 5530 5611 5689 6000 6019        |         |
|        |    | 6023 7203 7253 7291 7439 8063        |         |
|        |    | 8068 8532 9013 9150 9445 9449        |         |
|        |    | 9655 9730 9805 9847 9903             |         |
| LspI   | 2  | 65 5180                              | tt/cgaa |
| MaeI   | 28 | 166 181 208 651 690 962 1220         | c/tag   |
|        |    | 1397 1464 1481 1497 1871 2342        |         |
|        |    | 3258 3452 3616 4437 4690 5024        |         |
|        |    | 6039 6595 7013 7207 8007 8375        |         |

*FIG. 20 (Cont'd)*

|         |    |                                      |           |
|---------|----|--------------------------------------|-----------|
| MaeII   | 24 | 8570 9782 9800<br>1152 2316 2589 2802 2973 3764<br>4645 4778 5559 5746 6637 6747<br>6790 6802 7492 7663 7876 7985<br>8011 8168 8212 8283 8504 9436 | a/cgt |
| MaeIII  | 22 | 694 919 1124 1399 2707 3196 3391<br>3822 4298 4361 4477 4743 5433<br>5739 6558 6570 7071 7266 7755<br>8500 8949 9003 | /gtnac |
| MamI    | 4  | 2352 3265 6005 7202 | gatnn/nnatc |
| MboI    | 48 | 47 89 399 646 1469 1933 2023<br>2067 2170 2353 2500 3024 3172<br>3210 3260 3621 4508 4583 4594<br>4602 4680 4692 5051 5067 5443<br>5521 5530 5611 5689 6000 6019<br>6023 7203 7253 7291 7439 8063<br>8068 8532 9013 9150 9445 9449<br>9655 9730 9805 9847 9903 | /gatc |
| MboII   | 25 | 1935 1962 2199 2779 2824 3002<br>4596 4687 4839 5039 5206 5306<br>5516 6393 6621 7470 7645 7693<br>8297 8396 8987 9099 9404 9635<br>9866 | gaaga |
| MfeI    | 2  | 3353 7110 | c/aattg |
| MflI    | 20 | 47 399 646 1469 2500 3024 3621<br>4583 4594 4680 4692 5051 5443<br>5689 7439 8068 8532 9655 9730<br>9805 | r/gatcy |
| MluI    | 1  | 1878 | a/cgcgt |
| MluNI   | 3  | 5782 7951 9021 | tgg/cca |
| MnlI    | 87 | 103 177 229 318 364 413 425 440<br>745 790 909 915 934 1082 1117<br>1375 1392 1420 1470 1550 2162<br>2201 2315 2543 2624 2630 2707<br>2861 2873 2924 3044 3292 3315<br>3324 3663 4060 4117 4384 4754<br>5020 5068 5274 5450 5807 5943<br>6007 6047 6059 6086 6092 6099<br>6105 6383 6714 7147 7156 7179<br>7427 7547 7598 7610 7764 7841<br>7847 7928 8026 8058 8129 8233<br>8313 8364 8419 8522 8528 8725<br>8868 8937 9432 9470 9543 9579<br>9617 9650 9806 9844 9874 9945 | cctc |
| Mph1103I | 5 | 731 3893 6224 6296 9603 | atgca/t |
| MroNI   | 3  | 5077 5360 6643 | g/ccggc |
| MscI    | 3  | 5782 7951 9021 | tgg/cca |
| MseI    | 35 | 265 864 1521 1542 1565 1700 2094<br>3304 3365 3486 3507 3518 3530<br>3541 3558 3879 4648 4700 4705 | t/taa |

FIG. 20 (Cont'd)

|   |   |   |   |
|---|---|---|---|
|  |  | 4719 6538 6809 6907 6924 6935 |  |
|  |  | 6947 6958 6979 7100 7161 8019 |  |
|  |  | 8577 8662 8677 9301 |  |
| MslI | 17 | 328 1664 1773 2031 2525 2555 | caynn/nnrtg |
|  |  | 2705 2882 5427 7456 7585 7762 |  |
|  |  | 7912 7945 8677 9364 9596 |  |
| Msp17I | 8 | 1650 2187 3764 5081 5160 5862 | gr/cgyc |
|  |  | 9436 9892 |  |
| MspA1I | 13 | 97 1021 1205 2237 4284 4529 5758 | cmg/ckg |
|  |  | 6366 8259 8545 8610 9795 9838 |  |
| MspCI | 2 | 3485 6978 | c/ttaag |
| MspI | 45 | 328 547 1191 1315 1333 1475 2177 | c/cgg |
|  |  | 2384 2390 2506 2513 2553 2616 |  |
|  |  | 2676 3207 4149 4296 4322 4512 |  |
|  |  | 4986 5078 5086 5361 5542 5609 |  |
|  |  | 5699 5830 5858 5880 5957 6644 |  |
|  |  | 7258 7789 7849 7912 8410 8473 |  |
|  |  | 8537 8883 8928 9459 9734 9811 |  |
|  |  | 9856 9968 |  |
| MspR9I | 74 | 236 255 328 335 394 404 548 636 | cc/ngg |
|  |  | 642 677 722 940 1036 1048 1142 |  |
|  |  | 1158 1191 1309 1316 1333 1377 |  |
|  |  | 1393 1430 1475 2177 2285 2384 |  |
|  |  | 2391 2506 2554 2570 2695 2722 |  |
|  |  | 2807 2882 2936 3208 3797 3970 |  |
|  |  | 4091 4104 4322 4794 4897 5086 |  |
|  |  | 5476 5699 5859 6255 6272 6327 |  |
|  |  | 7258 7530 7584 7659 7771 7896 |  |
|  |  | 7912 8244 8403 8411 8537 8884 |  |
|  |  | 8929 8990 8996 9128 9459 9525 |  |
|  |  | 9735 9811 9856 9899 9968 |  |
| MunI | 2 | 3353 7110 | c/aattg |
| Mva1269I | 6 | 3353 3452 7021 7120 8351 8384 | gaatgc |
| MvaI | 47 | 236 255 335 394 404 636 642 677 | cc/wgg |
|  |  | 722 940 1036 1048 1142 1158 1309 |  |
|  |  | 1377 1393 1430 2285 2570 2695 |  |
|  |  | 2722 2807 2882 2936 3797 3970 |  |
|  |  | 4091 4104 4794 4897 5476 6255 |  |
|  |  | 6272 6327 7530 7584 7659 7771 |  |
|  |  | 7896 8244 8403 8990 8996 9128 |  |
|  |  | 9525 9899 |  |
| MvnI | 32 | 1880 2114 2124 2128 2218 2237 | cg/cg |
|  |  | 2248 2339 2853 3171 3252 3527 |  |
|  |  | 3828 3989 4570 4843 4912 4975 |  |
|  |  | 5059 5497 5798 6489 6520 6544 |  |
|  |  | 6564 6940 7215 7296 7614 8545 |  |
|  |  | 9789 9838 |  |
| MwoI | 53 | 311 482 600 722 807 1027 1052 | gcnnnnn/nngc |
|  |  | 1067 1266 1297 1642 1886 2042 |  |

FIG. 20 (Cont'd)

|         |    |                                              |          |
|---------|----|----------------------------------------------|----------|
|         |    | 2207 2616 2676 2689 2733 3801                |          |
|         |    | 3995 4567 4766 4970 5157 5424                |          |
|         |    | 5507 5624 5769 5792 5876 6092                |          |
|         |    | 6177 6228 6300 6539 6583 6610                |          |
|         |    | 6640 7728 7781 7794 7854 8192                |          |
|         |    | 8230 8494 8607 8709 9074 9417                |          |
|         |    | 9476 9716 9841 9889                          |          |
| NaeI    | 3  | 5079 5362 6645                               | gcc/ggc  |
| NarI    | 1  | 5862                                         | gg/cgcc  |
| NciI    | 27 | 328 548 1191 1316 1333 1475 2177             | cc/sgg   |
|         |    | 2384 2391 2506 2554 3208 4322                |          |
|         |    | 5086 5699 5859 7258 7912 8411                |          |
|         |    | 8537 8884 8929 9459 9735 9811                |          |
|         |    | 9856 9968                                    |          |
| NcoI    | 8  | 356 504 1284 2523 5428 6131 7940             | c/catgg  |
|         |    | 8621                                         |          |
| NdeI    | 1  | 2072                                         | ca/tatg  |
| NdeII   | 48 | 47 89 399 646 1469 1933 2023                 | /gatc    |
|         |    | 2067 2170 2353 2500 3024 3172                |          |
|         |    | 3210 3260 3621 4508 4583 4594                |          |
|         |    | 4602 4680 4692 5051 5067 5443                |          |
|         |    | 5521 5530 5611 5689 6000 6019                |          |
|         |    | 6023 7203 7253 7291 7439 8063                |          |
|         |    | 8068 8532 9013 9150 9445 9449                |          |
|         |    | 9655 9730 9805 9847 9903                     |          |
| NgoAIV  | 3  | 5077 5360 6643                               | g/ccggc  |
| NgoMI   | 3  | 5077 5360 6643                               | g/ccggc  |
| NheI    | 2  | 961 3615                                     | g/ctagc  |
| NlaIII  | 51 | 221 278 360 508 729 733 806 927              | catg/    |
|         |    | 1043 1187 1288 1495 1625 2333                |          |
|         |    | 2365 2527 2761 2791 3181 3226                |          |
|         |    | 3895 3946 4666 5050 5406 5432                |          |
|         |    | 5463 5649 5994 6135 6226 6298                |          |
|         |    | 6438 7245 7290 7485 7680 7710                |          |
|         |    | 7944 8039 8048 8599 8625 9020                |          |
|         |    | 9138 9186 9363 9601 9684 9726                |          |
|         |    | 9777                                         |          |
| NlaIV   | 55 | 113 160 332 401 648 702 1139                 | ggn/ncc  |
|         |    | 1243 1313 1330 1368 1415 1471                |          |
|         |    | 1679 2110 2214 2265 2388 2502                |          |
|         |    | 2511 2562 3100 3743 3974 4013                |          |
|         |    | 4856 4901 4980 5828 5863 6252                |          |
|         |    | 6324 6485 6676 6688 6709 7367                |          |
|         |    | 7905 8004 8059 8086 8234 8255                |          |
|         |    | 8414 8534 8541 8549 8932 9732                |          |
|         |    | 9738 9807 9816 9834 9854 9973                |          |
| NotI    | 2  | 3247 7216                                    | gc/ggccgc|
| NsiI    | 5  | 731 3893 6224 6296 9603                      | atgca/t  |
| NspBII  | 13 | 97 1021 1205 2237 4284 4529 5758             | cmg/ckg  |
|         |    | 6366 8259 8545 8610 9795 9838                |          |

FIG. 20 (Cont'd)

```
NspI       13  278 729 927 1625 2333 2365 3946           rcatg/y
               5463 6226 6298 8039 8048 9601
NspV        2  65 5180                                    tt/cgaa
PaeI        5  729 2333 5463 6226 6298                    gcatg/c
PaeR7I      2  43 51                                      c/tcgag
PalI       61  161 234 429 640 934 984 1140               gg/cc
               1201 1283 1369 1458 1804 2058
               2163 2264 2438 2598 2698 3014
               3099 3249 3569 3804 3957 3968
               3986 4420 4765 4798 4855 5364
               5391 5782 5956 6043 6086 6095
               6101 6756 6898 7218 7368 7480
               7769 7869 7951 8005 8058 8224
               8401 8414 8476 8497 8541 8712
               8806 9021 9666 9738 9835 9941
Pfl23II     1  2129                                       c/gtacg
PflMI       3  154 8079 9127                              ccannnn/ntgg
PinAI       1  2512                                       a/ccggt
PleI       16  697 1166 1227 2412 3258 4317               gagtc
               5194 6390 6800 6822 7214 8144
               8596 9199 9231 9353
PmaCI       1  8213                                       cac/gtg
Pme55I      3  234 6043 9941                              agg/cct
PmlI        1  8213                                       cac/gtg
Ppu10I      5  727 3889 6220 6292 9599                    a/tgcat
PpuMI       1  8931                                       rg/gwccy
PshAI       1  2276                                       gacnn/nngtc
PshBI       2  3879 8677                                  at/taat
Psp124BI    5  58 2298 9824 9928 9981                     gagct/c
Psp1406I    1  8504                                       aa/cgtt
Psp5II      1  8931                                       rg/gwccy
PspAI       7  1332 1474 2383 2505 8536 9810              c/ccggg
               9967
PspALI      7  1334 1476 2385 2507 8538 9812              ccc/ggg
               9969
PspLI       1  2129                                       c/gtacg
PspN4I     55  113 160 332 401 648 702 1139               ggn/ncc
               1243 1313 1330 1368 1415 1471
               1679 2110 2214 2265 2388 2502
               2511 2562 3100 3743 3974 4013
               4856 4901 4980 5828 5863 6252
               6324 6485 6676 6688 6709 7367
               7905 8004 8059 8086 8234 8255
               8414 8534 8541 8549 8932 9732
               9738 9807 9816 9834 9854 9973
PspOMI      4  1367 8412 8539 9736                        g/ggccc
PstI        2  85 8562                                    ctgca/g
PstNHI      2  961 3615                                   g/ctagc
PvuII       6  97 1021 1205 5758 6366 9795                cag/ctg
RcaI        3  4662 6434 8595                             t/catga8
```

FIG. 20 (Cont'd)

| | | | |
|---|---|---|---|
| RsaI | 22 | 352 1788 2117 2131 2489 2511<br>2954 3236 3670 5558 7231 7513<br>8086 8549 9173 9280 9442 9574<br>9772 9816 9952 9973 | gt/ac |
| RsrII | 1 | 5345 | cg/gwccg |
| SacI | 5 | 58 2298 9824 9928 9981 | gagct/c |
| SacII | 3 | 2238 8546 9839 | ccgc/gg |
| SalI | 3 | 2257 8553 8589 | g/tcgac |
| SapI | 2 | 5306 5516 | gctcttc |
| Sau3AI | 48 | 47 89 399 646 1469 1933 2023<br>2067 2170 2353 2500 3024 3172<br>3210 3260 3621 4508 4583 4594<br>4602 4680 4692 5051 5067 5443<br>5521 5530 5611 5689 6000 6019<br>6023 7203 7253 7291 7439 8063<br>8068 8532 9013 9150 9445 9449<br>9655 9730 9805 9847 9903 | /gatc |
| Sau96I | 36 | 159 638 983 1138 1199 1312 1367<br>2109 2161 2263 2387 2697 3098<br>3181 3802 4763 4796 4854 4900<br>5345 6754 7283 7366 7767 8003<br>8057 8399 8412 8539 8710 8931<br>8992 9664 9736 9833 9852 | g/gncc |
| ScrFI | 74 | 236 255 328 335 394 404 548 636<br>642 677 722 940 1036 1048 1142<br>1158 1191 1309 1316 1333 1377<br>1393 1430 1475 2177 2285 2384<br>2391 2506 2554 2570 2695 2722<br>2807 2882 2936 3208 3797 3970<br>4091 4104 4322 4794 4897 5086<br>5476 5699 5859 6255 6272 6327<br>7258 7530 7584 7659 7771 7896<br>7912 8244 8403 8411 8537 8884<br>8929 8990 8996 9128 9459 9525<br>9735 9811 9856 9899 9968 | cc/ngg |
| SduI | 33 | 58 1326 1333 1371 1437 2298 2565<br>2694 2943 3134 4260 4793 5503<br>5565 5755 5829 5922 6677 7337<br>7528 7777 7906 8052 8416 8543<br>8603 8743 8902 9134 9740 9824<br>9928 9981 | gdgch/c |
| SexAI | 1 | 6270 | a/ccwggt |
| SfaNI | 25 | 254 1946 2472 2637 2896 2911<br>3010 3414 4034 5236 5426 5511<br>5575 5642 5897 6223 6295 7058<br>7462 7561 7576 7835 8100 9500<br>9723 | gcatc |
| SfcI | 15 | 81 480 566 584 598 683 972 1408<br>1806 4207 4398 6525 8277 8558<br>9353 | c/tryag |

*FIG. 20 (Cont'd)*

```
SfiI      1   6092                                    ggccnnnn/nggcc
Sfr274I   2   43 51                                   c/tcgag
Sfr303I   3   2238 8546 9839                          ccgc/gg
SfuI      2   65 5180                                 tt/cgaa
SinI      10  1312 2109 2387 3181 4900 5345           g/gwcc
              7283 8931 8992 9852
SmaI      7   1334 1476 2385 2507 8538 9812           ccc/ggg
              9969
SpeI      1   8569                                    a/ctagt
SphI      5   729 2333 5463 6226 6298                 gcatg/c
SplI      1   2129                                    c/gtacg
SrfI      1   1334                                    gccc/gggc
Sse9I     36  67 75 262 496 666 861 1484 1838         /aatt
              2015 2063 2140 2478 3353 3417
              3495 3521 3532 3866 4702 6120
              6212 6284 6931 6942 6968 7046
              7110 8563 8579 8630 8778 8800
              9079 9297 9548 9826
SseBI     3   234 6043 9941                           agg/cct
SspBI     3   350 3234 7229                           t/gtaca
SspI      3   3511 6403 6956                          aat/att
SstI      5   58 2298 9824 9928 9981                  gagct/c
SstII     3   2238 8546 9839                          ccgc/gg
StuI      3   234 6043 9941                           agg/cct
StyI      17  180 356 504 650 775 1262 1284           c/cwwgg
              2029 2473 2523 5023 5428 6038
              6131 7940 8374 8621
SunI      1   2129                                    c/gtacg
TaqI      49  2 44 52 65 73 1557 1647 1830            t/cga
              2013 2157 2169 2258 2352 2445
              2574 2868 2895 2910 3039 4042
              4880 5135 5180 5371 5533 5569
              5593 5749 6022 6713 7426 7555
              7570 7597 7891 8025 8554 8590
              8857 9448 9824 9963 9981 10023
              10065 10107 10149 10191 10233
TfiI      11  1554 2378 3917 5095 5132 5242           g/awtc
              5376 8887 8972 9061 9156
ThaI      32  1880 2114 2124 2128 2218 2237           cg/cg
              2248 2339 2853 3171 3252 3527
              3828 3989 4570 4843 4912 4975
              5059 5497 5798 6489 6520 6544
              6564 6940 7215 7296 7614 8545
              9789 9838
Tru1I     35  265 864 1521 1542 1565 1700 2094        t/taa
              3304 3365 3486 3507 3518 3530
              3541 3558 3879 4648 4700 4705
              4719 6538 6809 6907 6924 6935
              6947 6958 6979 7100 7161 8019
              8577 8662 8677 9301
```

*FIG. 20 (Cont'd)*

```
Tru9I      35   265  864 1521 1542 1565 1700 2094   t/taa
                3304 3365 3486 3507 3518 3530
                3541 3558 3879 4648 4700 4705
                4719 6538 6809 6907 6924 6935
                6947 6958 6979 7100 7161 8019
                8577 8662 8677 9301
Tsp45I     10   694 1399 2707 3196 5433 5739        /gtsac
                6570 7266 7755 8949
Tsp509I    36   67 75 262 496 666 861 1484 1838     /aatt
                2015 2063 2140 2478 3353 3417
                3495 3521 3532 3866 4702 6120
                6212 6284 6931 6942 6968 7046
                7110 8563 8579 8630 8778 8800
                9079 9297 9548 9826
TspEI      36   67 75 262 496 666 861 1484 1838     /aatt
                2015 2063 2140 2478 3353 3417
                3495 3521 3532 3866 4702 6120
                6212 6284 6931 6942 6968 7046
                7110 8563 8579 8630 8778 8800
                9079 9297 9548 9826
TspRI      28   27 526 664 716 1250 1615 2736       cagtg
                3447 4348 4361 4632 5742 7025
                7736 8178 9094 9126 9220 9420
                9645 9664 10006 10048 10090
                10132 10174 10216 10258
Tth111I     2   840 5745                            gacn/nngtc
TthHB8I    49   2 44 52 65 73 1557 1647 1830        t/cga
                2013 2157 2169 2258 2352 2445
                2574 2868 2895 2910 3039 4042
                4880 5135 5180 5371 5533 5569
                5593 5749 6022 6713 7426 7555
                7570 7597 7891 8025 8554 8590
                8857 9448 9824 9963 9981 10023
                10065 10107 10149 10191 10233
Van91I      3   154 8079 9127                       ccannnn/ntgg
Vha464I     2   3485 6978                           c/ttaag
VneI        3   4256 8048 8739                      g/tgcac
VspI        2   3879 8677                           at/taat
XbaI        4   1463 1496 3257 7206                 t/ctaga
XhoI        2   43 51                               c/tcgag
XhoII      20   47 399 646 1469 2500 3024 3621      r/gatcy
                4583 4594 4680 4692 5051 5443
                5689 7439 8068 8532 9655 9730
                9805
XmaI        7   1332 1474 2383 2505 8536 9810       c/ccggg
                9967
XmaIII      3   3247 5954 7216                      c/ggccg
XmnI        1   8317                                gaann/nnttc
Zsp2I       5   731 3893 6224 6296 9603             atgca/t
```

FIG. 20 (Cont'd)

The following endonucleases were selected but don't cut this sequence:

Acc113I, AccIII, AhdI, AscI, AspEI, BseAI, BsiMT, Bsp13I, Bsp68I, BspCI, BspEI, BstEII, BstPI, BstSNI, Eam1105I, EclHKI, Eco105I, Eco255I, Eco32I, Eco91I, EcoO65I, EcoRV, FseI, Kpn2I, MroI, NruI, PacI, Ple19I, PmeI, PspEI, PvuI, SbfI, ScaI, SgfI, SgrAI, SmiI, SnaBI, Sse8387I, SwaI, XcmI

FIG. 20 (Cont'd)

pMCK/Tet-ON-BFP/TRE/HA-Mst/IRES-EGFP (23)

(pFinal)

1.) Open both pBlue$_{MNN}$ and pLong with Bgl II. Get the 6.3 kb and 6.6 kb plasmid opened and ligate them. Search for the 13 kb fusion plasmid which has the opposite orientation.

pfusion 13.4 kb test : EcoR I  0.5
1.1
1.3
10.5
13.4 kb

2.) Restriction digest the pfusion with NheI enzyme : get the ≈3.3 kb and ≈10.1 kb fragment. Cut the 10.1 kb fragment and self-ligate.

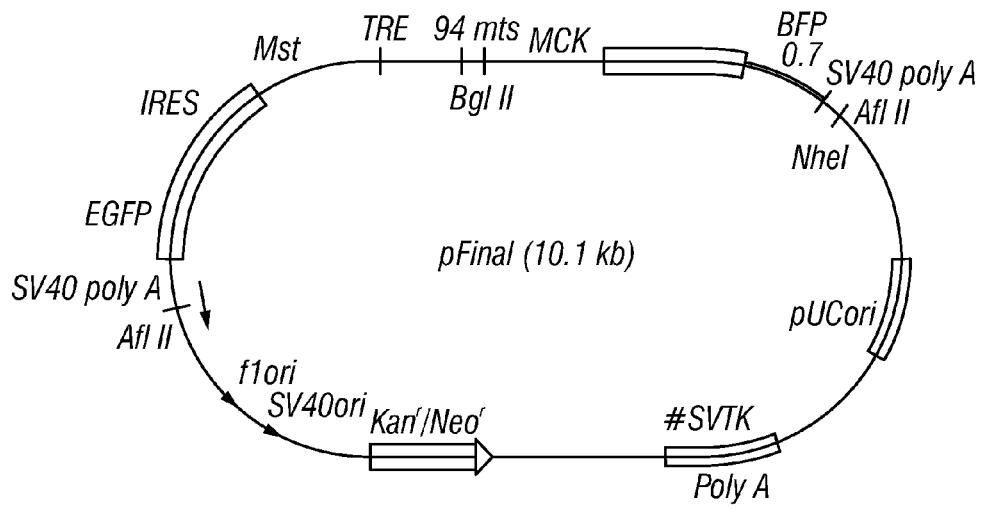

Constructed by Suzanne Porszasz - Reisz

Test: Afl II → 6.5 kb
3.6 kb

\* unique sit to release:
cut out the
construct with
Afl II

FIG. 21

CMOT transgene

6786 base pairs

Graphic map | Table by enzyme name

```
MspCI                                                                 Tsp509I
Bst98I                              BsaMI                             TspEI
BspTI MseI             MaeI   BsmI                                    Sse9I
cttaagatacattgatgagtttggacaaaccacaactagaatgcagtgaaaaaaatgctttatttgtgaaatttg base pairs
gaattctatgtaactactcaaacctgtttggtgttgatcttacgtcacttttttttacgaaataaacactttaaac 1 to 75
AflII TruII               BfaI   Mva1269I                             AcsI
Vha464I                          TspRI                                ApoI
BfrI Tru9I ItaI         HincII  Tsp509I
                              BsoFI        TruII   MunI      BsaMI
      SfaNI        MaeIII     CviJI        Tru9I   MfeI      BsmI
tgatgctattgctttatttgtaaccattataagctgcaataaacaagttaacaacaacaattgcattcatttttat base pairs
actacgataacgaaataaacattggtaatattcgacgttatttgttcaattgttgttgttaacgtaagtaaaata 76 to 150
                              AluI Bst71I  MseI    Sse9I    Mva1269I
                              Fsp4HI       HpaI    TspEI
                                BbvI       HindII TruII
              MnlI   MnlI Tru9I           MnlI           CviJI
gtttcaggttcaggggaggtgtgggaggttttttaaagcaagtaaaaacctctacaaatgtggtatggctgatta base pairs
caaagtccaagtcccccctccacaccctccaaaaaatttcgttcattttggagatgtttacaccataccgactaat 151 to 225
                        MseI
                        DraI Bse8I Sau3AI BfaI MvnI BsoFI Eco52I BsiEI Bsp1407I Hsp92II NciI AclWI Fsp4HI
BsrBRI Bsp143I ThaI BstZI NotI HaeIII Bsh1285I CviJI MboI DpnI HpaII BsoFI
MamI NdeII XbaI AccII CfrI Fsp4HI CviJI BsaOI Csp6I NdeII Kzo9I MspI AlwI BslI
tgatctagagtcgcggccgctttacttgtacagctcgtccatgccgagagtgatcccggcggcggtcacgaactc base pairs
actagatctcagcgccggcgaaatgaacatgtcgagcaggtacggctctcactagggccgccgccagtgcttgag 226 to 300
BsaBI MooI MaeI BstJI CciNI XmaIII AciI AciI BsrGI AluI Sau3AI BcnI ScrFI BsiYI
Bsh1365I DpnI PleI Bsh1236I EclXI PalI BstMCI RsaI NlaIII BsiSI HapII Bsc4I
 DpnII Kzo9I HinfI EaeI EagI ItaI BsuRI SspBI AfaI DpnII Bsp143I MspR9I ItaI MaeIII AsuI AspS9I Sau3AI Hin6I CfoI             DdeI Bbv12I
AciI  SinI AvaII NdeII DpnI AccII AspLEI       BseII BmyI BsiHKAI
    BpmI HgiEI NlaIII Kzo9I ThaI HhaI   DdeI   AciI BsrSI Bsp1286I
cagcaggaccatgtgatcgcgcttctcgttggggtctttgctcagggcgactgggtgctcaggtagtggttgtc base pairs
gtcgtcctggtacactagcgcgaagagcaaccccagaaacgagtcccgcctgacccacgagtccatcaccaacag 301 to 375
         Cfr13I Eco47I MboI HspAI Bsh1236I  BstDEI        BseNI AspHI
  Tsp45I Bme18I Hsp92II HinP1I MvnI                       BsrI SduI Alw21I
    GsuI Sau96I DpnII Bsp143I BstUI                       BstDEI
```

FIG. 22

```
      Bst71I  NlaIV                                              Fsp4HI Fsp4HI
   ItaI    AsuI HaeIII                                       AluI Bst71I      TaqI
 BsoFI    Cfr13I CviJI                                  Cac8I BbvI ItaI     TthHB8I
gggcagcagcacggggccgtcgccgatgggggtgttctgctggtagtggtcggcgagctgcacgctgccgtcctc base pairs
cccgtcgtcgtgccccggcagcggctaccccacaagacgaccatcaccagccgctcgacgtgcgacggcaggag 376 to 450
   Fsp4HI    Sau96I PalI                                    CviJI Cac8I Bst71I
      BbvI   AspS9I BsuRI                                      BsoFI BsoFI
             PspN4I                                             ItaI BsgI BbvI MboI Bsp143I                          PalI
          BstX2I AciI       HphI                HaeIII
          BstYI MflI AclWI MslI   SfaNI   MboII   EaeI   NlaIII MaeII     CviJI
gatgttgtggcggatcttgaagttcaccttgatgccgttcttctgcttgtcggccatgatatagacgttgtggct base pairs
ctacaacaccgcctagaacttcaagtggaactacggcaagaagacgaacagccggtactatatctgcaacaccga 451 to 525
          DpnII XhoII AlwI                     CfrI   Hsp92II
MnlI      NdeII Kzo9I                                 CviJI
          Sau3AI DpnI                                 BsuRI BseDI Bst2UI                              TaqI
          AfaI   GsuI  BmyI BstOI FokI                           AluI
          Cso6I  CviJI SduI BstNI BstF5I MnlI      TthHB8I       Eco57I   SfaNI
gttgtagttgtactccagcttgtgccccaggatgttgccgtcctccttgaagtcgatgcccttcagctcgatgcg base pairs
caacatcaacatgaggtcgaacacggggtcctacaacggcaggaggaacttcagctacgggaagtcgagctacgc 526 to 600
          RsaI   AluI   Bsp1286I MvaI              TaqI  SfaNI  CviJI
                 BpmI   BsaJI MspR9I                             TthHB8I
                        EcoRII ScrFI BstOI MslI                    HinP1I MvnI AciI
   BseDI ScrFI      MnlI         HhaI BslI HhaI CfoI
  EcoRII Bst2UI  TthHB8I       BsaJI Bsc4I AccII FauI                   MboII
gttcaccagggtgtcgccctcgaacttcacctcggcgcgggtcttgtagttgccgtcgtccttgaagaagatggt base pairs
caagtggtcccacagcgggagcttgaagtggagccgcgcccagaacatcaacggcagcaggaacttcttctacca 601 to 675
AciI BsaJI HphI   TaqI        BseDI Hin6I BstUI
     BstNI MvaI               MnlI BsiYI AspLEI
     MspR9I                   HspAI ThaI Bsh1236I AspLEI ScrFI                                  Bst71I                  AciI
  Hin6I BstNI MvaI                   AciI         ItaI                    ItaI
  HinP1I BstOI MaeII         NlaIII         MboII     BsoFI    NlaIII    BsoFI
gcgctcctggacgtagccttcgggcatggcggacttgaagaagtcgtgctgcttcatgtggtcggggtagcggct base pairs
cgcgaggacctgcatcggaagcccgtaccgcctgaacttcttcagcacgacgaagtacaccagccccatcgccga 676 to 750
 HspAI EcoRII    CviJI       Hsp92II               Fsp4HI   Hsp92II     Fsp4HI
    HhaI MspR9I                                      BbvI                CviJI
    CfoI Bst2UI Sau96I EcoRII MvaI BsiYI ItaI Cac8I
  MwoI      BsgI          BssSI HaeIII BstNI Bsc4I MwoI AluI BssAI
   Eco57I Cac8I        Tsp45I MslI Cfr13I BsuRI MspR9I SduI Fsp4HI BsrFI
gaagcactgcacgccgtaggtcagggtggtcacgagggtgggccagggcacgggcagcttgccggtggtgcagat base pairs
```

FIG. 22 (Cont'd)

```
                                                                                                    751 to 825
cttcgtgacgtgcggcatccagtcccaccagtgctcccacccggtcccgtgcccgtcgaacggccaccacgtcta
     TspRI               MaeIII  BsiI AspS9I BsaJI Bst2UI BmyI CviJI Bse118I
                                 MnlI CviJI BseDI ScrFI Bsp1286I Bst71I
                                 AsuI PalI BstOI BslI BsoFI BbvI Cfr1

HpaII                                              HapII              PalI
  MspI        AluI                                   HpaII              HaeIII
    HapII Eco57I Cac8I          SfaNI MnlI MnlI      MwoI       EaeI    MaeII
gaacttcagggtcagcttgccgtaggtggcatcgccctcgccctcgccggacacgctgaacttgtggccgtttac  base pairs
cttgaagtcccagtcgaacggcatcgccgtagcgggagcgggcctgtgcgacttgaacaccggcaaatg       826 to 900
    BsgI        CviJI                        BcgI    BsiSI              CfrI
  BsiSI                                              MspI               CviJI
  OI MwoI                                                               BsuRI MspR9I  Eco64I Bsp1286I MspI CviJI          NcoI BstDSI
           TthHB8I ScrFI BshNI BmyI MslI ScrFI    BseRI   StyI BseDI NlaIII
         CviJI BstNI BstF5I SduI BsiSI HapII      MnlI    Eco130I HphI
gtcgccgtccagctcgaccaggatgggcaccaccccggtgaacagctcctcgcccttgctcaccatggttgtggc  base pairs
cagcggcaggtcgagctggtcctacccgtggtgggccacttgtcgaggagcgggaacgagtggtaccaacaccg  901 to 975
         AluI EcoRII MvaI AccBlI BsaJI BcnI HphI          ErhI EcoT14I
          TaqI BstOI FokI NlaIV BseDI HpaII AluI          BssT1I Bsp19I
              Bst2UI BanI PspN4I NciI MspR9I              BsaJI DsaI Hsp92II MslI HaeIII                         BsmFI        DraII PspN4I
   PalI BalI                        BstDSI       AsuI NlaIV MaeI MseI   MnlI
BstXI BsuRI              MaeII BsaJI BslI  Cfr13I HaeIII    Tru9I TthHB8I
catattatcatcgtgtttttcaaaggaaaaccacgtcccgtggttcgggggcctagacgttttttttaacctcg  base pairs
gtataatagtagcacaaaaagtttcctttggtgcaggggcaccaagcccccggatctgcaaaaaaattggagc  976 to
                                                                             1050
EaeI CviJI                       BseDI BsiYI Sau96I CviJI MaeII    TaqI
  CfrI MscI                      DsaI Bsc4I Eco0109I BsuRI  Tru1I
    MluNI                                AspS9I PalI BfaI NspI    VneI Bsp1286I Sau96I PalI NlaIV Bsp143I MflI AclWI BsiYI
        NlaIII  Hsp92II Alw21I AsuI HaeIII NdeII DpnI BstX2I DpnI BslI
      BspLU11I  NlaIII BmyI BsaJI Eco0109I PspN4I BstYI Sau3AI AlwI Esp1396I
actaaacacatgtaaagcatgtgcaccgaggccccagatcagatcccatacaatgggtaccttctgggcatcct  base pairs
tgatttgtgtacatttcgtacacgtggctccggggtctagtctagggtatgttaccccatggaagacccgtagga 1051 to
                                                                             1125
         AflIII     Alw44I BbvI2I Cfr13I CviJI DpnII Kzo9I MooI XhoII AccB7I
         Hsp92II    NspI SduI BsiHKAI DraII MnlI MooI DpnII Bsp143I Bsc4I
                  ApaLI AspHI BseDI AspS9I BsuRI Sau3AI NdeII Kzo9I PflMI Acc65I RsaI FokI
  Eco64I NlaIV SfaNI          CviJI
    BshNI PspN4I        MnlI       HinfI                            MaeII
tcagcccttgttgaatacgcttgaggagagccatttgactctttccacaactatccaactcacaacgtggcact  base pairs
agtcgggaacaacttatgcgaactcctctcggtaaactgagaaaggtgttgataggttgagtgttgcaccgtga  1126 to
                                                                             1200
```

FIG. 22 (Cont'd)

```
    Asp718I AfaI Eco57I       BseRI          PleI                          DraIII
Van91I AccB1I BstF5I
  BanI Csp6I KpnI CviJI

BsrI                             PmlI     PalI ItaI BshNI      MspR9I BsiYI
  BseNI    ItaI MwoI                Eco72I  EaeI BsoFI Eco64I    BstOI BslI
 TspRI     BsoFI       BspMI    AflIII BbrPI HaeIII MwoI NlaIV EcoRII MvaI
ggggttgtgccgcctttgcaggtgtatcttatacacgtggcttttggccgcagaggcacctgtcgccaggtggg base pairs
ccccaacacggcggaaacgtccacatagaatatgtgcaccgaaaaccggcgtctccgtggacagcggtccacccc 1201 to
                                                                             1275
  EsrSI    Fsp4HI                 MaeII CviJI CviJI AciI Acc31I  BstNI BsC4I
  BseII    AciI                    BsaAI   CfrI Fsp4HI BanI PspN4I ScrFI
                                   PmaCI   BsuRI BglI MnlI      Bst2UI BsoFI   BslI                       MboII
  PspN4I ItaI Bsc4I                     BbsI  AluI            XmnI
   NlaIV AciI BbvI      SfcI  MaeII     BpuAI CviJI      MnlI
ggttccgctgcctgcaaagggtcgctacagacgttgtttgtcttcaagaagcttccagaggaactgcttccttca base pairs
ccaaggcgacggacgtttcccagcgatgtctgcaacaaacagaagttcttcgaaggtctccttgacgaaggaagt 1276 to
                                                                             1350
     NspBII Bst71I     BstSFI            Bbv16II            Asp700I
     MspA1I Cac8I                        BpiI
      Fsp4HI  BsiYI                       HindIII BlnI BseDI         BpiI
                    BsaMI              ErhI BsaJI BsaMI   Bbv16II
                    BsmI      MnlI     AvrII MaeI Mva1269I  MboII cgacattcaacagaccttgcattcctttggcgagaggggaaagaccccctaggaatgctcgtcaagaagacagggc base pairs
gctgtaagttgtctggaacgtaaggaaaccgctctcccctttctggggatccttacgagcagttcttctgtcccg 1351 to
                                                                             1425
                Mva1269I                 Eco13OI   BsmI      BpuAI
                                         StyI EcoT14I        BbsI
                                         BssT1I BfaI              Cfr13I AspS9I BstNI MvaI BcnI Sau96I HaeIII BmyI ApaI BslI                BsiSI
   CviJI MspR9I MspI Cfr13I EcoO109I Bsp1286I Bsc4I                Bse118I
Sau96I EcoRII BsiSI MspR9I AspS9I PalI Eco24I BsrDI                BssAI
caggtttccgggccctcacattgccaaaagacggcaatatggtggaaaataacatatagacaaacgcacaccggc base pairs
gtccaaaggcccgggagtgtaacggttttctgccgttataccacctttattgtatatctgtttgcgtgtggccg 1426 to
                                                                             1500
 HaeIII BstCI HpaII ScrFI AsuI CviJI SduI BanII                    BsrFI
AsuI BsuRI ScrFI NciI Bsp120I NlaIV PspN4I MnlI                    Cfr10I
    PalI Bst2UI HapII PspOMI DraII BsuRI FriOI BsiYI                HpaII CviJI     AciI PalI BsrSI                NceII BstI NlaIV Eco88I
    BsuRI   ItaI MwoI BsuRI MaeII           DpnII MflI AciI PspAI
 MspI       BsoFI EaeI MaeIII Psp1406I    MnlI MnlI Sau3AI Kzo9I BcoI AclWI
cttattccaagcggcttcggccagtaacgttaggggggggggaggggagagggggcggatcccgggcccgcggtacc base pairs
gaataaggttcgccgaagccggtcattgcaatcccccccccctccctctccccgcctagggcccgggcgccatgg 1501 to
```

FIG. 22 (Cont'd)

```
                                        1575
  HapII     Fsp4HI  HaeIII BsrI                      BstYI BamHI DpnI Cfr9I
   HaeIII       CviJI CviJI BseII                    BstX2I XhoI PspN4I
   PalI            CfrI  BseNI                       MboI Bsp143I Ama87I

XmaI MspI Cfr13I NlaIV SduI BsaJI DsaI MvnI FauI AciI Acc65I PspN4I SfcI
 BseDI HpaII SmaI AsuI HaeIII Eco24I BstDSI Bsh1236I Eco64I Csp6I SalI HindII
    BsoBI HapII Bsp120I PalI Bsp1286I ApaI NspBII SstII BanI NlaIV TthHB8I
gtcgactgcagaattcactagtgattaaattatattgtcgactcatgagcacccacagcggtctactaccatggc base pairs
cagctgacgtcttaagtgatcactaatttaatataacagctgagtactcgtgggtgtcgccagatgatggtaccg 1576 to
                                                                             1650
   AlwI BcnI PspALI AspS9I PspN4I BseDI ThaI MspA1I Cfr42I AccB1I KpnI HincII
 BsaJI NciI MspR9I Sau96I BsuRI Cac8I BanII BstUI Sfr303I Asp718I AfaI TaqI
 AvaI BsiSI ScrFI PspOMI CviJI BmyI FriOI AccII KspI SacII BshNI RsaI AccI BstSFI AcsI SpeI MseI TthHB8I PleI BmyI BsiHKAI StyI BseDI Hsp92II TruII PshBI DrdI
    TspEI BfaI Tsp509I HinfI SduI Bbv12I AccI BsaJI Bsp19I TspEI VspI TruII
   Sse9I AclNI TruII AccI BspHI Bsp1286I MspA1I BssT1I NlaIII ApoI AsnI MseI
tggaattttcccatatattatttgttctttgccattaaaatatagcatattaatgggagacatttttgtcggagt base pairs
accttaaaagggtatataataaacaagaaacggtaattttatatcgtataattaccctctgtaaaaacagcctca 1651 to
                                                                             1725
   EcoRI MaeI Sse9I TaqI RcaI AspHI MwoI AciI NcoI DsaI CviJI Tru9I Tru9I BsmAI
 PstI ApoI Tru9I SalI HindII Hsp92II NspBII ErhI EcoT14I Sse9I MseI MslI Alw26I
     Tsp509I TspEI HincII NlaIII Alw21I Eco130I BstDSI AcsI Tsp509I AseI Bst71I DraII BsuRI Bsp1720I         Bsp1286I
  Fsp4HI Sau96I PalI CelII            ApaLI Bbv12I
   BsoFI Cfr13I CviJI DdeI CviJI      Alw44I Alw21I         AciI
gcagcaagggcctgctgagcctctggggtttgcttggtgcacaagatgagtatgcggatattttgtaaaaacac base pairs
cgtcgttcccggacgactcggagaccccaaacgaaccacgtgttctactcatacgcctataaaaacattttgtg 1726 to
                                                                            1800
     BbvI EcoO109I Cac8I BstDEI        VneI BmyI
       BsgI AsuI HaeIII BlpI MnlI         SduI BsiHKAI
     ItaI MwoI AspS9I Bpu1102I             AspHI Tsp509I                   BsuRI                        BsmFI
  TspEI                     Tsp509I                    BseII Bsc4I
   Sse9I        DdeI     Sse9I HaeIII                  BsrSI BstF5I
aaattcacactctcctgagcagtaattggccttatatcttttgggtgcgataatccagtcccatccaaaggcttc base pairs
tttaagtgtgagaggactcgtcattaaccggaatatagaaaacccacgctattaggtcagggtaggtttccgaag 1801 to
                                                                             1875
  AcsI        BstDEI  TspEI CviJI                      BseNI  FokI CviJI
  ApoI                      PalI                       BsrI   BsII
                                                                BsiYI BstMCI MnlI        MspI MspR9I            Bbv12I
           BsiEI BsiYI    ItaI Bst71I BcnI BseDI   AspHI
    TthHB8I  Bsc4I     BsoFI BbvI NciI BsaJI    SduI BsiHKAI CviJI       Alw26I
aaaatcgaccgtgaggggtagcggcagcaccgggattccgtggagtgctcatcgcagtcaagcccaaagtctct base pairs
```

FIG. 22 (Cont'd)

```
tttagctggcactccccatcgccgtcgtggccctaaggcacctcacgagtagcgtcagttcgggtttcagaga 1876 to
                                                                        1950
    TaqI      BslI    Fsp4HI  BsiSI ScrFI DsaI    Bsp1286I              BsmAI
      Bsh1285I        AciI    HpaII HinfI         BmyI
      BsaOI                   HapII TfiI  BstDSI  Alw21I MspI MspR9I AsuI Psp5II MnlI                                MspR9I Bme18I
BsiSI ScrFI HgiEI Eco47I Tsp45I                             BstNI Cfr13I
    BcnI PpuMI DraII NlaIV HphI         HinfI CviJI   MboII ScrFI HgiEI
ccgggacctcttgggtgtgtctgtcaccttgacttctaaaaagggattcagcccatcttctcctggtcctgggaa base pairs
ggccctggagaacccacacagacagtggaactgaagattttccctaagtcgggtagaagaggaccaggacccct 1951 to
                                                                        2025
      NciI Bme18I AvaII PspN4I           TfiI         EcoRII MvaI AsuI
    HpaII Cfr13I EcoO109I BsmFI                       BstOI SinI AvaII
    HapII SinI Sau96I AspS9I MaeIII                   Bst2UI Sau96I AspS9I BstOI DpnII Kzo9I HaeIII FokI
 Eco47I BseDI MvaI Sau3AI NlaIII MluNI
    EcoRII MspR9I NdeII EaeI CviJI BalI AluI      DdeI    HinfI  CviJI MwoI
ggttacagcaagatcatggccattctcatccaaagctttgatttcaatgcctaagttggattcaggctgtttgag base pairs
ccaatgtcgttctagtaccggtaagagtaggtttcgaaactaaagttacggattcaacctaagtccgacaaactc 2026 to
                                                                        2100
    BslI BsaJI ScrFI Bsp143I PalI MscI CviJI         BstDEI  TfiI
      BsiYI Bst2UI MboI CfrI BsuRI BstF5I
    Bsc4I BstNI MaeIII DpnI Hsp92II HindIII BpiI                 Bsc4I PflMI BstNI ScrFI FriOI
    TspEI              Bov16II              BseII BslI BsaJI MspR9I Bsp1286I
      Sse9I           TspRI                 PsrSI AlwNI Esp1396I SduI BanII
ccaattttgcaacactgtcttcacatcaatactctgccaaataccagtgcctgggctcatgtcaagtttcagaga base pairs
ggttaaaacgttgtgacagaagtgtagttatgagacggtttatggtcacggaccgagtacagttcaaagtctct 2101 to
                                                                        2175
CviJI                 BpuAI                 BseNI AccB7I Van91I CviJI NlaIII
    Tsp509I           BpsI                  BsrI EcoRII BseDI Bst2UI Eco24I
                        MboII                 TspRI BsiYI BstOI MvaI BmyI DpnII DpnI BseNI                       BsmAI
       Bsp143I AccI   RsaI                    PleI
      NdeII TfiI BseII           NlaIII  HinfI Alw26I         TspRI
tcggattccagtatacccttgtaccgtctttcatgggtttgatgagtctcaggatttgcacaaacactgttgtagg base pairs
agcctaaggtcatatggaacatggcagaaagtacccaaactactcagagtcctaaacgtgtttgtgacaacatcc 2176 to
                                                                        2250
      Sau3AI BsrSI  Csp6I       Hsp92II   DdeI
        MboI Kzo9I  BsrI AfaI              BstDEI
      Hsp92II HinfI Bst1107I TspEI
                       BsiYI              AfaI                  Sse9I
 HinfI     DdeI        Bsc4I              Csp6I        CviJI Tru9I
agtcttgacgggtctgagatatatccacagttgggcttttactactttgttgtactgtattttagagctaaattt base pairs
```

FIG. 22 (Cont'd)

```
tcagaactgcccagactctatataggtgtcaacccgaaaatgatgaaacaacatgacataaaatctcgatttaaa 2251 to
                                                                             2325
      PleI     BstDEI          BslI              RsaI        AluI Tsp509I
                            CviJI                                 AcsI
                                                                  ApoI BstSFI
  DraI                  AcII                   SfcI       MslI
              CviJI        BstF5I             HinfI      NlaIII
aaaaaagcaacatttgggcttgccatccgcttgcattagaaagtcagactctgtaggcatggtaatgattgtttc base pairs
ttttttcgttgtaaacccgaacggtaggcgaacgtaatctttcagtctgagacatccgtaccattactaaaaag 2326 to
                                                                             2400
                Cac8I   FokI            AlwNI       Hsp92II
MseI                 Cac8I              PleI
TruII Hsp92I   DpnII  DpnI
BstDSI                                   MnlI BsaHI AfaI Sau3AI
BsaJI           MboII CviJI MwoI    BstF5I HinlI AcyI NdeII
cgtggtagcgtgataatcgtcatcttccaaagagccatcactgctgtcatccctctggacgtcgtactgatcgat base pairs
gcaccatcgcactattagcagtagaaggtttctcggtagtgacgacagtagggagacctgcagcatgactagcta 2401 to
                                                                             2475
BseDI                               TspRI    FokI   Mso17I RsaI MboI
DsaI                                                BciII AatII Bsp143I
                                                    MaeII Csp6I Kzo9I BspXI BseCI Kzo9I HpaII Hin6I HaeII                             Bst2JI
   Bsp106I ClaI Bsp143I MspR9I AspLEI                               BstOI
  TthHB8I Bsu15I Sau3AI MspI HspAI CfoI       SfaNI          CviJI EcoRII
cagttcccggagtggaggcgctcttggcagaagttgtcttatagcatctttgctgatgttaggagctgtttccag base pairs
gtcaagggcctcacctccgcgagaaccgtcttcaacagaatatcgtagaaacgactacaatcctcgacaaaggtc 2476 to
                                                                             2550
 BanIII BscI NdeII NciI HapII MnlI BstH2I                  AluI    BstNI
   Bsa29I DpnII DpnI BcnI HinP1I Bsp143II                          MspR9I
 BspDI TaqI MboI BsiSI ScrFI HhaI MwoI                             ScrFI AspLEI AluI    TspEI              AfaI
    HspAI BsoFI DdeI AcsI              BpmI     BssSI      MslI Hsp92II
   MvaI CfoI BcvI   Sse9I    CviJI    Csp6I MnlI      Alw26I Ppu1
gcgcagcttactgaggatttgaatttttatggcttctattctggagtacctcgtgttttgtctccacgcacatgc base pairs
cgcgtcgaatgactcctaaacttaaaaataccgaagataagacctcatggagcacaaaacagaggtgcgtgtacg 2551 to
                                                                             2625
     HinP1I CviJI BstDEI                 CsuI     BsiI    BsmAI     Nl
       HhaI Fsp4HI MnlI ApoI             RsaI                       NspI
       Hin6I ItaI Bst71I Tsp509I Zsp2I                                       MboI Bsp143I AsuI BseII
                                             BstX2I DpnI Sau96I HaeIII
  OI EcoT22I   MnlI          MboII   TspRI   BstYI MflI AlwI BsrSI
attacacagcccctcttttccacatttctcttctctctcactgccctcatttagatccactgggccagcagcaat base pairs
```

FIG. 22 (Cont'd)

```
taatgtgtcggggagaaaaaggtgtaaaagaagagagagtgacgggagtaaatctaggtgacccggtcgtcgtta 2626 to
                                                                             2700
 aIII    CviJI                             MnlI DpnII XhoII Cfr13I BsrI
    Mph1103I                                  NdeII Kzo9I TspRI BseNI
 NsiI                                      Sau3AI AclWI AspS9I CviJI BsoFI Hsp92II                          DpnII BamHI NlaIV AclWI
    Fsp4HI                             Hsp92II Sau3AI Kzo9I MspI
 PalI BbvI                      MwoI  SfaNI  BstYI Bsp143I BsiSI AlwI
cagcatgaacaggtaaatataaacatacatttgcagtttttgcatcatggctggatccgggcccataagagcgta base pairs
gtcgtacttgtccatttatatttgtatgtaaacgtcaaaaacgtagtaccgacctaggcccgggtattctcgcat 2701 to
                                                                             2775
 BsuRI Bst71I                            NlaIII NdeII XhoII HpaII BcnI
 Cac8I NlaIII                             CviJI MooI BstI PspN4I NciI
    ItaI                                   BstX2I MflI DpnI HapII Cfr13I NlaIV SduI BanII Hsp92II    AccII AluI BfaI MboI Bsp143I AclWI BcoI
MspR9I AsuI BsuRI FriOI RsaI  BfaI   ThaI   PvuII    BstX2I XhoII PspN4I Cfr9I Bsp120I CviJI BmyI Csp6I    MaeI Cac8I HgaI MspA1I BstYI BamHI DpnI AlwI
atctggaacatcgtatgggtacatggtgtctagctcgcgtcagctgactagaggatccccgggtaccgagctcga base pairs
tagaccttgtagcatacccatgtaccacagatcgagcgcagtcgactgatctcctaggggcccatggctcgagct 2776 to
                                                                             2850
     Sau96I PalI Bsp1286I NlaIII   CviJI Bsh1236I MaeI DpnII MflI MnlI BseDI
    PspOMI HaeIII Eco24I AfaI    AluI MvnI CviJI    NdeII BstI NlaIV Ama87I
  ScrFI AspS9I PspN4I ApaI          BstUI NspBII    Sau3AI Kzo9I BsaJI PspAI BsoBI HapII BanI Csp6I Ecl136II Bbv12I BanII AcsI Cfr13I HaeIII BstDSI MspA1I
    NciI MspR9I Acc65I AfaI EcoICRI Eco24I Alw21I ApoI NlaIV BsuRI DsaI BstUI
 Eco88I HpaII Eco64I NlaIV CviJI Bsp1286I FriOI Sse9I Sau96I CviJI BseDI AccII
attcgggccgcggaggctggatcggtcccggtgtcttctatggaggtcaaaacagcgtggatggcgtctccagg base pairs
taagcccggcgcctccgacctagccagggccacagaagatacctccagttttgtcgcacctaccgcagaggtcc 2851 to
                                                                             2925
AvaI BcnI PspALI BshNI RsaI AluI AspHI SacI SstI TspEI AspS9I BsoFI ItaI NspBII
  XmaI MspI SmaI AccBlI KpnI SduI BmyI TaqI BsiHKAI Tsp509I PalI Fsp4HI MvnI
  BsiSI ScrFI Asp718I PspN4I TthHB8I Psp124BI EcoRI AsuI PspN4I BsaJI ThaI SacII MnlI Bsp143I AsuI Eco47I HpaII Bbv16II HinII HgaI BstNI GsuI Sau3AI
   SstII BglI MboI AlwI Sau96I BsiSI HapII BbsI BstF5I AcyI BsmBI ScrFI MboI
   Sfr303I CviJI Kzo9I SinI AvaII NciI ScrFI MboII Msp17I EcoRII BstOI BomI
cgatctgacggttcactaaacgagctctgcttatataggcctcccaccgtacacgcctactcgacccgggtaccg base pairs
gctagactgccaagtgatttgctcgagacgaatatatccggagggtggcatgtgcggatgagctgggcccatggc 2926 to
                                                                             3000
     Cfr42I DpnII DpnI Bme18I NlaIV BcnI BsmFI MnlI BblII Alw26I MspR9I NdeII
    KspI AciI NdeII AclWI HgiEI PspN4I MspR9I BpiI FokI BsaHI Esp3I MvaI DpnII
   Bsh1236I MwoI Sau3AI Cfr13I AspS9I MspI BpuAI MwoI Hsp92I BsmAI Bst2UI Bsp143I AluI BmyI SacI BsiHKAI Eco147I TaqI Eco88I NciI MspR9I BshNI RsaI AluI
  DpnI Bsp1286I BanII StuI PalI RsaI BcoI AvaI BsiSI PspALI AccBlI KpnI SduI
  Kzo9I SduI Eco24I SstI HaeIII MnlI Ama87I BseDI MspI SmaI Asp718I PspN4I Bsp1286I
```

FIG. 22 (Cont'd)

```
                                                                                 base pairs
agctcgactttcacttttctctatcactgatagggagtggtaaactcgactttcacttttctctatcactgatag      3001 to
tcgagctgaaagtgaaaagagatagtgactatccctcaccatttgagctgaaagtgaaaagagatagtgactatc      3075
   CviJI AspHI FriOI Pme55I SseBI TthHB8I BsaJI BcnI ScrFI Acc65I AfaI EcoICRI
    Ecl136II Bbv12I Alw21I CviJI Csp6I PspAI XmaI HpaII Eco64I Csp6I Ecl136II
       EcoICRI Psp124BI AatI BsuRI AfaI Cfr9I BsoBI HapII BanI NlaIV CviJI TthHB8I AspHI SacI SstI TspRI
  Bbv12I BanII TthHB8I
        FriOI TspRI                   TspRI                   TthHB8I
                                                                                 base pairs
ggagtggtaaactcgactttcacttttctctatcactgatagggagtggtaaactcgactttcacttttctctat      3076 to
cctcaccatttgagctgaaagtgaaaagagatagtgactatccctcaccatttgagctgaaagtgaaaagagata      3150
     Eco24I Alw21I TthHB8I                                    TaqI
 BmyI Psp124BI TaqI
    TaqI BsiHKAI TaqI TspRI         TthHB8I                  TspRI              TthHB8I
                                                                                 base pairs
cactgatagggagtggtaaactcgactttcacttttctctatcactgatagggagtggtaaactcgactttcact      3151 to
gtgactatccctcaccatttgagctgaaagtgaaaagagatagtgactatccctcaccatttgagctgaaagtga      3225
                       TaqI                                       TaqI TspRI         TthHB8I                  TspRI              TthHB8I
                                                                                 base pairs
tttctctatcactgatagggagtggtaaactcgactttcacttttctctatcactgatagggagtggtaaactcg      3226 to
aaagagatagtgactatccctcaccatttgagctgaaagtgaaaagagatagtgactatccctcaccatttgagc      3300
                        TaqI                                      TaqI Eco88I BstYI Sau3AI Sfr274I BsoBI EcoICRI
                                   XhoI PaeR7I MboI BglII XhoI PaeR7I SduI
                        TspRI      Sfr274I DpnII MflI DpnI BcoI TaqI AluI
                                                                                 base pairs
actttcacttttctctatcactgatagggagtggtaaactcgagatctcgagctcaagcttcgaattatcgaatt      3301 to
tgaaagtgaaaagagatagtgactatccctcaccatttgagctctagagctcgagttcgaagcttaatagcttaa      3375
                                    Ama87I TaqI NdeII XhoII Eco88I CviJI
                                    BcoI BsoBI BstX2I Kzo9I AvaI Ecl136II
                                    AvaI TthHB8I Bsp143I Ama87I TthHB8I Psp124BI CviJI Bsp119I TaqI TspEI Fsp4HI NdeII BstDEI DdeI PspN4I
   Eco24I SstI TthHB8I NspV TthHB8I Tsp509I BbvI Sau3AI PvuII MnlI       AluI
    Bbv12I Alw21I SfuI TaqI Sse9I AcsI SfcI PstI MboI DdeI NspBII NlaIV   CviJI
                                                                                 base pairs
cctgcagcccgatctcagctgaggtgcaaaaggctcctgtcatattgtgtcctgctctggtctgccttccacagc
```

FIG. 22 (Cont'd)

```
ggacgtcgggctagagtcgactccacgttttccgaggacagtataacacaggacgagaccagacggaaggtgtcg 3376 to
                                                                             3450
  AspHI SacI BsiHKAI LspI Bpu14I Sse9I BstSFI CviJI Bsp143I MspA1I          Bsc4I
   BmyI FriOI HindIII BstBI TspEI EcoRI BsoFI Bst71I DpnI CviJI CviJI
Bsp1286I BanII AluI Csp45I Tsp509I ApoI ItaI DpnII Kzo9I AluI BstDEI BslI Cfr13I HaeIII       StyI EcoT14I ItaI                  BbvI  BsiYI
   BsiYI AspS9I BsuRI    Eco130I BfaI  BsoFI         CviJI       Hsp92II
     Esp1396I PalI BfaI   AvrII MaeI FokI CviJI    MaeI BsoFI   NlaIII
ttgggggccacctagcccacctctccctagggatgagagcagccactacgggtctaggctgcccatgtaaggagg base pairs
aaccccccggtggatcgggtggagagggatccctactctcgtcggtgatgcccagatccgacgggtacattcctcc 3451 to
                                                                             3525
     Van91I NlaIV MaeI MnlI BssT1I BstF5I  BbvI        BfaI Fsp4HI Bsc4I
AccB7I AsuI PspN4I CviJI  ErhI BsaJI   Fsp4HI               ItaI    BslI
PflMI Sau96I CviJI        BlnI BseDI       Bst71I           Bst71I CviJI EcoRII MvaI BcoI SfaNI ScrFI TruII    Hsp92II Bst71I
     AatI BsuRI BstNI BsmFI EcoRII MvaI MseI AflIII CviJI
MnlI Pme55I BsaJI MspR9I AvaI BstOI TspEI    BspLU11I BsoFI
caaggcctggggacacccgagatgcctggttataattaacccagacatgtggctgcccccccccccccaacacct base pairs
gttccggaccccctgtgggctctacggaccaatattaattgggtctgtacaccgacggggggggggggttgtgga 3526 to
                                                                             3600
     StuI Eco147I Bst2UI Bso3I MspR9I Tsp509I    BstXI Fsp4HI
     HaeIII BseDI ScrFI Eco88I Bst2UI Tru9I       NlaIII BbvI
     PalI SseBI BstOI Ama87I BstNI Sse9I          NspI ItaI BbvI            BsiYI MspI BshNI BseDI ScrFI SspBI Eco130I BstDSI CviJI
  BspMI MwoI MnlI    BseDI BcnI Eco64I BsaJI MspR9I Bsp1407I BssT1I NlaIII
   BsoFI BstDEI  HphI Bsc4I NciI MspR9I EcoRII MvaI CviJI RsaI NcoI DsaI BseRI
gctgcctgagcctcaccccacccggtgcctgggtcttaggctctgtacaccatggaggagaagctcgctctaa base pairs
cgacggactcggagtgggggtggggccacggacccagaatccgagacatgtggtacctcctcttcgagcgagatt 3601 to
                                                                             3675
   Fsp4HI  CviJI        BsaJI MslI ScrFI NlaIV BstCI BstDEI AfaI BsaJI Bsp19I
    ItaI DdeI            BslI HpaII BanI PspN4I Bst2UI BsrGI ErhI EcoT14I MnlI
     Bst71I              BsiSI HapII Acc3I BstNI DdeI Csp6I StyI BseDI Hsp92II BslI Bst2UI NdeII BstI DpnI BsaJI ScrFI MnlI EaeI HaeIII MnlI
   Cac8I       BseDI MspR9I DpnII MflI NlaIV AlwI Bst2UI Cac8I CfrI PalI BstDEI
               Bsc4I BstNI MvaI Sau3AI Kzo9I BseDI MvaI HphI BstDEI CviJI CviJI
aaataaccctgtccctggtggatccaggtgaggggcaggctgagggcggccacttccctcagccgcaggtttgt base pairs
tttattgggacagggaccacctaggtcccactccccgtccgactcccgccggtgaagggagtcggcgtccaaaca 3676 to
                                                                             3750
   AluI        BsaJI BstOI BstYI Bsp143I EcoRII MspR9I BsiYI MnlI ItaI AciI Fsp4HI
               EcoRII ScrFI BstX2I XhoII AclWI BstCI BslI CviJI Fsp4HI DdeI ItaI
```

FIG. 22 (Cont'd)

```
                    BsiYI BsmFI MboI BamHI PspN4I BstNI Bsc4I DdeI BsoFI BsuRI BsoFI

AciI                                            NcoI BstDSI Fsp4HI BsgI
        BsiYI                 MwoI         Tsp509I StyI BseDI Hsp92II Bsc4I
  BspMI Bsc4I            SfcI CviJI           Sse9I Eco130I NlaIII BbvI BslI
tttcccaagaatggttttttctgcttctgtagcttttcctgtcaattctgccatggtggagcagcctgcactgggc base pairs
aaagggttcttaccaaaaagacgaagacatcgaaaaggacagttaagacggtaccacctcgtcggacgtgacccg 3751 to
3825
          BslI                BstSFI            TspEI   ErhI EcoT14I ItaI Cac8I TspRI
                                AluI                    BssT1I Bsp19I CviJI BsiYI
                                                        BsaJI DsaI BsoFI Bst71I BsrSI BsrI                  NciI
BseII                 MspI MspR9I        SfcI                    Bsc4I          MwoI
BseNI                 BsiSI ScrFI        CviJI             SfcI BslI       SfcI CviJI
ttctgggagaaaccaaaccggggttctaacctttcagctacagttattgcctttcctgtagatgggcgactacagc base pairs
aagaccctctttggtttggcccaagattggaaagtcgatgtcaataacggaaaggacatctacccgctgatgtcg 3826 to
                                                                                3900
                      HpaII             AluI              BstSFI          BstSFI
CviJI                 HapII             BstSFI             BsiYI
                      BcnI BstOI Sau96I BsuRI BstNI BstYI Bsp143I NlaIV
              BsmBI      BseDI MvaI AspS9I EcoRII Bst2UI Sau3AI Kzo9I
              Alw26I     EcoRII Bst2UI CviJI BslI BstOI DpnII BamHI DpnI
cccaccccccaccccccgtctcctgtatccttcctgggcctggggatcctaggctttcactggaaatttcccccag base pairs
gggtgggggtgggggcagaggacataggaaggaccccggaccccctaggatccgaaagtgacctttaaaggggggtc 3901 to
                                                                                3975
               BsmAI      BsaJI ScrFI HaeIII BsiYI MspR9I MboI MflI PspN4I
               Esp3I      BstNI Cfr13I PalI BsaJI ScrFI NdeII BstI AvrII
                          MspR9I AsuI Bsc4I BseDI MvaI BstX2I XhoII Eco13

StyI EcoT14I BseNI Tsp509I Bst2UI BfaI PleI Cac8I ScrFI NlaIII EcoT22I
 ErhI BsaJI CviJI Sse9I EcoRII MvaI MaeI MaeIII BstOI MwoI BbuI Zso2I
  BlnI AlwI TspRI AcsI BseDI ScrFI CviJI CviJI EcoRII Cac8I NspI Mph1103I
gtgctgtaggctagagtcacggctcccaagaacagtgcttgcctggcatgcatggttctgaacctccaactgcaa base pairs
cacgacatccgatctcagtgccgagggttcttgtcacgaacggaccgtacgtaccaagacttggaggttgacgtt 3976 to
                                                                                4050
    Ac1WI MaeI BseII BsaJI MspR9I BstSFI NlaIV BstNI MvaI Hsp92II NlaIII
  BssT1I BfaI BsrI ApoI BstOI SfcI HinfI PspN4I MspR9I Ppu10I NsiI MnlI
  OI BseDI BsrSI TspEI BstNI AlwNI Tsp45I TspRI Bst2UI PaeI SphI Hsp92II BsaJI BslI
                  StyI Bsc4I                    MwoI             BseII
                  Eco130I CviJI MnlI         NlaIII  CviJI       BsrSI
aaaatgacacatacccttgacccttggaaggctgaggcaggggattgccatgagtgcaaagccagactggtggc base pairs
ttttactgtgtatgggaactgggaaccttccgactccgtcccccctaacggtactcacgtttcggtctgacccaccg 4051 to
                                                                                4125
                  ErhI BseDI BstDEI             Hsp92II          BseNI
                  BssT1I BsiYI                                    BsrI
```

FIG. 22 (Cont'd)

```
                        EcoT14I   DdeI

MseI                                BsoBI
           AtsI    BsmAI        Tsp509I                             Eco88I
        Ith111I                 Sse9I                               Ama87I
atagttagaccctgtctcaaaaaaccaaaaacaattaaataactaaagtcaggcaagtaatcctactcgggagac base pairs
tatcaatctgggacagagttttttggtttttgttaatttattgatttcagtccgttcattaggatgagccctctg 4126 to
                                                                              4200
           AspI    Alw26I       TspEI                               BcoI
                                Tru9I                               AvaI
                                Tru1I NspI    PalI CviJI ScrFI         BfaI BsmAI              AflIII BstDEI Cac8I Bst2JI       PstNHI      BstSFI
Alw26I    MnlI     BspLU11I HaeIII BstOI            CviJI       AccI
tgaggcagagggattgttacatgtctgaggccagcctggactacatagggtttcaggctagccctgtctacagag base pairs
actccgtctccctaacaatgtacagactccggtcggacctgatgtatcccaaagtccgatcgggacagatgtctc 4201 to
                                                                              4275
DdeI MnlI      MaeIII  NlaIII CviJI BstNI MvaI        NheI CviJI SfcI
BstDEI                 Hsp92II BsuRI MspR9I           MaeI
                         DdeI MnlI EcoRII                   Cac8I DraII CviJI                     MspAlI MwoI    Bst2UI   EcoRII MvaI
   AsuI HaeIII                     AluI Fsp4HI    BstOI Hsp92II Bst2JI
   Cfr13I PalI                     PvuII ItaI     EcoRII ScrFI  BstNI
taaggccctatttcaaaaacacaaacaaaatggttctcccagctgctaatgctcaccaggcatgaagcctggtga base pairs
attccgggataaagttttttgtgtttgttttaccaagagggtcgacgattacgagtggtccgtacttcggaccact 4276 to
                                                                              4350
   Sau96I BsuRI                     CviJI BbvI      PstNI NlaIII MspR9I
   EcoO109I                         NspBII Bst71I   MspR9I    CviJI ScrFI
   AspS9I                           BsoFI           HphI Mval    BstOI BstDEI     MaeIII
MwoI     BsrDI     BsrDI  MnlI Cac8I      CviJI  DdeI MnlI CviJI
gcattagcaatgaaggcaatgaaggagggtgctggctacaatcaaggctgtgggggactgagggcaggctgtaac base pairs
cgtaatcgttacttccgttacttcctcccacgaccgatgttagttccgacaccccctgactcccgtccgacattg 4351 to
                                                                              4425
          MwoI                  CviJI             BsmFI   Cac8I HphI NlaIV EcoRII Bst2UI BsaJI Bst2JI            BcnI ScrFI Sau96I
      AsuI HaeIII BstNI CviJI BstNI HinfI            BsiSI Bsc4I AspS9I
   CviJI Cfr13I CviJI BstOI MaeII BstOI BsmFI        NlaIII MspI BsiYI
aggcttgggggccagggcttatacgtgcctgggactcccaaagtattactgttccatgttcccggcgaagggcca base pairs
tccgaaccccggtcccgaatatgcacggaccctgagggtttcataatgacaaggtacaagggccgcttcccggt 4426 to
                                                                              4500
       Sau96I PalI BseDI MvaI BseDI MvaI              Hsp92II HapII Cfr13I
```

FIG. 22 (Cont'd)

```
      AspS9I BsuRI MspR9I BsaAI MspR9I PleI              NciI MspR9I HaeIII
    PspN4I BsaJI ScrFI EcoRII ScrFI                     HpaII BslI AsuI

Cac8I BsmFI    DdeI                  BsrI           BssT1I Fsp4HI
     PvuII AciI BfaI                    BseNI          ErhI BseDI CviJI
 CviJI AluI FauI AluI  PleI DdeI    NlaIV BsrSI        CviJI EcoT14I Bst71I
gctgtcccccgccagctagactcagcacttagtttaggaaccagtgagcaagtcagcccttggggcagcccatac base pairs
cgacagggggcggtcgatctgagtcgtgaatcaaatccttggtcactcgttcagtcgggaaccccgtcgggtatg 4501 to
4575
   BsuRI MspA1I MaeI       BstDEI     PspN4I TspRI      Eco130I BsoFI    Bsc4I
     CviJI  Cac8I HinfI                BseII           StyI BglI ItaI
   PalI NspBII CviJI BstDEI                            BsaJI MwoI BcvI CviJI BssT1I NlaIII CviJI Cac8I BstNI Cfr13I Eco47I BsiYI BseDI BmyI NlaIV
 BslI Eco130I BseDI Hsp92II ItaI BsgI BstCI SinI AvaII BslI HapII ScrFI AccB1I
    HaeIII NcoI DsaI BstXI Fsp4HI BsaJI ScrFI Sau96I PspN4I BsaJI SduI BanI
aaggccatggggctgggcaagctgcacgcctgggtccggggtgggcacggtgcccgggcaacgagctgaaagctc base pairs
ttccggtaccccgaccgttcgacgtgcggacccaggccccacccgtgccacgggcccgttgctcgactttcgag 4576 to
4650
    BsuRI BsaJI Bsp19I Cac8I BbvI BseDI MvaI HgiEI Bsc4I HpaII MspR9I BshNI
 BsiYI ErhI EcoT14I CviJI AluI Bst71I MspR9I Bme18I AspS9I MspI NciI Bsp1286I
    PalI StyI BstDSI MwoI BsoFI EcoRII Bst2UI AsuI NlaIV BsiSI BcnI Eco64I Eco88I SduI HpaII SrfI AluI Sau96I HaeIII BmyI Bsc4I BsiYI MvaI EcoRII
  Cfr9I BsoBI BcnI ScrFI CviJI PspOMI PspN4I Bsp1286I BsaJI BstOI CviJI Bst2UI
 Ama87I BseDI BmyI HapII CviJI Cfr13I DraII CviJI FriOI MnlI BstNI BsmFI MspR9I
atctgctctcaggggcccctccctgggacagcccctcctggctagtcacaccctgtaggctcctctatataacc base pairs
tagacgagagtccccggggagggaccctgtcggggaggaccgatcagtgtgggacatccgaggagatatattgg 4651 to
4725
 BcoI BsaJI BsiSI MspR9I AluI Bsp120I NlaIV BsuRI ApaI BseDI Bst2UI BstNI
   PspAI XmaI NciI MspI SmaI DdeI AsuI AspS9I SduI BanII EcoRII ScrFI BstOI
 PspN4I AvaI Bsp1286I PspALI BstDEI EcoO109I PalI Eco24I BslI MspR9I MnlI ScrFI MaeI BstSFI BseDI ScrFI BmyI ItaI CviJI HaeIII XbaI BstYI Sau3AI Kzo9I BsaJI
    SfcI PspN4I BstOI Bsp1286I Bsc4I EaeI BsuRI AccBSI NdeII BstI NlaIV Ama87I
    Tsp45I MnlI BstNI SduI Fsp4HI BsiYI CviJI AciI BfaI MboI MflI MnlI BseDI
cagggggcacagggggctgcccccaagctggccgctctagaggatccccgggactagaattcaccatgtctagatta base pairs
gtccccgtgtcccgacgggggttcgaccggcgagatctcctaggggccctgatcttaagtggtacagatctaat 4726 to
4800
 MvaI MaeIII BseRI MspR9I AlwNI BbvI AluI PalI ItaI MaeI BstX2I XhoII AclWI
 CviJI CviJI BsaJI Bst2UI CviJI Bst71I CfrI BsoFI BsrBI DpnII BamHI DpnI AlwI
    BfaI NlaIV EcoRII MvaI BsoFI BslI Cac8I Fsp4HI BstD102I Bsp143I PspN4I Eco88I HpaII MaeI TspEI XbaI Tru9I AspLEI BbvI  HinfI
     BsoBI HapII BfaI ApoI MaeI MseI HhaI Fsp4HI MnlI         Tru1I
    AvaI NciI ScrFI BsmFI Tsp509I HinP1I CviJI Tru9I TfiI     Tru9I
gataaaagtaaagtgattaacagcgcattagagctgcttaatgaggtcggaatcgaaggtttaacaacccgtaaa base pairs
ctattttcatttcactaattgtcgcgtaatctcgacgaattactccagccttagcttccaaattgttgggcattt 4801 to
4875
BcoI XmaI MspI SmaI AcsI HphI BfaI Hin6I BsoFI MseI   TthH38I MseI
```

```
    Cfr9I  BcnI  PspALI  EcoRI  Hsp92II  HspAI  AluI  Bst71I   TaqI
PspAI  BsiSI  MspR9I  Sse9I   NlaIII   TruII  CfoI  ItaI  TruII

BbvI                           MwoI    BbiII
            AluI           ItaI                NspI       FauI    HinII
         HindIII          BsoFI       TspRI    NlaIII     Cac8I   TthHB8I
ctcgcccagaagcttggtgtagagcagcctacactgtattggcatgtaaaaaataagcgggctttgctcgacgcc base pairs
gagcgggtcttcgaaccacatctcgtcggatgtgacataaccgtacatttttattcgcccgaaacgagctgcgg 4876 to
4950
           CviJI          Fsp4HI              Hsp92II            AciI    TaqI BsaHI
          BstXI           CviJI                                  CviJI   Msp17I
                          Bst71I                                         Hsp92I DdeI                 NlaIV               DraI
      HgaI                 BshNI               TruII              Cac8I
   AcyI      MslI          Eco64I              Tru9I BsiYI        CviJI
ttagccattgagatgttagataggcaccatactcacttttgcccttaaaaggggaaagctggcaagatttttta base pairs
aatcggtaactctacaatctatccgtggtatgagtgaaaacgggaaattttcccctttcgaccgttctaaaaat 4951 to
5025
      CviJI                BanI                MseI BslI     AluI
      BstDEI                AccB1I              EcoNI
                           PspN4I                Bsc4I AfaI
                                DdeI       MslI BsrDI Csp6I
cgcaataacgctaaaagtttttagatgtgctttactaagtcatcgcaatggagcaaaagtacattcagatacacgg base pairs
gcgttattgcgatttttcaaaatctacacgaaatgattcagtagcgttacctcgttttcatgtaagtctatgtgcc 5026 to
5100
                                 BstDEI                      RsaI SfcI
   PalI                        Tsp509I
   HaeIII              TthHB8I Sse9I CviJI                    MaeI    AflIII
cctacagaaaaacagtatgaaactctcgaaaatcaattagccttttatgccaacaaggttttcactagagaac base pairs
ggatgtcttttgtcatactttgagagcttttagttaatcggaaaaatacggttgttccaaaaagtgatctcttg 5101 to
5175
CviJI                TaqI    TspEI                            BfaI    MluI
```

FIG. 22 (Cont'd)

```
BsuRI
  BstSFI

BstUI          Hin6I AspLEI                          Bsp143I
 ThaI           HinP1I CfoI                           MboI DpnI
     MwoI  DdeI Aor51HI HaeII                         DpnII MboII  SfaNI
gcgttatatgcactcagcgctgtggggcatttttactttaggttgcgtattggaagatcaagagcatcaagtcgct  base pairs
cgcaatatacgtgagtcgcgacacccccgtaaaatgaaatccaacgcataaccttctagttctcgtagttcagcga  5176 to
                                                                              5250
      Bsh1236I BstDEI AfeI Bsp143II               NdeII
 AccII          HspAI HhaI                        Sau3AI
 MvnI           Eco47III BstH2I                   Kzo9I Tsp509I MboI Kzo9I
                                         ItaI        TthHB8I Bc1I Bsp143I
         MboII                         BsoFI       CviJI Sse9I FbaI Sau3AI
aaagaagaaagggaaacacctactactgatagtatgccgccattattacgacaagctatcgaattatttgatcac  base pairs
tttcttctttccctttgtggatgatgactatcatacggcggtaataatgctgttcgatagcttaataaactagtg  5251 to
                                                                             5325
                                     Fsp4HI        AluI TspEI  DpnII
                                      AciI          TaqI      NdeII
                                                               Ksp22I BssT1I CviJI            TspEI MboI DpnI
          BseDI MwoI          PalI Sse9I NdeII FauNDI           Tru1I
        BsaJI BsgI             HaeIII  FbaI Sau3AI AciI         Tru9I
caaggtgcagagccagccttcttattcggccttgaattgatcatatgcggattagaaaaacaacttaaatgtgaa  base pairs
gttccacgtctcggtcggaagaataagccggaacttaactagtatacgcctaatcttttgttgaatttacactt  5326 to
                                                                            5400
DpnI StyI MslI  CviJI          CviJI  DpnII Kzo9I               MseI
Eco130I HphI Cac8I             BsuRI  BclI Bsp143I
ErhI EcoT14I                          Tsp509I Ksp22I NdeI HgiEI AspS9I AciI BsoFI ThaI MvnI Cac8I Bsh1236I AfaI TaqI Eco0109I Cac8I
    Bme18I PspN4I Csp6I Fsp4HI AccII HhaI AccII Pf123II Tsp509I DraII PalI
     Cfr13I NlaIV Bsh1236I ItaI BsePI AciI ThaI PspLI RsaI TthHB8I AspS9I TthHB8I
agtgggtccgcgtacagccgcgcgcgtacgaaaaacaattacgggtctaccatcgagggcctgctcgatctcccg  base pairs
tcacccaggcgcatgtcggcgcgcgcatgcttttgttaatgcccagatggtagctcccggacgagctagagggc  5401 to
                                                                             5475
       SinI AvaII AccII RsaI HinP1I BstUI CfoI BstUI SunI Sse9I Cfr13I HaeIII
       Sau96I ThaI BstUI CviJI BssHII Bsh1236I MvnI BsiWI TspEI Sau96I CviJI
       AsuI Eco47I MvnI AfaI HspAI Hin6I AspLEI SplI Csp6I AccI AsuI MnlI BsuRI Sau3AI BcnI Hin1I HgaI Ksp632I BsoFI PspN4I BstUI    BseDI MvnI FauI AciI
   NdeII BsiSI HapII Hsp92I Eam1104I Cac8I NlaIV Hin6I AspLEI AccII KspI SacII
      Kzo9I MspI Msp17I BslI EarI CviJI AciI ThaI AciI BsaJI BstJI Sfr303I
gacgacgacgcccccgaagaggcggggctggcggctccgcgcctgtcctttctccccgcgggacacacgcgcaga  base pairs
ctgctgctgcgggggcttctccgccccgaccgccgaggcgcggacaggaaagaggggcgccctgtgtgcgcgtct  5476 to
                                                                              5550
  DpnII DpnI HpaII BbiII Bsc4I MnlI MwoI CviJI AccII HhaI BstDSI Bsh1236I BsmFI
```

*FIG. 22 (Cont'd)*

```
TaqI Bsp143I MspR9I AcyI BsiYI AciI Fsp4HI HspAI Bsh1236I DsaI NspBII SstII
   MboI NciI ScrFI BsaHI MboII FauI ItaI HinP1I MvnI CfoI ThaI MspA1I Cfr42I

AccII AspLEI HindII CviJI Bsh1285I BstOI Ecl136II BmyI SacI BsiHKAI
    ThaI MvnI TthHB8I AspS9I PspN4I CviJI MspR9I AluI AspHI BanII BstDEI     Hin6I
     HinP1I HhaI AccI Sau96I NlaIV PshAI BstNI BsmFI Bsp1286I FriOI DdeI    HinP1I
ctgtcgacggcccccccgaccgatgtcagcctgggggacgagctccacttagacggcgaggacgtggcgatggcg base pairs
gacagctgccggggggggctggctacagtcggaccccctgctcgaggtgaatctgccgctcctgcaccgctaccgc 5551 to
5625
     BstUI SalI HincII HaeIII BstMCI BseDI MvaI CviJI Bbv12I Alw21I        HspAI
  HspAI Bsh1236I Cfr13I PalI BsiEI EcoRII Bst2UI SduI Eco24I SstI MaeII
     Hin6I CfoI TaqI AsuI BsuRI BsaOI BsaJI ScrFI EcoICRI Psp124BI MnlI AspLEI NspI AccII HhaI MamI Bse8I Bsp143I NspI          BcoI XmaI HpaII SmaI
     PaeI SphI BstUI CfoI TthHB8I MboI AflIII     TfiI Ama87I NciI HapII SinI
       NlaIII ThaI Bsh1236I BsaBI DpnII DpnI    BsmFI   BsaJI Eco88I MspI Cfr13I
catgccgacgcgctagacgatttcgatctggacatgttgggggacggggattccccgggtccgggatttaccccc base pairs
gtacggctgcgcgatctgctaaagctagacctgtacaaccccctgcccctaagggggcccaggccctaaatgggg 5626 to
5700
      Cac8I HinP1I HgaI BfaI TaqI NdeII BspLU11I    HinfI Cfr9I BsiSI ScrFI Bme18I
   HhaI Hsp92II Hin6I AspLEI BsrBRI Sau3AI NlaIII      BseDI AvaI BcnI PspALI
   CfoI BbuI HspAI MvnI MaeI Bsh1365I Kzo9I Hsp92II       PspAI BsoBI MspR9I Sau96I HgiEI PspN4I NciI PleI HspAI      CfrI                                BssT1I
   AvaII BslI HapII AciI AspLEI EaeI     TaqI                         ErhI BseDI
     Eco47I BsiYI BcnI HinP1I Bsp143II BsuRI                          SfaNI EcoT14I
cacgactccgccccctacggcgctctggatatggccgacttcgagtttgagcagatgtttaccgatgcccttgga base pairs
gtgctgaggcggggatgccgcgagacctataccggctgaagctcaaactcgtctacaaatggctacgggaacct 5701 to
5775
      AspS9I HpaII HinfI HhaI HaeII CviJI TthHB8I                  Eco130I
   AsuI Bsc4I MspI MspR9I CfoI BstH2I PalI                         StyI Sse9I
      NlaIV BsiSI ScrFI Hin6I    HaeIII                            BsaJI Tsp509I           NdeII BamHI DpnI BseDI AvaI NciI ScrFI Acc65I RsaI PinAI
          AfaI      DpnII Bsp143I AclWI PspAI BsiSI MspR9I Asp718I AfaI BsaWI
          Csp6I     BstYI Sau3AI PspN4I BcoI XmaI HpaII Eco64I NlaIV BslI
attgacgagtacggtgggatggatccccgggtaccggtcgccaccatggtgagcaagggcgaggagctgttcacc base pairs
taactgctcatgccaccctacctaggggcccatggccagcggtggtaccactcgttcccgctcctcgacaagtgg 5776 to
5850
          RsaI     BstF5I MflI Kzo9I AlwI Eco88I MspI SmaI BshNI Bsc4I BssAI
                   BstX2I BstI NlaIV Ama87I BsoBI HapII BanI Csp6I AgeI BsrFI
  TspEI            MboI FokI XhoII BsaJI Cfr9I BcnI PspALI AccB1I PspN4I Cfr10I BsaCI BssT1I Bsp19I BseRI BsaJI ScrFI PspN4I BstOI TthH38I HaeIII
    HpaII Bsh1285I EcoT14I Hsp92II MspI MspR9I AccB1I BstF5I MvaI CviJI PalI
  BsiYI HapII Eco130I BseDI NlaIII BsiSI NciI Eco64I Bsp1286I MspR9I AluI CviJI
ggggtggtgcccatcctggtcgagctggacggcgacgtaaacggccacaagttcagcgtgtccggcgagggcgag base pairs
ccccaccacgggtaggaccagctcgacctgccgctgcatttgccggtgttcaagtcgcacaggccgctcccgctc 5851 to
5925
    BsiSI BsiEI StyI BstDSI MnlI HpaII BcnI BanI SduI EcoRII ScrFI MaeII HpaII
```

*FIG. 22 (Cont'd)*

```
     MspI BstMCI NcoI DsaI HphI AluI BseDI MslI NlaIV BstNI Bst2UI EaeI BsuRI
Bse118I KpnI ErhI BsaJI MslI CviJI HapII HphI BshNI BmyI FokI TaqI CfrI BsiSI

MspI                                       Cfr10I MwoI ItaI BsaJI BsiYI
  HapII           AluI                     BsrFI HapII Fsp4HI EcoRII BstOI
    MwoI SfaNI    Cac8I       Eco57I       BsgI HpaII AluI Bst71I Bsp1286I
ggcgatgccacctacggcaagctgaccctgaagttcatctgcaccaccggcaagctgcccgtgccctggcccacc base pairs
ccgctacggtggatgccgttcgactgggacttcaagtagacgtggtggccgttcgacgggcacgggaccgggtgg 5926 to
                                                                             6000
      BcgI       CviJI                    BssAI MspI BsoFI Bsc4I BslI
  MnlI                                    Bse118I CviJI MwoI SduI BmyI
  MnlI                                      BsiSI Cac8I BbvI BseDI BstNI MvaI AsuI MslI Bsc4I BstNI Cac8I     ItaI              ItaI
       Sau96I BsuRI BssSI BseDI MvaI     CviJI             BsoFI
    ScrFI AspS9I MaeIII BsaJI ScrFI TspRI BsoFI       NlaIII BcvI
ctcgtgaccaccctgacctgggcgtgcagtgcttcagccgctaccccgaccacatgaagcagcacgacttcttc base pairs
gagcactggtgggactggaccccgcacgtcacgaagtcggcgatggggctggtgtacttcgtcgtgctgaagaag 6001 to
                                                                             6075
MspR9I HaeIII BsiI BslI BstOI MwoI    Eco57I        Hsp92II
Bst2UI CviJI MnlI EcoRII MspR9I BsgI   Fsp4HI       Fsp4HI
  Cfr13I PalI Tsp45I BsiYI Bst2UI       AciI        Bst71I MspR9I HhaI                              Hin6I
            Hsp92II   BstNI HinP1I                            ThaI
MboII  AciI      CviJI EcoRII MvaI CfoI  MboII                HinP1I
aagtccgccatgcccgaaggctacgtccaggagcgcaccatcttcttcaaggacgacggcaactacaagacccgc base pairs
ttcaggcggtacgggcttccgatgcaggtcctcgcgtggtagaagaagttcctgctgccgttgatgttctgggcg 6076 to
                                                                             6150
         NlaIII      MaeII ScrFI Hin6I                     HspAI
                           BstOI HspAI                     AccII
                           Bst2UI AspLEI                   BstJI AciI BsaJI TthHB8I     BstNI HphI        AluI
   MvnI CfoI MnlI         EcoRII ScrFI   TaqI        TaqI
    AspLEI BslI MnlI      BsaJI MspR9I AciI CviJI Eco57I           MnlI
gccgaggtgaagttcgagggcgacaccctggtgaaccgcatcgagctgaagggcatcgacttcaaggaggacggc base pairs
cggctccacttcaagctcccgctgtgggaccacttggcgtagctcgacttcccgtagctgaagttcctcctgccg 6151 to
                                                                             6225
   Bsh1236I BsiYI       BseDI Bst2UI    TthHB8I      TthHB8I
   FauI Bsc4I HphI      MslI MvaI       SfaNI        SfaNI
   HhaI BseDI TaqI      BstOI BstNI ScrFI          BpmI
   BseDI Bst2UI AluI Csp6I
    EcoRII FokI Bsp1286I             CviJI MaeII    HphI        MboII
aacatcctggggcacaagctggagtacaactacatcagccacaacgtctatatcaccgccgacaagcagaagaac base pairs
ttgtaggacccgtgttcgacctcatgttgatgtagtcggtgttgcagatatagtggcggctgttcgtcttcttg 6226 to
                                                                             6300
```

FIG. 22 (Cont'd)

```
       BsaJI MspR9I CviJI RsaI                                  AciI
        BstF5I SduI    GsuI
        BstOI MvaI BmyI  AfaI

BsuRI     MboI Bsp143I                         Bst71I AluI
         CviJI     BstX2I DpnI    TthHB8I    ItaI   ItaI BbvI
   SfaNI           BstYI MflI AlwI     MnlI BsoFI  BsoFI Bst71I
ggcatcaaggccaacttcaagatccgccacaacatcgaggacggcagcgtgcagctcgccgaccactaccagcag base pairs
ccgtagttccggttgaagttctaggcggtgttgtagctcctgccgtcgcacgtcgagcggctggtgatggtcgtc  6301 to
                                                                             6375
         HaeIII    DpnII XhoII AciI            Fsp4HI Fsp4HI Cac8I
         PalI      NdeII Kzo9I    TaqI          BbvI CviJI
                   Sau3AI AclWI                 Cac8I BsgI HaeIII  BsoFI                      BmyI  BseNI BstDEI
              AsuI PalI ItaI                     Bsp1286I  AciI
              Cfr13I BsuRI BbvI                  DdeI  SduI BsiHKAI
aacaccccccatcggcgacggccccgtgctgctgcccgacaaccactacctgagcacccagtccgccctgagcaaa base pairs
ttgtgggggtagccgctgccggggcacgacgacgggctgttggtgatggactcgtgggtcaggcgggactcgttt  6376 to
                                                                             6450
              Sau96I NlaIV Bst71I           BstDEI Alw21I BsrI
              AspS9I PspN4I                 AspHI BsrSI DdeI
              CviJI   Fsp4HI                Bbv12I BseII ThaI Bsh1236I DpnI Hsp92II BomI  Fsp4HI HapII NdeII AlwI
         Hin6I MvnI NdeII NlaIII AsuI GsuI  BsoFI MspI BcnI Sau3AI NlaIII
         HinP1I AspLEI Bsp143I Sau96I AspS9I ItaI HpaII ScrFI Bsp143I
gaccccaacgagaagcgcgatcacatggtcctgctggagttcgtgaccgccgccgggatcactctcggcatggac base pairs
ctggggttgctcttcgcgctagtgtaccaggacgacctcaagcactggcggcggccctagtgagagccgtacctg  6451 to
                                                                             6525
         HspAI BstUI MboI Cfr13I HgiEI Tsp45I Bsc4I BsiYI MboI DpnI Hsp92II
         HhaI CfoI Sau3AI SinI AvaII MaeIII  BslI NciI DpnII AclWI
         AccII DpnII Kzo9I Bme18I Eco47I  AciI BsiSI MspR9I Kzo9I Bsp1407I   BsoFI ItaI CviJI BsaCI Bsh1236I Sau3AI BsrBI
    SspBI      CfrI Fsp4HI BsuRI AccII Hinfl DpnII MamI      MnlI
   CviJI AfaI  EaeI NotI HaeIII Bsh1285I PleI MboI DpnI CviJI
gagctgtacaagtaaagcggccgcgactctagatcataatcagccataccacatttgtagaggttttacttgctt base pairs
ctcgacatgttcatttcgccggcgctgagatctagtattagtcggtatggtgtaaacatctccaaaatgaacgaa  6526 to
                                                                             6600
      Csp6I      BstZI EclXI PalI BstMCI AciI BfaI Kzo9I Bsh1365I
   AluI RsaI     CciNI Eco52I BsiEI BstUI XbaI NdeII BsaBI
      BsrGI      EagI XmaIII AciI ThaI MvnI MaeI Bsp143I Bse8I MunI         HincII
   TruII                                     Mva1269I     MseI
   Tru9I         MnlI       MnlI              MfeI BsaMI Tru9I
taaaaaaccctcccacacctcccctgaacctgaaacataaaatgaatgcaattgttgttgttaacttgtttattg base pairs
atttttggagggtgtggagggggacttggactttgtattttacttacgttaacaacaacaattgaacaaataac  6601 to
                                                                            6675
```

FIG. 22 (Cont'd)

```
             MseI                            BsmI Tsp509I HpaI
          DraI                               Sse9I         TruII
                                             TspEI         HindII AluI                     ApoI                           BsaMI
         ItaI Bst71I                 AcsI                           Mva1269I
         BsoFI     MaeIII         SfaNI                           TspRI
cagcttataatggttacaaataaagcaatagcatcacaaatttcacaaataaagcattttttttcactgcattcta  base pairs
gtcgaatattaccaatgtttatttcgttatcgtagtgtttaaagtgtttatttcgtaaaaaaagtgacgtaagat  6676 to
                                                                              6750
         Fsp4HI                       Sse9I                         BsmI
           CviJI                      TspEI                         MaeI
              BbvI                    Tsp509I                       BfaI
                              MspCI
                              Bst98I
                              BspTI MseI
gttgtggtttgtccaaactcatcaatgtatcttaag    base pairs
caacaccaaacaggtttgagtagttacatagaattc    6751 to 6786
                              AflII TruII
                              Vha464I
                              BfrI Tru9I
```

FIG. 22 (Cont'd)

Table by Enzyme Name

| Enzyme name | No. cuts | Positions of sites | Recognition sequence |
|---|---|---|---|
| AatI | 2 | 2964 3530 | agg/cct |
| AatII | 1 | 2462 | gacgt/c |
| Acc65I | 5 | 1107 1570 2837 2994 5805 | g/gtacc |
| AccB1I | 11 | 926 1107 1255 1570 2837 2994 3626 4624 4973 5805 5856 | g/gyrcc |
| AccB7I | 3 | 1102 2150 3450 | ccannnn/ntgg |
| AccBSI | 1 | 4760 | gagcgg |
| AccI | 7 | 1577 1613 1637 2187 4267 5446 5554 | gt/mkac |
| AccII | 17 | 238 319 637 1568 2812 2861 5176 5410 5420 5424 5514 5533 5544 5635 6149 6467 6548 | cg/cg |
| AciI | 44 | 241 245 287 350 463 601 640 707 748 1213 1251 1283 1514 1556 1569 1636 1782 1900 2355 2862 3725 3742 4512 4758 4935 5290 5375 5411 5421 5500 5509 5515 5534 5711 6042 6083 6150 6189 6284 6327 6440 6500 6545 6549 | ccgc |
| AclNI | 1 | 1592 | a/ctagt |
| AclWI | 14 | 281 466 1096 1559 2683 2757 2832 2874 3699 3946 4769 5800 6325 6510 | ggatc |
| AcsI | 11 | 69 1586 1653 1801 2320 2571 2849 3371 3962 4780 6713 | r/aatty |
| AcyI | 4 | 2459 2915 4946 5483 | gr/cgyc |
| AfaI | 20 | 254 536 1109 1572 2196 2303 2465 2597 2795 2839 2975 2996 3648 5084 5413 5427 5785 5807 6250 6532 | gt/ac |
| AfeI | 1 | 5193 | agc/gct |
| AflII | 2 | 1 6781 | c/ttaag |
| AflIII | 6 | 1058 1233 3570 4219 5174 5657 | a/crygt |
| AgeI | 1 | 5808 | a/ccggt |
| AluI | 47 | 108 258 432 543 591 807 840 912 945 1326 2060 2317 2540 2556 2808 2818 2845 2949 3002 3352 3358 3393 3449 3665 3781 3861 4317 4501 4515 4596 4640 4647 4750 4833 4887 5009 5305 5592 5841 5874 5946 5979 6195 6243 6354 6528 6678 | ag/ct |
| Alw21I | 11 | 360 1075 1626 1766 1925 2847 2951 3004 3354 5594 6430 | gwgcw/c |
| Alw26I | 8 | 1711 1949 2224 2614 2921 3920 | gtctc |

FIG. 22 (Cont'd)

|           |    |                                          |            |
|-----------|----|------------------------------------------|------------|
|           |    | 4143 4200                                |            |
| Alw44I    | 2  | 1071 1762                                | g/tgcac    |
| AlwI      | 14 | 281 466 1096 1559 2683 2757 2832 2874 3699 3946 4769 5800 6325 6510 | ggatc |
| AlwNI     | 4  | 2150 2375 3978 4739                      | cagnnn/ctg |
| Ama87I    | 11 | 1559 2833 2990 3339 3347 3541 4191 4628 4770 5679 5801 | c/ycgrg |
| Aor51HI   | 1  | 5193                                     | agc/gct    |
| ApaI      | 4  | 1439 1566 2763 4667                      | gggcc/c    |
| ApaLI     | 2  | 1071 1762                                | g/tgcac    |
| ApoI      | 11 | 69 1586 1653 1801 2320 2571 2849 3371 3962 4780 6713 | r/aatty |
| AseI      | 1  | 1700                                     | at/taat    |
| AsnI      | 1  | 1700                                     | at/taat    |
| Asp700I   | 1  | 1340                                     | gaann/nttc |
| Asp718I   | 5  | 1107 1570 2837 2994 5805                 | g/gtacc    |
| AspHI     | 11 | 360 1075 1626 1766 1925 2847 2951 3004 3354 5594 6430 | gwgcw/c |
| AspI      | 1  | 4136                                     | gacn/nngtc |
| AspLEI    | 16 | 321 637 678 2495 2553 4825 5194 5422 5516 5546 5625 5637 5722 6110 6151 6467 | gcg/c |
| AspS9I    | 29 | 306 389 790 1026 1080 1422 1435 1562 1733 1954 2015 2687 2759 2856 2875 3455 3934 4279 4434 4495 4608 4663 5405 5457 5559 5683 5993 6394 6477 | g/gncc |
| AsuI      | 29 | 306 389 790 1026 1080 1422 1435 1562 1733 1954 2015 2687 2759 2856 2875 3455 3934 4279 4434 4495 4608 4663 5405 5457 5559 5683 5993 6394 6477 | g/gncc |
| AtsI      | 1  | 4136                                     | gacn/nngtc |
| AvaI      | 11 | 1559 2833 2990 3339 3347 3541 4191 4628 4770 5679 5801 | c/ycgrg |
| AvaII     | 8  | 306 1954 2015 2875 4608 5405 5683 6477   | g/gwcc     |
| AvrII     | 3  | 1397 3476 3946                           | c/ctagg    |
| BalI      | 2  | 974 2044                                 | tgg/cca    |
| BamHI     | 7  | 1555 2753 2828 3695 3942 4765 5796       | g/gatcc    |
| BanI      | 11 | 926 1107 1255 1570 2837 2994 3626 4624 4973 5805 5856 | g/gyrcc |
| BanII     | 10 | 1439 1566 2157 2763 2847 2951 3004 3354 4667 5594 | grgcy/c |
| BanIII    | 1  | 2471                                     | at/cgat    |
| BbiII     | 4  | 2459 2915 4946 5483                      | gr/cgyc    |
| BbrPI     | 1  | 1236                                     | cac/gtg    |
| BbsI      | 4  | 1320 1420 2122 2889                      | gaagac     |

FIG. 22 (Cont'd)

```
BbuI        2   4025 5629                              gcatg/c
Bbv12I      11  360 1075 1626 1766 1925 2847           gwgcw/c
                2951 3004 3354 5594 6430
Bbv16II     4   1320 1420 2122 2889                    gaagac
BbvI        29  112 382 436 443 727 808 1286           gcagc
                1730 1904 2557 2697 3383 3493
                3512 3581 3605 3814 4321 4569
                4600 4743 4837 4903 5983 6064
                6348 6355 6406 6679
BcgI        2   865 5933                               cgannnnnntgc
BclI        2   5319 5363                              t/gatca
BcnI        23  281 935 1434 1560 1907 1952 2482       cc/sgg
                2758 2834 2879 2991 3624 3844
                4487 4612 4629 4771 5473 5680
                5687 5802 5850 6504
BcoI        11  1559 2833 2990 3339 3347 3541          c/ycgrg
                4191 4628 4770 5679 5801
BfaI        22  36 230 1030 1398 1593 2805 2823        c/tag
                3462 3477 3504 3947 3986 4258
                4516 4693 4760 4777 4793 5167
                5638 6554 6748
BfrI        2   1 6781                                 c/ttaag
BglI        3   1253 2864 4562                         gccnnnn/nggc
BglII       1   3343                                   a/gatct
BlnI        3   1397 3476 3946                         c/ctagg
BlpI        1   1740                                   gc/tnagc
Bme18I      8   306 1954 2015 2875 4608 5405           g/gwcc
                5683 6477
BmyI        25  360 551 800 929 1075 1439 1566         gdgch/c
                1626 1766 1925 2157 2763 2847
                2951 3004 3354 4622 4629 4667
                4733 5594 5861 5990 6239 6430
BpiI        4   1320 1420 2122 2889                    gaagac
BpmI        6   303 543 2596 2924 6249 6489            ctggag
Bpu1102I    1   1740                                   gc/tnagc
Bpu14I      1   3361                                   tt/cgaa
BpuAI       4   1320 1420 2122 2889                    gaagac
Bsa29I      1   2471                                   at/cgat
BsaAI       2   1236 4449                              yac/gtr
BsaBI       3   225 5648 6561                          gatnn/nnatc
BsaHI       4   2459 2915 4946 5483                    gr/cgyc
BsaJI       55  551 606 630 793 933 963 1014           c/cnngg
                1076 1397 1559 1566 1644 1914
                2018 2150 2400 2832 2859 2990
                3476 3531 3622 3630 3652 3688
                3699 3800 3931 3937 3946 3971
                4071 4437 4453 4558 4580 4604
                4611 4628 4671 4724 4769 5325
                5531 5580 5678 5769 5800 5819
                5849 5989 6017 6152 6176 6231
```

*FIG. 22 (Cont'd)*

```
BsaMI       6    44  143 1374 1407 6649 6748        gaatgc
BsaOI       5   242 1884 5570 5813 6546             cgry/cg
BsaWI       1  5808                                  w/ccggw
Bsc4I      36   285  635  798 1019 1101 1271 1291   ccnnnn/nnngg
               1454 1866 1889 2017 2149 2280
               3449 3517 3622 3688 3704 3759
               3819 3884 3936 4075 4491 4574
               4609 4671 4749 4998 5492 5684
               5807 5989 6016 6152 6502

BscI        1  2471                                 at/cgat
Bse118I     4   811 1495 5808 5971                  r/ccggy
Bse1I      12   355 1202 1525 1859 2148 2187        actgg
               2688 3823 3961 4120 4545 6436
Bse8I       3   225 5648 6561                       gatnn/nnatc
BseCI       1  2471                                 at/cgat
BseDI      55   551  606  630  793  933  963 1014   c/cnngg
               1076 1397 1559 1566 1644 1914
               2018 2150 2400 2832 2859 2990
               3476 3531 3622 3630 3652 3688
               3699 3800 3931 3937 3946 3971
               4071 4437 4453 4558 4580 4604
               4611 4628 4671 4724 4769 5325
               5531 5580 5678 5769 5800 5819
               5849 5989 6017 6152 6176 6231
BseNI      12   355 1202 1525 1859 2148 2187        actgg
               2688 3823 3961 4120 4545 6436
BsePI       1  5420                                 g/cgcgc
BseRI       5   951 1154 3662 4716 5841             gaggag
BsgI       10   438  762  823 1729 3820 4602 5335   gtcag
               5969 6030 6354
Bsh1236I   17   238  319  637 1568 2812 2861 5176   cg/cg
               5410 5420 5424 5514 5533 5544
               5635 6149 6467 6548
Bsh1285I    5   242 1884 5570 5813 6546             cgry/cg
Bsh1365I    3   225 5648 6561                       gatnn/nnatc
BshNI      11   926 1107 1255 1570 2837 2994        g/gyrcc
               3626 4624 4973 5805 5856
BsiEI       5   242 1884 5570 5813 6546             cgry/cg
BsiHKAI    11   360 1075 1626 1766 1925 2847        gwgcw/c
               2951 3004 3354 5594 6430
BsiI        3   786 2605 6006                       ctcgtg
BsiSI      29   281  812  872  935 1433 1496 1560   c/cgg
               1906 1951 2482 2757 2834 2879
               2991 3624 3843 4487 4611 4629
               4771 5473 5680 5686 5802 5809
               5849 5912 5972 6503
BsiWI       1  5425                                 c/gtacg
BsiYI      36   286  636  799 1020 1102 1272 1292   ccnnnnn/nngg
               1455 1867 1890 2018 2150 2281
               3450 3518 3623 3689 3705 3760
```

FIG. 22 (Cont'd)

|         |    |                                                                                                                                                  |            |
|---------|----|--------------------------------------------------------------------------------------------------------------------------------------------------|------------|
|         |    | 3820 3885 3937 4076 4492 4575<br>4610 4672 4750 4999 5493 5685<br>5808 5990 6017 6153 6503                                                       |            |
| BslI    | 36 | 286  636  799 1020 1102 1272 1292<br>1455 1867 1890 2018 2150 2281<br>3450 3518 3623 3689 3705 3760<br>3820 3885 3937 4076 4492 4575<br>4610 4672 4750 4999 5493 5685<br>5808 5990 6017 6153 6503 | ccnnnnn/nngg |
| BsmAI   | 8  | 1711 1949 2224 2614 2921 3920<br>4143 4200                                                                                                       | gtctc      |
| BsmBI   | 2  | 2921 3920                                                                                                                                        | cgtctc     |
| BsmFI   | 14 | 1014 1862 1957 2880 3539 3690<br>4408 4460 4508 4680 4777 5539<br>5589 5670                                                                      | gggac      |
| BsmI    | 6  | 44 143 1374 1407 6649 6748                                                                                                                       | gaatgc     |
| BsoBI   | 11 | 1559 2833 2990 3339 3347 3541<br>4191 4628 4770 5679 5801                                                                                        | c/ycgrg    |
| BsoFI   | 45 | 109  239  285  379  433  440  724  746<br>805 1210 1248 1283 1512 1727<br>1898 2554 2694 2859 3380 3490<br>3509 3578 3602 3723 3739 3811<br>4318 4566 4597 4740 4755 4834<br>4900 5287 5418 5507 5980 6039<br>6061 6345 6352 6403 6500 6543<br>6676 | gc/ngc     |
| Bsp106I | 1  | 2471                                                                                                                                             | at/cgat    |
| Bsp119I | 1  | 3361                                                                                                                                             | tt/cgaa    |
| Bsp120I | 4  | 1435 1562 2759 4663                                                                                                                              | g/ggccc    |
| Bsp1286I| 25 | 360  551  800  929 1075 1439 1566<br>1626 1766 1925 2157 2763 2847<br>2951 3004 3354 4622 4629 4667<br>4733 5594 5861 5990 6239 6430             | gdgch/c    |
| Bsp1407I| 3  | 252 3646 6530                                                                                                                                    | t/gtaca    |
| Bsp143I | 31 | 226  276  314  462 1086 1091 1555<br>2036 2173 2468 2472 2678 2753<br>2828 2870 2926 3343 3385 3695<br>3942 4765 5229 5319 5363 5466<br>5649 5796 6320 6468 6506 6556 | /gatc      |
| Bsp143II| 3  | 2496 5195 5723                                                                                                                                   | rgcgc/y    |
| Bsp1720I| 1  | 1740                                                                                                                                             | gc/tnagc   |
| Bsp19I  | 6  | 963 1644 3652 3800 4580 5819                                                                                                                     | c/catgg    |
| BspDI   | 1  | 2471                                                                                                                                             | at/cgat    |
| BspHI   | 1  | 1618                                                                                                                                             | t/catga    |
| BspLU11I| 4  | 1058 3570 4219 5657                                                                                                                              | a/catgt    |
| BspMI   | 3  | 1223 3602 3746                                                                                                                                   | acctgc     |
| BspTI   | 2  | 1 6781                                                                                                                                           | c/ttaag    |
| BspXI   | 1  | 2471                                                                                                                                             | at/cgat    |
| BsrBI   | 1  | 4760                                                                                                                                             | gagcgg     |
| BsrBRI  | 3  | 225 5648 6561                                                                                                                                    | gatnn/nnatc|

FIG. 22 (Cont'd)

| | | | |
|---|---|---|---|
| BsrDI | 4 | 1449 4362 4371 5074 | gcaatg |
| BsrFI | 4 | 811 1495 5808 5971 | r/ccggy |
| BsrGI | 3 | 252 3646 6530 | t/gtaca |
| BsrI | 12 | 355 1202 1525 1859 2148 2187 2688 3823 3961 4120 4545 6436 | actgg |
| BsrSI | 12 | 355 1202 1525 1859 2148 2187 2688 3823 3961 4120 4545 6436 | actgg |
| BssAI | 4 | 811 1495 5808 5971 | r/ccggy |
| BssHII | 1 | 5420 | g/cgcgc |
| BssSI | 3 | 786 2605 6006 | ctcgtg |
| BssT1I | 13 | 963 1397 1644 3476 3652 3800 3946 4071 4558 4580 5325 5769 5819 | c/cwwgg |
| Bst1107I | 1 | 2188 | gta/tac |
| Bst2UI | 37 | 553 607 682 794 919 1267 1426 2013 2019 2151 2548 2922 3532 3551 3631 3690 3700 3932 3938 3973 4018 4236 4332 4344 4438 4454 4605 4673 4689 4726 5581 5866 5991 6018 6103 6178 6232 | cc/wgg |
| Bst71I | 29 | 112 382 436 443 727 808 1286 1730 1904 2557 2697 3383 3493 3512 3581 3605 3814 4321 4569 4600 4743 4837 4903 5983 6064 6348 6355 6406 6679 | gcagc |
| Bst98I | 2 | 1 6781 | c/ttaag |
| BstBI | 1 | 3361 | tt/cgaa |
| BstD102I | 1 | 4760 | gagcgg |
| BstDEI | 27 | 341 359 1740 1815 2076 2222 2264 2561 3389 3394 3606 3637 3716 3734 4081 4200 4225 4408 4521 4528 4658 4950 5059 5188 5598 6424 6442 | c/tnag |
| BstDSI | 12 | 963 1014 1566 1644 1914 2400 2859 3652 3800 4580 5531 5819 | c/crygg |
| BstF5I | 12 | 559 925 1124 1866 2056 2353 2452 2914 3485 5796 5866 6232 | ggatg |
| BstH2I | 3 | 2496 5195 5723 | rgcgc/y |
| BstI | 7 | 1555 2753 2828 3695 3942 4765 5796 | g/gatcc |
| BstMCI | 5 | 242 1884 5570 5813 6546 | cgry/cg |
| BstNI | 37 | 553 607 682 794 919 1267 1426 2013 2019 2151 2548 2922 3532 3551 3631 3690 3700 3932 3938 3973 4018 4236 4332 4344 4438 4454 4605 4673 4689 4726 5581 5866 5991 6018 6103 6178 6232 | cc/wgg |
| BstOI | 37 | 553 607 682 794 919 1267 1426 2013 2019 2151 2548 2922 3532 3551 3631 3690 3700 3932 3938 | cc/wgg |

*FIG. 22 (Cont'd)*

| | | | |
|---|---|---|---|
| | | 3973 4018 4236 4332 4344 4438 | |
| | | 4454 4605 4673 4689 4726 5581 | |
| | | 5866 5991 6018 6103 6178 6232 | |
| BstSFI | 12 | 1300 1581 2376 3377 3776 3862 | c/tryag |
| | | 3880 3894 3979 4268 4704 5102 | |
| BstUI | 17 | 238 319 637 1568 2812 2861 5176 | cg/cg |
| | | 5410 5420 5424 5514 5533 5544 | |
| | | 5635 6149 6467 6548 | |
| BstX2I | 12 | 462 1091 1555 2678 2753 2828 | r/gatcy |
| | | 3343 3695 3942 4765 5796 6320 | |
| BstXI | 4 | 970 3573 4587 4888 | ccannnnn/ntgg |
| BstYI | 12 | 462 1091 1555 2678 2753 2828 | r/gatcy |
| | | 3343 3695 3942 4765 5796 6320 | |
| BstZI | 2 | 239 6543 | c/ggccg |
| Bsu15I | 1 | 2471 | at/cgat |
| BsuRI | 42 | 241 391 503 792 892 974 1028 | gg/cc |
| | | 1081 1247 1424 1437 1499 1520 | |
| | | 1564 1735 1829 2044 2689 2761 | |
| | | 2858 2964 3457 3530 3725 3936 | |
| | | 4230 4280 4436 4497 4579 4665 | |
| | | 4754 5100 5354 5459 5560 5734 | |
| | | 5894 5994 6310 6395 6545 | |
| Cac8I | 38 | 430 437 761 809 842 1287 1566 | gcn/ngc |
| | | 1737 2345 2356 2691 2810 3667 | |
| | | 3713 3815 4014 4023 4232 4259 | |
| | | 4383 4416 4499 4513 4594 4601 | |
| | | 4752 4934 5011 5339 5422 5461 | |
| | | 5504 5627 5944 5977 6025 6349 | |
| | | 6356 | |
| CciNI | 2 | 239 6543 | gc/ggccgc |
| CelII | 1 | 1740 | gc/tnagc |
| CfoI | 16 | 321 637 678 2495 2553 4825 5194 | gcg/c |
| | | 5422 5516 5546 5625 5637 5722 | |
| | | 6110 6151 6467 | |
| Cfr10I | 4 | 811 1495 5808 5971 | r/ccggy |
| Cfr13I | 29 | 306 389 790 1026 1080 1422 1435 | g/gncc |
| | | 1562 1733 1954 2015 2687 2759 | |
| | | 2856 2875 3455 3934 4279 4434 | |
| | | 4495 4608 4663 5405 5457 5559 | |
| | | 5683 5993 6394 6477 | |
| Cfr42I | 3 | 1569 2862 5534 | ccgc/gg |
| Cfr9I | 7 | 1559 2833 2990 4628 4770 5679 | c/ccggg |
| | | 5801 | |
| CfrI | 12 | 239 501 890 972 1245 1518 2042 | y/ggccr |
| | | 3723 4752 5732 5892 6543 | |
| ClaI | 1 | 2471 | at/cgat |
| Csp45I | 1 | 3361 | tt/cgaa |
| Csp6I | 20 | 253 535 1108 1571 2195 2302 2464 | g/tac |
| | | 2596 2794 2838 2974 2995 3647 | |
| | | 5083 5412 5426 5784 5806 6249 | |

FIG. 22 (Cont'd)

|  |  |  |  |
|---|---|---|---|
| CviJI | 160 | 6531<br>108 218 241 258 391 432 503 523<br>543 591 691 748 792 807 840 892<br>912 945 974 1028 1081 1129 1156<br>1240 1247 1326 1424 1437 1499<br>1514 1520 1564 1649 1735 1744<br>1829 1871 1938 2001 2044 2060<br>2091 2100 2155 2285 2317 2343<br>2434 2540 2556 2582 2634 2689<br>2750 2761 2808 2818 2845 2858<br>2867 2949 2964 3002 3352 3358<br>3382 3393 3408 3449 3457 3465<br>3492 3508 3530 3577 3610 3642<br>3665 3715 3725 3738 3781 3813<br>3824 3861 3899 3936 3951 3985<br>3997 4080 4111 4230 4234 4257<br>4261 4280 4317 4342 4385 4397<br>4418 4428 4436 4442 4497 4501<br>4515 4556 4568 4579 4587 4596<br>4640 4647 4665 4682 4692 4710<br>4739 4750 4754 4833 4887 4902<br>4936 4954 5009 5100 5140 5305<br>5337 5341 5354 5417 5459 5502<br>5509 5560 5579 5592 5734 5841<br>5874 5894 5946 5979 5994 6038<br>6095 6195 6243 6263 6310 6354<br>6395 6528 6545 6568 6678 | rg/cy |
| DdeI | 27 | 341 359 1740 1815 2076 2222 2264<br>2561 3389 3394 3606 3637 3716<br>3734 4081 4200 4225 4408 4521<br>4528 4658 4950 5059 5188 5598<br>6424 6442 | c/tnag |
| DpnI | 31 | 228 278 316 464 1088 1093 1557<br>2038 2175 2470 2474 2680 2755<br>2830 2872 2928 3345 3387 3697<br>3944 4767 5231 5321 5365 5468<br>5651 5798 6322 6470 6508 6558 | ga/tc |
| DpnII | 31 | 226 276 314 462 1086 1091 1555<br>2036 2173 2468 2472 2678 2753<br>2828 2870 2926 3343 3385 3695<br>3942 4765 5229 5319 5363 5466<br>5649 5796 6320 6468 6506 6556 | /gatc |
| DraI | 4 | 185 2325 4997 6601 | ttt/aaa |
| DraII | 8 | 1026 1080 1436 1733 1954 4279<br>4663 5457 | rg/gnccy |
| DraIII | 1 | 1192 | cacnnn/gtg |
| DrdI | 1 | 1715 | gacnnnn/nngtc |
| DsaI | 12 | 963 1014 1566 1644 1914 2400<br>2859 3652 3800 4580 5531 5819 | c/crygg |
| EaeI | 12 | 239 501 890 972 1245 1518 2042 | y/ggccr |

FIG. 22 (Cont'd)

|  |  |  |  |
|---|---|---|---|
|  |  | 3723 4752 5732 5892 6543 |  |
| EagI | 2 | 239 6543 | c/ggccg |
| Eam1104I | 1 | 5496 | ctcttc |
| EarI | 1 | 5496 | ctcttc |
| Ecl136II | 5 | 2845 2949 3002 3352 5592 | gag/ctc |
| EclXI | 2 | 239 6543 | c/ggccg |
| Eco130I | 13 | 963 1397 1644 3476 3652 3800 3946 4071 4558 4580 5325 5769 5819 | c/cwwgg |
| Eco147I | 2 | 2964 3530 | agg/cct |
| Eco24I | 10 | 1439 1566 2157 2763 2847 2951 3004 3354 4667 5594 | grgcy/c |
| Eco47I | 8 | 306 1954 2015 2875 4608 5405 5683 6477 | g/gwcc |
| Eco47III | 1 | 5193 | agc/gct |
| Eco52I | 2 | 239 6543 | c/ggccg |
| Eco57I | 7 | 591 754 834 1129 5958 6038 6201 | ctgaag |
| Eco64I | 11 | 926 1107 1255 1570 2837 2994 3626 4624 4973 5805 5856 | g/gyrcc |
| Eco72I | 1 | 1236 | cac/gtg |
| Eco88I | 11 | 1559 2833 2990 3339 3347 3541 4191 4628 4770 5679 5801 | c/ycgrg |
| EcoICRI | 5 | 2845 2949 3002 3352 5592 | gag/ctc |
| EcoNI | 1 | 4997 | cctnn/nnnagg |
| EcoO109I | 8 | 1026 1080 1436 1733 1954 4279 4663 5457 | rg/gnccy |
| EcoRI | 4 | 1586 2849 3371 4780 | g/aattc |
| EcoRII | 37 | 551 605 680 792 917 1265 1424 2011 2017 2149 2546 2920 3530 3549 3629 3688 3698 3930 3936 3971 4016 4234 4330 4342 4436 4452 4603 4671 4687 4724 5579 5864 5989 6016 6101 6176 6230 | /ccwgg |
| EcoT14I | 13 | 963 1397 1644 3476 3652 3800 3946 4071 4558 4580 5325 5769 5819 | c/cwwgg |
| EcoT22I | 2 | 2626 4027 | atgca/t |
| ErhI | 13 | 963 1397 1644 3476 3652 3800 3946 4071 4558 4580 5325 5769 5819 | c/cwwgg |
| Esp1396I | 3 | 1102 2150 3450 | ccannnn/ntgg |
| Esp3I | 2 | 2921 3920 | cgtctc |
| FauI | 7 | 641 1569 4512 4936 5501 5534 6150 | cccgc |
| FauNDI | 1 | 5368 | ca/tatg |
| FbaI | 2 | 5319 5363 | t/gatca |
| FokI | 12 | 559 925 1124 1866 2056 2353 2452 2914 3485 5796 5866 6232 | ggatg |
| FriOI | 10 | 1439 1566 2157 2763 2847 2951 3004 3354 4667 5594 | grgcy/c |

*FIG. 22 (Cont'd)*

```
Fsp4HI      45   109  239  285  379  433  440  724  746    gc/ngc
                 805  1210 1248 1283 1512 1727
                 1898 2554 2694 2859 3380 3490
                 3509 3578 3602 3723 3739 3811
                 4318 4566 4597 4740 4755 4834
                 4900 5287 5418 5507 5980 6039
                 6061 6345 6352 6403 6500 6543
                 6676
GsuI        6    303  543  2596 2924 6249 6489            ctggag
HaeII       3    2496 5195 5723                            rgcgc/y
HaeIII      42   241  391  503  792  892  974  1028        gg/cc
                 1081 1247 1424 1437 1499 1520
                 1564 1735 1829 2044 2689 2761
                 2858 2964 3457 3530 3725 3936
                 4230 4280 4436 4497 4579 4665
                 4754 5100 5354 5459 5560 5734
                 5894 5994 6310 6395 6545
HapII       29   281  812  872  935  1433 1496 1560        c/cgg
                 1906 1951 2482 2757 2834 2879
                 2991 3624 3843 4487 4611 4629
                 4771 5473 5680 5686 5802 5809
                 5849 5912 5972 6503
HgaI        5    2816 2919 4949 5486 5636                  gacgc
HgiEI       8    306  1954 2015 2875 4608 5405             g/gwcc
                 5683 6477
HhaI        16   321  637  678  2495 2553 4825 5194        gcg/c
                 5422 5516 5546 5625 5637 5722
                 6110 6151 6467
Hin1I       4    2459 2915 4946 5483                       gr/cgyc
Hin6I       16   319  635  676  2493 2551 4823 5192        g/cgc
                 5420 5514 5544 5623 5635 5720
                 6108 6149 6465
HinP1I      16   319  635  676  2493 2551 4823 5192        g/cgc
                 5420 5514 5544 5623 5635 5720
                 6108 6149 6465
HincII      5    124  1578 1614 5555 6662                  gty/rac
HindII      5    124  1578 1614 5555 6662                  gty/rac
HindIII     4    1324 2058 3356 4885                       a/agctt
HinfI       17   233  1163 1615 1910 1995 2084             g/antc
                 2179 2218 2250 2372 3989 4458
                 4519 4850 5674 5704 6550
HpaI        2    124  6662                                 gtt/aac
HpaII       29   281  812  872  935  1433 1496 1560        c/cgg
                 1906 1951 2482 2757 2834 2879
                 2991 3624 3843 4487 4611 4629
                 4771 5473 5680 5686 5802 5809
                 5849 5912 5972 6503
HphI        17   478  607  631  941  964  1978 3617        ggtga
                 3707 4332 4350 4788 5326 5827
                 5850 6160 6184 6282
```

FIG. 22 (Cont'd)

```
Hsp92I      4   2459 2915 4946 5483                    gr/cgyc
Hsp92II    38   268 313 508 703 733 967 1062           catg/
                1071 1622 1648 2043 2161 2209
                2386 2624 2707 2749 2800 3517
                3574 3656 3804 4025 4029 4102
                4223 4339 4483 4584 4791 4921
                5629 5661 5823 6057 6087 6477
                6522
HspAI      16   319 635 676 2493 2551 4823 5192        g/cgc
                5420 5514 5544 5623 5635 5720
                6108 6149 6465
ItaI       45   109 239 285 379 433 440 724 746        gc/ngc
                805 1210 1248 1283 1512 1727
                1898 2554 2694 2859 3380 3490
                3509 3578 3602 3723 3739 3811
                4318 4566 4597 4740 4755 4834
                4900 5287 5418 5507 5980 6039
                6061 6345 6352 6403 6500 6543
                6676
KpnI        5   1111 1574 2841 2998 5809               ggtac/c
Ksp22I      2   5319 5363                              t/gatca
Ksp632I     1   5496                                   ctcttc
KspI        3   1569 2862 5534                         ccgc/gg
Kzo9I      31   226 276 314 462 1086 1091 1555         /gatc
                2036 2173 2468 2472 2678 2753
                2828 2870 2926 3343 3385 3695
                3942 4765 5229 5319 5363 5466
                5649 5796 6320 6468 6506 6556
LspI        1   3361                                   tt/cgaa
MaeI       22   36 230 1030 1398 1593 2805 2823        c/tag
                3462 3477 3504 3947 3986 4258
                4516 4693 4760 4777 4793 5167
                5638 6554 6748
MaeII      15   515 686 899 1008 1034 1191 1235        a/cgt
                1306 1527 2459 4448 5612 5885
                6098 6269
MaeIII     13   94 289 778 1523 1972 2026 3990         /gtnac
                4215 4420 4695 6003 6492 6687
MamI        3   225 5648 6561                          gatnn/nnatc
MboI       31   226 276 314 462 1086 1091 1555         /gatc
                2036 2173 2468 2472 2678 2753
                2828 2870 2926 3343 3385 3695
                3942 4765 5229 5319 5363 5466
                5649 5796 6320 6468 6506 6556
MboII      16   493 668 716 1320 1419 2010 2122        gaaga
                2427 2658 2889 5231 5258 5495
                6075 6120 6298
MfeI        2   133 6649                               c/aattg
MflI       12   462 1091 1555 2678 2753 2828           r/gatcy
                3343 3695 3942 4765 5796 6320
```

*FIG. 22 (Cont'd)*

```
MluI      1   5174                                          a/cgcgt
MluNI     2   974 2044                                      tgg/cca
MnlI      67  170 179 202 450 570 621 633 787              cctc
              864 870 951 1049 1081 1152 1256
              1336 1387 1442 1545 1551 1748
              1891 1960 2455 2493 2566 2602
              2640 2673 2829 2867 2897 2968
              3399 3473 3525 3614 3660 3709
              3721 3736 4041 4086 4205 4211
              4230 4378 4413 4671 4688 4716
              4766 4846 5458 5497 5611 5839
              5920 5926 6003 6157 6169 6220
              6340 6588 6611 6620
Mph1103I  2   2626 4027                                     atgca/t
MscI      2   974 2044                                      tgg/cca
MseI      18  2 123 184 1042 1600 1685 1700                 t/taa
              2324 3561 4160 4817 4838 4861
              4996 5390 6600 6661 6782
MslI      16  479 608 785 935 968 1700 2387                 caynn/nnrtg
              2619 3624 4960 5069 5327 5821
              5851 6001 6178
Msp17I    4   2459 2915 4946 5483                           gr/cgyc
MspA1I    9   1282 1568 1633 2818 2861 3393                 cmg/ckg
              4317 4501 5533
MspCI     2   1 6781                                        c/ttaag
MspI      29  281 812 872 935 1433 1496 1560                c/cgg
              1906 1951 2482 2757 2834 2879
              2991 3624 3843 4487 4611 4629
              4771 5473 5680 5686 5802 5809
              5849 5912 5972 6503
MspR9I    60  281 553 607 682 794 919 935 1267              cc/ngg
              1426 1434 1560 1907 1952 2013
              2019 2151 2482 2548 2758 2834
              2879 2922 2991 3532 3551 3624
              3631 3690 3700 3844 3932 3938
              3973 4018 4236 4332 4344 4438
              4454 4487 4605 4612 4629 4673
              4689 4726 4771 5473 5581 5680
              5687 5802 5850 5866 5991 6018
              6103 6178 6232 6504
MunI      2   133 6649                                      c/aattg
Mva1269I  6   44 143 1374 1407 6649 6748                    gaatgc
MvaI      37  553 607 682 794 919 1267 1426                 cc/wgg
              2013 2019 2151 2548 2922 3532
              3551 3631 3690 3700 3932 3938
              3973 4018 4236 4332 4344 4438
              4454 4605 4673 4689 4726 5581
              5866 5991 6018 6103 6178 6232
MvnI      17  238 319 637 1568 2812 2861 5176               cg/cg
              5410 5420 5424 5514 5533 5544
```

FIG. 22 (Cont'd)

| | | | |
|---|---|---|---|
| | | 5635 6149 6467 6548 | |
| MwoI | 33 | 751 804 817 877 1215 1253 1517<br>1630 1732 2097 2440 2499 2739<br>2864 2912 3607 3778 3896 4018<br>4103 4323 4348 4363 4562 4593<br>4938 5182 5338 5503 5912 5972<br>5985 6029 | gcnnnnn/nngc |
| NciI | 23 | 281 935 1434 1560 1907 1952 2482<br>2758 2834 2879 2991 3624 3844<br>4487 4612 4629 4771 5473 5680<br>5687 5802 5850 6504 | cc/sgg |
| NcoI | 6 | 963 1644 3652 3800 4580 5819 | c/catgg |
| NdeI | 1 | 5368 | ca/tatg |
| NdeII | 31 | 226 276 314 462 1086 1091 1555<br>2036 2173 2468 2472 2678 2753<br>2828 2870 2926 3343 3385 3695<br>3942 4765 5229 5319 5363 5466<br>5649 5796 6320 6468 6506 6556 | /gatc |
| NheI | 1 | 4257 | g/ctagc |
| NlaIII | 38 | 268 313 508 703 733 967 1062<br>1071 1622 1648 2043 2161 2209<br>2386 2624 2707 2749 2800 3517<br>3574 3656 3804 4025 4029 4102<br>4223 4339 4483 4584 4791 4921<br>5629 5661 5823 6057 6087 6477<br>6522 | catg/ |
| NlaIV | 41 | 390 928 1027 1082 1109 1257 1278<br>1437 1557 1564 1572 1955 2755<br>2761 2830 2839 2857 2877 2996<br>3409 3456 3628 3697 3944 3998<br>4435 4539 4609 4626 4664 4711<br>4767 4975 5406 5510 5561 5684<br>5798 5807 5858 6396 | ggn/ncc |
| NotI | 2 | 239 6543 | gc/ggccgc |
| NsiI | 2 | 2626 4027 | atgca/t |
| NspBII | 9 | 1282 1568 1633 2818 2861 3393<br>4317 4501 5533 | cmg/ckg |
| NspI | 9 | 1062 1071 2624 3574 4025 4223<br>4921 5629 5661 | rcatg/y |
| NspV | 1 | 3361 | tt/cgaa |
| PaeI | 2 | 4025 5629 | gcatg/c |
| PaeR7I | 2 | 3339 3347 | c/tcgag |
| PalI | 42 | 241 391 503 792 892 974 1028<br>1081 1247 1424 1437 1499 1520<br>1564 1735 1829 2044 2689 2761<br>2858 2964 3457 3530 3725 3936<br>4230 4280 4436 4497 4579 4665<br>4754 5100 5354 5459 5560 5734<br>5894 5994 6310 6395 6545 | gg/cc |
| Pfl23II | 1 | 5425 | c/gtacg |

FIG. 22 (Cont'd)

```
PflMI      3   1102 2150 3450                          ccannnn/ntgg
PinAI      1   5808                                    a/ccggt
PleI       11  237 1167 1619 2222 2254 2376            gagtc
               3993 4462 4523 5708 6554
PmaCI      1   1236                                    cac/gtg
Pme55I     2   2964 3530                               agg/cct
PmlI       1   1236                                    cac/gtg
Ppu10I     2   2622 4023                               a/tgcat
PpuMI      1   1954                                    rg/gwccy
PshAI      1   5572                                    gacnn/nngtc
PshBI      1   1700                                    at/taat
Psp124BI   5   2847 2951 3004 3354 5594                gagct/c
Psp1406I   1   1527                                    aa/cgtt
Psp5II     1   1954                                    rg/gwccy
PspAI      7   1559 2833 2990 4628 4770 5679           c/ccggg
               5801
PspALI     7   1561 2835 2992 4630 4772 5681           ccc/ggg
               5803
PspLI      1   5425                                    c/gtacg
PspN4I     41  390 928 1027 1082 1109 1257 1278        ggn/ncc
               1437 1557 1564 1572 1955 2755
               2761 2830 2839 2857 2877 2996
               3409 3456 3628 3697 3944 3998
               4435 4539 4609 4626 4664 4711
               4767 4975 5406 5510 5561 5684
               5798 5807 5858 6396
PspOMI     4   1435 1562 2759 4663                     g/ggccc
PstI       2   1585 3381                               ctgca/g
PstNHI     1   4257                                    g/ctagc
PvuII      4   2818 3393 4317 4501                     cag/ctg
RcaI       1   1618                                    t/catga
RsaI       20  254 536 1109 1572 2196 2303 2465        gt/ac
               2597 2795 2839 2975 2996 3648
               5084 5413 5427 5785 5807 6250
               6532
SacI       5   2847 2951 3004 3354 5594                gagct/c
SacII      3   1569 2862 5534                          ccgc/gg
SalI       3   1576 1612 5553                          g/tcgac
Sau3AI     31  226 276 314 462 1086 1091 1555          /gatc
               2036 2173 2468 2472 2678 2753
               2828 2870 2926 3343 3385 3695
               3942 4765 5229 5319 5363 5466
               5649 5796 6320 6468 6506 6556
Sau96I     29  306 389 790 1026 1080 1422 1435         g/gncc
               1562 1733 1954 2015 2687 2759
               2856 2875 3455 3934 4279 4434
               4495 4608 4663 5405 5457 5559
               5683 5993 6394 6477
ScrFI      60  281 553 607 682 794 919 935 1267        cc/ngg
               1426 1434 1560 1907 1952 2013
```

FIG. 22 (Cont'd)

|       |    |                                                                                                                                                        |         |
|-------|----|--------------------------------------------------------------------------------------------------------------------------------------------------------|---------|
|       |    | 2019 2151 2482 2548 2758 2834<br>2879 2922 2991 3532 3551 3624<br>3631 3690 3700 3844 3932 3938<br>3973 4018 4236 4332 4344 4438<br>4454 4487 4605 4612 4629 4673<br>4689 4726 4771 5473 5581 5680<br>5687 5802 5850 5866 5991 6018<br>6103 6178 6232 6504 |         |
| SduI  | 25 | 360 551 800 929 1075 1439 1566<br>1626 1766 1925 2157 2763 2847<br>2951 3004 3354 4622 4629 4667<br>4733 5594 5861 5990 6239 6430 | gdgch/c |
| SfaNI | 16 | 81 485 584 599 858 1123 2523<br>2746 3550 5242 5768 5933 6192<br>6207 6306 6710 | gcatc   |
| SfcI  | 12 | 1300 1581 2376 3377 3776 3862<br>3880 3894 3979 4268 4704 5102 | c/tryag |
| Sfr274I | 2 | 3339 3347 | c/tcgag |
| Sfr303I | 3 | 1569 2862 5534 | ccgc/gg |
| SfuI  | 1  | 3361 | tt/cgaa |
| SinI  | 8  | 306 1954 2015 2875 4608 5405<br>5683 6477 | g/gwcc |
| SmaI  | 7  | 1561 2835 2992 4630 4772 5681<br>5803 | ccc/ggg |
| SpeI  | 1  | 1592 | a/ctagt |
| SphI  | 2  | 4025 5629 | gcatg/c |
| SplI  | 1  | 5425 | c/gtacg |
| SrfI  | 1  | 4630 | gccc/gggc |
| Sse9I | 25 | 69 133 1586 1602 1653 1801 1823<br>2102 2320 2571 2849 3363 3371<br>3558 3792 3962 4157 4780 5134<br>5311 5359 5436 5774 6649 6713 | /aatt |
| SseBI | 2  | 2964 3530 | agg/cct |
| SspBI | 3  | 252 3646 6530 | t/gtaca |
| SstI  | 5  | 2847 2951 3004 3354 5594 | gagct/c |
| SstII | 3  | 1569 2862 5534 | ccgc/gg |
| StuI  | 2  | 2964 3530 | agg/cct |
| StyI  | 13 | 963 1397 1644 3476 3652 3800<br>3946 4071 4558 4580 5325 5769<br>5819 | c/cwwgg |
| SunI  | 1  | 5425 | c/gtacg |
| TaqI  | 38 | 449 578 593 620 914 1048 1577<br>1613 1880 2471 2847 2986 3004<br>3046 3088 3130 3172 3214 3256<br>3298 3340 3348 3361 3369 4853<br>4943 5126 5309 5453 5465 5554<br>5648 5741 5870 6164 6191 6206<br>6335 | t/cga |
| TfiI  | 6  | 1910 1995 2084 2179 4850 5674 | g/awtc |
| ThaI  | 17 | 238 319 637 1568 2812 2861 5176 | cg/cg |

FIG. 22 (Cont'd)

|         |    |                                              |            |
|---------|----|----------------------------------------------|------------|
|         |    | 5410 5420 5424 5514 5533 5544                |            |
|         |    | 5635 6149 6467 6548                          |            |
| Tru1I   | 18 | 2 123 184 1042 1600 1685 1700                | t/taa      |
|         |    | 2324 3561 4160 4817 4838 4861                |            |
|         |    | 4996 5390 6600 6661 6782                     |            |
| Tru9I   | 18 | 2 123 184 1042 1600 1685 1700                | t/taa      |
|         |    | 2324 3561 4160 4817 4838 4861                |            |
|         |    | 4996 5390 6600 6661 6782                     |            |
| Tsp45I  | 7  | 289 778 1972 3990 4695 6003 6492             | /gtsac     |
| Tsp509I | 25 | 69 133 1586 1602 1653 1801 1823              | /aatt      |
|         |    | 2102 2320 2571 2849 3363 3371                |            |
|         |    | 3558 3792 3962 4157 4780 5134                |            |
|         |    | 5311 5359 5436 5774 6649 6713                |            |
| TspEI   | 25 | 69 133 1586 1602 1653 1801 1823              | /aatt      |
|         |    | 2102 2320 2571 2849 3363 3371                |            |
|         |    | 3558 3792 3962 4157 4780 5134                |            |
|         |    | 5311 5359 5436 5774 6649 6713                |            |
| TspRI   | 24 | 48 759 1201 2117 2149 2243 2443              | cagtg      |
|         |    | 2668 2687 3029 3071 3113 3155                |            |
|         |    | 3197 3239 3281 3323 3822 3960                |            |
|         |    | 4012 4546 4911 6032 6743                     |            |
| Tth111I | 1  | 4136                                         | gacn/nngtc |
| TthHB8I | 38 | 449 578 593 620 914 1048 1577                | t/cga      |
|         |    | 1613 1880 2471 2847 2986 3004                |            |
|         |    | 3046 3088 3130 3172 3214 3256                |            |
|         |    | 3298 3340 3348 3361 3369 4853                |            |
|         |    | 4943 5126 5309 5453 5465 5554                |            |
|         |    | 5648 5741 5870 6164 6191 6206                |            |
|         |    | 6335                                         |            |
| Van91I  | 3  | 1102 2150 3450                               | ccannnn/ntgg |
| Vha464I | 2  | 1 6781                                       | c/ttaag    |
| VneI    | 2  | 1071 1762                                    | g/tgcac    |
| VspI    | 1  | 1700                                         | at/taat    |
| XbaI    | 4  | 229 4759 4792 6553                           | t/ctaga    |
| XhoI    | 2  | 3339 3347                                    | c/tcgag    |
| XhoII   | 12 | 462 1091 1555 2678 2753 2828                 | r/gatcy    |
|         |    | 3343 3695 3942 4765 5796 6320                |            |
| XmaI    | 7  | 1559 2833 2990 4628 4770 5679                | c/ccggg    |
|         |    | 5801                                         |            |
| XmaIII  | 2  | 239 6543                                     | c/ggccg    |
| XmnI    | 1  | 1340                                         | gaann/nnttc |
| Zsp2I   | 2  | 2626 4027                                    | atgca/t    |

*FIG. 22 (Cont'd)*

The following endonucleases were selected but don't cut this sequence:

Acc113I, Acc16I, AccIII, AhdI, AocI, AscI, AspEI, AviII, BbeI, BsaI, Bse21I,
BseAI, BsiMI, Bsp13I, Bsp68I, BspCI, BspEI, BstEII, BstPI, BstSNI, Bsu36I,
CpoI, CspI, CvnI, Eam1105I, EclHKI, Eco105I, Eco255I, Eco31I, Eco32I, Eco81I,
Eco91I, EcoO65I, EcoRV, EheI, FseI, FspI, KasI, Kpn2I, MroI, MroNI, NaeI,
NarI, NgoAIV, NgoMI, NruI, PacI, Ple19I, PmeI, PspEI, PvuI, RsrII, SapI,
SbfI, ScaI, SexAI, SfiI, SgfI, SgrAI, SmiI, SnaBI, Sse8387I, SspI, SwaI,
XcmI

FIG. 22 (Cont'd)

CONDITIONAL MST OVEREXPRESSING CONSTRUCT AND CONDITIONAL MYOSTATIN OVEREXPRESSING TRANSGENIC MOUSE

CROSS-REFERENCE TO RELATED APPLICATIONS

This application claims priority under 35 U.S.C. §119(e) from U.S. Provisional Application Ser. No. 61/034,083 filed Mar. 5, 2008, the contents of which are hereby incorporated by reference in their entirety.

A Sequence Listing is provided in electronic form in the text file named "CDU-0001US.txt" and being 37.45 kB in size, which was filed with the United States Patent and Trademark Office on Mar. 12, 2010, the contents of which are hereby incorporated by reference in their entirety.

GOVERNMENT SUPPORT

This work was made possible, in part, with support from the United States government, NIH/MBRS Score Program Grant: S06 GM 0685510-01 and NIH/NIASMD grant 1R21AR0541010-01A2. The government of the United States Government may have certain rights in this invention.

FIELD OF THE INVENTION

The instant invention relates to the field of molecular genetics, in particular to the generation of transgenic mice, and most particularly to the generation of conditional transgenic mice which allows for the study of myostatin gene expression at different stages of development.

BACKGROUND OF THE INVENTION

Myostatin—a Member of the (TGF)-β Superfamily

Myostatin (Mst), a member of the transforming growth factor (TGF)-β superfamily, is thought to be a negative regulatory protein of skeletal muscle mass during embryological development (McPherron et al. Nature 387:83-90 1997) and to be a genetic determinant of skeletal muscle mass in mice, cattle, and humans. Mst is also referred to as growth and differentiation factor-8 (GDF-8). Specifically, Mst is thought to be a negative regulator of skeletal muscle mass; to modulate transcription of muscle-specific genes; to keep muscle progenitor (satellite) cells in a quiescent state; to inhibit muscle regeneration; to inhibit proliferation and differentiation of myoblast; and to downregulate DNA and protein synthesis. All members of the (TGF)-β superfamily share a common structure including a short peptide signal for secretion and an N-terminal peptide fragment that is separated from the bioactive carboxy-terminal fragment by proteolytic cleavage at a highly conserved proteolytic cleavage site.

Since myostatin belongs to the TGF-β superfamily, it is likely to share many features to different members of this family. The biologically active forms of TGF-β are dimers and have been shown to signal by binding receptors followed by activation of Smad proteins. The myostatin gene is composed of three exons. Mst is a 376 amino acid long protein including a signal sequence for secretion, a proteolytic processing site and a C-terminal cysteine residue, like other members of TGF-β superfamily. The biological activation mechanism includes a proteolytic process yielding a 110 amino acid at the C-terminal region, capable of forming a disulfide-linked dimer. The bioactive carboxy-terminal domain is encoded by the third exon and is characterized by cysteine residues at highly conserved positions which are involved in intra- and intermolecular disulfide bridges. Functional myostatin protein molecules are covalently linked (via a S—S bond) dimers of the carboxy-terminal domain.

Myostatin is expressed in skeletal muscle and its precursors from early embryonic stages until adulthood. Myostatin expression is also observed at a lower level in adipose tissue (McPherron et al Nature 387:83-90 1997). Myostatin mRNA has also been observed in the mammary gland (Ji et al. American Journal of Physiology 275:part 2, R1265-1273, 1998) and in cardiac muscle (Sharma et al. Journal of Cell Physiology 180:1-9 1999).

MHC Isoforms

The pathomechanism of muscle wasting is not completely understood, but it is characterized, among other things, by the derangement in size and number of muscle fibers. Muscle function depends on fiber numbers and size, and its myosin heavy chain (MHC) isoform composition. Mst has an effect on these muscle determinants, although data are contradictory. Myosin, the most abundant protein expressed in striated muscle cells, was first isolated by Kuhne in 1864. Years later, its central role in the contractile process was elucidated. Myosin comprises ~25% of the total protein pool and exists as a complex molecule. An important feature concerning muscle structural/functional properties is the existence of the MHC gene family of motor proteins in which specific genes encode MHC protein isoforms. These isoforms have distinctly different ATPase (and shortening velocity) properties, which impact the intrinsic functional properties of the individual myofibers in which they are expressed, and provide the molecular basis of a muscle fiber's functional diversity. Four different fiber types, each with different mechanical properties, have been reported in rodent muscle: slow type I, and fast types IIA, IIX and IIB. It is well recognized that muscles are capable of undergoing significant transition in MHC isoform expression, and several animal models have been developed to determine this plastic feature during different mechanical conditions. After endurance exercise training, MHC type I and IIA increase, and MHC IIX decreases. Mechanical unloading upregulates the fast MHC protein isoform content while concomitantly downregulating the content of the slow MHC protein isoform. In contrast, mechanical overloading produces a significant reduction in the relative proportion of the fast type IIB MHC isoform and a concomitant increase in the slow type I MHC isoform. Removal of load bearing via hindlimb unloading results in similar changes.

Overloading and Unloading the Muscle

In skeletal muscle, interventions that unload or reduce the weight-bearing activity of the muscle cause slow-to-fast MHC conversions, whereas fast-to-slow conversions are seen when the muscles become either chronically overloaded or subjected to intermittent loading, as occurs during resistance training and endurance exercise. How physiological conditions change muscle function and muscle composition has been investigated. Overloading muscle in wild type rats by removing almost all muscle in the hind limb except the plantaris, and then unloading that muscle by casting the animal's limb in order to immobilize it, yields unexpected results. Over time, the plantaris fast muscle, which originally contains 65% MHC isoform IIB type MHC isoform, shifted to slow type muscle. Using antibodies against all 4 different MHC isoforms, it was possible to identify a shift in MHC isoform composition. Prior to overloading, the muscle contained 60-65% fast type IIB fibers, but after six weeks of overloading, the ratio of the IIB:IIX had increased. During those six weeks it was found that the concentration of the type IIB MHC isoform gradually decreased, the ratio of the IIB:IIX increased, and thereafter, the rate of IIX:IIA also increased. By the end of experiment, the majority of the muscle contained isoform type I (slow type). These findings demonstrate a partial shift toward a slower phenotype; however, the high degree of polymorphism found in the plantaris muscle represents a unique design that appears to minimize the functional consequences of these MHC transitions, and could be a characteristic of fibers with high adaptive potential, i.e., hybrid fibers are more suitable to switch phenotype to meet new functional demands.

Shifting Myosin Heavy Chain (MHC) Isoforms

It has also been shown that Mst knockout mice lose more muscle mass after hindlimb suspension, and it is not clear whether this is a consequence of the modified muscle development during embryogenesis or a consequence of an Mst-independent mechanism. To date, there is no direct evidence that Mst can influence muscle plasticity in adulthood. The effect of Mst on fiber type alterations had been investigated by comparing adult muscles from the Mst knockout mice with wild-type controls. Based on myofibrillar ATPase staining, the soleus of Mst knockout mice displays a larger proportion of fast type II fibers and a reduced proportion of slow type I fibers, compared with wild-type animals. Using a staining for succinate dehydrogenase (SDH) activity, a larger proportion of glycolytic (fast) fibers and a reduced proportion of oxidative (slow) fibers occur in the extensor digitorum longus (EDL) of Mst knockouts. These differences in distribution of fiber types are accompanied by differences in the expression of MHC isoforms. In both Mst knockout soleus and EDL, larger numbers of faster MHC isoforms are expressed at the expense of slower isoforms, when compared with wild-type littermates. Proteomic analysis supported these findings. The differences in the proportion of fiber types in Compact mice (natural Mst mutant strain) vs. WT are similar to differences observed between double-muscled and normal cattle. Hypermuscularity seems to be associated with a shift in the metabolic pathway of energy production toward glycolysis, and lower capillary density which could have negative consequences for physical fitness. Another study with similar results compared MHC composition in normal- and double-muscled animals during prenatal development. It was concluded that Mst downregulates the fast type MHC isoform expression and is associated with changes in both skeletal muscle fiber type and fiber size during muscle development. This muscle phenotype is likely a consequence of developmental processes. It is not known for certain whether inhibition of Mst in adults drives the shift towards a glycolytic (faster) phenotype or not.

Embryogenesis

Myostatin plays a critical role during embryogenesis. The ontogeny of Mst coincides with the periods of the primary and secondary muscle fiber formation. Since myofiber number is mostly completed by the end of embryogenesis, the reduction of Mst prior to this stage could be due to the reduction in myogenic and mytogenic events. Skeletal myogenesis is a precisely orchestrated process by which committed but proliferating myoblasts irreversibly exit from the cell cycle, and differentiate to multinucleated myotubes. Myofibers are permanently differentiated after birth and cannot undergo mitotic division. Satellite cells (muscle stem cells) are the probable source of new myonuclei, and their proliferation is required to support muscle hypertrophy, while inhibition of satellite cell proliferation maintains muscle atrophy. Several studies indicate that Mst acts to keep muscle progenitor cells in a quiescent state, and when Mst levels are reduced, these progenitor cells are released from growth arrest.

Adult Skeletal Muscle Atrophy

Regulation of muscle size and number is essential for proper development and homeostasis of adult musculature. A number of genetic factors, growth factors, hormones, nutritional factors, and a network of signal transduction pathways are important in the regulation of skeletal muscle mass. However, their precise role in the integrated, in vivo regulation of skeletal muscle homeostasis and its pathology, muscle wasting, remains poorly understood. It can cause generalized weakness and debilitation and, when respiratory muscles are involved, asphyxia and even death. Pathological atrophy or muscle wasting is a characteristic of a number of diseases, including cancer, cachexia, sepsis, HIV-infection, diabetes, and end-stage kidney, heart and pulmonary disease. Both serum and intramuscular concentrations of Mst are increased in HIV-infected men with weight loss, and correlate inversely with fat-free mass index. Chronic disuse, prolonged bed rest, cachexia, spaceflight, glucocorticoid treatment are all coupled with elevated levels of Mst, and as a consequence, with muscle atrophy. These data support the hypothesis that Mst diminishes adult skeletal muscle growth and contributes to adult muscle wasting. The changes in Mst expression in conditions associated with skeletal muscle loss in adult animals and humans, although suggesting an inverse correlation between myostatin levels and muscle mass, have not established a clear cause/effect relationship. Therefore, the precise functional role of Mst protein in regulating muscle growth in adult animals remains poorly understood.

Mst Knock-Out Mice

Homozygous Mst-null mice have 30 to 50% more muscle mass than the wild type mice, and have larger cross-sectional fiber area (hypertrophy) and higher fiber number (hyperplasia). Similarly, the dominant negative transgenic mice which express an Mst precursor mutated at its cleavage site under the control of a muscle specific promoter, results in myofiber hypertrophy, but not hyperplasia. However, these studies do not clarify the role of Mst in the adult wild type animal.

Transgenic Animal Models

In the last decade transgenic animals have become a powerful research tool for studying the molecular mechanisms underlying cellular and physiological processes such as cell growth, differentiation, and regulation of specific gene expression. Transgenic mice (McPherron et al. Nature 387: 83-90 1997) previously disclosed have been used to exhibit reduced or completely disrupted expression of Mst. However, it is possible that Mst protein plays an important role in regulating skeletal muscle mass and function in postnatal life, by reducing the number and size of muscle fibers, and decreasing muscle function even further than what could be expected from the loss of muscle mass. This role has not been elucidated by using regular transgenic mice because changes in Mst expression and/or function in these animals may be compensated by ancillary pathways that may obscure results obtained in adult animals.

Constitutive loss of Mst function results in a dramatic increase in skeletal muscle mass as a result of combined muscle hyperplasia and hypertrophy. Both myostatin knockout mice along as well as mice (McPherron et al. Nature 387:83-90 1997; Szabo et al. Mammalian Genome 9:671-672 1998 and Varga et al. Genetics 147:755-764 1997) and cattle (Grobet et al. Nature Genetics 17:71-74 1997; Grobet et al. Mammalian Genome 9:210-213 1998; Kambadur et al. Genome Research 7:910-915 1997 and McPherron et al. PNAS USA 94:12457-12461 1997) which are homozygous for naturally occurring Mst loss-of-function mutations share this phenotype commonly referred to as "double-muscling."

Myostatin Overexpression in Adult

One report has tested Mst overexpression directly in adult mice, by injecting a CHO cell line expressing recombinant Mst into the thighs of athymic nude mice, which resulted in a dramatic weight loss (33% of total body weight), partially due to a global decline in skeletal muscle mass. Morphometric analysis revealed that fiber diameter was reduced by 25% in Mst overexpressing animals. The question remains as to whether these wasting effects occurred as a result of Mst secretion into the circulation, or as an unspecific response either to cytokines produced by the Mst-transformed cell line, or as a B-cell immunogenic reaction.

Conditional Mst Inactivation

In the mdx mouse model of muscle dystrophy, inactivation of Mst with an antibody, and also crossing the mdx with the Mst knockout animals resulted in an increase in skeletal muscle mass and a reduction of muscle degeneration.

US20040158884 discloses a transgenic mouse model for conditional inactivation, as opposed to conditional overexpression, of Mst in an adult mouse. This model utilized a non-tissue specific cre-lox system to conditionally inactivate Mst in the mouse, to effect muscular hypertrophy. Conditional inactivation of Mst in mice has demonstrated that early postnatal inactivation of the Mst gene causes generalized muscular hypertrophy, of a magnitude similar to that observed for constitutive Mst knock out (KO) mice, primarily due to muscle fiber hypertrophy. But when adult mice (7-8 weeks old) were treated with an antibody against Mst, they also showed increased muscle mass as a result of fiber hypertrophy, and increased grip strength. No sex differences were detected in this study although others have suggested that Mst has a more prominent effect on male than on female muscle.

Thus, these studies looking at Mst expression levels in adult skeletal muscle suggest that regulation of muscle mass is controlled by Mst at the level of fiber size and/or at the level of cell growth, and that inactivating Mst in adult animals also increases muscle mass. However, these studies do not provide direct evidence that Mst is a negative regulator of adult muscle, but, rather, merely provide an indication that inactivating Mst causes muscle hypertrophy. It still remains to be demonstrated whether or not the presence of Mst is responsible for muscle atrophy or waste.

Such gaps have impaired the ability to develop appropriate treatments to improve muscle size and strength, and muscle atrophy-related conditions which continue to pose a substantial burden to patients as well as to public health. Understanding Mst and its effect in altered physiological conditions is crucial to advance discovery towards much-needed treatments of diseases associated with muscle wasting.

There is thus a need in the art for animal models for studying Mst activation and the associated effects on skeletal muscle.

SUMMARY OF THE INVENTION

Provided herein are novel nucleic acid sequences, vectors comprising such nucleic acid sequences, host cells comprising such vectors, and transgenic animals comprising such nucleic acid sequences, and related molecules and methods relating thereto.

In an embodiment, a conditional eukaryotic gene expression system may comprise two separate constructs:

a regulatory construct which includes a promoter sequence and a transactivation protein sequence with a polyA tail at the 3' end; and a response construct which includes a promoter such as a transactivator response element (TRE) and the gene of interest with a polyA tail at the 3' end.

In exemplary embodiments of a conditional myostatin overexpression system these two essential, basic structure may have the following parts:

the regulatory construct has a tissue (muscle) specific promoter MCK (muscle specific creatine kinase) and a doxycyclin inducible reverse transactivation protein sequence rtTA (also called Tet-ON): 5'-MCK-rtTA-polyA-3'; and the response construct has the TRE promoter and the mouse myostatin sequence: 5'-TRE-Mst-polyA-3'.

When the two constructs apply separately, it is called monocistronic version. When the two constructs put together in one, it is called bicistronic version. In the bicistronic version, the order and orientation of the elements (e.g., the order and/or orientation of the two constructs) is not critical, and may be altered or re-arranged in any suitable manner. For example, any of the possible structure/order of the bicistronic model listed below are suitable for the practice of the invention:

a. 5'-MCK-rtTA-polyA//TRE-Mst-polyA-3'
b. 5'-MCK-rtTA-polyA//polyA-Mst-TRE-5'
c. 3'-polyA-rtTA-MCK//TRE-Mst-polyA-3'
d. 5'-TRE-Mst-polyA//MCK-rtTA-polyA-3'
e. 5'-TRE-Mst-polyA//polyA rtTA-MCK-5'
f. 3'-polyA-Mst-TRE//MCK-rtTA-polyA-3'

In some embodiments, it may be desirable to include or append a label and/or a tags to either or to both sequences. For example, in an embodiment of the conditional myostatin overexpressing system, the structure example "f" from the above list, may be labeled as follows:

3'-polyA-EGFP/IRES-Mst/HA-TRE//-MCK-rtTA/BFP-polyA-3'

(where EGFP stands for a nucleic acid sequence encoding "enhanced green fluorescent protein"; IRES stands for a nucleic acid sequence encoding an "internal ribosome entry site" sequence; Mst stands for a nucleic acid sequence encoding myostatin; HA stands for a nucleic acid sequence encoding hemagglutinin; TRE stands for a nucleic acid sequence encoding a tetracycline response element; MCK stands for a nucleic acid sequence encoding muscle creatine kinase; rtTA stands for a nucleic acid sequence encoding reverse tetracycline transactivator; and BFP stands for a nucleic acid sequence encoding blue fluorescence protein).

For example, in a construct such as the one disclosed above, the BFP (blue fluorescence protein) and the IRES/EGFP (green fluorescence protein) were used for easy detection of gene expression, and HA (hemagglutinin) sequence was used to tag the Mst and to detect/quantify Mst expression on western blot. It will be understood that labels and tags are not an essential part of the system, but may be useful, and that any suitable label, tag, or other identifiable element may be used in the practice of the invention.

In further embodiments, transgenic animals are provided. Transgenic animals of the instant application provide tissue specific, conditional overexpression of Mst at any stage of development, allowing normal embryonic development, if desired, before triggering Mst overexpression, while allowing external manipulation of Mst levels and of muscle mass in the animals when desired. These transgenic animals having increased Mst expression provide decreased muscle mass compared to wild-type animals, and may be used to elucidate the functional role of myostatin in the regulation of skeletal muscle mass and muscle performance in the adult animal. Transgenic animals having features of the invention provide a conditional increase-of-function animal model that keeps Mst levels under physiological control via administration or withdrawal of a pharmacological modulator that can modify recombinant Mst expression in skeletal muscle. Specifically, the invention provides muscle tissue specific expression of Mst. Expression of Mst may be regulated, for example, by a control sequence such as a promoter, which may be a conditional promoter. A control sequence may be regulated by administration or by withdrawal of a control factor that affects the action of the control sequence. For example, Mst expression in a transgenic animal having features of the invention may be regulated by an rtTA-TRE2 regulatory and response sequence controlled via administration and withdrawal of doxycycline or tetracycline. Transgenic animals having features of the invention may be induced, upon administration or withdrawal of a control factor or control factors, to increase Mst expression. Such controlled increase in Mst expression leads to decreased muscle mass. In embodiments, transgenic animals having features of the invention may be induced, upon administration or withdrawal of a control factor or control factors, to increase Mst expression in a particular target tissue or multiple particular target tissues. Such controlled increase in Mst expression in the particular tissue(s) leads to decreased muscle mass in the particular tissue(s) as a result of the administration or withdrawal of a control factor or control factors.

Transgenic animals having features of the invention and having increased Mst expression, at least at some time during their life, may be used to provide animals with decreased muscle mass, or decreased muscle strength, and may provide animals with decreased muscle mass or strength in one or more target muscle(s). In alternative embodiments, transgenic animals having features of the invention and having decreased Mst expression, at least at some time during their life, may be used to provide animals with enhanced muscle mass, or increased muscle strength, and may provide animals with enhanced muscle mass or strength in one or more target muscle(s). Transgenic animals having features of the invention may be used for investigating whether the transient increase of Mst level reduces muscle mass and function, and whether ageing affects this process, as well as restoring physiological level of Mst corrects and/or normalizes the changes, and whether or not there are sex differences in Mst effects. Because the expression of Mst during embryogenesis is not affected in the conditionally Mst overexpressing transgenic (CMOT) animal, such as a CMOT mouse, the animals develop normally. Since the Mst gene may be allowed to function normally during development, transgenic animals of the instant application thus do not have some of the problems associated with overexpression, or knocking out, of a regulatory protein during embryogenesis. Alternatively, administering or withdrawing a control factor during embryogenesis or other developmental stage allows manipulation of Mst levels during development if desired.

EMBODIMENTS, ASPECTS AND VARIATIONS OF THE INVENTION

The present application provides multiple embodiments, aspects and variations, including, but not limited to, the following embodiments, aspects and variations:

The application provides a transgenic non-human animal for conditionally overexpressing Mst. These animals comprise cells comprising a DNA transgene. The DNA transgene may comprise SEQ ID NO. 1, or variants thereof having greater than 80%, 90%, 95%, 99% sequence identity to SEQ ID No. 1, and may be operably linked to a tissue specific promoter. In one embodiment, the DNA transgene further comprises a regulatory sequence. The regulatory sequence may comprise, for example, reverse tetracycline transcription activator (rtTA). The transgene may further comprise a response sequence. In embodiments, the tissue specific promoter may comprise nucleic acid sequences encoding muscle creatine kinase (MCK), including a MCK promoter sequence (e.g., SEQ ID NO: 8) or Troponin I (e.g., TNNI1, found in slow twitch skeletal muscle, or TNNI2, found in fast-twitch skeletal muscle).

The application also provides a Mst expression response construct comprising a transgenic nucleotide sequence comprising SEQ ID NO. 1, or Mst cDNA (e.g., SEQ ID NO: 5), or variations thereof. For example, the transgene sequence SEQ ID NO: 1 includes a nucleic acid sequence encoding Mst (SEQ ID NO: 5).

The application also provides a bicistronic Mst expression construct comprising a regulatory sequence and a Mst response sequence. The application also provides a method of producing a Mst expression vector comprising cloning the Mst expression response construct for conditionally overexpressing Mst operably linked to a tissue specific promoter into a vector.

The application also provides a method of producing a bicistronic Mst expression vector comprising cloning a bicistronic Mst expression construct comprising a regulatory sequence and a Mst response construct into a vector.

The application also provides a method of producing a transgenic non-human animal comprising introducing the conditional monocistronic Mst expression response construct of any of the above embodiments into a non-human animal.

The application also provides a method of producing a double-transgenic non-human animal comprising i) introducing a conditional monocistronic Mst expression response construct of any of the previous embodiments into a non-human animal and ii) introducing a regulatory sequence in a second non-human animal and iii) crossing the first and second non-human animals to produce an offspring having both the regulatory and the response sequences.

The application also provides a method of producing a transgenic non-human animal comprising introducing a bicistronic Mst expression construct into a non-human animal.

In one embodiment, the vector comprises a fluorescent marker coding sequence. In variations of the above embodiment, the fluorescent marker coding sequence is selected from the group consisting of GFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1, luciferase, and aequorin, and other fluorescent marker polypeptides. Fluorescent proteins are disclosed in, for example, U.S. Pat. Nos. 5,981,200; 6,054,321; 6,077,707; 6,172,188; 6,194,548; 6,172,188; 6,803,188; 7,022,826; 7,091,317; 7,157,566; 7,314,915; 7,329,735; and 7,332,598.

The application also provides a method of transfecting cells with the construct of any of the above embodiments by electroporation or injection. The application also provides a construct of any of the above embodiments further comprising a fluorescent marker coding sequence. The fluorescent marker coding sequence may be, for example, a coding sequence coding for GFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1, luciferase, aequorin, or other fluorescent marker polypeptide.

The application also provides a construct of any of the above embodiments in a vector. In one embodiment, the vector is pEGFP-1; an EGFP sequence is found within the CMOT transgene exemplified in SEQ ID NO: 1; for example, an EGFP sequence is found in the IRES/EGFP sequence SEQ ID NO: 4 and in the blue fluorescent protein sequence SEQ ID NO: 10. The application also provides a construct of any of the above embodiments wherein the transgenic nucleotide sequence comprises SEQ ID NO. 1 or SEQ ID NO: 13 or Mst cDNA (e.g., SEQ ID NO: 5) operably linked to a promoter. The promoter may be, for example, a TRE2 promoter. In another embodiment, the application provides a bicistronic Mst expression construct such as, for example, SEQ ID NO: 13 wherein the transgenic nucleotide sequence may comprise SEQ ID NO. 1 or SEQ ID NO: 13 or Mst cDNA operably linked to a promoter, such as a TRE2 promoter.

In one embodiment, the application provides a transgenic nucleotide sequence comprising SEQ ID NO. 1 or SEQ ID NO: 13 or Mst cDNA (e.g., SEQ ID NO: 5) operably linked to a TRE2 promoter, in cells engineered to express rtTA protein in the presence of tetracycline or doxycycline. In another embodiment, the application provides a method of decreasing Mst expression in a cell comprising withdrawal or removal of tetracycline or doxycycline from a cell comprising the Mst expression response construct of any of the above embodiments. In another embodiment, the application provides a method of decreasing Mst expression in a cell comprising withdrawal or removal of tetracycline or doxycycline from a cell comprising the bicistronic Mst expression response construct of any of the above embodiments.

In another embodiment the application provides a Mst expression response construct wherein the nucleotide sequence comprises SEQ ID NO. 1 or SEQ ID NO: 13 or Mst cDNA (e.g., SEQ ID NO: 5) operably linked to TRE2. In one embodiment, the application provides a bicistronic Mst expression construct wherein the nucleotide sequence comprises SEQ ID NO. 1 or SEQ ID NO: 13 or Mst cDNA (e.g., SEQ ID NO: 5) operably linked to TRE2.

In another embodiment, the application provides a Mst expression regulatory construct wherein the nucleotide sequence comprises SEQ ID NO. 1 or SEQ ID NO: 13 or Mst cDNA (e.g., SEQ ID NO: 5) operably linked to MCK or Troponin I. For example, MCK is discussed in Shield et al., "E-box sites and a proximal regulatory region of the muscle creatine kinase gene differentially regulate expression in diverse skeletal muscles and cardiac muscle of transgenic mice" *Mol Cell Biol* 16:5058-5068 (1996).

In another embodiment, the application provides a bicistronic Mst expression construct wherein the nucleotide sequence comprises SEQ ID NO. 1 or SEQ ID NO: 13 or Mst cDNA (e.g., SEQ ID NO: 5) and is operably linked to MCK or Troponin I.

In another embodiment, the application provides a Mst expression regulatory construct further comprising a tissue specific promoter. In another embodiment, the application provides a bicistronic Mst expression construct further comprising a tissue specific promoter. In another embodiment, the application provides a Mst expression construct wherein the tissue specific promoter is skeletal muscle specific. In another embodiment, the application provides a bicistronic Mst expression construct wherein the tissue specific promoter is skeletal muscle specific.

In another embodiment, the application provides a Mst expression regulatory construct wherein the promoter is an MCK promoter. In another embodiment, the application provides a bicistronic Mst expression construct wherein the promoter is an MCK promoter. In another embodiment, the application provides a Mst expression response construct further comprising Mst regulating promoter TRE2. In another embodiment, the application provides a bicistronic Mst expression construct further comprising Mst regulating promoter TRE2.

In another embodiment, the application provides a Mst expression regulatory construct further comprising reverse tetracycline transactivator (rtTA) e.g., SEQ ID NO: 9. In another embodiment, the application provides a bicistronic Mst expression construct further comprising reverse tetracycline transactivator (rtTA) e.g., SEQ ID NO: 9.

In another embodiment, the application provides a method of modulating the expression of Mst (e.g., SEQ ID NO. 5) in a non-human animal comprising the construct of any of the above embodiments by increasing or decreasing the concentration of doxycycline in the non-human animal. In another embodiment, the application provides a transgenic non-human animal comprising a transgenic nucleotide sequence that comprises SEQ ID NO. 1 or SEQ ID NO: 13 or Mst cDNA (e.g., SEQ ID NO: 5) that is operably linked to a muscle tissue specific promoter. In one embodiment, the animal is a mouse. In one embodiment, the transgenic nucleotide sequence comprising SEQ ID NO. 1 or SEQ ID NO: 13 or Mst cDNA (e.g., SEQ ID NO: 5) integrated into the genome of the animal.

The application also provides the above embodiment wherein the transgenic nucleotide sequence comprising SEQ ID NO. 1 or SEQ ID NO: 13 or Mst cDNA (e.g., SEQ ID NO: 5) is operably linked to MCK promoter. The application also provides the above embodiment wherein the animal is a mouse. The application also provides a transgenic non-human animal of any of the above embodiments wherein the transgenic nucleotide sequence comprising SEQ ID NO. 1 or SEQ ID NO: 13 or Mst cDNA (e.g., SEQ ID NO: 5) is operably linked to a reverse transcription activator.

The application also provides a transgenic non-human animal of any of the above embodiments wherein the animal exhibits a Mst associated phenotype in the presence of a transcription activator.

The application also provides a transgenic non-human animal of any of the above embodiments wherein the phenotype can be reversed or ameliorated upon decrease or removal of said transcription activator. The application also provides a transgenic non-human animal of any of the above embodiments wherein the nucleotide sequence comprises SEQ ID NO. 1 or SEQ ID NO: 13 or Mst cDNA (e.g., SEQ ID NO: 5) is regulated by a transactivator. The application also provides a transgenic non-human animal of any of the above embodiments wherein the nucleotide sequence comprises SEQ ID NO. 1 or SEQ ID NO: 13 or Mst cDNA (e.g., SEQ ID NO: 5) is linked to a promoter. The application also provides a transgenic non-human animal of any of the above embodiments wherein the promoter is a tissue specific promoter. The application also provides a transgenic non-human animal of any of the above embodiments wherein the tissue specific promoter is skeletal muscle specific.

The application also provides a transgenic non-human animal of any of the above embodiments wherein the Mst phenotype is a skeletal muscle phenotype. The application also provides a transgenic non-human animal of any of the above embodiments wherein the skeletal muscle phenotype is aplasia. The application also provides a transgenic non-human animal of any of the above embodiments wherein the promoter is an MCK promoter.

The application also provides a transgenic non-human animal of any of the above embodiments wherein the transactivator is reverse tetracycline transactivator (rtTA) (e.g., SEQ ID NO: 9). The application also provides a transgenic non-human animal of any of the above embodiments wherein the transcription activator is tetracycline or doxycycline.

The application also provides a transgenic non-human animal of any of the above embodiments wherein the animal is a mouse. The application also provides a transgenic non-human animal of any of the above embodiments wherein the transcription activator is doxycycline.

The application also provides a method for screening for therapeutic agents that inhibit Mst activity comprising (a) administering test agents to a transgenic animal of any of the above embodiments, (b) evaluating the effects of the test agent on the muscular phenotype of the transgenic animal.

The application also provides a transgenic non-human animal produced by: (a) crossing a first transgenic non-human animal comprising a first construct that expresses rtTA operably linked to promoter MCK with a second non-human animal comprising a second construct comprising Mst or Mst cDNA operably linked to a promoter TRE2 and (b) selecting from the first generation offspring a transgenic non-human animal having a genome comprising both the first construct and the second construct.

The application also provides any of the above embodiments wherein the transgenic non-human animal is a mouse.

IN THE DRAWINGS

FIG. 1A. Structure of the fragments carrying the transgene for generating transgenic animals expressing EGFP and overexpressing myostatin, respectively, in the skeletal muscle. A: MCK1.3/EGFP-1 construct, B: MCK1.3/mMst construct. Asterisks show the position of 5' and 3' primers used. FIG. 1B. top: myostatin overexpressing construct (prior art); bottom: novel bicistronic conditional myostatin overexpressing construct. A novel bicistronic conditional myostatin overexpressing construct as disclosed herein may thus have a regulatory sequence comprising, e.g., polyA, rtTA and MCK; and a response sequence comprising TRE, Mst/IRES-EGFP, polyA. In a novel bicistronic conditional myostatin overexpressing construct having features of the invention, nucleic acids encoding a fluorescent protein, (e.g., blue fluorescent protein (BFP), tag (e.g., hemagglutinin (HA) or other marker may be inserted or included between the polyA and rtTA regions and/or between the TRE and Mst/IRES-EGFP regions. For example, a BFP-encoding sequence may be inserted between the polyA and rtTA regions, and an HA-encoding sequence may be inserted between the TRE and Mst/IRES-EGFP regions.

Figures 1, 1A, 2:
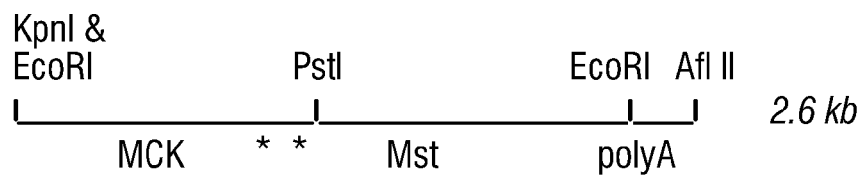
Figures 1, 1B:
Figures 1, 1B, 2:
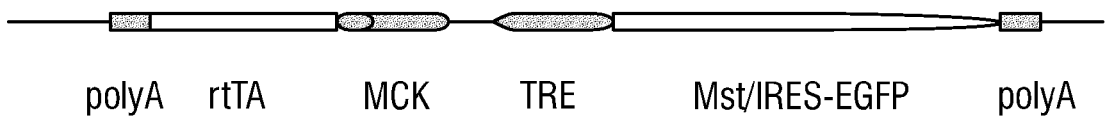

FIG. 2. EGFP expression in C2C12 cells and skeletal muscle. A: Myoblast, B: Myotube, C: Control tissue, D: Transgenic animal muscle.

FIG. 3. Genotyping of transgenic and control mice. A: PCR, B: Southern blot.

FIG. 4: Muscle weight of transgenic and control mice. A: male, B: female.

FIG. 5. RT-PCR results of transgenic and control mice. A: agarose gel, B: densitometry FIG. 6. Western blot analysis of mice. A) male, B) female, C) densitometry FIG. 7. Histomorphometry results from transgenic and control mice. A: cross-sectional area of fibers, B: myonuclei numbers mice' skeletal muscle.

Figure 8:
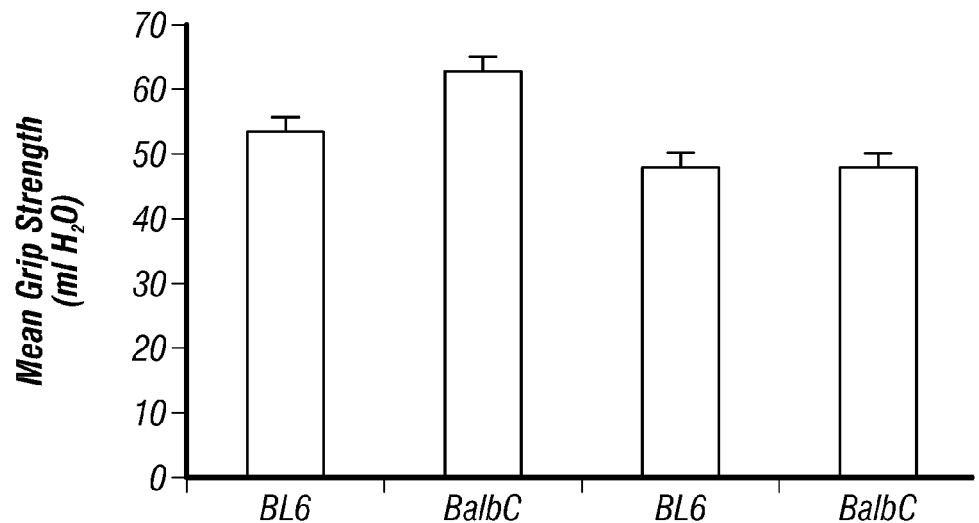

FIG. 8. Comparison of grip strength between mouse strains and gender

Figure 9:
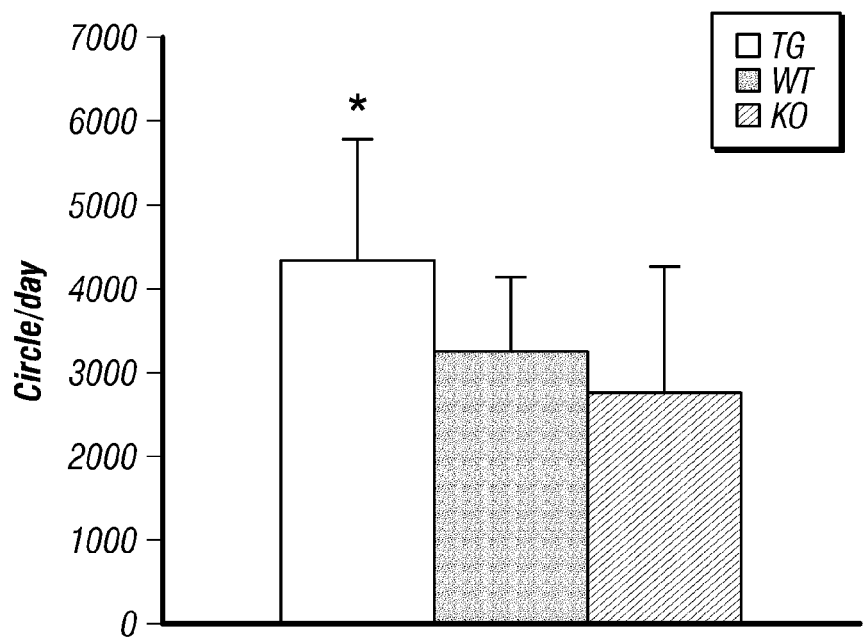

FIG. 9. Spontaneous daily activity measured by rodent activity wheel.

FIG. 10. CT scan images of 6 months-old male mice. A: Whole body 3D reconstructed image of a WT animal; B: a representative slice from raw data of Tg mouse; C: a representative slice from raw data of KO mouse.

FIG. 11. Force-velocity relationship measured in Mst Tg, KO and WT mice on gastrocnemius muscle.

Figure 12:
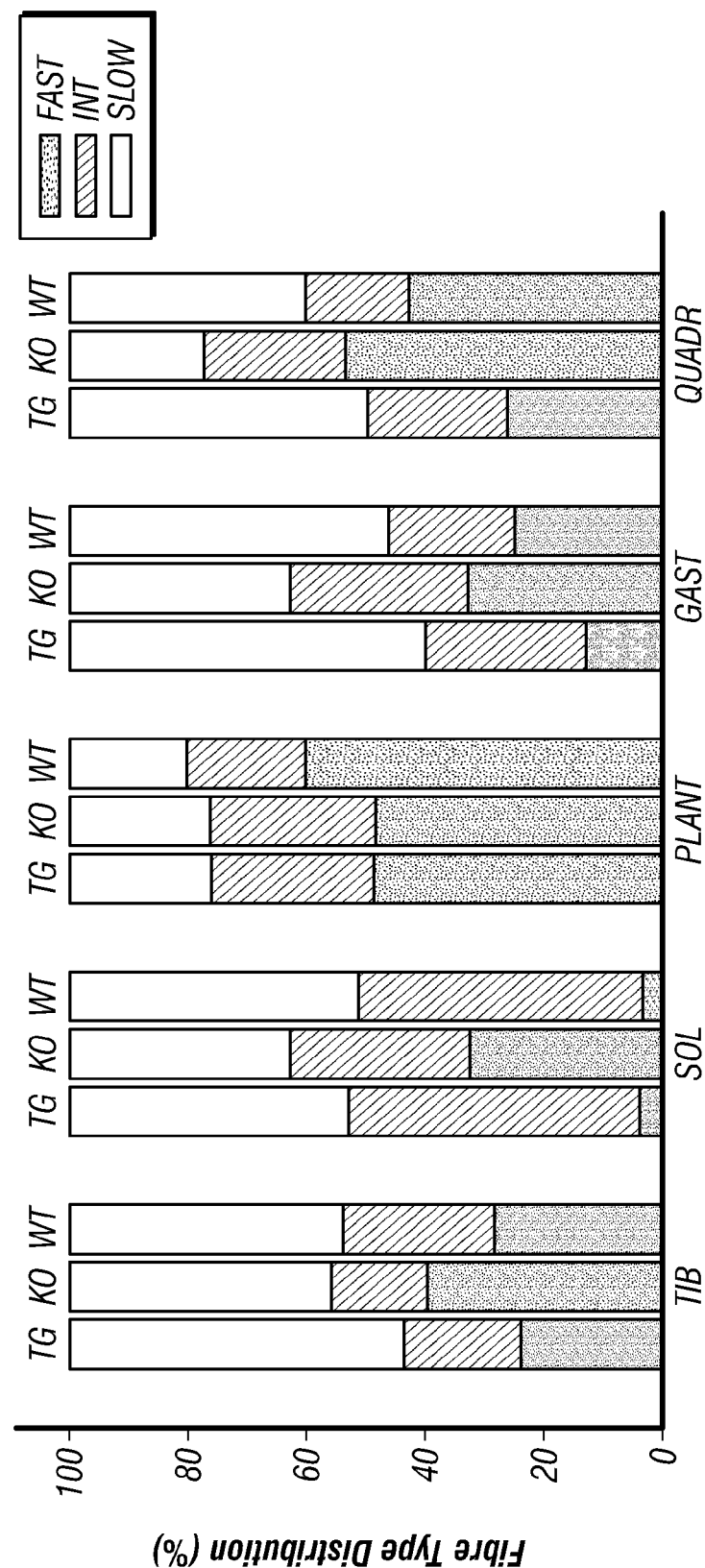

FIG. 12. Fiber type distribution in skeletal muscles.

Figure 13:
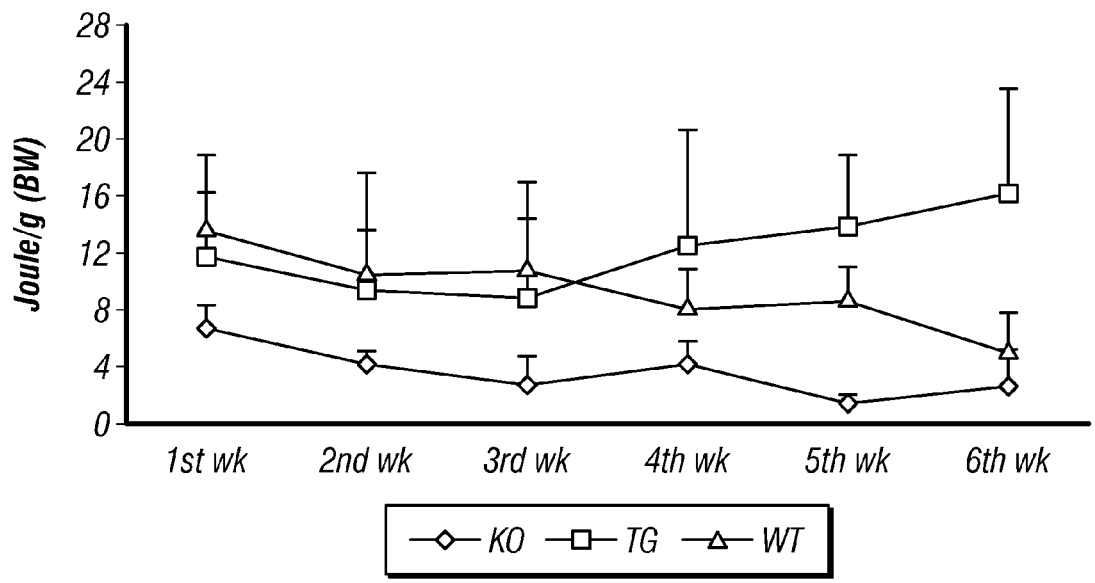

FIG. 13. Treadmill exercise tolerance.

Figure 14:
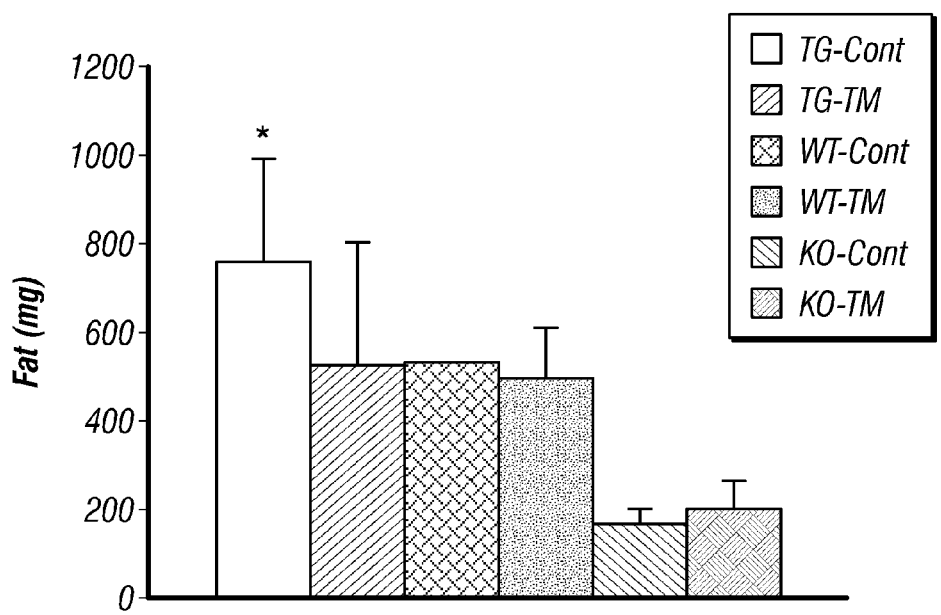

FIG. 14. Changes in abdominal fat mass followed by 8 weeks treadmill exercise test on Mst Tg, KO and WT mice compared with non-treadmill tested animals.

Figure 15A:
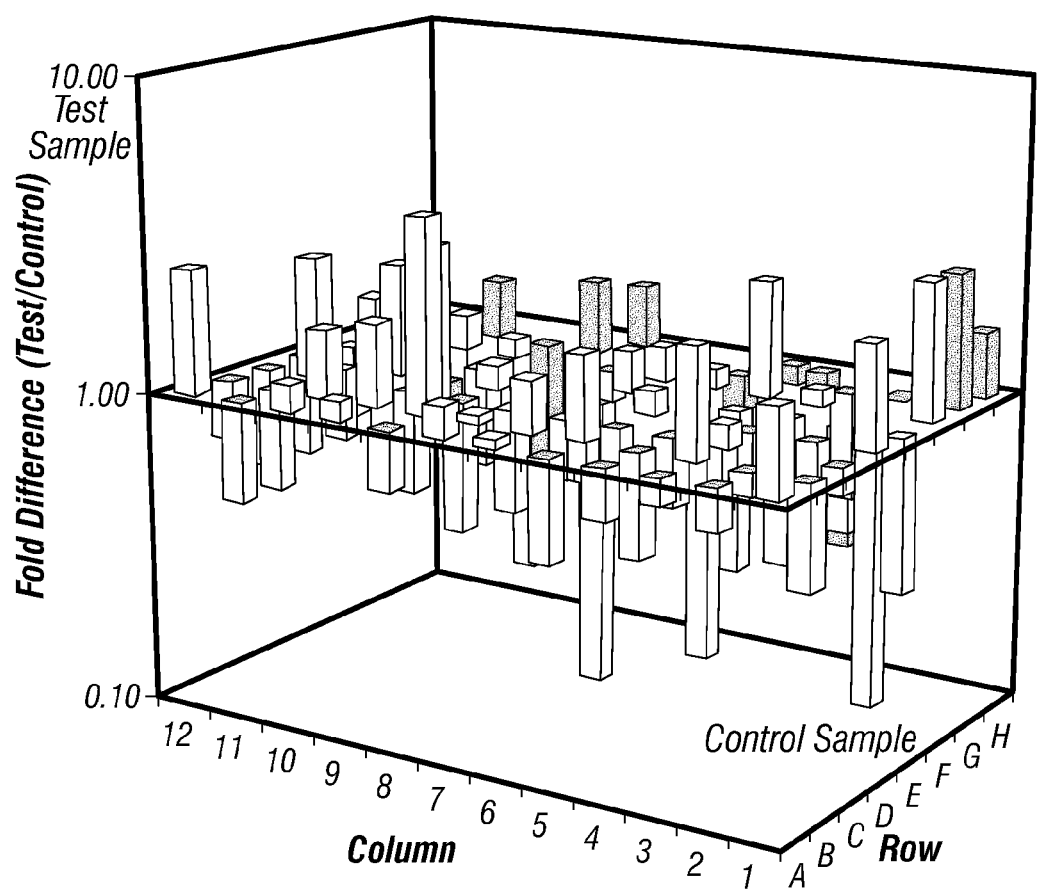
Figure 15B:
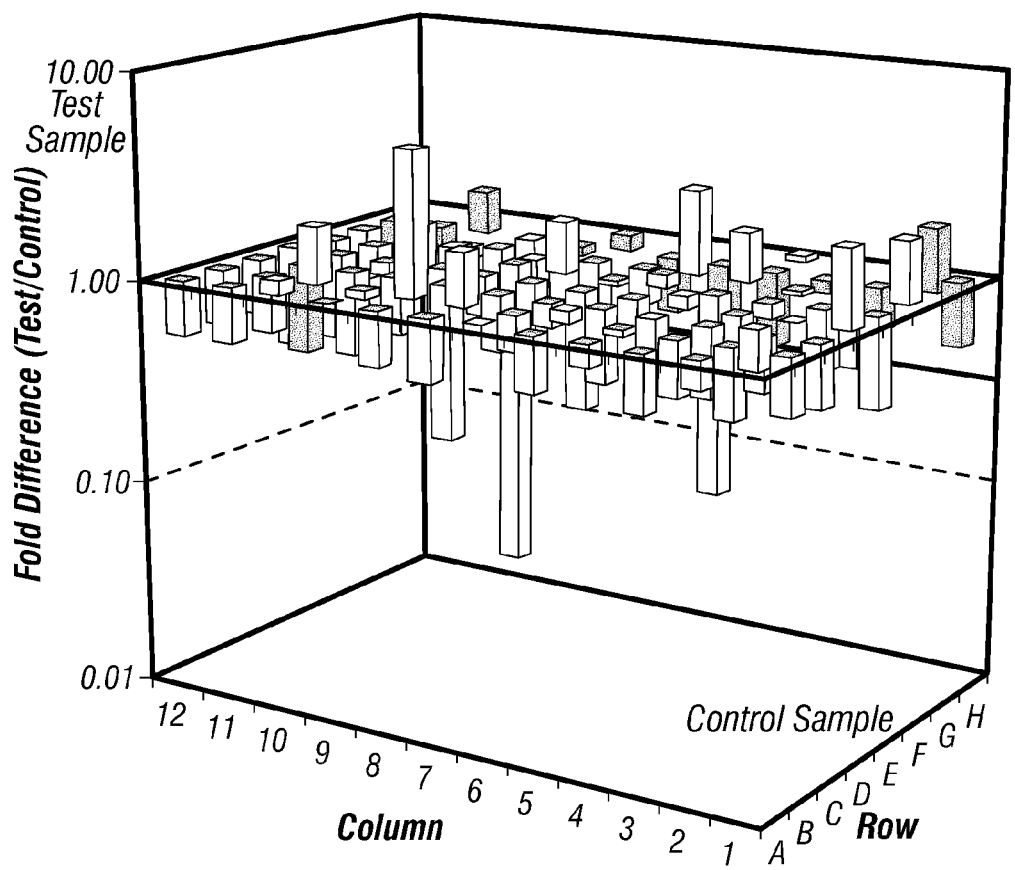

FIG. 15. Superarray pathway analysis data show changes in gene expression influenced by Mst. A: Tg mice; B: KO mice relative to WT controls.

Figure 16A:
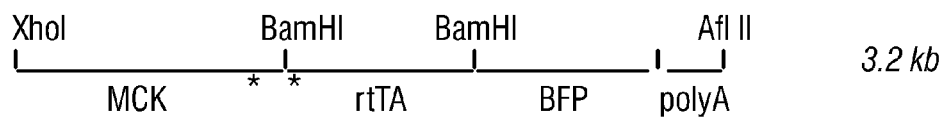
Figure 16B:
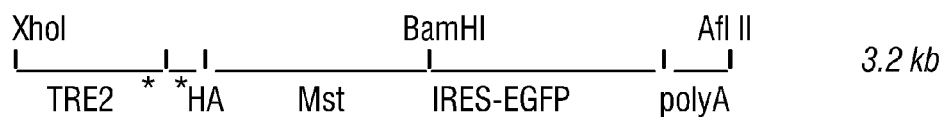

FIG. 16. Structure of the Tet-ON gene expression system carrying the sequences for conditional Mst overexpressing transgenic animals. A: MCK1.3/Tet-ON/Blue construct, B: TRE2/HA-mMst/IRES-EGFP construct. Asterisks show the position of 5' and 3' primers used.

Figure 17:
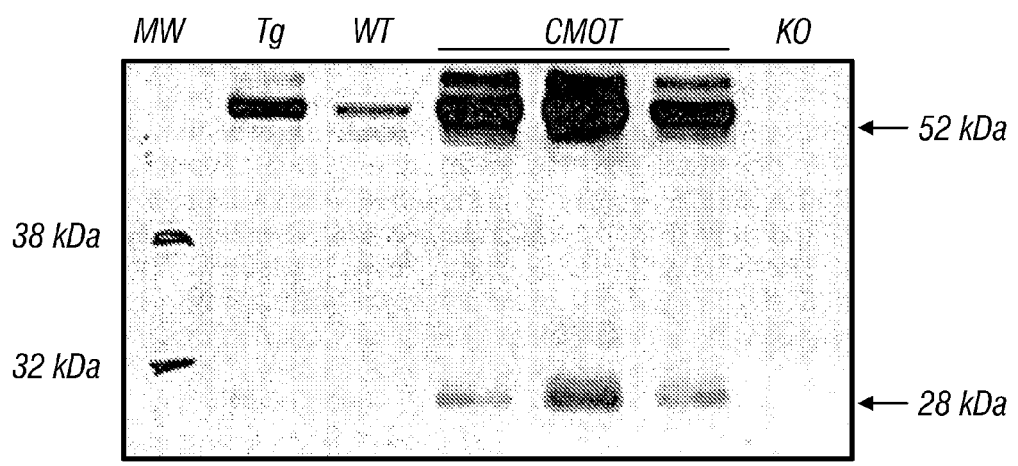

FIG. 17. Western blot of Mst expression in CMOT mice quadriceps muscle followed by Doxycylin induction (200 mg/kg Dox in chow) for 8 weeks.

FIG. 18. CMOT Transgene (SEQ ID NO:1), including MCK promoter, Tet-ON (rtTA), ECFP (Blue FP), SV40 polyA, Plasmid backbone sequences (including pUC, HSV TK/polyA, Kan/Neo, SV40 ori, flori) SV40 polyA, IRES/EGFP, Myostatin (Mst), HA-tag on Mst, and TRE. The two "bold" sequences are the Afl II restriction site that was used to release the sequence from the plasmid.

FIG. 19. CMOT=pFin plasmid sequence (SEQ ID NO: 13); note that "Tet-on polyA." in the figure refers to SEQ ID NO: 9 (tet-on) and SEQ ID NO: 11 (polyA).

FIG. 20. CMOT plasmid (10273 base pairs) (SEQ ID NO: 13) Graphic map and Table by enzyme name.

FIG. 21. Schematic of Plasmid

FIG. 22. CMOT transgene (6786 base pairs) (SEQ ID NO: 1) Graphic map and Table by enzyme name.

DETAILED DESCRIPTION

All publications, patents, and patent applications cited herein, both supra and infra, are hereby incorporated by reference herein in their entireties.

The present application includes a listing of sequences following the abstract of the invention.

As used in the present specification the following terms have the meanings indicated:

The abbreviation "Tg" as used herein means transgenic.

The term "transgenic non-human animal" as used herein means a non-human animal, for example a mouse, having a cell or cells that contain a transgene, which transgene is either introduced into the animal or an ancestor of the animal. Such introduction of a transgene may be at a prenatal stage, for example, an embryonic stage.

The term "mouse" is used herein to include an individual mouse in all stages of development, including embryonic and fetal stages.

A "transgenic mouse" is any mouse containing one or more cells bearing genetic information altered or received, directly or indirectly, by deliberate genetic manipulation at a subcellular level, such as by targeted recombination or microinjection or infection with recombinant virus. The term "transgenic mouse" is intended to encompass classical cross-breeding or in vitro fertilization, as well as meant to encompass mice in which one or more cells are altered by, or receive, a recombinant DNA molecule. This recombinant DNA molecule may be specifically targeted to a defined genetic locus, may be randomly integrated within a chromosome, or it may be extrachromosomally replicating DNA.

The alteration or genetic information may be foreign to the animal (e.g. species of mouse) to which the recipient belongs, or foreign only to the particular individual recipient, or may be genetic information already possessed by the recipient. In the last case, the altered or introduced gene may be expressed differently than the native gene, or not expressed at all. Various types of nucleotide sequences can be used to generate transgenic animals, for example, mutant sequences and heterologous sequences. "Knock out" animals can also be generated, wherein entire genes or parts of genes are deleted or "knocked-out" to discern function. Methods for generating transgenic animals, particularly animals such as mice, have become conventional in the art and are described, for example, in U.S. Pat. No. 4,736,866.

The term "Mst" as used herein means myostatin protein. A nucleic acid encoding Mst is disclosed as SEQ ID NO: 5.

The terms "control sequences" and "regulatory sequences" refer to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer. A control sequence may be or include, for example, a rtTA-TRE2 regulatory and response sequence (which may interact, for example with tetracycline or a tetracycline derivative such as doxocycline).

The terms "control factor" and "regulatory factor" refer to a factor that affects a control sequence (also termed a regulatory sequence). A control factor may be administered, or may be withdrawn, in order to affect a control sequence. A control factor may be, for example, tetracycline or a tetracycline derivative such as doxocycline (e.g., for use with a rtTA-TRE2 regulatory and response sequence).

Control sequences may be modified, for example by the addition of further transcriptional regulatory elements to make the level of transcription directed by the control sequences more responsive to transcriptional modulators. Control sequences operably linked to sequences encoding a polypeptide described herein include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Thus, the terms "control sequence" and "regulatory sequence" as used herein means nucleotide sequences located upstream (T), within, and/or downstream (Y) to a coding sequence or "response sequence," which control the transcription and/or expression of the coding sequences or "response sequences," potentially in conjunction with the protein biosynthetic apparatus of the cell. These nucleotide sequences include a promoter sequence, a translation leader sequence, a transcription termination sequence, and a polyadenylation sequence.

The term "promoter" as used herein means a nucleic acid sequence which may be effective at increase transcription of nearby nucleic acid coding sequences, which are functional in mammalian cells, although prokaryotic promoters and promoters functional in other eukaryotic cells, such as insect cells, may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner or, alternatively, a tissue-specific manner, such as the "tissue specific promoter" MCK which is the gene for muscle creatine kinase, as disclosed herein. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

Promoters are untranslated sequences located upstream from the start codon of a structural gene (generally within about 100 to 1000 base pairs (bp)) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for trk receptor is not usable. However, heterologous promoters generally will result in greater transcription and higher yields of expressed trk receptor as compared to the native trk receptor promoter.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT (SEQ ID NO: 14) region where X may be any nucleotide. At the 3' end of most eukaryotic genes is an AATAAA (SEQ ID NO: 15) sequence that may be the signal for addition of the poly A tail to the 3' end of the coding sequence. All of these sequences are suitably inserted into mammalian expression vectors.

Transcription from vectors in mammalian host cells may be, for example, controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the trk receptor sequence, provided such promoters are compatible with the host cell systems.

The early and late promoters of the SV40 virus are conveniently obtained as an SV40 restriction fragment which also contains the SV40 viral origin of replication [Fiers et al., Nature 273:113 (1978), Mulligan and Berg, Science 209, 1422-1427 (1980); Pavlakis et al., Proc. Natl. Acad. Sci. USA 78, 7398-7402 (1981)]. The immediate early promoter of the human cytomegalovirus is conveniently obtained as a HindIII E restriction fragment [Greenaway et al., Gene 18, 355-360 (1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., Nature 295, 503-508 (1982) on expressing cDNA encoding human immune interferon in monkey cells; Reyes et al., Nature 297, 598-601 (1982) on expressing human .beta.-interferon cDNA in mouse cells under the control of a thymidine kinase promoter from herpes simplex virus; Canaani and Berg, Proc. Natl. Acad. Sci. USA 79, 5166-5170 (1982) on expression of the human interferon β1 gene in cultured mouse and rabbit cells; and Gorman et al., Proc. Natl. Acad. Sci., USA 79, 6777-6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter. The actual plasmid used in the course of cloning the murine trk receptor contains the promoter of the murine 3-hydroxy-3-methylglutaryl coenzyme A reductase gene [Gautier et al., Nucleic Acids Res. 17, 8389 (1989)], whereas the reporter plasmid [pUMS (GT)$_8$-Tac] used during expression cloning contained an artificial multimerized trk recepto-inducible promoter element [McDonald et al., Cell 60, 767-779 (1990)].

The term "operably linked" as used herein means that the components described are in a relationship permitting them to function in their intended manner. A regulatory sequence "operably linked" to a coding sequence is ligated in such a way that expression of the coding sequence is achieved under conditions compatible with the control sequences.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

The term "vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized. Expression vectors, unlike cloning vectors, should contain a promoter which is recognized by the host organism and is operably linked to the nucleic acid encoding the desired polypeptide.

The term "variants" as used herein indicates a molecule, such as a polypeptide or polynucleotide, that has substantial sequence identity to a different (parent) molecule, but differs from the parent sequence by one or more different residues (e.g., different amino acids for polypeptides, or different nucleotides, for nucleic acids). Variants may be, for example, substitution, insertion, or deletion variants, in which one or more residue(s) is/are replaced by (an)other residue(s) (substitution variants), or in which one or more additional residue(s) is/are included in the sequence (an insertion variant), or in which one or more residue(s) is/are lacking (a deletion variant).

A substitution variant in a polypeptide may be a conservative substitution variant, in which an amino acid is replaced by a different amino acid with similar properties. Standard amino acid naming terminology is used herein. For example, conservative substitutions for the amino acid Ala (A) include: val, leu, ile, val. Conservative substitutions for the amino acid Arg (R) include: lys, gln, asn, lys. Conservative substitutions for the amino acid Asn (N) include: gln, his, asp, lys, arg, gln. Conservative substitutions for the amino acid Asp (D) include: glu, asn, glu. Conservative substitutions for the amino acid Cys (C) include ser, ala, ser. Conservative substitutions for the amino acid Gln (Q) include: asn, glu, asn. Conservative substitutions for the amino acid Glu (E) include: asp, gln, asp. Conservative substitutions for the amino acid Gly (G) include: ala. Conservative substitutions for the amino acid His (H) include: asn, gln, lys, arg. Conservative substitutions for the amino acid Ile (I) include: leu, val, met, ala, len phe, norleucine. Conservative substitutions for the amino acid Leu (L) include: norleucine, ile, val, ile, met, ala, phe. Conservative substitutions for the amino acid Lys (K) include: arg, gln, asn, arg. Conservative substitutions for the amino acid Met (M) include: leu, phe, ile, leu. Conservative substitutions for the amino acid Phe (F) include: leu, val, ile, ala, tyr. Conservative substitutions for the amino acid Pro (P) include: ala. Conservative substitutions for the amino acid Ser (S) include thr. Conservative substitutions for the amino acid Thr (T) include: ser. Conservative substitutions for the amino acid Trp (W) include: tyr, phe. Conservative substitutions for the amino acid Tyr (Y) include: trp, phe, thr, ser, phe. Conservative substitutions for the amino acid Val (V) include: ile, leu, met, phe, leu, ala, norleucine.

Variants that maintain (a) the structure of the polypeptide backbone in the area of the substitution, for example, as a sheet or helical conformation, (b) the charge or hydrophobicity of the molecule at the target site, or (c) the bulk of the side chain are expected to substantially maintain the properties of the parent polypeptide. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions will typically entail exchanging a member of one of these classes for another of the same class. Any cysteine residue not involved in maintaining the proper conformation of the parent polypeptide also may be substituted, generally with serine, to improve the oxidative stability of the molecule and prevent aberrant crosslinking. Conversely, cysteine bond(s) may be added to the polypeptide to improve its stability.

As used herein, "tetO" means a tetracycline operator comprising sequence which can be present in a promoter. Thus, a "tetO promoter" means a promoter having one or more such sequences.

As used herein, "tTA" means a fusion protein comprising the repressor of the Tn10 tetracycline-resistance operon of *Escheria coli* and a C-terminal portion of protein 16 of herpes simplex virus that functions as a strong transcriptional activator. This fusion protein is a tetracycline-controlled transactivator. For example, tTA will bind to the tetO region of a promoter and function as a strong activator of transcription in the absence of doxycycline. Doxycycline may therefore be used to suppress transcription from a promoter having tetO sequences.

As used herein, "rtTA" means a protein that is a variant of the tTA protein, and plays a role opposite that of tTA, i.e., rtTA protein requires doxycycline in order to activate transcription from a tetO promoter such as TRE2. Doxycycline can thus be used as an activator of transcription in conjunction with rtTA and a transgene operatively linked to a tetO-containing promoter such as TRE2, to effect controlled transactivation. SEQ ID NO: 9 provides an example of a rtTA.

The term "TRE2" as used herein means tetracycline response element.

As used herein "tetracycline controlled transactivation" refers to the tetracycline (Tc)-controlled gene expression system which permits the at will control of individual gene activities quantitatively and reversibly. In the reverse Tc-controlled transactivator (rtTA) system, Tc or doxycycline (Dox) acts as an inducer of transcription that works well in vitro, with reported induction levels of gene expression (like luciferase reporter gene, erythropoietin, ecdysone receptor, retinoid X receptor, etc.) ranging from 3 to 4 orders of magnitude above basal level.

It is well known that in transgenic and knock-out (KO) animals the irreversibility of genetic transfer may lead to compensatory upregulation, developmental defects, embryonic mortality, and others. Such limitations could be overcome by utilizing a "genetic switch" system, such as the rtTA-TRE2 system, that can be operated at will and permit the control of individual gene activities quantitatively and reversibly, in a temporal and spatial manner.

Several reports have successfully demonstrated how a drug-regulated gene expression system can be used to study gene function, and can be operated in a quantitative way in cell culture and transgenic mice. In many of these studies, the expression system is driven by the cytomegalovirus (CVM) promoter, which frequently causes leakiness in gene expression due to lack of tissue specificity, which can be overcome by using a strong muscle-specific promoter such as MCK.

The term "MCK" as used herein means muscle creatine kinase. Tissue-specific gene expression requires a well-characterized, strong, tissue specific promoter. Many muscle-specific regulatory sequences have been mapped, such as α-skeletal actin, α-cardiac actin, troponin I, myosin light chain 2, myosin heavy chain (MHC) and muscle creatine kinase (MCK). Both MCK and troponin I have high expression levels in muscle, and their promoter/enhancer regions are small enough to make them suitable for gene transfer. Within the mouse MCK gene, several regions are required for muscle-specific expression in myocytes and cardiomyocytes. Of particular interest is a 206 bp enhancer located approximately 1 kb upstream of the transcription start site which contains two E-box sequences. The 1 kb region immediately 3' of the 206 bp enhancer (called proximal regulatory region) has an E-box sequence as well, and plays an important role in tissue-specific gene expression. Simultaneous mutation of the three E-boxes in the 1,256 bp region of MCK promoter resulted in a substantial loss of reporter gene activity in cardiac and tongue muscle. SEQ ID NO: 8 provides an example of MCK promoter. To date, this mutated version of the MCK promoter is the only one which is truly skeletal muscle-specific, the E-box mutations had not dramatically affected transgene expression in fast muscles in CAT-transgenic mice.

The term "cDNA" as used herein means complementary deoxyribonucleic acid.

The term "construct" as used herein means a recombinant nucleic acid, generally recombinant DNA, that has been generated for the purpose of the expression of a specific nucleotide sequence(s), or is to be used in the construction of other recombinant nucleotide sequences.

The term "monocistronic myostatin expression" as used herein refers to a myostatin expression system wherein the regulatory sequence is not ligated into the same construct as the myostatin coding response element. Conditional eukaryote gene expression system requires a regulatory construct sequence and a response construct sequence. If the two sequences are used separately to generate transgenic animals, then they are termed the monocistronic gene expression system that further requires breeding the two transgenic animals. If their offsprings are genotyped as double transgenic, these animals can be used to test the conditional gene expression system in vivo.

The term "bicistronic myostatin expression construct" as used herein refers to a myostatin expression system wherein the regulatory sequence has been ligated into the same construct as the myostatin coding response element. Thus, in vivo, the method for bicistronic gene expression system requires that the regulatory and response sequences to be located on the same DNA fragment that is used to generate the transgenic animal. Once the animal is genotyped positively for the transgene, it can be used for testing the conditional gene expression without any further breeding with another transgenic animal.

The term "expression vector" as used herein means a plasmid comprising a transcriptional unit. The unit comprises (a) a genetic element or elements having a regulatory role in gene expression, for example, promoters or enhancers, (b) a structural or coding sequence which is transcribed into mRNA and translated into protein, and (c) appropriate transcription and translation initiation and termination sequences. Structural elements used in yeast expression systems preferably include a leader sequence enabling extracellular secretion of translated protein by a host cell.

The term "double-transgenic" as used herein is used to describe a non-human animal, for example a mouse, having a cell or cells that contain two transgenes, which transgenes are either introduced into the animal or an ancestor of the animal at a prenatal stage, for example, an embryonic stage.

The term "fluorescent marker coding sequence" as used herein means the nucleic acid sequence that codes for fluorescent and/or luminescent markers such as GFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1, luciferase, aequorin, and other fluorescent and/or luminescent polypeptides. Fluorescent proteins are disclosed in, for example, U.S. Pat. Nos. 5,981,200; 6,054,321; 6,077,707; 6,172,188; 6,194,548; 6,172,188; 6,803,188; 7,022,826; 7,091,317; 7,157,566; 7,314,915; 7,329,735; and 7,332,598.

The term "transfecting" as used herein means causing the nucleic acid to be taken up by the cell.

The term "electroporation" as used herein means the temporary creation of holes or aqueous pores in the surface of a cell membrane by an applied electrical potential and through which therapeutic agents may pass into the cell. Electroporation is now widely used in biology, particularly for transfection studies, where plasmids, DNA fragments and other genetic material are introduced into living cells. During electroporation pulsing, molecules which are not normally membrane permeant are able to pass from the extracellular environment into the cells during the period of induced reversible membrane permeabilization. The permeabilized state is caused by the generation of an electrical field in the cell suspension or tissue of sufficient field strength to perturb the cell surface membrane's proteolipid structure. This perturbation (sometimes referred to as dielectric breakdown) is believed to be due to both a constituent charge separation and the effect of viscoelastic compression forces within the membrane and it's sub-adjacent cytoskeletal structures. The result is a localized membrane thinning. At a critical external field strength, pores or small domains of increased permeability are formed in the membrane proteolipid bi-layer.

The term "Mst associated phenotype" as used herein means any of one or more characteristics of an organism, tissue, or cell associated with the expression of Mst.

The term "transcription activator" as used herein means any substance capable of inducing the transcription of a gene.

The term "transactivator" as used herein means a protein that binds to regulatory regions of DNA and enhances the expression of its associated gene.

The term "aplasia" as used herein means a decrease in muscle fiber number compared to a normal fiber number or a previously determined fiber number.

The term "atrophy" as used herein means is the partial or complete wasting away of a part of the body.

The term "test agent" as used herein means any compound or agent that is being examined for the ability to modulate myostatin expression. A test agent can be any type of molecule, including, for example a peptide, a polynucleotide (including antisense or RNAi), an antibody, a glycoprotein, a carbohydrate, a small organic molecule, or a peptidomimetic.

EXEMPLARY EMBODIMENTS

The invention comprises, in part, constructs, transgenicn animals, and methods, some of which are listed in the following exemplary list of embodiments. It is noted that this exemplary list of embodiments is not restrictive, but provides examples of the embodiments of the invention disclosed herein.

1. A conditional bicistronic myostatin expression construct comprising polyA-EGFP/IRES-Mst/HA-TRE//MCK-rtTA/BFP-polyA, where MCK is a promoter selected from MCK and MCK-3E.
2. A conditional bicistronic myostatin expression construct comprising polyA-BFP/rtTA-MCK//TRE-HA/Mst-IRES/EGFP-polyA.
3. A conditional bicistronic myostatin expression construct comprising TRE-HA/Mst-IRES/EGFP-polyA//MCK-rtTA/BFP-polyA.
4. A conditional bicistronic myostatin expression construct comprising MCK-rtTA/BFP-polyA//-TRE-HA/Mst-IRES/EGFP-polyA.
5. A conditional monocistronic construct of any of embodiments 1-4 comprising two sequences: a: the regulatory construct MCK-rtTA/BFP-polyA, and b: the response construct TRE-HA/Mst-IRES/EGFP-polyA.
6. A conditional bicistronic myostatin expression construct comprising a construct of any of claims 1-4 lacking a HA tag at the 5' end of Mst sequence.
7. A conditional monocistronic construct of embodiment 6 where the response construct lacks a HA tag on Mst sequence.
8. A conditional bicistronic myostatin expression construct comprising a construct of any of claims 1-4 lacking an IRES/EGFP sequence downstream of Mst sequence.
9. A conditional monocistronic construct of embodiment 8 where the response construct has no IRES/EGFP sequence.
10. A conditional bicistronic myostatin expression construct comprising a construct of any of embodiments 1-4 lacking BFP fusion to the rtTA sequence.
11. A conditional monocistronic construct of embodiment 10 wherein the regulatory construct lacks a BFP fusion at the 3' end of the rtTA sequence.
12. A construct of any of embodiments 1-11 wherein said construct comprises a plasmid.
13. A method of producing a transgenic non-human animal comprising introducing the construct of any of embodiments 1-11 into a non-human animal.
14. A transgenic non-human animal for conditionally overexpressing Mst comprising cells comprising a construct of any of embodiments 1-11.
15. A transgenic non-human animal produced by: (a) crossing a first transgenic non-human animal comprising a first (regulatory) construct that expresses rtTA operably linked to promoter MCK or MCK-3E with a second non-human animal comprising a second (response) construct comprising Mst or Mst cDNA operably linked to a promoter TRE and (b) selecting from the first generation offspring a transgenic non-human animal having a genome comprising both the first regulatory construct and the second response construct.
16. A method for screening for therapeutic agents that inhibit Mst activity comprising (a) administering test agents to the transgenic animal of embodiments 14 or 15, (b) evaluating the effects of the test agent on the Mst associated phenotype of the animal.
17. A conditional bicistronic myostatin expression construct comprising a regulatory sequence and a myostatin (Mst) response sequence, wherein said bicistronic myostatin expression construct comprises a DNA transgene, said DNA transgene comprising SEQ ID NO. 13, or variants thereof with greater than 80%, 90%, 95%, 99% sequence identity operably linked to the TRE promoter, as a response sequence, and a regulatory sequence comprising a tissue specific promoter.
18. The conditional bicistronic myostatin expression construct of embodiment 1-4, 6, 8 and 10 wherein the regulatory sequence comprises reverse tetracycline transcription activator (rtTA).
19. The conditional bicistronic myostatin expression construct of embodiment 1-4, 6, 8 and 10 wherein the response sequence comprises TRE promoter.
20. The conditional bicistronic myostatin expression construct of embodiment 1-4, 6, 8 and 10 wherein the tissue specific promoter is selected from MCK, MCK-3E and Troponin I.
21. A transgenic non-human animal for conditionally overexpressing Mst comprising cells comprising a bicistronic myostatin expression construct comprising a regulatory sequence and a myostatin response sequence, wherein said bicistronic myostatin expression construct comprises a DNA transgene, said DNA transgene comprising SEQ ID NO. 13, or variants thereof with greater than 80%, 90%, 95%, 99% sequence identity operably linked to the TRE promoter, as a response sequence, and a regulatory sequence comprising a tissue specific promoter.
22. The transgenic non-human animal of embodiment 21 wherein the regulatory sequence comprises reverse tetracycline transcription activator (rtTA).
23. The transgenic non-human animal of embodiment 21 wherein the response sequence comprises TRE.
24. The transgenic non-human animal of embodiment 21 wherein the tissue specific promoter is MCK, MCK-3E or Troponin I.
25. A conditional bicistronic myostatin expression vector comprising the myostatin expression response construct of embodiment 17 cloned into a vector.
26. A method of producing a conditional bicistronic myostatin expression vector comprising cloning the myostatin expression construct of any of embodiments 1-4, 6, 8 and 10 into a vector.
27. A method of producing a transgenic non-human animal comprising introducing the conditional bicistronic myostatin expression construct of embodiment 17 into a non-human animal.

28. A conditional monocistronic myostatin expression construct comprising polyA-EGFP/IRES-Mst/HA-TRE//MCK-rtTA/BFP-polyA, where MCK is a promoter selected from MCK and MCK-3E.

29. A conditional monocistronic myostatin expression construct comprising polyA-BFP/rtTA-MCK//TRE-HA/Mst-IRES/EGFP-polyA.

30. A conditional monocistronic myostatin expression construct comprising TRE-HA/Mst-IRES/EGFP-polyA//MCK-rtTA/BFP-polyA.

31. A conditional monocistronic myostatin expression construct comprising MCK-rtTA/BFP-polyA//TRE-HA/Mst-IRES/EGFP-polyA.

32. A conditional monocistronic construct of any of embodiments 28-31 comprising sequences: a: the regulatory construct MCK-rtTA/BFP-polyA, and b: the response construct TRE-HA/Mst-IRES/EGFP-polyA.

33. A conditional monocistronic myostatin expression construct comprising any of embodiments 28-31 lacking a HA tag at the 5' end of Mst sequence.

34. A construct of embodiment 33 wherein the response construct lacks an HA tag on Mst sequence.

35. A conditional monocistronic myostatin expression construct comprising a construct of any of embodiments 28-31 lacking IRES/EGFP sequence downstream of Mst sequence.

36. A conditional monocistronic construct of embodiment 35 wherein the response construct lacks a IRES/EGFP sequence.

37. A conditional monocistronic myostatin expression construct comprising a construct of any of embodiments 28-31 lacking a BFP fusion to the rtTA sequence.

38. A conditional monocistronic construct of embodiment 37 wherein the regulatory construct lacks a BFP fusion at the 3' end of the rtTA sequence.

39. A construct of any of embodiments 28-38 wherein said construct comprises a plasmid.

40. A method of producing a double-transgenic non-human animal comprising introducing the monocistronic myostatin expression constructs of embodiment 28-39 into a non-human animal.

41. A myostatin expression vector of any of the preceding embodiments, further comprising a fluorescent marker coding sequence selected from the group consisting of GFP, EGFP, dsRed, dsRed2, CFP, ECFP, YFP, EYFP, BFP, dsRed1, dsRed2, DsRed-Express, AsRed2, HcRed1, AmCyan, ZsYellow, ZsGreen, AcGFP-1, luciferase, and aequorin.

42. The method of embodiment 13 or 26 wherein the vector comprises the conditional bicistronic myostatin expression vector of any of the preceding embodiments.

43. The conditional bicistronic myostatin expression vector of any of the preceding embodiments wherein the vector is pEGFP-1.

44. The conditional bicistronic myostatin expression response construct of embodiment 1 wherein the transgenic nucleotide sequence comprises SEQ ID NO. 5 or Mst cDNA operably linked to a TRE2 promoter in cells engineered to express rtTA protein in the presence of tetracycline or doxycycline.

45. A method of decreasing Mst expression in a cell comprising withdrawal or removal of tetracycline or doxycycline from a cell comprising a myostatin expression response construct of a preceding embodiment.

46. The conditional bicistronic myostatin expression response construct of embodiment 1 wherein the tissue specific promoter is skeletal muscle specific.

47. The conditional bicistronic myostatin expression response construct of a preceding embodiment wherein the promoter is an MCK-3E promoter.

48. A method of modulating the expression of Mst (SEQ ID NO. 5) in a non-human animal comprising inserting the construct of a preceding embodiment into cells of said animal and further by increasing or decreasing the concentration of doxycycline in the non-human animal.

49. A transgenic non-human animal comprising a transgenic nucleotide sequence of embodiment 1, wherein said tissue specific promoter comprises a muscle tissue specific promoter.

50. The transgenic non-human animal of embodiment 49 wherein the transgenic nucleotide sequence comprising SEQ ID NO. 5 or Mst cDNA is integrated into the genome of the animal.

51. The transgenic non-human animal of embodiment 50 wherein the transgenic nucleotide sequence comprising SEQ ID NO. 5 or Mst cDNA is operably linked MCK-3E promoter.

52. The transgenic non-human animal of embodiment 51 wherein the transgenic nucleotide sequence comprising SEQ ID NO. 5 or Mst cDNA operably linked to a reverse transcription activator.

53. The transgenic non-human animal of embodiment 52 wherein the animal exhibits an Mst associated phenotype in the presence of a transcription activator.

54. The transgenic non-human animal of embodiment 53 wherein the phenotype can be reversed or ameliorated upon decrease or removal of said transcription activator 55. The transgenic non-human animal of embodiment 53 wherein the nucleotide sequence comprises SEQ ID NO. 5 or Mst cDNA is regulated by a transactivator.

56. The transgenic non-human animal of embodiment 55 wherein the nucleotide sequence comprises SEQ ID NO. X or Mst cDNA is linked to a promoter.

57. The transgenic non-human animal of embodiment 53 wherein the Mst associated phenotype is a muscular phenotype selected from aplasia and atrophy.

58. The transgenic non-human animal of embodiment 55 wherein the transactivator is reverse tetracycline transactivator (rtTA).

59 A method for screening for therapeutic agents that inhibit Mst activity comprising (a) administering test agents to the transgenic animal of any of the above embodiments, (b) evaluating the effects of the test agent on the Mst associated phenotype of the animal.

60. A transgenic non-human animal produced by: (a) crossing a first transgenic non-human animal comprising a first construct that expresses rtTA operably linked to promoter MCK-3E with a second non-human animal comprising a second construct comprising Mst or Mst cDNA operably linked to a promoter TRE2 and (b) selecting from the first generation offspring a transgenic non-human animal having a genome comprising both the first construct and the second construct.

61. A method of producing a double-transgenic non-human animal comprising introducing the conditional monocistronic Mst expression response construct of any of embodiments 28-31 into a non-human animal.

62. The transgenic non-human animal of embodiment 49 or 60 wherein the animal is a mouse.

63. A method for screening for therapeutic agents that inhibit Mst activity comprising (a) administering test agents to a transgenic mouse of any of the above embodiments, (b) evaluating the effects of the test agent on the Mst associated phenotype of the mouse.

The following examples provide further disclosure and illustration of the embodiments of the invention disclosed herein.

EXAMPLES

Example 1

The following experiments were done to investigate the role of Mst in processes that result in muscle atrophy and hypertrophy. The data support the following conclusions: 1.) an Mst overexpressing construct allows the quantification of Mst expression levels in myoblasts and myotubes in vitro, using a muscle-specific MCK promoter; 2.) the Mst overexpressing transgenic mouse is a good model for muscle atrophy, and has been characterized using: (a) PCR and Southern blot techniques to genotype the mouse; (b) RT-PCR and western blotting to quantify Mst expression levels in skeletal muscle; (c) CT scanning to quantify the muscle mass; (d) force-velocity, grip strength and activity wheel measurements to quantify muscle power; (e) SDS-PAGE to quantify the relative MHC composition of muscle; (f) immunohistochemistry to identify changes in muscle fiber distribution and structure; and (g) forced exercise test to evaluate muscle function.

Mst Overexpression Construct Expresses High Levels of Mst In Vitro

Preparation of EGFP and Myostatin Expression Constructs:

pMCK1.3/EGFP-1 plasmid: Generation of this construct has been described (Reisz-Porszasz, S. et al. Am. J. Physiol. Endocrinol. Metab. 285(4):E876-888, 2003) and may be accomplished as follows: A muscle specific creatine kinase (MCK) enhancer/promoter containing the region from −1354 to +1 bp from the transcription initiation site, cloned into the pEGFP-1 vector (Clontech) was used (FIG. 1A/A). The MCK fragment (1.3 kb) was released from pMCKG plasmid by restriction digest with SpeI/EcoRI. The vector was digested with HindIII. The two DNA fragments were blunt end ligated. A 2.2 kb construct containing the MCK, the EGFP and the SV40 polyA sequence was released by XhoI/Afl II digestion for animal pronuclei injection (FIG. 1A). Larochelle et al., "Efficient muscle-specific transgene expression after adenovirus-mediated gene transfer in mice using a 1.35 kb muscle creatine kinase promoter/enhancer" Gene Ther 4:465-472 (1997).

pMCK-3E/EGFP-1 plasmid: Another construct for generating the MCK promoter with the three point mutations was also used. The MCK promoter (from −1256 to −1 nucleotide) harbors three point mutations in its three conserved E-box site. The locations of the point mutations are: nt −1178, −1153 and −249 (Donoviel et al., "Analysis of muscle creatine kinase gene regulatory elements in skeletal and cardiac muscles of transgenic mice" Mol Cell Biol. 16:1649-1658 (1996)). These mutations prevent gene expression in the heart muscle and have been shown to restrict the expression of the protein to the skeletal muscle. A 2.2 kb fragment containing the mutated version of the MCK promoter and EGFP sequences was released with BglII/AflII restriction digest and used for pronuclei injection.

pMCK-3E/mMst plasmid: The mMst sequence was PCR amplified in order to introduce 5' AgeI site and 3' NotI site. Primers for mMst cloning: forward 5'-atg atg caa aaa ctg caa atg tat-3' (SEQ ID NO: 16); reverse 5'-tca tga gca ccc aca-3' (SEQ ID NO: 17). The PCR product and the pMCK-3E/EGFP-1 plasmid were restriction digested with AgeI/NotI enzymes, and ligated. A 2.6 kb fragment was released with Bgl II/Afl II digestion and used for pronuclei injection.

pMCK1.3/mMst plasmid: Mst cDNA from the mouse skeletal muscle was cloned and sequenced. This 1.1 kb sequence was subcloned into the pEGFP-1 vector by substituting the EGFP (725 bp) sequence to mMst sequence (FIG. 1A/B). The MCK promoter was cloned into this construct in a similar way as described above. The MCK promoter-Mst cDNA-polyA construct (2.6 kb) was released with KpnI/Afl II digestion and used for mouse pronuclei injection.

Figure 2A:
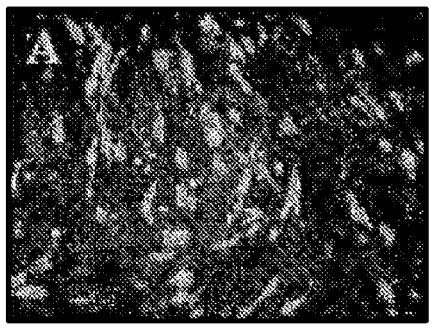
Figure 2B:

In Vitro Expression of Construct:

The C3H murine myoblast cell line C2C12 was propagated in DME medium with 10% fetal bovine serum. For differentiation into myotubes, myoblasts were allowed to grow to approx. 90-100% confluence. After 2 days the medium was changed to DMEM with 5% horse serum. Myotubes began to form after 3 or 4 days. Cells were transiently transfected with 2 μg of the using Lipofectamine according to the manufacturer's protocol. Green fluorescence protein synthesis was monitored every day under fluorescence microscopy (FIGS. 2A and 2B).

Transfection experiment was repeated by using the bicistronic conditional Mst overexpressing transgene (FIG. 1B bottom) and Mst/EGFP expression was able to be switched on and off by adding (2.5 μg/ml doxycyclin as the optimized concentration) or withdrawing doxycycline from the media. When the gene was turned on, EGFP expression was observed in 5 days, while turning off the gene resulted in zero EGFP expression during one week. This experiment was repeated several times, showing that the gene induction system is unlikely to be leaking. Stable transfectants are maintained in G418 selection media. After 48 hours of infection we got high expression level of GFP in both myoblasts and myotubes. The mutated MCK promoter (MCK-3E) provided higher expression level in vitro, than the wild type (pMCK-3E/EGFP-1: 57%; versus pMCK1.3/EGFP-1: 25%).

Mst Overexpressing Transgenic Mice as a Model for Muscle Atrophy

Generation and identification of transgenic animals: Purified MCK1.3/EGFP and MCK1.3/mMst transgene sequences were sent to UC Irvine Transgenic Facility, and 300-300 pronuclei were injected with each DNA construct and transplanted into CB6F1 mice. Transgenic animals were identified by PCR reaction of ear (or tail) DNA. The size of the PCR product was 290 bp using the 5' primer located at −209 bp upstream, and the 3' primer located at +60 bp downstream of the transcriptional start site as shown in FIG. 1A (asterisks show primer locations). Primers for the ear DNA genotyping: forward 5'-aac cag tga gca agt cag cc-3' (SEQ ID NO: 18); reverse 5'-gcc agc agc aat cag cat-3' (SEQ ID NO: 19). These primers overlap the joint sequences of the MCK promoter 3' end and the EGFP or Mst gene 5' end. Female and male animals carrying the transgene and their age-matched controls were sacrificed at 7 weeks of age, 10 animals in each group. Genotyping of mice was performed by PCR (FIG. 3A) and Southern blot analysis (FIG. 3B) of 30 μg EcoRI digested genomic DNA prepared from liver (representative samples are shown).

Figure 2C:
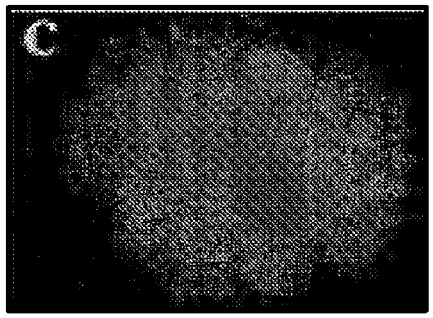
Figure 2D:
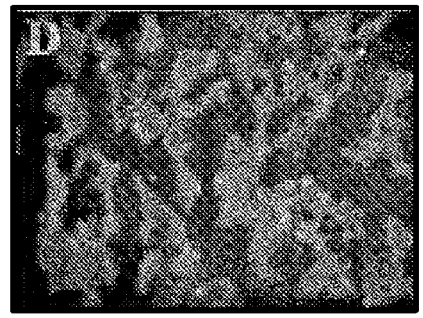
Figure 4A:
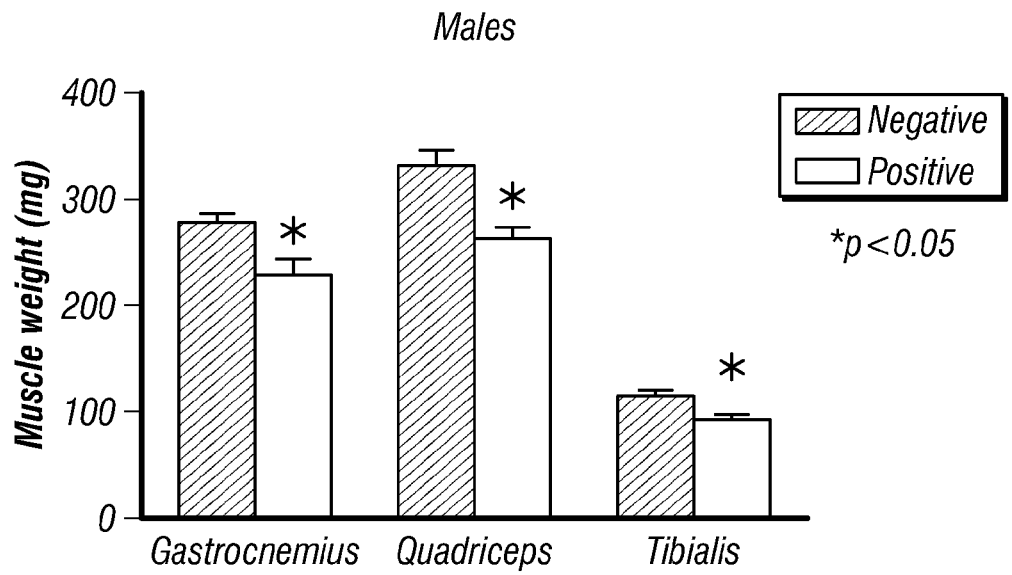
Figure 4B:
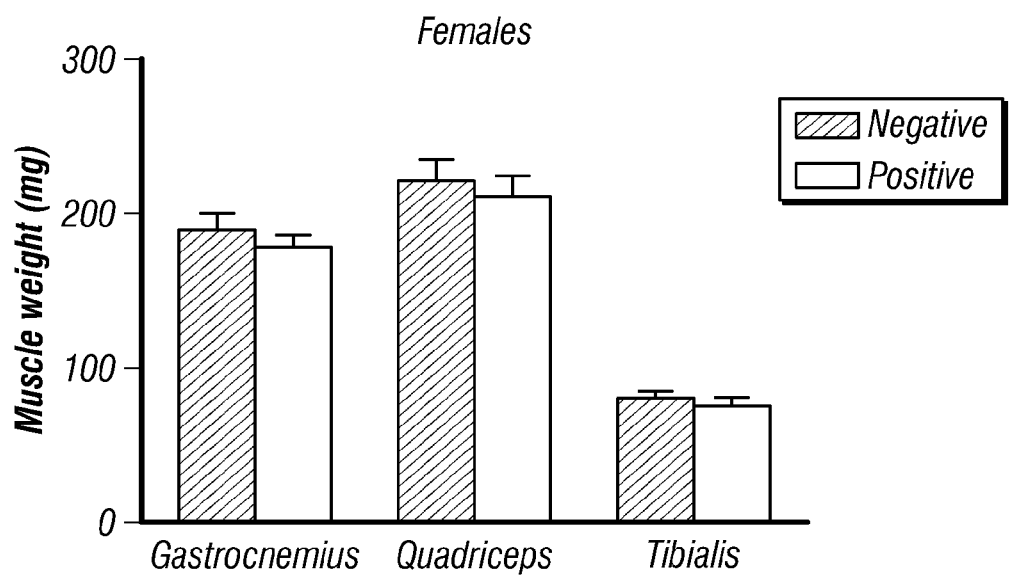

Skeletal muscles (tibialis, gastrocnemius, quadriceps, diaphragm, biceps, forearm muscle) were collected, and selected tissues were used for further investigation. Transgenic animals carrying the EGFP transgene showed green fluorescence only in muscles (FIGS. 2C and 2D). Results of different muscle weights collected from myostatin overexpressing and wild type animals are shown in FIG. 4. Although there was no significant difference between the body weights of transgenic and control males (22.3±2.1 and 24.8±2 g, respectively), there was a 17% decrease in gastrocnemius weight, a 21% decrease in quadriceps weight, and an 18% decrease in tibialis muscle weight (FIG. 4A). Significant differences in body weights (19.1±1.1 and 19.3±2.1 g), or in muscle weights between transgenic and control females were not found (FIG. 4B).

Determination of EGFP and Myostatin Expression

Transgenic animals show 2.2 fold increase in Mst expression in skeletal muscle: Mst expression was analyzed by RT-PCR, northern and western blotting. Total RNA was extracted from gastrocnemius, tibialis and quadriceps of transgenic and control mice. Aliquots were submitted to RT-PCR reaction. Two primer sets for Mst were chosen. A first primer set for endogenous Mst included: forward 5'-aga caa aac acg agg tact c-3' (SEQ ID NO: 20) and reverse 5'-tgg att cag gct gtt tga gc-3' (SEQ ID NO: 21). A second primer set for Mst transgene included: forward 5'-gtc tcc cat taa tat gct at-3' ((SEQ ID NO: 22) and reverse 5'-atc ata ccc tcc taa ctc ag-3' (SEQ ID NO: 23).

Figure 6B:
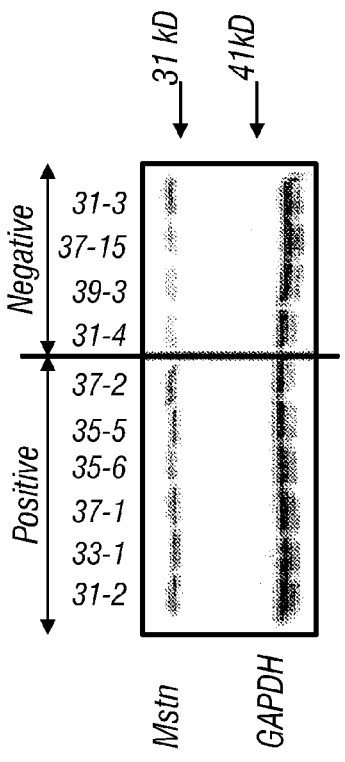
Figure 6C:
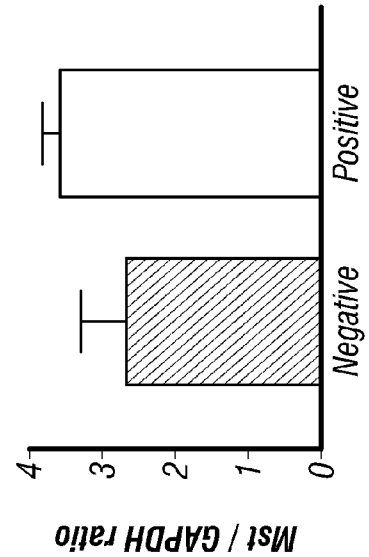
Figure 6A:
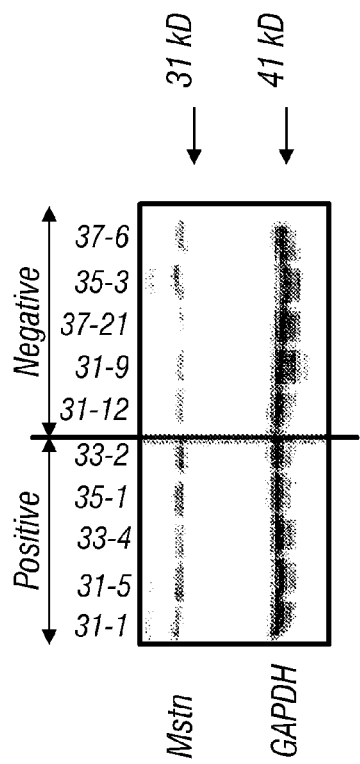

The first primer set was used to measure the total Mst present, but to avoid possible cross-reaction with GDF-11 mRNA, the second was used to differentiate the endogenous and exogenous Mst. The housekeeping gene GAPDH was employed, and was evenly expressed in all samples. There was a significant increase (37%) in Mst mRNA expression in transgenic animals (FIG. 5). Protein was extracted from the same muscles mentioned above. Denatured proteins were separated on SDS gel, transferred to NC membrane, and immunodetected with costume made Mst monoclonal antibody. This antibody recognizes the full length, unprocessed 52 kDa Mst protein and the 28 kDa biologically active Mst protein. Quantification of the Western blot results indicated a significantly higher (2.2 fold) Mst protein levels in transgenic animals' skeletal muscle. The relative expression levels within each animal followed this order: gastrocnemius>quadriceps>tibialis anterior. No detectable Mst protein was found in Mst KO animals. Mst proteins were also immunodetected with myostatin polyclonal antibody that recognized the 38 kDa form of Mst (FIG. 6). Significantly lower (41%) Mst protein was detectable in male skeletal muscle, than in female's (25%). The figure shows the western blot from gastrocnemius, but similar results were found in other muscles.

Quantification of muscle atrophy: Groups of animals of different ages (2 months, 6 months, 12 months and 18 months) were anaesthetized and scanned in CT scanner (MicroCAT II). The X-ray source, X-ray detector and video camera were mounted to a rotating stage that moved around the animal 360 degrees. The exposure time was about 29 minutes per animal. Amira 3.1 version software was used to obtain a 3D image from the raw data. Skeletal tissue and fat mass were quantified on the images. A significant reduction (24%) in hind limb muscle mass and an increase in abdominal fat (1.7 fold) in transgenic animals at age 6 months or older compared to control was identified. Representative 3D images and cross sections are shown on FIG. 10. Detailed quantification of the data is in progress.

Comparison of Muscle Strength Measurements:

A pulley apparatus was constructed in which one end of the pulley system consisted of a weight container, while the other end attached to the base of the animal tail. Mice were dangled over a horizontal pull bar assembly, and were allowed to grasp the bar. Once the grasp was secure, a steady stream of water flowed into the weight container. The volume of water required for the mouse to release the pull bar was measured. The difference in grip strength between females and males in two different mouse strains, C57B16 and BalbC, was measured (FIG. 8). Gender differences within the strains (B16: p=0.02193; BalbC: p=7.9E-07), differences between males (first two columns) of the two strains (p=0.00377), but not between female (last two columns, p=0.393) were observed.

The daily spontaneous activity was also analyzed on a rodent running wheel for four weeks and surprisingly found that Mst Tg mice had significantly greater daily activity compared KO and WT male animals as shown on FIG. 9.

Modified Mst expression does not change single fiber tension: Contractile measurements on 7 week-old male WT, transgenic and KO animals, 10 mice in each group were performed. Under anesthesia, the tendon of the plantaris muscle was attached to a computer controlled Cambridge 305B ergometer. The optimal muscle length (i.e., $L_0$) was determined from measurements of isometric tension made at various muscle lengths. All subsequent measurements were made with the muscle starting at an initial length of $L_0$. The muscle was then tested at a minimum of 15 different after load conditions (3 to 100% of $P_0$) so that the force-velocity relationship could be determined. The after load of the ergometer was controlled using the DAC-08 digital-to-analog board of the computer. Specific-tension was determined by normalizing maximal isometric tension to the cross-sectional area of the muscle. Force-velocity data was fitted using a linear version of the Hill equation. Using this equation, $V_{max}$ was estimated by determining the y-intercept of the force-velocity relationship. All of the above contractile measurements were made with a rest interval of 1 min. between each contraction. FIG. 11 shows the results of the force-velocity measurements. Plantaris muscle of the KO mice produced ~40% more force than the WT and transgenic mice. Specific-tension provides insight regarding the physiology of the system, and, in this case, demonstrated that the muscles in both the transgenic and KO groups were capable of producing a normal amount of specific tension. No differences were found in isometric tension normalized to cross-sectional area and isometric twitches.

Fast type whole muscle MHC protein isoform composition in transgenic animals is not altered: Proteins were isolated from plantaris muscle from the same animals used for the contractile measurements. Approximately 0.1 µg of myofibrillar protein from each muscle sample were electrophoresed using a constant voltage of 275 V for 5 hrs. The four MHC isoforms, type I, type IIA, IIX and IIB proteins were stained using a silver staining kit and scanned for quantification using a laser densitometer. We found significant differences in MHC isoform composition in KO animals where the MHC type JIB protein levels were significantly higher by 17.5±1.7% compared to WT, and the type IIA protein levels were decreased by 10.5±1.3% in plantaris muscles. Transgenic animal's plantaris muscle MHC isoform composition was not significantly different from WT.

Histomorphometry

The cross-sectional area of the muscle fibers was determined by point counting. A minimum of 30 type II fibers was analyzed in each muscle specimen. The fields were randomly selected to measure the fiber area, and all of the fibers encompassed in those fields were evaluated. Significant differences were observed between myostatin overexpressing and control animals in gastrocnemius, as well as in quadriceps (FIG. 7A). The number of myonuclei were counted in 20 randomly selected muscle fibers of each type in gastrocnemius and quadriceps samples. Myonuclei numbers are summarized in FIG. 7B. Statistically significant differences were observed between transgenic and control in gastrocnemius, and in quadriceps muscles as well. Gender differences were neither observed in cross-sectional area nor in myonuclei number.

Mst transgenic animals exhibit significant changes in fiber morphometry: A comprehensive analysis on fiber cross-sectional area (CSA), fiber number, and fiber type distribution in plantaris, gastrocnemius, soleus, quadriceps, tibialis and extensor digitorum longus (EDL) muscles isolated from WT, KO and transgenic animals (n=5/group) has been conducted. Muscle samples were frozen and sectioned in a cryostat. Tissue sections were probed with a monoclonal antibody specific to type IIB MHC isoform. 200-300 fibers per sample were analyzed and quantified applying image analysis (Table I and FIG. 12).

female rats. The overloaded muscle showed a significant reduction in fast type IIB MHC isoform, both at the mRNA and protein levels. This technique is adopted for corresponding experiments with mice.

Mst Changes Molecular Pathways in Muscle

In order to identify the pathways involved in the Mst overexpression induced muscle atrophy, muscle samples were collected from five animals in each group (gastrocnemuis muscles were used because it had mixed fiber types and were

TABLE I

MHC composition and fiber cross sectional area (CSA) analysis in Mst KO, Tg, and WT animals.

| | Plantaris | | | red gastrocnemius | | | Soleus | | | EDL | | |
|---|---|---|---|---|---|---|---|---|---|---|---|---|
| | CSA ($\mu m^2$) | | IIB/I | CSA ($\mu m^2$) | | IIB/I | CSA ($\mu m^2$) | | IIB/I | CSA ($\mu m^2$) | | IIB/I |
| | type IIB | Type I | Ratio | type IIB | type I | ratio | type IIB | type I | ratio | type IIB | type I | ratio |
| WT | 4432 ± 115 | 2271 ± 245 | 3.6 | 3772 ± 265 | 2234 ± 154 | 0.5 | 2118 ± 176 | 1970 ± 256 | 0.2 | 3577 ± 189 | 1848 ± 98 | 4.25 |
| KO | 6785 ± 221* | 3874 ± 211* | 2.0 | 5998 ± 326* | 3111 ± 319 | 0.9* | 2510 ± 152 | 2045 ± 344 | 1.1* | 5392 ± 137* | 1991 ± 119 | 6.4* |
| Tg | 3974 ± 153* | 2075 ± 237 | 2.0 | 3145 ± 105* | 2015 ± 167 | 0.16* | 1989 ± 187 | 1769 ± 233 | 0.2 | 2434 ± 121* | 1122 ± 197 | 1.8* |

*significant differences compared to WT when P < 0.05

The data show significant changes in CSA of Tg animal's fast and mixed type muscles, but not in slow type muscles. KO animals had more fast type fibers while Tg animals had more slow type fibers, compared to WT. Significant changes in the number of fibers were not detected.

Mst Tg animals exhibit significantly higher level of exercise tolerance: The exercise tolerance of these three groups of animals using treadmill to exhaustion were completed. Following a short training period, six months-old animals were forced to run on a flat treadmill at 8 m/min speed for 5 min. Then both the belt speed and the inclination angle were increased to 12 m/min, 5% increment for 5 min. The next step was at 16 m/min, 10% increment for 5 min, etc. Animals were forced to run with 1.5 mA electric shock, and the test ended when the animals did not avoid the electric shock. The test was performed every other day for six weeks. The work rate weekly (3 days, four animals in each groups) (WR=g*BW*v*sin(a), where WR=work rate (Watts), g=gravitation acceleration, BW=body weight (kg), v=speed (m/min), a=opening angle of the treadmill) was calculated. The results are shown on FIG. 13. Exercise tolerance for KO animals was significantly lower than for Tg animals each week. This difference started to increase on week 3, mainly because Tg animals begun to show increased exercise tolerance. The lower exercise tolerance in KO mice could be related to increased amount of fast type fibers, and the shift from oxidative to glycolytic metabolic activity in adult skeletal muscle.

Male mice overexpressing Mst in skeletal muscle showed increased levels of abdominal fat mass if older than 4 months. At the end of the treadmill exercise experiment described above, abdominal fat pads were collected from control (not running on treadmill) and experimental animals. As shown in FIG. 14, Mst Tg animals had significantly higher fat before exercise than WT. Following six weeks of treadmill, Tg animals not only ran longer and had higher exercise tolerance, but they lost more fat compared to WT and KO. WT and KO mice fat mass did not change significantly during exercise.

Mechanical overloading of the plantaris muscle: Mechanical overloading has been used on rats. Mechanical overloading produces substantial hypertrophy of the plantaris muscle (muscle mass increased by 63% compared to control), and substantial changes of MHC protein isoform distribution in large enough to isolate RNA in sufficient quantities). The isolated RNAs were pooled and subjected to cDNA synthesis, then applied on superarray Pathway Finder analysis. FIG. 15 shows the changes in gene expression levels in TG and KO animals relative to WT. Mst Tg animals TGF-β, p53, NF-kappaB, LDL and PI3K/Akt pathways were upregulated significantly, while the Hedgehog, retinoic acid, insulin and CREB pathways were downregulated. In Mst KO animals, the only upregulated pathway was TGF-β, while insulin and androgen pathways were significantly downregulated. These changes indicate that Mst is involved in cell proliferation, differentiation, cell cycle regulation (as already known), and also in cell metabolism and cell fate decision. Further analysis is needed to elucidate the exact role of Mst in these processes, and this is one of the goal of this project.

Generation of the CMOT Mouse

The data presented above shows that the Mst overexpressing mouse is a good model for muscle wasting. However, this model does not allow testing the mechanism of Mst action in the regulation of muscle in the adult. The Tg animals we have generated have a "developmental disorder", since Mst is overexpressed before birth. A more appropriate model to mimic atrophic pathology would be a conditional overexpressing transgenic (CMOT) animal, in which Mst could be turned on and off in a reversible way at any time during adulthood.

Example 2

Generation of the DNA Construct for Conditional Mst Overexpression pMCK1.3/Tet-ON/Blue plasmid: To produce a conditional Mst overexpressing transgenic animal, we have used two constructs, one is the regulatory plasmid (pTet-ON), and the other is the response plasmid (pTRE2). Both are available from Clontech, Inc. In the regulatory plasmid, the reverse transactivator protein (rtTA), which is a fusion of Tc repressor protein and VP16 protein of herpes simplex virus activation domain, expresses under the control of CMV promoter. First, this promoter was changed to the muscle specific promoter (MCK, SEQ ID NO: 8) to obtain rtTA expression only in skeletal muscle. A fusion protein of rtTA with blue-fluorescence protein was created to detect rtTA expression level both in vitro and in vivo (FIG. 16-A).

pTRE2/HA-mMst/IRES-EGFP plasmid: The response plasmid contains a multiple cloning site immediately downstream of the Tet-responsive $P_{hCMV-1}$ promoter. This site was used for cloning the Mst sequence (SEQ ID NO: 5), which was previously fused with hemagglutinin (HA) epitope on its 5' end (SEQ ID NO: 6). It is well-known that Mst goes through a posttranslational modification.[3] During this process, two C-terminal domains of the full length Mst protein form a dimer by covalent bond called the processed/mature Mst. This dimer was able to be detected with an antibody against the C-terminal domain. The N-terminal domain stays attached to the dimer, and has an inhibitory function on it. This complex is called latency associated protein. An antibody against the HA sequence allowed detection of and following of the path of the N-terminal domain, both within the muscle tissues and in the serum. An IRES (internal ribosome entry site) sequence with an EGFP sequence (SEQ ID NO: 4) was inserted to be able to express Mst and EGFP with the same promoter on a single transcript (FIG. 16-B).

Both constructs were tested in vitro on two different cell lines, the C2C12 mouse myoblast and the human skeletal muscle myoblast (HSMM) before use in producing transgenic animals. The regulatory and the response plasmids were co-transfected into the cells by electroporation. The transfected cell lines were used to determine the optimal doxycyclin concentration and the optimal time course for maximum EGFP expression. For in vivo application, this monocistronic model requires generation of two different transgenic animals (the regulatory and the response animals). Their offspring are genotyped, selected for the presence of the two transgenes, respectively, and cross-bred. The second generation is screened for double transgenic animals. Each step requires duplication, and more importantly, the number of the resulted double-transgenic animals is very low. The results of producing these animals are described below.

Bicistronic model: To increase the number of double-transgenic animals and decrease the time to generate offsprings, a novel, bicistronic gene expression system was developed where the regulatory and response sequences are cloned in the opposite orientation. The basic idea is similar to the one described above, but instead of using two constructs, only one fragment with the regulatory and the response sequences was used. A muscle creatine kinase (MCK) enhancer/promoter (SEQ ID NO: 8) containing the region from −1354 to +1 bp from the transcription initiation site was cloned into the pTet-ON vector carrying the rtTA sequence (Clontech). The MCK fragment (1.3 kb) was released from pMCKG plasmid by restriction digest with SpeI/EcoRI. The vector was digested with HindIII. Both fragments were filled up by Klenow polymerase reaction, and blunt end ligation was performed. Blue fluorescent protein sequence (SEQ ID NO: 10) was fused to the 3' end of the rtTA sequence in order to visualize the expression.

Next, the myostatin cDNA (SEQ ID NO: 5) from the mouse skeletal muscle was cloned and sequenced. Primers for mMst cloning were: forward 5'-atg atg caa aaa ctg caa atg tat-3' (SEQ ID NO: 16); reverse 5'-tca tga gca ccc aca-3' (SEQ ID NO: 17). This 1.1 kb sequence was subcloned into the pTRE/HA vector and then the TRA/HA-Mst sequence was subsequently cloned into the pIRES/EGFP vector.

Finally, the two sequences were cloned together in reverse orientation into a bicistronic gene expression system resulting the final construct named: pMCK/rtTA-BFP/SV40polyA//TRE/HA-Mst/IRES-EGFP/SV40polyA (SEQ ID NO: 13) (FIG. 1B).

The TRE promoter is silent in the absence of binding Tet-activated rtTA protein, and becomes activated upon binding the Doxycycline (Dox, also known as doxycyclin), and express HA-Mst and EGFP at the same time.

This construct (6.4 kb) has been developed, the in vitro tests are completed, and the construct was injected into pronuclei. Stable transfectant myoblast (C2C12) cells were isolated and experiments regarding to optimal Dox concentration and time course were repeated.

Example 3

CMOT animals: For the generation of transgenic mice, the 6.5 kb long MCK/rtTA-BFP/SV40polyA//TRE/HA-Mst/IRES-EGFP/SV40polyA fragment was released by AflII restriction endonuclease digestion and this fragment was used for pronuclei injection. Pronuclei injection was successfully completed. Three hundred and five pronuclei were injected with the bicistronic construct, and 24 pups were born. Five were identified positive for the transgene.

Transgenic (positive genotype) animals were used for breeding, and following an eighth weeks of Dox treatment in their chow, Mst and EGFP expression were monitored via collection of biopsy samples. Mst protein expression levels were detected by Western blot using monoclonal anti-Mst antibody that recognized the two forms of Mst protein: the 52 kDa and the 28 kDa. The representative result is shown on FIG. 17. Mst conditional expression was successfully repeated on these animals three times already by Dox treatment and Dox withdrawal.

Other non-human transgenic animals, such as transgenic rats, hamsters, rabbits, gerbils, sheep, goat, horse, cow, dog, cat, other mammal, chicken, turkey, goose, pheasant, other bird, salmon, trout, halibut, other fish, oyster, shrimp, or other animal, whether a domestic animal, laboratory animal, a game animal, or other animal, may be prepared by the same or analogous methods.

It will be appreciated by those skilled in the art that changes could be made to the embodiments described above without departing from the broad inventive concept thereof. It is understood, therefore that this invention is not limited to the particular embodiments disclosed, but it is intended to cover modifications that are within the spirit and scope of the invention, as defined by the appended claims.

What is claimed:

1. A transgenic non-human mammal that conditionally overexpresses myostatin (Mst) when provided with a control factor selected from tetracycline and doxycycline, said transgenic non-human mammal having a genome that comprises a conditional bicistronic myostatin expression nucleic acid construct selected from the group of nucleic acid constructs consisting of:
 a) i) polyA-green fluorescence protein (EGFP)/internal ribosome entry site (IRES)-Mst/hemagglutinin (HA)-tetracycline response element (TRE)//MCK-rtTA/blue fluorescence protein (BFP)-polyA,
  ii) polyA-BFP/rtTA-MCK//TRE-HA/Mst-IRES/EGFP-polyA,
  iii) TRE-HA/Mst-IRES/EGFP-polyA//MCK-rtTA/BFP-polyA,
  iv) MCK-rtTA/BFP-polyA//TRE-HA/Mst-IRES/EGFP-polyA,
  v) TRE-HA/Mst-IRES/EGFP-polyA//polyA-BFP/rtTA-MCK, or
  vi) MCK-rtTA/BFP-polyA//polyA-EGFP/IRES-Mst/HA-TRE;
 b) any one of the constructs of a) lacking a HA tag;
 c) any one of the constructs of a) lacking an IRES/EGFP or EGFP/IRES; and
 d) any one of the constructs of a) lacking a BFP fusion to the rtTA sequence;
 where MCK is a promoter selected from muscle specific creatine kinase, MCK-3E, and troponin I;
 wherein Mst expression is inducible by administration of said control factor; and
 wherein said transgenic non-human mammal overexpresses Mst in response to administration of said control factor to said transgenic non-human mammal, whereby, following said administration of said control factor, said Mst overexpression is detectable, and said transgenic non-human mammal has decreased muscle mass as compared to control wild-type mammals.

2. The transgenic non-human mammal that conditionally overexpresses Mst of claim 1, wherein said conditional bicistronic myostatin expression nucleic acid construct is selected from the group of nucleic acid constructs consisting of:
 i) polyA-EGFP)/internal ribosome entry site (IRES)-Mst/hemagglutinin (HA)-tetracycline response element (TRE)//MCK-rtTA/blue fluorescence protein (BFP),
 ii) polyA-BFP/rtTA-MCK//TRE-HA/Mst-IRES/EGFP-polyA, iii) TRE-HA/Mst-IRES/EGFP-polyA//MCK-rtTA/BFP-polyA,
iv) MCK-rtTA/BFP-polyA//TRE-HA/Mst-IRES/EGFP-polyA,
v) TRE-HA/Mst-IRES/EGFP-polyA//polyA-BFP/rtTA-MCK, and
vi) MCK-rtTA/BFP-polyA//polyA-EGFP/IRES-Mst/HA-TRE, where MCK is a promoter selected from muscle specific creatine kinase, MCK-3E, and troponin I.

3. A transgenic non-human mammal that conditionally overexpresses Mst comprising cells comprising a bicistronic myostatin expression nucleic acid construct comprising a regulatory sequence and a myostatin response sequence, wherein said bicistronic myostatin expression nucleic acid construct comprises a DNA transgene, said DNA transgene comprising SEQ ID NO7: 13, or variants thereof with greater than 95% or 99% sequence identity to SEQ ID NO: 13, operably linked to the tetracycline response element (TRE) promoter, as a response sequence, and to a regulatory sequence comprising a tissue specific promoter selected from muscle specific creatine kinase, MCK-3E, and troponin I, said tissue specific promoter being a conditional promoter influenced by a control factor selected from tetracycline and doxycycline,
wherein said transgenic non-human mammal overexpresses Mst in response to administration of said control factor to said transgenic non-human mammal,
whereby, following said administration of said control factor, said Mst overexpression is detectable, and said transgenic non-human mammal has decreased muscle mass as compared to control wild-type mammals.

4. The transgenic non-human mammal of claim 3 wherein the regulatory sequence comprises reverse tetracycline transcription activator (rtTA).

5. The transgenic non-human mammal of claim 3 wherein the response sequence comprises TRE.

6. The transgenic non-human mammal of claim 3 wherein the tissue specific promoter is muscle specific creatine kinase, MCK-3E or Troponin I.

* * * * *

UNITED STATES PATENT AND TRADEMARK OFFICE
CERTIFICATE OF CORRECTION

| | | |
|---|---|---|
| PATENT NO. | : 8,222,478 B2 | Page 1 of 1 |
| APPLICATION NO. | : 12/398994 | |
| DATED | : July 17, 2012 | |
| INVENTOR(S) | : Suzanne Porszasz-Reisz | |

It is certified that error appears in the above-identified patent and that said Letters Patent is hereby corrected as shown below:

Col. 59, line 17 should read,

-- comprising SEQ ID NO:13, or variants thereof with greater --

Signed and Sealed this

Eleventh Day of September, 2012

David J. Kappos
*Director of the United States Patent and Trademark Office*

SEQUENCE LISTING

```
<160> NUMBER OF SEQ ID NOS: 23

<210> SEQ ID NO 1
<211> LENGTH: 6786
<212> TYPE: DNA
<213> ORGANISM: Mus Musculus
```

```
<400> SEQUENCE: 1
cttaagatac attgatgagt ttggacaaac cacaactaga atgcagtgaa aaaaatgctt    60
tatttgtgaa atttgtgatg ctattgcttt atttgtaacc attataagct gcaataaaca   120
agttaacaac aacaattgca ttcattttat gtttcaggtt caggggggagg tgtgggaggt   180 tttttaaagc aagtaaaacc tctacaaatg tggtatggct gattatgatc tagagtcgcg   240
gccgctttac ttgtacagct cgtccatgcc gagagtgatc ccggcggcgg tcacgaactc   300
cagcaggacc atgtgatcgc gcttctcgtt ggggtctttg ctcagggcgg actgggtgct   360
caggtagtgg ttgtcgggca gcagcacggg gccgtcgccg atggggtgt tctgctggta    420 gtggtcggcg agctgcacgc tgccgtcctc gatgttgtgg cggatcttga agttcacctt   480
gatgccgttc ttctgcttgt cggccatgat atagacgttg tggctgttgt agttgtactc   540
cagcttgtgc cccaggatgt tgccgtcctc cttgaagtcg atgcccttca gctcgatgcg   600
gttcaccagg gtgtcgccct cgaacttcac ctcggcgcgg tcttgtagt tgccgtcgtc    660 cttgaagaag atggtgcgct cctggacgta gccttcgggc atggcggact tgaagaagtc   720
gtgctgcttc atgtggtcgg ggtagcggct gaagcactgc acgccgtagg tcagggtggt   780
cacgagggtg ggcagggca cgggcagctt gccggtggtg cagatgaact tcagggtcag    840
cttgccgtag gtggcatcgc cctcgccctc gccggacacg ctgaacttgt ggccgtttac   900
gtcgccgtcc agctcgacca ggatgggcac caccccggtg aacagctcct cgcccttgct   960
caccatggtt gtggccatat tatcatcgtg tttttcaaag gaaaaccacg tccccgtggt  1020 tcgggggggcc tagacgtttt tttaacctcg actaaacaca tgtaaagcat gtgcaccgag  1080
gccccagatc agatcccata caatgggta ccttctgggc atccttcagc cccttgttga   1140
atacgcttga ggagagccat ttgactcttt ccacaactat ccaactcaca acgtggcact  1200
ggggttgtgc cgccttttgca ggtgtatctt atacacgtgg cttttggccg cagaggcacc  1260
tgtcgccagg tgggggggttc cgctgcctgc aaagggtcgc tacagacgtt gtttgtcttc  1320
aagaagcttc cagaggaact gcttccttca cgacattcaa cagaccttgc attcctttgg  1380
cgagagggga aagaccccta ggaatgctcg tcaagaagac agggccaggt ttccgggccc  1440
tcacattgcc aaaagacggc aatatggtgg aaaataacat atagacaaac gcacaccggc  1500
cttattccaa gcggcttcgg ccagtaacgt taggggggggg ggagggagag gggcggatcc  1560
cgggcccgcg gtaccgtcga ctgcagaatt cactagtgat taaattatat gtcgactca   1620 tgagcaccca cagcggtcta ctaccatggc tggaattttc ccatatatta tttgttcttt  1680
gccattaaaa tatagcatat taatgggaga cattttgtc ggagtgcagc aagggcctgc   1740
tgagcctctg ggtttgctt ggtgcacaag atgagtatgc ggatattttt gtaaaaacac   1800
aaattcacac tctcctgagc agtaattggc cttatatctt tgggtgcga taatccagtc    1860 ccatccaaag gcttcaaaat cgaccgtgag ggggtagcgg cagcaccggg attccgtgga  1920
gtgctcatcg cagtcaagcc caaagtctct ccgggacctc ttgggtgtgt ctgtcacctt  1980
gacttctaaa aagggattca gcccatcttc tcctggtcct gggaaggtta cagcaagatc  2040 atgccattc tcatccaaag ctttgatttc aatgcctaag ttggattcag gctgtttgag   2100
ccaattttgc aacactgtct tcacatcaat actctgccaa ataccagtgc ctgggctcat  2160
gtcaagtttc agagatcgga ttccagtata ccttgtaccg tctttcatgg gtttgatgag  2220
tctcaggatt tgcacaaaca ctgttgtagg agtcttgacg ggtctgagat atatccacag  2280
ttgggctttt actactttgt tgtactgtat tttagagcta aatttaaaaa agcaacattt  2340
```

```
gggcttgcca tccgcttgca ttagaaagtc agactctgta ggcatggtaa tgattgtttc   2400
cgtggtagcg tgataatcgt catcttccaa agagccatca ctgctgtcat ccctctggac   2460
gtcgtactga tcgatcagtt cccggagtgg aggcgctctt ggcagaagtt gtcttatagc   2520
atctttgctg atgttaggag ctgttccag gcgcagctta ctgaggattt gaattttat    2580 ggcttctatt ctggagtacc tcgtgttttg tctccacgca catgcattac acagcccctc   2640 ttttccaca ttttcttctc tctcactgcc ctcatttaga tccactgggc cagcagcaat    2700
cagcatgaac aggtaaatat aaacatacat ttgcagtttt tgcatcatgg ctggatccgg   2760
gcccataaga gcgtaatctg gaacatcgta tgggtacatg tgtctagct cgcgtcagct    2820 gactagagga tccccgggta ccgagctcga attcggggcc gcggaggctg gatcggtccc   2880
ggtgtcttct atggaggtca aaacagcgtg gatggcgtct ccaggcgatc tgacggttca   2940
ctaaacgagc tctgcttata taggcctccc accgtacacg cctactcgac ccgggtaccg   3000
agctcgactt tcactttct ctatcactga taggagtgg taaactcgac tttcactttt     3060
ctctatcact gatagggagt ggtaaactcg actttcactt ttctctatca ctgataggga   3120
gtggtaaact cgactttcac ttttctctat cactgatagg gagtggtaaa ctcgactttc   3180
acttttctct atcactgata gggagtggta aactcgactt tcacttttct ctatcactga   3240
tagggagtgg taaactcgac tttcactttt ctctatcact gatagggagt ggtaaactcg   3300
actttcactt ttctctatca ctgataggga gtggtaaact cgagatctcg agctcaagct   3360
tcgaattatc gaattcctgc agcccgatct cagctgaggt gcaaaaggct cctgtcatat   3420
tgtgtcctgc tctggtctgc cttccacagc ttggggggcca cctagcccac ctctccctag   3480
ggatgagagc agccactacg ggtctaggct gcccatgtaa ggaggcaagg cctggggaca   3540
cccgagatgc ctggttataa ttaacccaga catgtggctg ccccccccc cccaacacct     3600 gctgcctgag cctcaccccc accccggtgc ctgggtctta ggctctgtac accatggagg   3660
agaagctcgc tctaaaaata accctgtccc tggtggatcc agggtgaggg gcaggctgag   3720
ggcggccact tccctcagcc gcaggtttgt tttcccaaga atggttttc tgcttctgta    3780 gcttttcctg tcaattctgc catggtggag cagcctgcac tgggcttctg ggagaaacca   3840
aaccgggttc taacctttca gctacagtta ttgccttttcc tgtagatggg cgactacagc   3900
cccaccccca ccccgtctc ctgtatcctt cctgggcctg gggatcctag gctttcactg     3960
gaaatttccc cccaggtgct gtaggctaga gtcacggctc caagaacag tgcttgcctg     4020 gcatgcatgt ttctgaacct ccaactgcaa aaatgacac ataccttgac ccttggaagg     4080
ctgaggcagg gggattgcca tgagtgcaaa gccagactgg gtggcatagt tagaccctgt   4140
ctcaaaaaac caaaaacaat taataacta aagtcaggca agtaatccta ctcgggagac     4200
tgaggcagag ggattgttac atgtctgagg ccagcctgga ctacataggg tttcaggcta   4260
gccctgtcta cagagtaagg ccctatttca aaaacacaaa caaatggtt ctcccagctg     4320 ctaatgctca ccaggcatga agcctggtga gcattagcaa tgaaggcaat gaaggagggt   4380
gctggctaca atcaaggctg tgggggactg agggcaggct gtaacaggct tggggccag     4440 ggcttatacg tgcctgggac tcccaaagta ttactgttcc atgttcccgg cgaagggcca   4500
gctgtccccc gccagctaga ctcagcactt agtttaggaa ccagtgagca agtcagccct   4560
tggggcagcc catacaaggc catggggctg ggcaagctgc acgcctgggt ccggggtggg   4620
cacggtgccc gggcaacgag ctgaaagctc atctgctctc aggggccct ccctggggac     4680 agcccctcct ggctagtcac accctgtagg ctcctctata taacccaggg gcacagggc    4740
```

| | |
|---|---|
| tgcccccaag ctggccgctc tagaggatcc ccgggactag aattcaccat gtctagatta | 4800 |
| gataaaagta aagtgattaa cagcgcatta gagctgctta atgaggtcgg aatcgaaggt | 4860 |
| ttaacaaccc gtaaactcgc ccagaagctt ggtgtagagc agcctacact gtattggcat | 4920 |
| gtaaaaaata agcgggcttt gctcgacgcc ttagccattg agatgttaga taggcaccat | 4980 |
| actcactttt gcccttaaa aggggaaagc tggcaagatt ttttacgcaa taacgctaaa | 5040 |
| agttttagat gtgctttact aagtcatcgc aatggagcaa aagtacattc agatacacgg | 5100 |
| cctacagaaa aacagtatga aactctcgaa aatcaattag ccttttatg ccaacaaggt | 5160 |
| ttttcactag agaacgcgtt atatgcactc agcgctgtgg ggcattttac tttaggttgc | 5220 |
| gtattggaag atcaagagca tcaagtcgct aaagaagaaa gggaaacacc tactactgat | 5280 |
| agtatgccgc cattattacg acaagctatc gaattatttg atcaccaagg tgcagagcca | 5340 |
| gccttcttat tcggccttga attgatcata tgcggattag aaaaacaact taaatgtgaa | 5400 |
| agtgggtccg cgtacagccg cgcgcgtacg aaaaacaatt acgggtctac catcgagggc | 5460 |
| ctgctcgatc tcccggacga cgacgccccc gaagaggcgg ggctggcggc tccgcgcctg | 5520 |
| tcctttctcc ccgcgggaca cacgcgcaga ctgtcgacgg ccccccgac cgatgtcagc | 5580 |
| ctgggggacg agctccactt agacggcgag gacgtggcga tggcgcatgc cgacgcgcta | 5640 |
| gacgatttcg atctggacat gttggggac ggggattccc cgggtccggg atttaccccc | 5700 |
| cacgactccg ccccctacgg cgctctggat atggccgact tcgagtttga gcagatgttt | 5760 |
| accgatgccc ttggaattga cgagtacggt gggatggatc cccgggtacc ggtcgccacc | 5820 |
| atggtgagca agggcgagga gctgttcacc ggggtggtgc ccatcctggt cgagctggac | 5880 |
| ggcgacgtaa acggccacaa gttcagcgtg tccggcgagg gcgagggcga tgccacctac | 5940 |
| ggcaagctga ccctgaagtt catctgcacc accggcaagc tgcccgtgcc ctggcccacc | 6000 |
| ctcgtgacca ccctgacctg gggcgtgcag tgcttcagcc gctaccccga ccacatgaag | 6060 |
| cagcacgact tcttcaagtc cgccatgccc gaaggctacg tccaggagcg caccatcttc | 6120 |
| ttcaaggacg acggcaacta caagacccgc gccgaggtga agttcgaggg cgacaccctg | 6180 |
| gtgaaccgca tcgagctgaa gggcatcgac ttcaaggagg acggcaacat cctggggcac | 6240 |
| aagctggagt acaactacat cagccacaac gtctatatca ccgccgacaa gcagaagaac | 6300 |
| ggcatcaagg ccaacttcaa gatccgccac aacatcgagg acggcagcgt gcagctcgcc | 6360 |
| gaccactacc agcagaacac ccccatcggc gacggccccg tgctgctgcc cgacaaccac | 6420 |
| tacctgagca cccagtccgc cctgagcaaa gaccccaacg agaagcgcga tcacatggtc | 6480 |
| ctgctggagt tcgtgaccgc cgccgggatc actctcggca tggacgagct gtacaagtaa | 6540 |
| agcggccgcg actctagatc ataatcagcc ataccacatt tgtagaggtt ttacttgctt | 6600 |
| taaaaaacct cccacacctc ccctgaacc tgaaacataa aatgaatgca attgttgttg | 6660 |
| ttaacttgtt tattgcagct tataatggtt acaataaag caatagcatc acaaatttca | 6720 |
| caaataaagc atttttttca ctgcattcta gttgtggttt gtccaaactc atcaatgtat | 6780 |
| cttaag | 6786 |

<210> SEQ ID NO 2
<211> LENGTH: 3131
<212> TYPE: DNA
<213> ORGANISM: Mus Musculus

<400> SEQUENCE: 2

| | |
|---|---|
| atgcatggcg gtaatacggt tatccacaga atcaggggat aacgcaggaa agaacatgtg | 60 |

-continued

```
agcaaaaggc cagcaaaagg ccaggaaccg taaaaaggcc gcgttgctgg cgttttttcca    120 taggctccgc cccctgacg agcatcacaa aaatcgacgc tcaagtcaga ggtggcgaaa       180
cccgacagga ctataaagat accaggcgtt tccccctgga agctccctcg tgcgctctcc      240
tgttccgacc ctgccgctta ccggatacct gtccgccttt ctcccttcgg gaagcgtggc      300
gctttctcat agctcacgct gtaggtatct cagttcggtg taggtcgttc gctccaagct      360
gggctgtgtg cacgaacccc ccgttcagcc cgaccgctgc gccttatccg gtaactatcg      420
tcttgagtcc aacccggtaa gacacgactt atcgccactg gcagcagcca ctggtaacag      480
gattagcaga gcgaggtatg taggcggtgc tacagagttc ttgaagtggt ggcctaacta      540
cggctacact agaaggacag tatttggtat ctgcgctctg ctgaagccag ttaccttcgg      600
aaaaagagtt ggtagctctt gatccggcaa acaaaccacc gctggtagcg gtggttttt      660 tgtttgcaag cagcagatta cgcgcagaaa aaaggatct caagaagatc ctttgatctt       720
ttctacgggg tctgacgctc agtggaacga aaactcacgt taagggattt tggtcatgag      780
attatcaaaa aggatcttca cctagatcct tttaaattaa aaatgaagtt ttaaatcaat      840
ctaaagtata tatgagtaac ctgaggctat ggcagggcct gccgcccga cgttggctgc       900 gagccctggg ccttcacccg aacttggggg gtggggtggg gaaaaggaag aaacgcgggc      960
gtattggccc caatgggtc tcggtggggt atcgacagag tgccagccct gggaccgaac       1020
cccgcgttta tgaacaaacg acccaacacc gtgcgtttta ttctgtcttt ttattgccgt      1080
catagcgcgg gttccttccg gtattgtctc cttccgtgtt tcagttagcc tcccctagg      1140 gtgggcgaag aactccagca tgagatcccc gcgctggagg atcatccagc cggcgtcccg      1200
gaaaacgatt ccgaagccca acctttcata gaaggcggcg gtggaatcga aatctcgtga      1260
tggcaggttg ggcgtcgctt ggtcggtcat ttcgaacccc agagtcccgc tcagaagaac      1320
tcgtcaagaa ggcgatagaa ggcgatgcgc tgcgaatcgg gagcggcgat accgtaaagc      1380
acgaggaagc ggtcagccca ttcgccgcca agctcttcag caatatcacg ggtagccaac      1440
gctatgtcct gatagcggtc cgccacaccc agccggccac agtcgatgaa tccagaaaag      1500
cggccatttt ccaccatgat attcggcaag caggcatcgc catgggtcac gacgagatcc      1560
tcgccgtcgg gcatgctcgc cttgagcctg gcgaacagtt cggctggcgc gagcccctga      1620
tgctcttcgt ccagatcatc ctgatcgaca agaccggctt ccatccgagt acgtgctcgc      1680
tcgatgcgat gtttcgcttg gtggtcgaat gggcaggtag ccggatcaag cgtatgcagc      1740
cgccgcattg catcagccat gatggatact ttctcggcag gagcaaggtg agatgacagg      1800
agatcctgcc ccggcacttc gcccaatagc agccagtccc ttcccgcttc agtgacaacg      1860
tcgagcacag ctgcgcaagg aacgcccgtc gtggccagcc acgatagccg cgctgcctcg      1920
tcttgcagtt cattcagggc accggacagg tcggtcttga caaaagaac cgggcgcccc       1980 tgcgctgaca gccggaacac ggcggcatca gagcagccga ttgtctgttg tgcccagtca      2040
tagccgaata gcctctccac ccaagcggcc ggagaacctg cgtgcaatcc atcttgttca      2100
atcatgcgaa acgatcctca tcctgtctct tgatcgatct ttgcaaaagc ctaggcctcc      2160
aaaaaagcct cctcactact tctggaatag ctcagaggcc gaggcggcct cggcctctgc      2220
ataaataaaa aaaattagtc agccatgggg cggagaatgg gcggaactgg gcggagttag      2280
gggcgggatg ggcggagtta ggggcgggac tatggttgct gactaattga gatgcatgct      2340
ttgcatactt ctgcctgctg gggagcctgg ggactttcca cacctggttg ctgactaatt      2400
gagatgcatg ctttgcatac ttctgcctgc tggggagcct ggggactttc cacaccctaa      2460
```

-continued

| | |
|---|---|
| ctgacacaca ttccacagct ggttctttcc gcctcaggac tcttccttt tcaatattat | 2520 |
| tgaagcattt atcagggtta ttgtctcatg agcggataca tatttgaatg tatttagaaa | 2580 |
| aataaacaaa taggggttcc gcgcacattt ccccgaaaag tgccacctga cgcgccctgt | 2640 |
| agcggcgcat taagcgcggc gggtgtgtgt gttacgcgca gcgtgaccgc tacacttgcc | 2700 |
| agcgccctag cgcccgctcc tttcgctttc ttcccttcct ttctcgccac gttcgccggc | 2760 |
| tttccccgtc aagctctaaa tcgggggctc cctttagggt tccgatttag tgctttacgg | 2820 |
| cacctcgacc ccaaaaaact tgattagggt gatggttcac gtagtgggcc atcgccctga | 2880 |
| tagacggttt tcgcccttt gacgttggag tccacgttct ttaatagtgg actcttgttc | 2940 |
| caaactggaa caacactcaa ccctatctcg gtctattctt ttgatttata agggattttg | 3000 |
| ccgatttcgg cctattggtt aaaaaatgag ctgatttaac aaaaatttaa cgcgaatttt | 3060 |
| aacaaaatat taacgcttac aatttacgcc ttaagataca ttgatgagtt tggacaaacc | 3120 |
| acaactagaa t | 3131 |

<210> SEQ ID NO 3
<211> LENGTH: 51
<212> TYPE: DNA
<213> ORGANISM: Mus Musculus

<400> SEQUENCE: 3

| | |
|---|---|
| gcagtgaaaa aaatgcttta tttgtgaaat tgtgatgct attgctttat t | 51 |

<210> SEQ ID NO 4
<211> LENGTH: 1308
<212> TYPE: DNA
<213> ORGANISM: Mus Musculus

<400> SEQUENCE: 4

| | |
|---|---|
| ttacttgtac agctcgtcca tgccgagagt gatcccggcg gcggtcacga actccagcag | 60 |
| gaccatgtga tcgcgcttct cgttggggtc tttgctcagg gcggactggg tgctcaggta | 120 |
| gtggttgtcg ggcagcagca cggggccgtc gccgatgggg gtgttctgct ggtagtggtc | 180 |
| ggcgagctgc acgctgccgt cctcgatgtt gtggcggatc ttgaagttca ccttgatgcc | 240 |
| gttcttctgc ttgtcggcca tgatatagac gttgtggctg ttgtagttgt actccagctt | 300 |
| gtgccccagg atgttgccgt cctccttgaa gtcgatgccc ttcagctcga tgcggttcac | 360 |
| cagggtgtcg ccctcgaact tcacctcggc gcgggtcttg tagttgccgt cgtccttgaa | 420 |
| gaagatggtg cgctcctgga cgtagccttc gggcatggcg gacttgaaga agtcgtgctg | 480 |
| cttcatgtgg tcggggtagc ggctgaagca ctgcacgccg taggtcaggg tggtcacgag | 540 |
| ggtgggccag ggcacgggca gcttgccggt ggtgcagatg aacttcaggg tcagcttgcc | 600 |
| gtaggtggca tcgccctcgc cctcgccgga cacgctgaac ttgtggccgt ttacgtcgcc | 660 |
| gtccagctcg accaggatgg gcaccacccc ggtgaacagc tcctcgccct tgctcaccat | 720 |
| ggttgtggcc atattatcat cgtgtttttc aaaggaaaac cacgtccccg tggttcgggg | 780 |
| ggcctagacg tttttttaac ctcgactaaa cacatgtaaa gcatgtgcac cgaggcccca | 840 |
| gatcagatcc catacaatgg ggtaccttct gggcatcctt cagccccttg ttgaatacgc | 900 |
| ttgaggagag ccatttgact cttttccaca ctatccaact cacaacgtgg cactgggggtt | 960 |
| gtgccgcctt tgcaggtgta tcttatacac gtggcttttg gccgcagagg cacctgtcgc | 1020 |
| caggtggggg gttccgctgc ctgcaaaggg tcgctacaga cgttgtttgt cttcaagaag | 1080 |
| cttccagagg aactgcttcc ttcacgacat tcaacagacc ttgcattcct ttggcgagag | 1140 |

```
gggaaagacc cctaggaatg ctcgtcaaga agacagggcc aggtttccgg gccctcacat    1200
tgccaaaaga cggcaatatg gtggaaaata acatatagac aaacgcacac cggccttatt    1260
ccaagcggct tcggccagta acgttagggg gggggagggg agaggggc                 1308
```

<210> SEQ ID NO 5
<211> LENGTH: 1131
<212> TYPE: DNA
<213> ORGANISM: Mus Musculus

<400> SEQUENCE: 5

```
tcatgagcac ccacagcggt ctactaccat ggctggaatt ttcccatata ttatttgttc     60
tttgccatta aaatatagca tattaatggg agacattttt gtcggagtgc agcaagggcc    120
tgctgagcct ctggggtttg cttggtgcac aagatgagta tgcggatatt tttgtaaaaa    180
cacaaattca cactctcctg agcagtaatt ggccttatat cttttgggtg cgataatcca    240
gtcccatcca aaggcttcaa aatcgaccgt gaggggtag cggcagcacc gggattccgt     300
ggagtgctca tcgcagtcaa gcccaaagtc tctccgggac ctcttgggtg tgtctgtcac    360
cttgacttct aaaaagggat tcagcccatc ttctcctggt cctgggaagg ttacagcaag    420
atcatggcca ttctcatcca aagctttgat ttcaatgcct aagttggatt caggctgttt    480
gagccaattt tgcaacactg tcttcacatc aatactctgc caaataccag tgcctgggct    540
catgtcaagt ttcagagatc ggattccagt ataccttgta ccgtctttca tgggtttgat    600
gagtctcagg atttgcacaa acactgttgt aggagtcttg acgggtctga gatatatcca    660
cagttgggct tttactactt tgttgtactg tattttagag ctaaatttaa aaaagcaaca    720
tttgggcttg ccatccgctt gcattagaaa gtcagactct gtaggcatgg taatgattgt    780
ttccgtggta gcgtgataat cgtcatcttc caaagagcca tcactgctgt catccctctg    840
gacgtcgtac tgatcgatca gttcccggag tggaggcgct cttggcagaa gttgtcttat    900
agcatctttg ctgatgttag gagctgtttc caggcgcagc ttactgagga tttgaatttt    960
tatggcttct attctggagt acctcgtgtt ttgtctccac gcacatgcat tacacagccc   1020 ctcttttttcc acattttctt ctctctcact gccctcattt agatccactg gccagcagc   1080 aatcagcatg aacaggtaaa tataaacata catttgcagt ttttgcatca t            1131
```

<210> SEQ ID NO 6
<211> LENGTH: 30
<212> TYPE: DNA
<213> ORGANISM: Mus Musculus

<400> SEQUENCE: 6

```
aagagcgtaa tctggaacat cgtatgggta                                      30
```

<210> SEQ ID NO 7
<211> LENGTH: 432
<212> TYPE: DNA
<213> ORGANISM: Mus Musculus

<400> SEQUENCE: 7

```
aggctggatc ggtcccggtg tcttctatgg aggtcaaaac agcgtggatg gcgtctccag     60
gcgatctgac ggttcactaa acgagctctg cttatatagg cctcccaccg tacacgccta    120
ctcgacccgg gtaccgagct cgactttcac tttttctctat cactgatagg gagtggtaaa    180
ctcgactttc acttttctct atcactgata gggagtggta aactcgactt tcactttttct    240 ctatcactga tagggagtgg taaactcgac tttcactttt ctctatcact gatagggagt    300
```

```
ggtaaactcg actttcactt ttctctatca ctgatagggc gtggtaaact cgactttcac        360
ttttctctat cactgatagg gagtggtaaa ctcgactttc acttttctct atcactgata        420
gggagtggta aa                                                            432
```

<210> SEQ ID NO 8
<211> LENGTH: 1357
<212> TYPE: DNA
<213> ORGANISM: Mus Musculus

<400> SEQUENCE: 8

```
cagctgaggt gcaaaaggct cctgtcatat tgtgtcctgc tctggtctgc cttccacagc         60
ttgggggcca cctagcccac ctctccctag ggatgagagc agccactacg ggtctaggct        120
gcccatgtaa ggaggcaagg cctggggaca cccgagatgc ctggttataa ttaacccaga        180
catgtggctg cccccccccc cccaacacct gctgcctgag cctcaccccc accccggtgc        240
ctgggtctta ggctctgtac accatggagg agaagctcgc tctaaaaata accctgtccc        300
tggtggatcc agggtgaggg gcaggctgag ggcggccact tccctcagcc gcaggtttgt        360
tttcccaaga atggttttttc tgcttctgta gcttttcctg tcaattctgc catggtggag        420
cagcctgcac tgggcttctg ggagaaacca accgggttc taacctttca gctacagtta         480
ttgcctttcc tgtagatggg cgactacagc cccacccccca ccccgtctc ctgtatcctt        540 cctgggcctg gggatcctag gctttcactg gaaatttccc cccaggtgct gtaggctaga        600
gtcacggctc ccaagaacag tgcttgcctg gcatgcatgg ttctgaacct ccaactgcaa        660
aaaatgacac ataccttgac ccttggaagg ctgaggcagg ggattgcca tgagtgcaaa         720 gccagactgg gtggcatagt tagaccctgt ctcaaaaaac caaaaacaat taaataacta        780
aagtcaggca agtaatccta ctcgggagac tgaggcagag ggattgttac atgtctgagg        840
ccagcctgga ctacataggg tttcaggcta gccctgtcta cagagtaagg ccctatttca        900
aaaacacaaa caaaatggtt ctcccagctg ctaatgctca ccaggcatga agcctggtga        960
gcattagcaa tgaaggcaat gaaggagggt gctggctaca atcaaggctg tgggggactg       1020
agggcaggct gtaacaggct gggggccag ggcttatacg tgcctgggac tcccaaagta       1080
ttactgttcc atgttcccgg cgaagggcca gctgtccccc gccagctaga ctcagcactt       1140
agtttaggaa ccagtgagca agtcagccct ggggcagcc catacaaggc catgggcctg        1200
ggcaagctgc acgcctgggt ccggggtggg cacggtgccc gggcaacgag ctgaaagctc       1260
atctgctctc agggggccct ccctggggac agccctcct ggctagtcac accctgtagg        1320
ctcctctata taacccaggg gcacaggggc tgccccc                                 1357
```

<210> SEQ ID NO 9
<211> LENGTH: 1005
<212> TYPE: DNA
<213> ORGANISM: Mus Musculus

<400> SEQUENCE: 9

```
atgtctagat tagataaaag taaagtgatt aacagcgcat tagagctgct taatgaggtc         60
ggaatcgaag gtttaacaac ccgtaaactc gcccagaagc ttggtgtaga gcagcctaca        120
ctgtattggc atgtaaaaaa taagcgggct ttgctcgacg ccttagccat tgagatgtta        180
gataggcacc atactcactt tgcccctta aaaggggaaa gctggcaaga ttttttacgc         240
aataacgcta aaagttttag atgtgcttta ctaagtcatc gcaatggagc aaaagtacat        300
tcagatacac ggcctacaga aaaacagtat gaaactctcg aaaatcaatt agccttttta        360
```

```
tgccaacaag gttttcact  agagaacgcg  ttatatgcac  tcagcgctgt  ggggcatttt    420
actttaggtt gcgtattgga agatcaagag  catcaagtcg  ctaaagaaga  aagggaaaca    480
cctactactg atagtatgcc gccattatta  cgacaagcta  tcgaattatt  tgatcaccaa    540
ggtgcagagc cagccttctt attcggcctt  gaattgatca  tatgcggatt  agaaaaacaa    600
cttaaatgtg aaagtgggtc cgcgtacagc  cgcgcgcgta  cgaaaaacaa  ttacgggtct    660
accatcgagg gcctgctcga  tctcccggac  gacgacgccc  cgaagaggc  ggggctggcg    720 gctccgcgcc tgtcctttct  ccccgcggga  cacacgcgca  gactgtcgac  ggccccccg    780 accgatgtca gcctggggga  cgagctccac  ttagacggcg  aggacgtggc  gatgcgcat    840 gccgacgcgc tagacgattt  cgatctggac  atgttggggg  acggggattc  cccgggtccg    900
ggatttaccc cccacgactc  cgcccccctac ggcgctctgg  atatggccga  cttcgagttt    960
gagcagatgt ttaccgatgc  ccttggaatt  gacgagtacg  gtggg                    1005

<210> SEQ ID NO 10
<211> LENGTH: 720
<212> TYPE: DNA
<213> ORGANISM: Mus Musculus

<400> SEQUENCE: 10
atggtgagca agggcgagga gctgttcacc  ggggtggtgc  ccatcctggt  cgagctggac     60
ggcgacgtaa acggccacaa gttcagcgtg  tccggcgagg  gcgagggcga  tgccacctac    120
ggcaagctga ccctgaagtt catctgcacc  accggcaagc  tgcccgtgcc  ctggcccacc    180
ctcgtgacca ccctgaccctg gggcgtgcag  tgcttcagcc  gctaccccga  ccacatgaag    240
cagcacgact tcttcaagtc cgccatgccc  gaaggctacg  tccaggagcg  caccatcttc    300
ttcaaggacg acggcaacta caagacccgc  gccgaggtga  agttcgaggg  cgacaccctg    360
gtgaaccgca tcgagctgaa gggcatcgac  ttcaaggagg  acggcaacat  cctggggcac    420
aagctggagt acaactacat cagccacaac  gtctatatca  ccgccgacaa  gcagaagaac    480
ggcatcaagg ccaacttcaa gatccgccac  aacatcgagg  acggcagcgt  gcagctcgcc    540
gaccactacc agcagaacac ccccatcggc  gacggccccg  tgctgctgcc  cgacaaccac    600
tacctgagca cccagtccgc cctgagcaaa  gaccccaacg  agaagcgcga  tcacatggtc    660
ctgctggagt tcgtgaccgc cgccgggatc  actctcggca  tggacgagct  gtacaagtaa    720

<210> SEQ ID NO 11
<211> LENGTH: 51
<212> TYPE: DNA
<213> ORGANISM: Mus Musculus

<400> SEQUENCE: 11
aataaagcaa tagcatcaca aatttcacaa  ataaagcatt  tttttcactg c              51

<210> SEQ ID NO 12
<211> LENGTH: 6
<212> TYPE: DNA
<213> ORGANISM: Mus Musculus

<400> SEQUENCE: 12 cttaag                                                                    6

<210> SEQ ID NO 13
<211> LENGTH: 10273
<212> TYPE: DNA
<213> ORGANISM: Mus Musculus
```

<400> SEQUENCE: 13

```
ctcgactttc acttttctct atcactgata gggagtggta aactcgagat ctcgagctca      60
agcttcgaat tatcgaattc ctgcagcccg atctcagctg aggtgcaaaa ggctcctgtc     120
atattgtgtc ctgctctggt ctgccttcca cagcttgggg gccacctagc ccacctctcc     180
ctagggatga gagcagccac tacgggtcta ggctgcccat gtaaggaggc aaggcctggg     240
gacacccgag atgcctggtt ataattaacc cagacatgtg gctgccccc cccccccaac     300
acctgctgcc tgagcctcac ccccaccccg gtgcctgggt cttaggctct gtacaccatg     360
gaggagaagc tcgctctaaa ataaccctg tccctggtgg atccagggtg aggggcaggc     420
tgagggcggc cacttccctc agccgcaggt ttgttttccc aagaatggtt tttctgcttc     480
tgtagctttt cctgtcaatt ctgccatggt ggagcagcct gcactgggct tctgggagaa     540
accaaaccgg gttctaacct ttcagctaca gttattgcct ttcctgtaga tgggcgacta     600
cagccccacc cccaccccg tctcctgtat ccttcctggg cctggggatc ctaggctttc     660
actgaaaatt tcccccagg tgctgtaggc tagagtcacg gctcccaaga acagtgcttg     720
cctggcatgc atggttctga acctccaact gcaaaaaatg acacatacct tgacccttgg     780
aaggctgagg caggggggatt gccatgagtg caaagccaga ctgggtggca tagttagacc     840
ctgtctcaaa aaaccaaaaa caattaaata actaaagtca ggcaagtaat cctactcggg     900
agactgaggc agagggattg ttacatgtct gaggccagcc tggactacat agggtttcag     960
gctagccctg tctacagagt aaggcccat ttcaaaaaca caaacaaaat ggttctccca    1020
gctgctaatg ctcaccaggc atgaagcctg gtgagcatta gcaatgaagg caatgaagga    1080
gggtgctggc tacaatcaag gctgtggggg actgagggca ggctgtaaca ggcttggggg    1140
ccagggctta tacgtgcctg ggactcccaa agtattactg ttccatgttc ccggcgaagg    1200
gccagctgtc ccccgccagc tagactcagc acttagtta ggaaccagtg agcaagtcag     1260
cccttggggc agcccataca aggccatggg gctgggcaag ctgcacgcct gggtccgggg    1320
tgggcacggt gccgggcaa cgagctgaaa gctcatctgc tctcagggggc ccctccctgg    1380
ggacagcccc tcctggctag tcacaccctg taggctcctc tatataaccc aggggcacag    1440
gggctgcccc caagctggcc gctctagagg atccccggga ctagaattca ccatgtctag    1500
attagataaa agtaaagtga ttaacagcgc attagagctg cttaatgagg tcggaatcga    1560
aggtttaaca acccgtaaac tcgcccagaa gcttggtgta gagcagccta cactgtattg    1620
gcatgtaaaa aataagcggg cttttgctcga cgccttagcc attgagatgt tagataggca    1680
ccatactcac ttttgccctt taaaagggga aagctggcaa gatttttac gcaataacgc    1740
taaaagtttt agatgtgctt tactaagtca tcgcaatgga gcaaaagtac attcagatac    1800
acggcctaca gaaaaacagt atgaaactct cgaaaatcaa ttagcctttt tatgccaaca    1860
aggtttttca ctagagaacg cgttatatgc actcagcgct gtgggcatt ttactttagg     1920
ttgcgtattg gaagatcaag agcatcaagt cgctaaagaa gaagggaaa cacctactac    1980
tgatagtatg ccgccattat tacgacaagc tatcgaatta tttgatcacc aaggtgcaga    2040
gccagccttc ttattcggcc ttgaattgat catatgcgga ttagaaaaac aacttaaatg    2100
tgaaagtggg tccgcgtaca gccgcgcgcg tacgaaaaac aattacgggt ctaccatcga    2160
gggcctgctc gatctcccgg acgacgacgc ccccgaagag gcggggctgg cggctccgcg    2220
cctgtccttt ctccccgcgg gacacacgcg cagactgtcg acggccccc cgaccgatgt    2280
cagcctgggg gacgagctcc acttagacgg cgaggacgtg gcgatggcgc atgccgacgc    2340
```

```
gctagacgat tcgatctgg acatgttggg ggacggggat tccccgggtc cgggatttac   2400
cccccacgac tccgccccct acggcgctct ggatatggcc gacttcgagt ttgagcagat   2460
gtttaccgat gcccttggaa ttgacgagta cggtgggatg gatccccggg taccggtcgc   2520
caccatggtg agcaagggcg aggagctgtt caccggggtg gtgcccatcc tggtcgagct   2580
ggacggcgac gtaaacggcc acaagttcag cgtgtccggc gagggcgagg gcgatgccac   2640
ctacggcaag ctgaccctga agttcatctg caccaccggc aagctgcccg tgccctggcc   2700
caccctcgtg accaccctga cctggggcgt gcagtgcttc agccgctacc ccgaccacat   2760
gaagcagcac gacttcttca gtccgccat gcccgaaggc tacgtccagg agcgcaccat   2820
cttcttcaag gacgacggca actacaagac ccgcgccgag gtgaagttcg agggcgacac   2880
cctggtgaac cgcatcgagc tgaagggcat cgacttcaag gaggacggca acatcctggg   2940
gcacaagctg gagtacaact acatcagcca caacgtctat atcaccgccg acaagcagaa   3000
gaacggcatc aaggccaact tcaagatccg ccacaacatc gaggacggca gcgtgcagct   3060
cgccgaccac taccagcaga cacccccat cggcgacggc cccgtgctgc tgcccgacaa   3120
ccactacctg agcacccagt ccgccctgag caaagacccc aacgagaagc gcgatcacat   3180
ggtcctgctg gagttcgtga ccgccgccgg gatcactctc ggcatggacg agctgtacaa   3240
gtaaagcggc cgcgactcta gatcataatc agccatacca catttgtaga ggttttactt   3300
gctttaaaaa acctcccaca cctcccctg aacctgaaac ataaaatgaa tgcaattgtt   3360
gttgttaact tgtttattgc agcttataat ggttacaaat aaagcaatag catcacaaat   3420
ttcacaaata aagcattttt ttcactgcat tctagttgtg gtttgtccaa actcatcaat   3480
gtatcttaag cgtaaattg taagcgttaa tattttgtta aaattcgcgt taaattttttg   3540
ttaaatcagc tcattttta accaataggc cgaaatcggc aaaatccctt ataaatcaaa   3600
agaatagacc gagagctagc ggatctgacg gttcactaaa ccagctctgc ttatatagac   3660
ctcccaccgt acacgcctac ccgccatttg cgtcaatggg gcggagttgt tatgacattt   3720
tggaaagtcc cgttgatttt ggtgccaaaa caaactccca ttgacgtcaa tgggcggggg   3780
tcgttgggcg gtcagccagg cgggccattt accgtaagtt atgtaacgcg gaactccata   3840
tatgggctat gaactaatga ccccgtaatt gattactatt ataactaat gcatggcggt   3900
aatacggtta tccacagaat cagggggataa cgcaggaaag aacatgtgag caaaaggcca   3960
gcaaaaggcc aggaaccgta aaaaggccgc gttgctggcg ttttttccata ggctccgccc   4020
ccctgacgag catcacaaaa atcgacgctc aagtcagagg tggcgaaacc cgacaggact   4080
ataaagatac caggcgtttc ccctggaag ctccctcgtg cgctctcctg ttccgaccct   4140
gccgcttacc ggatacctgt ccgcctttct cccttcggga agcgtggcgc tttctcatag   4200
ctcacgctgt aggtatctca gttcggtgta ggtcgttcgc tccaagctgg gctgtgtgca   4260
cgaaccccc gttcagcccg accgctgcgc cttatccgt aactatcgtc ttgagtccaa   4320
cccggtaaga cacgacttat cgccactggc agcagccact ggtaacagga ttagcagagc   4380
gaggtatgta ggcggtgcta cagagttctt gaagtggtgg cctaactacg gctacactag   4440
aaggacagta tttggtatct gcgctctgct gaagccagtt accttcggaa aaagagttgg   4500
tagctcttga tccggcaaac aaaccaccgc tggtagcggt ggttttttttg tttgcaagca   4560
gcagattacg cgcagaaaaa aaggatctca agaagatcct ttgatctttt ctacggggtc   4620
tgacgctcag tggaacgaaa actcacgtta agggatttg gtcatgagat tatcaaaaag   4680
gatcttcacc tagatccttt taaattaaaa atgaagtttt aaatcaatct aaagtatata   4740
```

-continued

```
tgagtaacct gaggctatgg cagggcctgc cgccccgacg ttggctgcga gccctgggcc    4800
ttcacccgaa cttgggggt ggggtgggga aaaggaagaa acgcgggcgt attggcccca     4860
atggggtctc ggtggggtat cgacagagtg ccagccctgg gaccgaaccc cgcgtttatg    4920
aacaaacgac ccaacaccgt gcgtttatt ctgtcttttt attgccgtca tagcgcgggt     4980
tccttccggt attgtctcct tccgtgtttc agttagcctc cccctagggt gggcgaagaa    5040
ctccagcatg agatcccgc gctggaggat catccagccg cgtcccgga aaacgattcc     5100 gaagcccaac ctttcataga aggcggcggt ggaatcgaaa tctcgtgatg cagggttggg    5160
cgtcgcttgg tcggtcattt cgaacccag agtcccgctc agaagaactc gtcaagaagg    5220
cgatagaagg cgatgcgctg cgaatcggga gcggcgatac cgtaaagcac gaggaagcgg    5280
tcagcccatt cgccgccaag ctcttcagca atatcacggg tagccaacgc tatgtcctga    5340
tagcggtccg ccacacccag ccggccacag tcgatgaatc cagaaaagcg gccattttcc    5400
accatgatat cggcaagca ggcatcgcca tgggtcacga cgagatcctc gccgtcgggc    5460
atgctcgcct tgagcctggc gaacagttcg gctggcgcga gcccctgatg ctcttcgtcc    5520
agatcatcct gatcgacaag accggcttcc atccgagtac gtgctcgctc gatgcgatgt    5580
ttcgcttggt ggtcgaatgg gcaggtagcc ggatcaagcg tatgcagccg ccgcattgca    5640
tcagccatga tggataccttt ctcggcagga gcaaggtgag atgacaggag atcctgcccc    5700
ggcacttcgc ccaatagcag ccagtcctt cccgcttcag tgacaacgtc gagcacagct    5760
gcgcaaggaa cgcccgtcgt ggccagccac gatagccgcg ctgcctcgtc ttgcagttca    5820
ttcagggcac cggacaggtc ggtcttgaca aaagaaccg ggcgccctg cgctgacagc     5880 cggaacacgg cggcatcaga gcagccgatt gtctgttgtg cccagtcata gccgaatagc    5940
ctctccaccc aagcggccgg agaacctgcg tgcaatccat cttgttcaat catgcgaaac    6000
gatcctcatc ctgtctcttg atcgatcttt gcaaaagcct aggcctccaa aaagcctcc     6060 tcactacttc tggaatagct cagaggccga ggcggcctcg gcctctgcat aaataaaaaa    6120
aattagtcag ccatggggcg gagaatgggc ggaactgggc ggagttaggg gcggatggg     6180 cggagttagg ggcgggacta tggttgctga ctaattgaga tgcatgcttt gcatacttct    6240
gcctgctggg gagcctgggg actttccaca cctggttgct gactaattga gatgcatgct    6300
ttgcatactt ctgcctgctg gggagcctgg ggacttccca caccctaact gacacacatt    6360
ccacagctgg ttcttccgc ctcaggactc ttccttttc aatattattg aagcatttat     6420
cagggttatt gtctcatgag cggatacata tttgaatgta tttagaaaaa taaacaaata    6480
ggggttccgc gcacatttcc ccgaaagtg ccacctgacg cgccctgtag cggcgcatta    6540
agcgcggcgg gtgtggtggt tacgcgcagc gtgaccgcta cacttgccag cgccctagcg    6600
cccgctcctt tcgctttctt cccttccttt ctcgccacgt tcgccggctt tccccgtcaa    6660
gctctaaatc gggggctccc tttagggttc cgatttagtg ctttacggca cctcgacccc    6720
aaaaaacttg attagggtga tggttcacgt agtgggccat cgccctgata acggttttt    6780 cgcccttga cgttggagtc cacgttcttt aatagtggac tcttgttcca aactggaaca    6840
acactcaacc ctatctcggt ctattctttt gatttataag gattttgcc gatttcggcc    6900 tattggttaa aaaatgagct gatttaacaa aaatttaacg cgaattttaa caaaatatta    6960
acgcttacaa tttacgcctt aagatacatt gatgagtttg gacaaaccac aactagaatg    7020
cagtgaaaaa aatgctttat ttgtgaaatt tgtgatgcta ttgctttatt tgtaaccatt    7080
ataagctgca ataaacaagt taacaacaac aattgcattc attttatgtt tcaggttcag    7140
```

```
ggggaggtgt gggaggtttt ttaaagcaag taaaacctct acaaatgtgg tatggctgat    7200
tatgatctag agtcgcggcc gctttacttg tacagctcgt ccatgccgag agtgatcccg    7260
gcggcggtca cgaactccag caggaccatg tgatcgcgct tctcgttggg gtctttgctc    7320
agggcggact gggtgctcag gtagtggttg tcgggcagca gcacggggcc gtcgccgatg    7380
ggggtgttct gctggtagtg gtcggcgagc tgcacgctgc cgtcctcgat gttgtggcgg    7440
atcttgaagt tcaccttgat gccgttcttc tgcttgtcgg ccatgatata gacgttgtgg    7500
ctgttgtagt tgtactccag cttgtgcccc aggatgttgc cgtcctcctt gaagtcgatg    7560
cccttcagct cgatgcggtt caccagggtg tcgccctcga acttcacctc ggcgcgggtc    7620
ttgtagttgc cgtcgtcctt gaagaagatg gtgcgctcct ggacgtagcc ttcgggcatg    7680
gcggacttga agaagtcgtg ctgcttcatg tggtcgggt agcggctgaa gcactgcacg    7740
ccgtaggtca gggtggtcac gagggtgggc cagggcacgg gcagcttgcc ggtggtgcag    7800
atgaacttca gggtcagctt gccgtaggtg gcatcgccct cgcccttcgcc ggacacgctg    7860
aacttgtggc cgtttacgtc gccgtccagc tcgaccagga tgggcaccac cccggtgaac    7920
agctcctcgc ccttgctcac catggttgtg gccatattat catcgtgttt ttcaaaggaa    7980
aaccacgtcc ccgtggttcg gggggcctag acgtttttt aacctcgact aaacacatgt    8040
aaagcatgtg caccgaggcc ccagatcaga tcccatacaa tggggtacct tctgggcatc    8100
cttcagcccc ttgttgaata cgcttgagga gagccatttg actctttcca caactatcca    8160
actcacaacg tggcactggg gttgtgccgc ctttgcaggt gtatcttata cacgtggctt    8220
ttggccgcag aggcacctgt cgccaggtgg ggggttccgc tgcctgcaaa gggtcgctac    8280
agacgttgtt tgtcttcaag aagcttccag aggaactgct tccttcacga cattcaacag    8340
accttgcatt cctttggcga gaggggaaag accccctagga atgctcgtca agaagacagg    8400
gccaggtttc cgggccctca cattgccaaa agacggcaat atggtggaaa ataacatata    8460
gacaaacgca caccggcctt attccaagcg gcttcggcca gtaacgttag ggggggggga    8520
gggagagggg cggatcccgg gcccgcggta ccgtcgactg cagaattcac tagtgattaa    8580
attatattgt cgactcatga gcacccacag cggtctacta ccatggctgg aattttccca    8640
tatattattt gttctttgcc attaaaatat agcatattaa tgggagacat ttttgtcgga    8700
gtgcagcaag ggcctgctga gcctctgggg tttgcttggt gcacaagatg agtatgcgga    8760
tattttgta aaaacacaaa ttcacactct cctgagcagt aattggcctt atatcttttg    8820
ggtgcgataa tccagtccca tccaaaggct tcaaaatcga ccgtgagggg gtagcggcag    8880
caccgggatt ccgtggagtg ctcatcgcag tcaagcccaa agtctctccg ggacctcttg    8940
ggtgtgtctg tcaccttgac ttctaaaaag ggattcagcc catcttctcc tggtcctggg    9000
aaggttacag caagatcatg gccattctca tccaaagctt tgatttcaat gcctaagttg    9060
gattcaggct gtttgagcca attttgcaac actgtcttca catcaatact ctgccaaata    9120
ccagtgcctg ggctcatgtc aagtttcaga gatcggattc cagtataccc tgtaccgtct    9180
ttcatgggtt tgatgagtct caggatttgc acaaacactg ttgtaggagt cttgacgggt    9240
ctgagatata tccacagttg ggcttttact actttgttgt actgtatttt agagctaaat    9300
ttaaaaagc aacatttggg cttgccatcc gcttgcatta gaaagtcaga ctctgtaggc    9360
atggtaatga ttgtttccgt ggtagcgtga taatcgtcat cttccaaaga gccatcactg    9420
ctgtcatccc tctggacgtc gtactgatcg atcagttccc ggagtggagg cgctcttggc    9480
agaagttgtc ttatagcatc tttgctgatg ttaggagctg tttccaggcg cagcttactg    9540
```

-continued

```
aggatttgaa tttttatggc ttctattctg gagtacctcg tgttttgtct ccacgcacat    9600
gcattacaca gcccctcttt ttccacattt tcttctctct cactgccctc atttagatcc    9660
actgggccag cagcaatcag catgaacagg taaatataaa catacatttg cagtttttgc    9720
atcatggctg gatccgggcc cataagagcg taatctggaa catcgtatgg gtacatggtg    9780
tctagctcgc gtcagctgac tagaggatcc ccgggtaccg agctcgaatt cggggccgcg    9840
gaggctggat cggtcccggt gtcttctatg gaggtcaaaa cagcgtggat ggcgtctcca    9900
ggcgatctga cggttcacta aacgagctct gcttatatag gcctcccacc gtacacgcct    9960
actcgacccg ggtaccgagc tcgactttca ctttttctcta tcactgatag ggagtggtaa   10020
actcgacttt cactttttctc tatcactgat agggagtggt aaactcgact ttcactttttc   10080 tctatcactg atagggagtg gtaaactcga ctttcacttt tctctatcac tgataggag   10140 tggtaaactc gactttcact tttctctatc actgataggg agtggtaaac tcgactttca   10200 ctttttctcta tcactgatag ggagtggtaa actcgactttt cactttttctc tatcactgat   10260 agggagtggt aaa                                                      10273
```

<210> SEQ ID NO 14
<211> LENGTH: 6
<212> TYPE: DNA
<213> ORGANISM: Mus musculus
<220> FEATURE:
<221> NAME/KEY: misc_feature
<222> LOCATION: (2)..(2)
<223> OTHER INFORMATION: x = any nucleotide

<400> SEQUENCE: 14

```
cncaat                                                                    6
```

<210> SEQ ID NO 15
<211> LENGTH: 6
<212> TYPE: DNA
<213> ORGANISM: Mus musculus

<400> SEQUENCE: 15

```
aataaa                                                                    6
```

<210> SEQ ID NO 16
<211> LENGTH: 24
<212> TYPE: DNA
<213> ORGANISM: Mus Musculus

<400> SEQUENCE: 16

```
atgatgcaaa aactgcaaat gtat                                               24
```

<210> SEQ ID NO 17
<211> LENGTH: 15
<212> TYPE: DNA
<213> ORGANISM: Mus Musculus

<400> SEQUENCE: 17

```
tcatgagcac ccaca                                                         15
```

<210> SEQ ID NO 18
<211> LENGTH: 20
<212> TYPE: DNA
<213> ORGANISM: Mus Musculus

<400> SEQUENCE: 18

```
aaccagtgag caagtcagcc                                                    20
```

```
<210> SEQ ID NO 19
<211> LENGTH: 18
<212> TYPE: DNA
<213> ORGANISM: Mus Musculus

<400> SEQUENCE: 19
gccagcagca atcagcat                                                 18

<210> SEQ ID NO 20
<211> LENGTH: 20
<212> TYPE: DNA
<213> ORGANISM: Mus Musculus

<400> SEQUENCE: 20
agacaaaaca cgaggtactc                                               20

<210> SEQ ID NO 21
<211> LENGTH: 20
<212> TYPE: DNA
<213> ORGANISM: Mus Musculus

<400> SEQUENCE: 21
tggattcagg ctgtttgagc                                               20

<210> SEQ ID NO 22
<211> LENGTH: 20
<212> TYPE: DNA
<213> ORGANISM: Mus Musculus

<400> SEQUENCE: 22
gtctcccatt aatatgctat                                               20

<210> SEQ ID NO 23
<211> LENGTH: 20
<212> TYPE: DNA
<213> ORGANISM: Mus Musculus

<400> SEQUENCE: 23
atcataccct cctaactcag                                               20
```